United States Patent
Dudek et al.

(10) Patent No.: US 7,708,998 B2
(45) Date of Patent: *May 4, 2010

(54) METHODS OF INHIBITING UNWANTED CELL PROLIFERATION USING HEDGEHOG ANTAGONISTS

(75) Inventors: Henryk Dudek, Wellesley, MA (US);
Irina Karavanov, Bethesda, MD (US);
Carmen Pepicelli, Lowell, MA (US);
Karen Kotkow, Jamaica Plain, MA (US); Lee L. Rubin, Wellesley, MA (US)

(73) Assignee: Curis, Inc., Cambridge, MA (US)

(*) Notice: Subject to any disclaimer, the term of this patent is extended or adjusted under 35 U.S.C. 154(b) by 181 days.

This patent is subject to a terminal disclaimer.

(21) Appl. No.: 10/652,298

(22) Filed: Aug. 29, 2003

(65) Prior Publication Data
US 2004/0110663 A1 Jun. 10, 2004

Related U.S. Application Data

(63) Continuation-in-part of application No. 09/977,864, filed on Oct. 15, 2001.

(60) Provisional application No. 60/240,564, filed on Oct. 13, 2000.

(51) Int. Cl.
*A61K 39/395* (2006.01)
*C12Q 1/68* (2006.01)
*G01N 33/574* (2006.01)

(52) U.S. Cl. .................. 424/138.1; 424/139.1; 435/6; 435/7.23; 800/10

(58) Field of Classification Search ............ None
See application file for complete search history.

(56) References Cited

U.S. PATENT DOCUMENTS

| | | | |
|---|---|---|---|
| 5,789,543 A | 8/1998 | Ingham et al. | |
| 5,837,538 A | 11/1998 | Scott et al. | |
| 5,844,079 A | 12/1998 | Ingham et al. | |
| 6,027,882 A | 2/2000 | Scott et al. | |
| 6,165,747 A | 12/2000 | Ingham et al. | |
| 6,172,200 B1 | 1/2001 | Scott et al. | |
| 6,261,786 B1 | 7/2001 | Marigo et al. | |
| 6,271,363 B1 | 8/2001 | Ingham et al. | |
| 6,384,192 B1 | 5/2002 | Ingham et al. | |
| 6,429,354 B1* | 8/2002 | Scott et al. | 800/18 |
| 6,545,005 B1 | 4/2003 | Baxter et al. | |
| 6,551,782 B1 | 4/2003 | Scott et al. | |

(Continued)

FOREIGN PATENT DOCUMENTS

WO WO 95/18856 7/1995

(Continued)

OTHER PUBLICATIONS

Heijstek et al, 2005. Dig Surg. 22: 16-25.*

(Continued)

*Primary Examiner*—Bridget E Bunner
*Assistant Examiner*—Zachary C Howard
(74) *Attorney, Agent, or Firm*—Ropes & Gray LLP

(57) ABSTRACT

The present application is directed to compositions and methods for inhibiting angiogenesis and treating or preventing unwanted cell proliferation, including tumors, by inhibiting the hedgehog pathway, e.g., with an antagonist of the hedgehog pathway such as those disclosed herein.

63 Claims, 54 Drawing Sheets

U.S. PATENT DOCUMENTS

| | | | |
|---|---|---|---|
| 6,552,016 | B1 | 4/2003 | Baxter et al. |
| 6,576,237 | B1 | 6/2003 | Ingham et al. |
| 6,607,913 | B1 | 8/2003 | Ingham et al. |
| 6,610,507 | B2 | 8/2003 | Scott et al. |
| 6,610,656 | B1 | 8/2003 | Ingham et al. |
| 6,630,148 | B1 | 10/2003 | Ingham et al. |
| 6,664,075 | B2 | 12/2003 | Ingham et al. |
| 6,867,216 | B1 | 3/2005 | Beachy et al. |
| 6,884,775 | B1 | 4/2005 | Tabin et al. |
| 6,921,646 | B2 | 7/2005 | Scott et al. |
| 6,946,257 | B1 | 9/2005 | Scott et al. |
| 7,060,450 | B1 | 6/2006 | Tabin et al. |
| 7,144,732 | B2 | 12/2006 | Ingham et al. |
| 7,445,778 | B2 | 11/2008 | Burkly et al. |
| 7,498,304 | B2 * | 3/2009 | Kotkow et al. ................. 514/12 |
| 2002/0015702 | A1 | 2/2002 | Burkly et al. |
| 2003/0022819 | A1 | 1/2003 | Ling et al. |
| 2004/0060568 | A1 | 4/2004 | Dudek et al. |
| 2004/0110663 | A1 | 6/2004 | Dudek et al. |
| 2004/0171546 | A1 | 9/2004 | Pepicelli et al. |
| 2005/0002933 | A1 | 1/2005 | Baron et al. |
| 2005/0054568 | A1 | 3/2005 | Ling et al. |
| 2005/0080138 | A1 | 4/2005 | Guicherit et al. |

FOREIGN PATENT DOCUMENTS

| | | |
|---|---|---|
| WO | WO-95/23223 | 8/1995 |
| WO | WO 96/17924 | 6/1996 |
| WO | WO-98/21227 | 5/1998 |
| WO | WO-98/35020 | 8/1998 |
| WO | WO-99/10004 A2 | 3/1999 |
| WO | WO-00/15246 | 3/2000 |
| WO | WO 00/18428 | 4/2000 |
| WO | WO-00/25725 | 5/2000 |
| WO | WO 00/41545 | 7/2000 |
| WO | WO-00/74706 | 12/2000 |
| WO | WO-01/19800 | 3/2001 |
| WO | WO-01/26644 | 4/2001 |
| WO | WO-01/74344 | 10/2001 |
| WO | WO-02/30462 | 4/2002 |
| WO | WO-02/080952 | 10/2002 |
| WO | WO 03/011219 | 2/2003 |

OTHER PUBLICATIONS

Kobaek-Larsen et al, 2000. Comp Med. 50(1): 16-26.*
Welt et al, 1999, Semin Oncol. 26(6): 683-90.*
Sanchez et al, 2004, PNAS, 101(34): 12561-12566.*
Taipale et al, 2000. Nature 406: 1005-1009.*
Tribbick et al. 2002. Journal of Immunological Methods. 267: 27-35.*
Unwin et al, 1999. Electrophoresis. 20: 3629-3637.*
Merseburger et al, World J Urol. 24: 579-584.*
Ericson et al (1996. Cell. 87: 661-673).*
Sheng et al, 2004. Molecular Cancer. 3: 29; 13 pages as printed.*
Schulz et al. 2006. Int J Cancer. 119: 1513-1518.*
Douard et al, 2006. Surgery. 139: 665-70.*
Bian et al, 2007. World J. Gastroenterol 13(11): 1659-1665.*
Thayer et al. 2003. Nature. 425: 851-856.*
Merseburger et al, World J Urol. 24: 579-584. 2006. (A copy of this reference provided previously with the Office Action mailed Aug. 22, 2007. Cited here solely because the date of this reference was missing on the Aug. 22, 2007 PTO-892).*
Alcedo, J. et al. The *Drosophila* smoothened Gene Encodes a Seven-Pass Membrane Protein, a Putative Receptor for the Hedgehog Signal. Cell 86, 221-232 (1996).
Apelqvist, A. et al. Sonic hedgehog directs specialized mesoderm differentiation in the intestine and pancreas. Curr. Biol. 7, 801-804 (1997).
Bellusci, S. et al. Involvement of Sonic hedgehog (Shh) in mouse embryonic lung growth and morphogenesis. Development 124, 53 (1997).
Berger, C.S. et al. Chromosomes in Kidney, Ureter, and Bladder Cancer. Cancer Genetics and Cytogenesis 23, 1-24 (1986).
Bitgood, M.J. & McMahon, A.P. Hedgehog and Bmp Genes are Coexpressed at Many Diverse Sites of Cell-Cell Interaction in the Mouse Embryo. Dev. Biol. 172, 126-138 (1995).
Bitgood, M.J. et al. Sertoli cell signaling by Desert hedgehog regulates the male germline. Curr. Biol. 6, 298 (1996).
Bumcrot, D.A. et al. Proteolytic Processing Yields Two Secreted Forms of Sonic hedgehog. Mol. Cell. Biol. 15, 2294-2303 (1995).
Cairns, P. et al. Initiation of bladder cancer may involve deletion of a tumour-suppressor gene on chromosome 9. Oncogene 8, 1083-1085 (1992).
Carter, B.S. et al. Allelic loss of chromosomes 16q and 10q in human prostate cancer. PNAS 87, 8751-8755 (1990).
Chang, D.E. et al. Products, genetic linkage and limb patterning activity of a murine hedgehog gene. Development 120, 3339-3353 (1994).
Chen, Y. & Struhl, G. Dual Roles for Patched in Sequestering and Transducing Hedgehog. Cell 87, 553 (1996).
Dahmane, N. et al: "Activation of the transcription factor Gli 1 and the Sonic hedgehog signalling pathway in skin tumors", Nature, MacMillan Journals Ltd., London, GB, vol. 389, Oct. 23, 1997, pp. 876-881.
Dalbagni, G. et al. Genetic alterations in bladder cancer. Lancet 342, 469-471 (1993).
Davidson, E. How embryos work: a comparative view of diverse modes of cell fate specification. Development 108, 365-389 (1990).
Echelard, Y. et al. Sonic Hedgehog, a Member of a Family of Putative Signaling Molecules, is Implicated in the Regulation of CNS Polarity. Cell 75, 1417-1430 (1993).
Ekker, S.C. et al. Patterning activities of vertebrate hedgehog proteins in the developing eye and brain. Curr. Biol. 5, 944-955 (1995).
Ekker, S.C. et al. Distinct expression and shared activities of members of the hedgehog gene family of *Xenopus laevis*. Development 121, 2337-2347 (1995).
Ericson, J. et al. Sonic Hedgehog Induces the Differentiation of Ventral Forebrain Neurons: A Common Signal for Ventral Patterning within the Neural Tube. Cell 81, 747-756 (1995).
Fan, C.-M. & Tessier-Lavigne, M. Patterning of Mammalian Somites by Surface Ectoderm and Notochord: Evidence for Sclerotome Induction by a Hedgehog Homolog. Cell 79, 1175-1186 (1994).
Fan, C.-M. et al. Long-Range Sclerotome Induction by Sonic Hedgehog: Direct Role of the Amino-Terminal Cleavage Product and Modulation by the Cyclic AMP Signaling Pathway. Cell 81, 457-465 (1995).
Fietz, M.J. et al. Secretion of the amino-terminal fragment of the Hedgehog protein is necessary and sufficient for hedgehog signaling in *Drosophila*. Curr. Biol. 5, 643-651 (1995).
Forbes, A.J. et al. hedgehog is required for the proliferation and specification of ovarian somatic cells prior to egg chamber formation in *Drosophila*. Development 122, 1125-1135 (1996).
Francis, P.H. et al. Bone morphogenetic proteins and a signaling pathway that controls patterning in the developing chick limb. Development 120, 209-218 (1994).
Fujita, E. et al. Involvement of Sonic hedgehog in the Cell Growth of LK-2 Cells, Human Lung Squamous Carcinoma Cells. Biochem. Biophys. Res. Comm. 238, 658 (1997).
Gibas, Z. et al. Nonrandom Chromosomal Changes in Transitional Cell Carcinoma of the Bladder. Cancer Res. 44, 1257-1264 (1984).
Goodrich, L.V. et al. Conservation of the hedgehog/patched signaling pathway from flies to mice: induction of a mouse patched gene by Hedgehog. Genes Dev. 10, 301-312 (1996).
Gurdon, J.B. The Generation of Diversity and Pattern in Animal Development. Cell 68, 185-199 (1992).
Hahn, H. et al. Mutations of the Human Homolog of *Drosophila* patched in the Nevoid Basal Cell Carcinoma Syndrome. Cell 85, 841 (1996).
Hammerschmidt, M. et al. Protein kinase A is a common negative regulator of Hedgehog signaling in the vertebrate embryo. Genes Dev. 10, 647-658 (1996).
Hammerschmidt, M. et al: "The world according to hedgehog", Trends in Genetics, Elsevier Science Publishers B.V. Amsterdam, NL, vol. 13, No. 1, 1997, pp. 14-21.

Hynes, M. et al. Induction of Midbrain Dopaminergic Neurons by Sonic Hedgehog. Neuron 15, 35-44 (1995).
Honig, L.S. Positional signal transmission in the developing chick limb. Nature 291, 72-73 (1981).
Hooper, J.E. & Scott, M.P. The *Drosophila* patched Gene Encodes a Putative Membrane Protein Required for Segmental Patterning. Cell 59, 751 (1989).
Jensen, A.M. & Wallace, V.A. Expression of Sonic hedgehog and its putative role as a precursor cell mitogen in the developing mouse retina. Development 124, 363 (1997).
Jessell, T.M. & Melton, D.A. Diffusible Factors in Vertebrate Embryonic Induction. Cell 68, 257-270 (1992).
Johnson, R.L. et al. Ectopic Expression of Sonic hedgehog Alters Dorsal-Ventral Patterning of Somites. Cell 79, 1165-1173 (1994).
Johnson, R.L. et al. Human Homolog of patched, a Candidate Gene for the Basal Cell Nevus Syndrome. Science 272, 1668 (1996).
Krauss, S. et al. A Functionally Conserved Homolog of the *Drosophila* Segment Polarity Gene hh is Expressed in Tissues with Polarizing Activity in Zebrafish Embryos. Cell 75, 1401-1416 (1993).
Lai, C.-J. et al. Patterning of the neural ectoderm of *Xenopus laevis* by the amino-terminal product of hedgehog autoproteolytic cleavage. Development 121, 2349-2360 (1995).
Laufer, E. et al. Sonic hedgehog and Fgf-4 Act through a Signaling Cascade and Feedback Loop to Integrate Growth and Patterning of the Developing Limb Bud. Cell 79, 993-1003 (1994).
Lee, J.J. et al. Secretion and Localized Transcription Suggest a Role in Positional Signaling for Products of the Segmentation Gene hedgehog. Cell 71, 33-50 (1992).
Lee, J.J. et al. Autoproteolysis in hedgehog Protein Biogenesis. Science 266, 1528-1537 (1994).
Lench, N.J. et al. Characterization of human patched gene line mutations in naevoid basal cell carcinoma syndrome. Hum. Genet. 100, 497-502 (Oct. 1997).
Levin, M. et al. A Molecular Pathway Determining Left-Right Asymmetry in Chick Embryogenesis. Cell 82, 803-814 (1995).
Levine, E.M. et al. Sonic Hedgehog Promotes Rod Photoreceptor Differentiation in Mammalian Retinal Cells in Vitro. J. Neurosci. 17, 6277 (1997).
Li, J. et al. PTEN, a Putative Protein Tyrosine Phosphatase Gene Mutated in Human Brain, Breast, and Prostate Cancer. Science 275, 1943-1947 (1997).
Lopez-Martinez, A. et al. Limb-patterning activity and restricted posterior localization of the amino-terminal product of Sonic hedgehog cleavage. Curr. Biol. 5, 791-795 (1995).
Marigo, V. et al. Biochemical evidence that Patched is the Hedgehog receptor. Nature 384, 177-179 (1996).
Marti, E. et al. Distribution of Sonic hedgehog peptides in the developing chick and mouse embryo. Development 121, 2537-2547 (1995).
Marti, E. et al. Requirement of 19K form of Sonic hedgehog for induction of distinct ventral cell types in CNS explants. Nature 375, 322-325 (1995).
McGarvey, T.W. et al. PTCH gene mutations in invasive transitional cell carcinoma of the bladder. Oncogene 17, 1167-1172 (1998).
Munsterberg, A.E. et al. Combinatorial signaling by Sonic hedgehog and Wnt family members induces myogenic bHLH gene expression in the somite. Genes Dev. 9, 2911-2922 (1995).
Nakano, Y. et al. A protein with several possible membrane-spanning domains encoded by the *Drosophila* segment polarity gene patched. Nature 341, 508 (1989).
Niswander, L. et al. A positive feedback loop coordinates growth and patterning in the vertebrate limb. Nature 371, 609-612 (1994).
Nusse, R. Patching up Hedgehog. Nature 384, 119-120 (1996).
Nusslein-Volhard, C. & Wieschaus, E. Mutations affecting segment number and polarity in *Drosophila*. Nature 287, 795-801 (1980).
Pepicelli, C.V. et al. Sonic hedgehog regulates branching morphogenesis in the mammalian lung. Curr. Biol. 8, 1083-1086 (1998).
Perrimon, N. Hedgehog and Beyond. Cell 80, 517 (1995).
Perrimon, N. Serpentine Proteins Slither into the Wingless and Hedgehog Fields. Cell 86, 513 (1996).
Placzek, M. et al. Induction of floor plate differentiation by contact-dependent, homiogenetic signals. Development 117, 205-218 (1993).
Podlasek, C.A. et al. Prostrate Development Requires Sonic Hedgehog Expressed by the Urogenital Sinus Epithelium. Dev. Biol. 209, 28-39 (1999).
Porter, J.A. et al. Hedgehog Patterning Activity: Role of a Lipophilic Modification Mediated by the Carboxy-Terminal Autoprocessing Domain. Cell 86, 21-34 (1996).
Porter, J.A. et al. The product of hedgehog autoproteolytic cleavage active in local and long-range signaling. Nature 374, 363-366 (1995).
Reifenberger, J. et al. Missense Mutations in SMOH in Sporadic Basal Cell Carcinomas of the Skin and Primitive Neuroectodermal Tumors of the Central Nervous System. Cancer Res. 58, 1798-1803 (1998).
Riddle, R.D. et al. Sonic hedgehog Mediates the Polarizing Activity of the ZPA. Cell 75, 1401-1416 (1993).
Roberts, D.J. et al. Sonic hedgehog is an endodermal signal inducing Bmp-4 and Hox genes during induction and regionalization of the chick hindgut. Development 121, 3163-3174 (1995).
Roelink, H. et al. Floor Plate and Motor Neuron Induction by vhh-1, a Vertebrate Homolog of hedgehog Expressed by the Notochord. Cell 76, 761-775 (1994).
Roelink, H. et al. Floor Plate and Motor Neuron Induction by Different Concentrations of the Amino-Terminal Cleavage Product of Sonic Hedgehog Autoproteolysis. Cell 81, 445-455 (1995).
Ruiz I. Altaba, A: "Gli proteins and Hedgehog signaling: development and cancer", Trends in Genetics, Elsevier Science Publishers B.V. Amsterdam, NL, vol. 15, No. 10, Oct. 1, 1999, pp. 418-425.
Ruiz i Altaba, A. et al. Restrictions to Floor Plate Induction by hedgehog and Winged-Helix Genes in the Neural Tube of Frog Embryos. Mol. Cell. Neurosci. 6, 106-121 (1995).
Smeets, W. et al. Chromosomal Analysis of Bladder Cancer. III. Nonrandom Alterations. Cancer Genetics and Cytogenesis 29, 29-41 (1987).
Stone, D.M. et al. The turmour-suppressor gene patched encodes a candidate receptor for Sonic hedgehog. Nature 384, 129-134 (1996).
Tabata, T. et al. The *Drosophila* hedgehog gene is expressed specifically in posterior compartment cells and is a target of engrailed regulation. Genes Dev. 6, 2635-2645 (1992).
Tanabe, Y. et al. Induction of motor neurons by Sonic hedgehog is independent of floor plate differentiation. Curr. Biol. 5, 651-658 (1995).
Urase, Koko et al: "Spatial expression of Sonic hedgehog in the lung epithelium during branching morphogenesis." Biochemical and Biophysical Research Communications, vol. 225, No. 1, 1996, pp. 161-166.
Wang, M.Z. et al. Induction of dopaminergic neuron phenotype in the midbrain by Sonic hedgehog protein. Nature Med. 1, 1184-1188 (1995).
Weinberg, E.S. et al. Developmental regulation of zebrafish MyoD in wild-type, no tail and spadetail embryos. Development 122, 271-280 (1996).
Wilkin, R.P. et al. Stromal 5alpha-reductase activity is elevated in benign prostatic hyperplasia. Acta Endocrinology 94, 284-288 (1980).
Xie, J. et al. Activating Smoothened mutations in sporadic basal-cell carcinoma. Nature 391, 90-92 (1998).
Yamada, T. et al. Control of Cell Pattern in the Neural Tube: Motor Neuron Induction by Diffusible Factors from Notochord and Floor Plate. Cell 73, 673-686 (1993).
Greenspan, N.S. and Di Cera, E., "Defining epitopes: It's not as easy as it seems," Nature Biotechnology, 17:936-937 (1999).
Stancovski, I., et al., "Mechanistic aspects of the opposing effects of monoclonal antibodies to the ERBB2 receptor on tumor growth," Proc. Natl. Acad. Sci, USA, 88:8691-8695 (1991).
Jiang, B., et al., "A Novel Peptide Isolated from a Phage Display Peptide Library with Trastuzumab Can Mimic Antigen Epitope of HER-2," J. Biol. Chem., 280(6):4656-4662 (2005).
Ericson, J., et al., "Two Critical Periods of Sonic Hedgehog Signaling Required for the Specification of Motor Neuron Identity," Cell, 87:661-673 (1996).
Nelson, et al., (J. Clin. Pathol: Mol. Pathol. 2000; 53:111-117).

Green, et al., "Basal cell carcinoma development is associated with induction of the expression of the transcription factor Gli-1", British Journal of Dermatology, vol. 139, pp. 911-915, (1998).

Roberts, et al., "Amplification of the gli Gene in Childhood Sarcomas", Cancer Research, vol. 49, pp. 5407-5413 (1989).

Dahmane, et al., "Sonic hedgehog regulates the growth and patterning of the cerebellum", Development, vol. 126, pp. 3089-3100 (1999).

Feng et al., "Overexpression of Hedgehog Signaling Molecules and Its Involvement in the Proliferation of Endometrial Carcinoma Cells", Human Cancer Biology, vol. 13, pp. 1389-1398 (2007).

Huang et al., "Activation of the hedgehog pathway in human hepatocellular carcinomas", Carcinogenesis, vol. 27(7), pp. 1334-1340 (2006).

Wallace, Valerie A., "Purkinje-cell-derived Sonic hedgehog regulates granule neuron precursor cell proliferation in the developing mouse cerebellum", Current Biology, vol. 9, p. 445-448 (1999).

Thievessen et al., "Hedgehog Signaling in Normal Urothelial Cells and in Urothelial Carcinoma Cell Lines", Journal of Cellular Physiology, vol. 230, pp. 372-377 (2005).

Wang et al., "Shifting paradigms in Hedgehog signaling", Current Opinion in Cell Biology, vol. 19, pp. 159-165 (2007).

Dermer, Gerald B., "The Last Word—Another Anniversary for the War on Cancer", Bio/Technology, vol. 12, p. 320 (1994).

Freshney, R. Ian, "Culture of Animal Cells, A Manual of Basic Technique", Alan R. Liss, Inc., pp. 3-4 (1983).

Yauch et al., "A paracrine requirement for hedgehog signalling in cancer"; available online Aug. 27, 2008 in advance of publication, doi:10.1038/nature07275 (2008).

Heijstek, et al., "Mouse Models of Colorectal Cancer and Liver Metastases", Digestive Surgery, 22: pp. 16-25 (2005).

Kobaek-Larsen, et al., "Review of Colorectal Cancer and Its Metastases in Rodent Models: Comparative Aspects with Those in Humans", Comparative Medicine, 50(1): pp. 16-26 (2000).

Taipale, et al., "Effects of oncogenic mutations in Smoothened and Patched can be reversed by cyclopamine", Letters to Nature, 406: pp. 1005-1009, year published: 2000.

Welt et al., "Antibodies in the Therapy of Colon Cancer", Seminars in Oncology, 26(6): pp. 683-690 (1999).

Schuger et al., "Retinoic Acid Stimulates Mouse Lung Development by a Mechanism Involving Epithelial-Mesenchymal Interaction and Regulation of Epidermal Growth Factor Receptors", Developmental Biology, vol. 159, pp. 462-473 (1993).

Watkins et al., "Hedgehog signalling within airway epithelial progenitors and in small-cell lung cancer", Nature, vol. 422, pp. 313-317 (2003).

Yuan et al., "Frequent requirement of hedgehog signaling in non-small cell lung carcinoma", Oncogene, vol. 26, pp. 1046-1055 (2007).

* cited by examiner

COMPOUND A

COMPOUND B

AGONIST Z

SEQUENCE LISTING

<160> NUMBER OF SEQ ID NOS: 22

<210> SEQ ID NO 1
<211> LENGTH: 1277
<212> TYPE: DNA
<213> ORGANISM: Gallus gallus

<400> SEQUENCE: 1

```
atggtcgaaa tgctgctgtt gacaagaatt ctcttggtgg gcttcatctg cgctcttta        60 gtctcctctg ggctgacttg tggaccaggc aggggcattg gaaaaaggag gcaccccaaa       120
aagctgaccc cgttagccta taagcagttt attcccaatg tggcagagaa gacccctaggg      180
```

| | |
|---|---|
| gccagtggaa gatatgaagg gaagatcaca agaaactccg agagatttaa agaactaacc | 240 |
| ccaaattaca accctgacat tatttttaag gatgaagaga acacgggagc tgacagactg | 300 |
| atgactcagc gctgcaagga caagctgaat gccctggcga tctcggtgat gaaccagtgg | 360 |
| cccggggtga agctgcgggt gaccgagggc tgggacgagg atggccatca ctccgaggaa | 420 |
| tcgctgcact acgagggtcg cgccgtggac atcaccacgt cggatcggga ccgcagcaag | 480 |
| tacggaatgc tggcccgcct cgccgtcgag gccggcttcg actgggtcta ctacgagtcc | 540 |
| aaggcgcaca tccactgctc cgtcaaagca gaaaactcag tggcagcgaa atcaggaggc | 600 |
| tgcttccctg gctcagccac agtgcacctg agcatggag gcaccaagct ggtgaaggac | 660 |
| ctgagccctg ggaccgcgt gctggctgct gacgcggacg gccggctgct ctacagtgac | 720 |
| ttcctcacct tcctcgaccg gatggacagc tcccgaaagc tcttctacgt catcgagacg | 780 |
| cggcagcccc gggcccggct gctactgacg gcggcccacc tgctctttgt ggcccccag | 840 |
| cacaaccagt cggaggccac agggtccacc agtggccagg cgctcttcgc cagcaacgtg | 900 |
| aagcctggcc aacgtgtcta tgtgctgggc gagggcgggc agcagctgct gccggcgtct | 960 |
| gtccacagcg tctcattgcg ggaggaggcg tccggagcct acgccccact caccgcccag | 1020 |
| ggcaccatcc tcatcaaccg ggtgttggcc tcctgctacg ccgtcatcga ggagcacagt | 1080 |
| tgggcccatt gggccttcgc accattccgc ttggctcagg gctgctggc cgccctctgc | 1140 |
| ccagatgggg ccatccctac tgccgccacc accaccactg gcatccattg gtactcacgg | 1200 |
| ctcctctacc gcatcggcag ctgggtgctg gatggtgacg cgctgcatcc gctgggcatg | 1260 |
| gtggcaccgg ccagctg | 1277 |

<210> SEQ ID NO 2
<211> LENGTH: 1190
<212> TYPE: DNA
<213> ORGANISM: Mus musculus

<400> SEQUENCE: 2

| | |
|---|---|
| atggctctgc cggccagtct gttgcccctg tgctgcttgg cactcttggc actatctgcc | 60 |
| cagagctgcg ggccgggccg aggaccggtt ggccggcggc gttatgtgcg caagcaactt | 120 |
| gtgcctctgc tatacaagca gtttgtgccc agtatgcccg agcggaccct gggcgcgagt | 180 |
| gggccagcgg aggggagggt aacaaggggg tcggagcgct tccgggacct cgtacccaac | 240 |
| tacaaccccg acataatctt caaggatgag gagaacagcg gcgcagaccg cctgatgaca | 300 |
| gagcgttgca aagagcgggt gaacgctcta gccatcgcgg tgatgaacat gtggcccgga | 360 |
| gtacgcctac gtgtgactga aggctgggac gaggacggcc accacgcaca ggattcactc | 420 |
| cactacgaag gccgtgcctt ggacatcacc acgtctgacc gtgaccgtaa taagtatggt | 480 |
| tgttggcgc gcctagctgt ggaagccgga ttcgactggg tctactacga gtcccgcaac | 540 |
| cacatccacg tatcggtcaa agctgataac tcactggcgg tccgagccgg aggctgcttt | 600 |
| ccgggaaatg ccacggtgcg cttgcggagc ggcgaacgga aggggctgag ggaactacat | 660 |
| cgtggtgact gggtactggc cgctgatgca gcggggccga tggtacccac gccagtgctg | 720 |
| ctcttcctgg accgggatct gcagcgccgc gcctcgttcg tggctgtgga accgagcgg | 780 |
| cctccgcgca aactgttgct cacacccctgg catctggtgt tcgctgctcg cgggccagcg | 840 |
| cctgctccag gtgactttgc accggtgttc gcgcgccgct acgtgctggc gactcggtg | 900 |
| ctggctcccg gcggggacgc gctccagccg gcgcgcgtag cccgcgtggc gcgcgaggaa | 960 |
| gccgtgggcg tgttcgcacc gctcactgcg cacgggacgc tgctggtcaa cgacgtcctc | 1020 |

```
gcctcctgct acgcggttct agagagtcac cagtgggccc accgcgcctt cgcccctttg    1080
cggctgctgc acgcgctcgg ggctctgctc cctgggggtg cagtccagcc gactggcatg    1140
cattggtact ctcgcctcct ttaccgcttg gccgaggagt taatgggctg               1190
```

<210> SEQ ID NO 3
<211> LENGTH: 1281
<212> TYPE: DNA
<213> ORGANISM: Mus musculus

<400> SEQUENCE: 3

```
atgtctcccg cctggctccg gccccgactg cggttctgtc tgttcctgct gctgctgctt     60
ctggtgccgg cggcgcgggg ctgcgggccg ggccgggtgg tgggcagccg ccggaggccg    120
cctcgcaagc tcgtgcctct tgcctacaag cagttcagcc ccaacgtgcc ggagaagacc    180
ctgggcgcca gcgggcgcta cgaaggcaag atcgcgcgca gctctgagcg cttcaaagag    240
ctcaccccca actacaatcc cgacatcatc ttcaaggacg aggagaacac gggtgccgac    300
cgcctcatga cccagcgctg caaggaccgt ctgaactcac tggccatctc tgtcatgaac    360
cagtggcctg tgtgaaaact gcgggtgacc gaaggccggg atgaagatgg ccatcactca    420
gaggagtctt tacactatga gggccgcgcg gtggatatca ccacctcaga ccgtgaccga    480
aataagtatg gactgctggc gcgcttagca gtggaggccg gcttcgactg ggtgtattac    540
gagtccaagg cccacgtgca ttgctctgtc aagtctgagc attcggccgc tgccaagaca    600
ggtggctgct ttcctgccgg agcccaggtg cgcctagaga acgggagcg tgtggccctg    660 tcagctgtaa agccaggaga ccgggtgctg gccatggggg aggatgggac ccccaccttc    720
agtgatgtgc ttatttttcct ggaccgcgag ccaaaccggc tgagagcttt ccaggtcatc    780
gagactcagg atcctccgcg tcggctggcg ctcacgcctg cccacctgct cttcattgcg    840
gacaatcata cagaaccagc agcccacttc cgggccacat tgccagcca tgtgcaacca    900 ggccaatatg tgctggtatc aggggtacca ggcctccagc ctgctcgggt ggcagctgtc    960
tccacccacg tggcccttgg gtcctatgct cctctcacaa ggcatgggac acttgtggtg   1020
gaggatgtgg tggcctcctg ctttgcagct gtggctgacc accatctggc tcagttggcc   1080
ttctggcccc tgcgactgtt tcccagtttg gcatggggca gctggacccc aagtgagggt   1140
gttcactcct accctcagat gctctaccgc ctgggcgtc tcttgctaga agagagcacc   1200
ttccatccac tgggcatgtc tgggggcagga agctgaaggg actctaacca ctgccctcct   1260
ggaactgctg tgcgtggatc c                                              1281
```

<210> SEQ ID NO 4
<211> LENGTH: 1313
<212> TYPE: DNA
<213> ORGANISM: Mus musculus

<400> SEQUENCE: 4

```
atgctgctgc tgctggccag atgttttctg gtgatccttg cttcctcgct gctggtgtgc    60
cccgggctgg cctgtgggcc cggcaggggg tttggaaaga ggcggcaccc caaaaagctg   120 accccttag cctacaagca gtttattccc aacgtagccg agaagaccct aggggccagc   180
ggcagatatg aagggaagat cacaagaaac tccgaacgat ttaaggaact cacccccaat   240
tacaaccccg acatcatatt taaggatgag gaaacacgg gagcagaccg gctgatgact   300
cagaggtgca agacaagtt aaatgccttg gccatctctg tgatgaacca gtggcctgga   360
```

-continued

```
gtgaggctgc gagtgaccga gggctgggat gaggacggcc atcattcaga ggagtctcta      420
cactatgagg tcgagcagt ggacatcacc acgtccgacc gggaccgcag caagtacggc       480
atgctggctc gcctggctgt ggaagcaggt ttcgactggg tctactatga atccaaagct     540
cacatccact gttctgtgaa agcagagaac tccgtggcgg ccaaatccgg cggctgtttc     600
ccgggatccg ccaccgtgca cctggagcag ggcggcacca agctggtgaa ggacttacgt     660
cccggagacc gcgtgctggc ggctgacgac cagggccggc tgctgtacag cgacttcctc     720
accttcctgg accgcgacga aggcgccaag aaggtcttct acgtgatcga gacgctggag     780
ccgcgcgagc gcctgctgct caccgccgcg cacctgctct tcgtggcgcc gcacaacgac     840
tcggggccca cgcccgggcc aagcgcgctc tttgccagcc gcgtgcgccc cgggcagcgc     900
gtgtacgtgg tggctgaacg cggcggggac cgccggctgc tgcccgccgc ggtgcacagc     960
gtgacgctgc gagaggagga ggcgggcgcg tacgcgccgc tcacggcgca cggcaccatt    1020
ctcatcaacc gggtgctcgc ctcgtgctac gctgtcatcg aggagcacag ctgggcacac    1080
cgggccttcg cgcctttccg cctggcgcac gcgctgctgg ccgcgctggc acccgcccgc    1140
acggacggcg gggcgggg cagcatccct gcagcgcaat ctgcaacgga agcgaggggc     1200
gcggagccga ctgcgggcat ccactggtac tcgcagctgc tctaccacat tggcacctgg    1260
ctgttggaca gcgagaccat gcatcccttg ggaatggcgg tcaagtccag ctg           1313
```

<210> SEQ ID NO 5
<211> LENGTH: 1256
<212> TYPE: DNA
<213> ORGANISM: Brachydanio rerio

<400> SEQUENCE: 5

```
atgcggcttt tgacgagagt gctgctggtg tctcttctca ctctgtcctt ggtggtgtcc       60
ggactggcct gcggtcctgg cagaggctac ggcagaagaa gacatccgaa gaagctgaca      120
cctctcgcct acaagcagtt catacctaat gtcgcggaga agaccttagg ggccagcggc      180
agatacgagg gcaagataac gcgcaattcg gagagattta agaacttac tccaaattac       240 aatcccgaca ttatctttaa ggatgaggag aacacgggag cggacaggct catgacacag      300
agatgcaaag acaagctgaa ctcgctggcc atctctgtaa tgaaccactg gccaggggtt      360
aagctgcgtg tgacagaggg ctgggatgag gacggtcacc attttgaaga atcactccac      420
tacgagggaa gagctgttga tattaccacc tctgaccgag acaagagcaa atacgggaca     480
ctgtctcgcc tagctgtgga ggctggattt gactgggtct attacgagtc caaagcccac     540
attcattgct ctgtcaaagc agaaaattcg gttgctgcga atctggggg ctgtttccca      600 ggttcggctc tggtctcgct ccaggacgga ggacagaagg ccgtgaagga cctgaacccc     660
ggagacaagg tgctggcggc agacagcgcg ggaaacctgg tgttcagcga cttcatcatg     720
ttcacagacc gagactccac gacgacgt gtgtttacg tcatagaaac gcaagaaccc       780
gttgaaaaga tcaccctcac cgccgctcac ctccttttg tcctcgacaa ctcaacggaa      840
gatctccaca ccatgaccgc cgcgtatgcc agcagtgtca gagccggaca aaaggtgatg     900
gttgttgatg atagcggtca gcttaaatct gtcatcgtgc agcggatata cacggaggag    960
cagcggggct cgttcgcacc agtgactgca catgggacca ttgtggtcga cagaatactg    1020
gcgtcctgtt acgccgtaat agaggaccag gggcttgcgc atttggcctt cgcgcccgcc    1080
aggctctatt attacgtgtc atcattcctg tcccccaaaa ctccagcagt cggtccaatg    1140
cgactttaca acaggagggg gtccactggt actccaggct cctgtcatca aatgggaacg    1200
```

```
<210> SEQ ID NO 6
<211> LENGTH: 1425
<212> TYPE: DNA
<213> ORGANISM: Homo sapiens
<220> FEATURE:
<221> NAME/KEY: modified_base
<222> LOCATION: (1387...1389)
<223> OTHER INFORMATION: n=a, c, g, or t

<400> SEQUENCE: 6
tggcttttgg acagcaacat gcttcatcct ttggggatgt cagtaaactc aagctg      1256 atgctgctgc tggcgagatg tctgctgcta gtcctcgtct cctcgctgct ggtatgctcg    60
ggactggcgt gcggaccggg cagggggttc gggaagagga ggcaccccaa aaagctgacc   120
cctttagcct acaagcagtt tatccccaat gtggccgaga agaccctagg cgccagcgga   180
aggtatgaag ggaagatctc cagaaactcc gagcgattta aggaactcac ccccaattac   240
aaccccgaca tcatatttaa ggatgaagaa acaccggag cggacaggct gatgactcag    300
aggtgtaagg acaagttgaa cgctttggcc atctcggtga tgaaccagtg gccaggagtg   360
aaactgcggg tgaccgaggg ctgggacgaa gatggccacc actcagagga gtctctgcac   420
tacgagggcc gcgcagtgga catcaccacg tctgaccgcg accgcagcaa gtacggcatg   480
ctggcccgcc tggcggtgga ggccggcttc gactgggtgt actacgagtc caaggcacat   540
atccactgct cggtgaaagc agagaactcg gtggcggcca atcggggagg ctgcttcccg   600
ggctcggcca cggtgcacct ggagcagggc ggcaccaagc tggtgaagga cctgagcccc   660
ggggaccgcg tgctggcggc ggacgaccag ggccggctgc tctacagcga cttcctcact   720
ttcctggacc gcgacgacgg cgccaagaag gtcttctacg tgatcgagac gcgggagccg   780
cgcgagcgcc tgctgctcac cgccgcgcac ctgctctttg tggcgccgca caacgactcg   840
gccaccgggg agcccgaggc gtcctcgggc tcggggccgc cttccggggg cgcactgggg   900
cctcgggcgc tgttcgccag ccgcgtgcgc ccgggccagc gcgtgtacgt ggtggccgag   960
cgtgacgggg accgccggct cctgcccgcc gctgtgcaca gcgtgaccct aagcgaggag  1020
gccgcgggcg cctacgcgcc gctcacggcc cagggcacca ttctcatcaa ccgggtgctg  1080
gcctcgtgct acgcggtcat cgaggagcac agctgggcgc accgggcctt cgcgcccttc  1140
cgcctggcgc acgcgctcct ggctgcactg gcgcccgcgc gcacggaccg cggcggggac  1200
agcggcggcg ggaccgcgg gggcggcggc ggcagagtag ccctaaccgc tccaggtgct  1260
gccgacgctc cgggtgcggg ggccaccgcg ggcatccact ggtactcgca gctgctctac  1320
caaataggca cctggctcct ggacagcgag gccctgcacc cgctgggcat ggcggtcaag  1380
tccagcnnna gccgggggc cggggaggg gcgcgggagg gggcc                   1425

<210> SEQ ID NO 7
<211> LENGTH: 1622
<212> TYPE: DNA
<213> ORGANISM: Homo sapiens

<400> SEQUENCE: 7
catcagccca ccaggagacc tcgcccgccg ctccccggg ctccccggcc atgtctcccg     60
cccggctccg gccccgactg cacttctgcc tggtcctgtt gctgctgctg gtggtgcccg   120
cggcatgggg ctgcgggccg ggtcgggtgg tgggcagccg ccggcgaccg ccacgcaaac   180
tcgtgccgct cgcctacaag cagttcagcc ccaatgtgcc cgagaagacc ctgggcgcca   240
```

-continued

| | |
|---|---|
| gcggacgcta tgaaggcaag atcgctcgca gctccgagcg cttcaaggag ctcaccccca | 300 |
| attacaatcc agacatcatc ttcaaggacg aggagaacac aggcgccgac cgcctcatga | 360 |
| cccagcgctg caaggaccgc ctgaactcgc tggctatctc ggtgatgaac cagtggcccg | 420 |
| gtgtgaagct gcgggtgacc gagggctggg acgaggacgc ccaccactca gaggagtccc | 480 |
| tgcattatga gggccgcgcg gtggacatca ccacatcaga ccgcgaccgc aataagtatg | 540 |
| gactgctggc gcgcttggca gtggaggccg gctttgactg ggtgtattac gagtcaaagg | 600 |
| cccacgtgca ttgctccgtc aagtccgagc actcggccgc agccaagacg ggcggctgct | 660 |
| tccctgccgg agcccaggta cgcctggaga gtggggcgcg tgtggccttg tcagccgtga | 720 |
| ggccgggaga ccgtgtgctg gccatggggg aggatgggag ccccaccttc agcgatgtgc | 780 |
| tcattttcct ggaccgcgag ccccacaggc tgagagcctt ccaggtcatc gagactcagg | 840 |
| acccccacg ccgcctggca ctcacacccg ctcacctgct ctttacggct gacaatcaca | 900 |
| cggagccggc agcccgcttc cgggccacat ttgccagcca cgtgcagcct ggccagtacg | 960 |
| tgctggtggc tggggtgcca ggcctgcagc ctgcccgcgt ggcagctgtc tctacacacg | 1020 |
| tggccctcgg ggcctacgcc ccgctcacaa agcatgggac actggtggtg gaggatgtgg | 1080 |
| tggcatcctg cttcgcggcc gtggctgacc accacctggc tcagttggcc ttctggcccc | 1140 |
| tgagactctt tcacagcttg gcatggggca gctggacccc gggggagggt gtgcattggt | 1200 |
| accccagct gctctaccgc ctggggcgtc tcctgctaga gagggcagc ttccacccac | 1260 |
| tgggcatgtc cggggcaggg agctgaaagg actccaccgc tgccctcctg gaactgctgt | 1320 |
| actgggtcca gaagcctctc agccaggagg gagctggccc tggaagggac ctgagctggg | 1380 |
| ggacactggc cctgccatc tcctctgcca tgaagataca ccattgagac ttgactgggc | 1440 |
| aacaccagcg tcccccaccc cgtcgtggt gtagtcatag agctgcaagc tgagctggcg | 1500 |
| aggggatggt tgttgacccc tctctcctag agaccttgag gctggcacgg cgactcccaa | 1560 |
| ctcagcctgc tctcactacg agttttcata ctctgcctcc cccattggga gggcccattc | 1620 |
| cc | 1622 |

<210> SEQ ID NO 8
<211> LENGTH: 1191
<212> TYPE: DNA
<213> ORGANISM: Homo sapiens

<400> SEQUENCE: 8

| | |
|---|---|
| atggctctcc tgaccaatct actgcccttg tgctgcttgg cacttctggc gctgccagcc | 60 |
| cagagctgcg ggccgggccg gggccggtt ggcggcgcc gctatgcgcg caagcagctc | 120 |
| gtgccgctac tctacaagca atttgtgccc ggcgtgccag agcggaccct gggcgccagt | 180 |
| gggccagcgg aggggagggt ggcaaggggc tccgagcgct ccgggaccct cgtgcccaac | 240 |
| tacaaccccg acatcatctt caaggatgag agaacagtg gagccgaccg cctgatgacc | 300 |
| gagcgttgca aggagagggt gaacgctttg gccattgccg tgatgaacat gtggcccgga | 360 |
| gtgcgcctac gagtgactga ggctgggac gaggacggcc accacgctca ggattcactc | 420 |
| cactacgaag gccgtgcttt ggacatcact acgtctgacc gcgaccgcaa caagtatggg | 480 |
| ttgctggcgc gcctcgcagt ggaagccggc ttcgactggg tctactacga gtcccgcaac | 540 |
| cacgtccacg tgtcggtcaa agctgataac tcactggcgg tccgggcggg cggctgcttt | 600 |
| ccgggaaatg caactgtgcg cctgtggagc ggcgagcgga aagggctgcg ggaactgcac | 660 |
| cgcggagact gggttttggc ggccgatgcg tcaggccggg tggtgcccac gccggtgctg | 720 |

-continued

```
ctcttcctgg accgggactt gcagcgccgg gcttcatttg tggctgtgga gaccgagtgg      780
cctccacgca aactgttgct cacgccctgg cacctggtgt ttgccgctcg agggccggcg      840
cccgcgccag gcgactttgc accggtgttc gcgcgccggc tacgcgctgg ggactcggtg      900
ctggcgcccg gcggggatgc gcttcggcca gcgcgcgtgg cccgtgtggc gcggaggaa       960 gccgtgggcg tgttcgcgcc gctcaccgcg cacgggacgc tgctggtgaa cgatgtcctg     1020
gcctcttgct acgcggttct ggagagtcac cagtgggcgc accgcgcttt tgccccttg     1080 agactgctgc acgcgctagg ggcgctgctc cccggcgggg ccgtccagcc gactggcatg     1140
cattggtact ctcggctcct ctaccgctta gcggaggagc tactgggctg a             1191
```

<210> SEQ ID NO 9
<211> LENGTH: 1251
<212> TYPE: DNA
<213> ORGANISM: Brachydanio rerio

<400> SEQUENCE: 9

```
atggacgtaa ggctgcatct gaagcaattt gctttactgt gttttatcag cttgcttctg       60
acgccttgtg gattagcctg tggtcctggt agaggttatg gaaaacgaag acacccaaag      120
aaattaaccc cgttggctta caagcaattc atccccaacg ttgctgagaa aacgcttgga      180
gccagcggca aatacgaagg caaaatcaca aggaattcag agagatttaa agagctgatt      240
ccgaattata atcccgatat catctttaag gacgaggaaa acacaaacgc tgacaggctg      300
atgaccaagc gctgtaagga caagttaaat tcgttggcca tatccgtcat gaaccactgg      360
cccggcgtga aactgcgcgt cactgaaggc tgggatgagg atggtcacca tttagaagaa      420
tctttgcact atgagggacg ggcagtgac  atcactacct cagacaggga taaaagcaag      480
tatgggatgc tatccaggct tgcagtggag gcaggattcg actgggtcta ttatgaatct      540
aaagcccaca tacactgctc tgtcaaagca gaaaattcag tggctgctaa atcaggagga      600
tgttttcctg ggtctgggac ggtgacactt ggtgatggga cgaggaaacc catcaaagat      660
cttaaagtgg gcgaccgggt tttggctgca gacgagaagg gaaatgtctt aataagcgac      720
tttattatgt ttatagacca cgatccgaca acgagaaggc aattcatcgt catcgagacg      780
tcagaacctt tcaccaagct caccctcact gccgcgcacc tagttttcgt tggaaactct      840
tcagcagctt cgggtataac agcaacattt gccagcaacg tgaagcctgg agatacagtt      900
ttagtgtggg aagacacatg cgagagcctc aagagcgtta cagtgaaaag gatttacact      960
gaggagcacg agggctcttt tgcgccagtc accgcgcacg gaaccataat agtggatcag     1020
gtgttggcat cgtgctacgc ggtcattgag aaccacaaat gggcacattg ggcttttgcg     1080
ccggtcaggt tgtgtcacaa gctgatgacg tggcttttt cggctcgtga atcaaacgtc     1140
aattttcagg aggatggtat ccactggtac tcaaatatgc tgtttcacat cggctcttgg     1200
ctgctggaca gagactcttt ccatccactc gggattttac acttaagttg a             1251
```

<210> SEQ ID NO 10
<211> LENGTH: 425
<212> TYPE: PRT
<213> ORGANISM: Gallus gallus

<400> SEQUENCE: 10

```
Met Val Glu Met Leu Leu Leu Thr Arg Ile Leu Leu Val Gly Phe Ile
  1               5                  10                  15

Cys Ala Leu Leu Val Ser Ser Gly Leu Thr Cys Gly Pro Gly Arg Gly
```

```
                20                  25                  30
Ile Gly Lys Arg Arg His Pro Lys Lys Leu Thr Pro Leu Ala Tyr Lys
            35                  40                  45

Gln Phe Ile Pro Asn Val Ala Glu Lys Thr Leu Gly Ala Ser Gly Arg
        50                  55                  60

Tyr Glu Gly Lys Ile Thr Arg Asn Ser Glu Arg Phe Lys Glu Leu Thr
65                  70                  75                  80

Pro Asn Tyr Asn Pro Asp Ile Ile Phe Lys Asp Glu Glu Asn Thr Gly
                85                  90                  95

Ala Asp Arg Leu Met Thr Gln Arg Cys Lys Asp Lys Leu Asn Ala Leu
            100                 105                 110

Ala Ile Ser Val Met Asn Gln Trp Pro Gly Val Lys Leu Arg Val Thr
        115                 120                 125

Glu Gly Trp Asp Glu Asp Gly His His Ser Glu Glu Ser Leu His Tyr
            130                 135                 140

Glu Gly Arg Ala Val Asp Ile Thr Thr Ser Asp Arg Asp Arg Ser Lys
145                 150                 155                 160

Tyr Gly Met Leu Ala Arg Leu Ala Val Glu Ala Gly Phe Asp Trp Val
                165                 170                 175

Tyr Tyr Glu Ser Lys Ala His Ile His Cys Ser Val Lys Ala Glu Asn
            180                 185                 190

Ser Val Ala Ala Lys Ser Gly Gly Cys Phe Pro Gly Ser Ala Thr Val
        195                 200                 205

His Leu Glu His Gly Gly Thr Lys Leu Val Lys Asp Leu Ser Pro Gly
    210                 215                 220

Asp Arg Val Leu Ala Ala Asp Ala Asp Gly Arg Leu Leu Tyr Ser Asp
225                 230                 235                 240

Phe Leu Thr Phe Leu Asp Arg Met Asp Ser Ser Arg Lys Leu Phe Tyr
                245                 250                 255

Val Ile Glu Thr Arg Gln Pro Arg Ala Arg Leu Leu Leu Thr Ala Ala
            260                 265                 270

His Leu Leu Phe Val Ala Pro Gln His Asn Gln Ser Glu Ala Thr Gly
        275                 280                 285

Ser Thr Ser Gly Gln Ala Leu Phe Ala Ser Asn Val Lys Pro Gly Gln
    290                 295                 300

Arg Val Tyr Val Leu Gly Glu Gly Gly Gln Gln Leu Leu Pro Ala Ser
305                 310                 315                 320

Val His Ser Val Ser Leu Arg Glu Glu Ala Ser Gly Ala Tyr Ala Pro
                325                 330                 335

Leu Thr Ala Gln Gly Thr Ile Leu Ile Asn Arg Val Leu Ala Ser Cys
            340                 345                 350

Tyr Ala Val Ile Glu Glu His Ser Trp Ala His Trp Ala Phe Ala Pro
        355                 360                 365

Phe Arg Leu Ala Gln Gly Leu Leu Ala Leu Cys Pro Asp Gly Ala
    370                 375                 380

Ile Pro Thr Ala Ala Thr Thr Thr Gly Ile His Trp Tyr Ser Arg
385                 390                 395                 400

Leu Leu Tyr Arg Ile Gly Ser Trp Val Leu Asp Gly Asp Ala Leu His
                405                 410                 415

Pro Leu Gly Met Val Ala Pro Ala Ser
            420                 425

<210> SEQ ID NO 11
```

<211> LENGTH: 396
<212> TYPE: PRT
<213> ORGANISM: Mus musculus

<400> SEQUENCE: 11

```
Met Ala Leu Pro Ala Ser Leu Leu Pro Leu Cys Cys Leu Ala Leu Leu
 1               5                  10                  15

Ala Leu Ser Ala Gln Ser Cys Gly Pro Gly Arg Gly Pro Val Gly Arg
            20                  25                  30

Arg Arg Tyr Val Arg Lys Gln Leu Val Pro Leu Leu Tyr Lys Gln Phe
        35                  40                  45

Val Pro Ser Met Pro Glu Arg Thr Leu Gly Ala Ser Gly Pro Ala Glu
    50                  55                  60

Gly Arg Val Thr Arg Gly Ser Glu Arg Phe Arg Asp Leu Val Pro Asn
 65                  70                  75                  80

Tyr Asn Pro Asp Ile Ile Phe Lys Asp Glu Glu Asn Ser Gly Ala Asp
                85                  90                  95

Arg Leu Met Thr Glu Arg Cys Lys Glu Arg Val Asn Ala Leu Ala Ile
            100                 105                 110

Ala Val Met Asn Met Trp Pro Gly Val Arg Leu Arg Val Thr Glu Gly
        115                 120                 125

Trp Asp Glu Asp Gly His His Ala Gln Asp Ser Leu His Tyr Glu Gly
    130                 135                 140

Arg Ala Leu Asp Ile Thr Thr Ser Asp Arg Asp Arg Asn Lys Tyr Gly
145                 150                 155                 160

Leu Leu Ala Arg Leu Ala Val Glu Ala Gly Phe Asp Trp Val Tyr Tyr
                165                 170                 175

Glu Ser Arg Asn His Ile His Val Ser Val Lys Ala Asp Asn Ser Leu
            180                 185                 190

Ala Val Arg Ala Gly Gly Cys Phe Pro Gly Asn Ala Thr Val Arg Leu
        195                 200                 205

Arg Ser Gly Glu Arg Lys Gly Leu Arg Glu Leu His Arg Gly Asp Trp
    210                 215                 220

Val Leu Ala Ala Asp Ala Ala Gly Arg Val Val Pro Thr Pro Val Leu
225                 230                 235                 240

Leu Phe Leu Asp Arg Asp Leu Gln Arg Arg Ala Ser Phe Val Ala Val
                245                 250                 255

Glu Thr Glu Arg Pro Pro Arg Lys Leu Leu Leu Thr Pro Trp His Leu
            260                 265                 270

Val Phe Ala Ala Arg Gly Pro Ala Pro Ala Pro Gly Asp Phe Ala Pro
        275                 280                 285

Val Phe Ala Arg Arg Leu Arg Ala Gly Asp Ser Val Leu Ala Pro Gly
    290                 295                 300

Gly Asp Ala Leu Gln Pro Ala Arg Val Ala Arg Val Ala Arg Glu Glu
305                 310                 315                 320

Ala Val Gly Val Phe Ala Pro Leu Thr Ala His Gly Thr Leu Leu Val
                325                 330                 335

Asn Asp Val Leu Ala Ser Cys Tyr Ala Val Leu Glu Ser His Gln Trp
            340                 345                 350

Ala His Arg Ala Phe Ala Pro Leu Arg Leu Leu His Ala Leu Gly Ala
        355                 360                 365

Leu Leu Pro Gly Gly Ala Val Gln Pro Thr Gly Met His Trp Tyr Ser
    370                 375                 380

Arg Leu Leu Tyr Arg Leu Ala Glu Glu Leu Met Gly
```

```
385              390              395
```

<210> SEQ ID NO 12
<211> LENGTH: 411
<212> TYPE: PRT
<213> ORGANISM: Mus musculus

<400> SEQUENCE: 12

| | | | | | | | | | | | | | | |
|---|---|---|---|---|---|---|---|---|---|---|---|---|---|---|
| Met | Ser | Pro | Ala | Trp | Leu | Arg | Pro | Arg | Leu | Arg | Phe | Cys | Leu | Phe Leu |
| 1 | | | | 5 | | | | | 10 | | | | | 15 |
| Leu | Leu | Leu | Leu | Leu | Val | Pro | Ala | Ala | Arg | Gly | Cys | Gly | Pro | Gly Arg |
| | | | 20 | | | | | 25 | | | | | 30 | |
| Val | Val | Gly | Ser | Arg | Arg | Pro | Arg | Lys | Leu | Val | Pro | Leu | Ala | |
| | | 35 | | | | | 40 | | | | | 45 | | |
| Tyr | Lys | Gln | Phe | Ser | Pro | Asn | Val | Pro | Glu | Lys | Thr | Leu | Gly | Ala Ser |
| | 50 | | | | | 55 | | | | | 60 | | | |
| Gly | Arg | Tyr | Glu | Gly | Lys | Ile | Ala | Arg | Ser | Ser | Glu | Arg | Phe | Lys Glu |
| 65 | | | | | 70 | | | | | 75 | | | | | 80 |
| Leu | Thr | Pro | Asn | Tyr | Asn | Pro | Asp | Ile | Ile | Phe | Lys | Asp | Glu | Glu Asn |
| | | | | 85 | | | | | 90 | | | | | 95 |
| Thr | Gly | Ala | Asp | Arg | Leu | Met | Thr | Gln | Arg | Cys | Lys | Asp | Arg | Leu Asn |
| | | | 100 | | | | | 105 | | | | | 110 | |
| Ser | Leu | Ala | Ile | Ser | Val | Met | Asn | Gln | Trp | Pro | Gly | Val | Lys | Leu Arg |
| | | | 115 | | | | | 120 | | | | | 125 | |
| Val | Thr | Glu | Gly | Arg | Asp | Glu | Asp | Gly | His | His | Ser | Glu | Glu | Ser Leu |
| | 130 | | | | | 135 | | | | | 140 | | | |
| His | Tyr | Glu | Gly | Arg | Ala | Val | Asp | Ile | Thr | Thr | Ser | Asp | Arg | Asp Arg |
| 145 | | | | | 150 | | | | | 155 | | | | | 160 |
| Asn | Lys | Tyr | Gly | Leu | Leu | Ala | Arg | Leu | Ala | Val | Glu | Ala | Gly | Phe Asp |
| | | | | 165 | | | | | 170 | | | | | 175 |
| Trp | Val | Tyr | Tyr | Glu | Ser | Lys | Ala | His | Val | His | Cys | Ser | Val | Lys Ser |
| | | | 180 | | | | | 185 | | | | | 190 | |
| Glu | His | Ser | Ala | Ala | Lys | Thr | Gly | Gly | Cys | Phe | Pro | Ala | Gly | Ala |
| | | | 195 | | | | | 200 | | | | | 205 | |
| Gln | Val | Arg | Leu | Glu | Asn | Gly | Glu | Arg | Val | Ala | Leu | Ser | Ala | Val Lys |
| | 210 | | | | | 215 | | | | | 220 | | | |
| Pro | Gly | Asp | Arg | Val | Leu | Ala | Met | Gly | Glu | Asp | Gly | Thr | Pro | Thr Phe |
| 225 | | | | | 230 | | | | | 235 | | | | | 240 |
| Ser | Asp | Val | Leu | Ile | Phe | Leu | Asp | Arg | Glu | Pro | Asn | Arg | Leu | Arg Ala |
| | | | | 245 | | | | | 250 | | | | | 255 |
| Phe | Gln | Val | Ile | Glu | Thr | Gln | Asp | Pro | Pro | Arg | Arg | Leu | Ala | Leu Thr |
| | | | | 260 | | | | | 265 | | | | | 270 |
| Pro | Ala | His | Leu | Leu | Phe | Ile | Ala | Asp | Asn | His | Thr | Glu | Pro | Ala Ala |
| | | | 275 | | | | | 280 | | | | | 285 | |
| His | Phe | Arg | Ala | Thr | Phe | Ala | Ser | His | Val | Gln | Pro | Gly | Gln | Tyr Val |
| | | | 290 | | | | | 295 | | | | | 300 | |
| Leu | Val | Ser | Gly | Val | Pro | Gly | Leu | Gln | Pro | Ala | Arg | Val | Ala | Ala Val |
| 305 | | | | | 310 | | | | | 315 | | | | | 320 |
| Ser | Thr | His | Val | Ala | Leu | Gly | Ser | Tyr | Ala | Pro | Leu | Thr | Arg | His Gly |
| | | | | 325 | | | | | 330 | | | | | 335 |
| Thr | Leu | Val | Val | Glu | Asp | Val | Val | Ala | Ser | Cys | Phe | Ala | Ala | Val Ala |
| | | | 340 | | | | | 345 | | | | | 350 | |
| Asp | His | His | Leu | Ala | Gln | Leu | Ala | Phe | Trp | Pro | Leu | Arg | Leu | Phe Pro |
| | | | 355 | | | | | 360 | | | | | 365 | |

```
Ser Leu Ala Trp Gly Ser Trp Thr Pro Ser Glu Gly Val His Ser Tyr
    370                 375                 380

Pro Gln Met Leu Tyr Arg Leu Gly Arg Leu Leu Glu Glu Ser Thr
385                 390                 395                 400

Phe His Pro Leu Gly Met Ser Gly Ala Gly Ser
                405                 410

<210> SEQ ID NO 13
<211> LENGTH: 437
<212> TYPE: PRT
<213> ORGANISM: Mus musculus

<400> SEQUENCE: 13

Met Leu Leu Leu Ala Arg Cys Phe Leu Val Ile Leu Ala Ser Ser
1               5                   10                  15

Leu Leu Val Cys Pro Gly Leu Ala Cys Gly Pro Gly Arg Gly Phe Gly
            20                  25                  30

Lys Arg Arg His Pro Lys Lys Leu Thr Pro Leu Ala Tyr Lys Gln Phe
        35                  40                  45

Ile Pro Asn Val Ala Glu Lys Thr Leu Gly Ala Ser Gly Arg Tyr Glu
    50                  55                  60

Gly Lys Ile Thr Arg Asn Ser Glu Arg Phe Lys Glu Leu Thr Pro Asn
65                  70                  75                  80

Tyr Asn Pro Asp Ile Ile Phe Lys Asp Glu Glu Asn Thr Gly Ala Asp
                85                  90                  95

Arg Leu Met Thr Gln Arg Cys Lys Asp Lys Leu Asn Ala Leu Ala Ile
            100                 105                 110

Ser Val Met Asn Gln Trp Pro Gly Val Arg Leu Arg Val Thr Glu Gly
        115                 120                 125

Trp Asp Glu Asp Gly His His Ser Glu Glu Ser Leu His Tyr Glu Gly
    130                 135                 140

Arg Ala Val Asp Ile Thr Thr Ser Asp Arg Asp Arg Ser Lys Tyr Gly
145                 150                 155                 160

Met Leu Ala Arg Leu Ala Val Glu Ala Gly Phe Asp Trp Val Tyr Tyr
                165                 170                 175

Glu Ser Lys Ala His Ile His Cys Ser Val Lys Ala Glu Asn Ser Val
            180                 185                 190

Ala Ala Lys Ser Gly Gly Cys Phe Pro Gly Ser Ala Thr Val His Leu
        195                 200                 205

Glu Gln Gly Gly Thr Lys Leu Val Lys Asp Leu Arg Pro Gly Asp Arg
    210                 215                 220

Val Leu Ala Ala Asp Asp Gln Gly Arg Leu Leu Tyr Ser Asp Phe Leu
225                 230                 235                 240

Thr Phe Leu Asp Arg Asp Glu Gly Ala Lys Lys Val Phe Tyr Val Ile
                245                 250                 255

Glu Thr Leu Glu Pro Arg Glu Arg Leu Leu Leu Thr Ala Ala His Leu
            260                 265                 270

Leu Phe Val Ala Pro His Asn Asp Ser Gly Pro Thr Pro Gly Pro Ser
        275                 280                 285

Ala Leu Phe Ala Ser Arg Val Arg Pro Gly Gln Arg Val Tyr Val Val
    290                 295                 300

Ala Glu Arg Gly Gly Asp Arg Arg Leu Leu Pro Ala Ala Val His Ser
305                 310                 315                 320

Val Thr Leu Arg Glu Glu Glu Ala Gly Ala Tyr Ala Pro Leu Thr Ala
                325                 330                 335
```

```
His Gly Thr Ile Leu Ile Asn Arg Val Leu Ala Ser Cys Tyr Ala Val
            340                 345                 350

Ile Glu Glu His Ser Trp Ala His Arg Ala Phe Ala Pro Phe Arg Leu
            355                 360                 365

Ala His Ala Leu Leu Ala Ala Leu Ala Pro Ala Arg Thr Asp Gly Gly
            370                 375                 380

Gly Gly Gly Ser Ile Pro Ala Ala Gln Ser Ala Thr Glu Ala Arg Gly
385                 390                 395                 400

Ala Glu Pro Thr Ala Gly Ile His Trp Tyr Ser Gln Leu Leu Tyr His
            405                 410                 415

Ile Gly Thr Trp Leu Leu Asp Ser Glu Thr Met His Pro Leu Gly Met
            420                 425                 430

Ala Val Lys Ser Ser
            435

<210> SEQ ID NO 14
<211> LENGTH: 418
<212> TYPE: PRT
<213> ORGANISM: Brachydanio rerio

<400> SEQUENCE: 14

Met Arg Leu Leu Thr Arg Val Leu Leu Val Ser Leu Leu Thr Leu Ser
1               5                   10                  15

Leu Val Val Ser Gly Leu Ala Cys Gly Pro Gly Arg Gly Tyr Gly Arg
                20                  25                  30

Arg Arg His Pro Lys Lys Leu Thr Pro Leu Ala Tyr Lys Gln Phe Ile
            35                  40                  45

Pro Asn Val Ala Glu Lys Thr Leu Gly Ala Ser Gly Arg Tyr Glu Gly
        50                  55                  60

Lys Ile Thr Arg Asn Ser Glu Arg Phe Lys Glu Leu Thr Pro Asn Tyr
65                  70                  75                  80

Asn Pro Asp Ile Ile Phe Lys Asp Glu Glu Asn Thr Gly Ala Asp Arg
                85                  90                  95

Leu Met Thr Gln Arg Cys Lys Asp Lys Leu Asn Ser Leu Ala Ile Ser
            100                 105                 110

Val Met Asn His Trp Pro Gly Val Lys Leu Arg Val Thr Glu Gly Trp
        115                 120                 125

Asp Glu Asp Gly His His Phe Glu Glu Ser Leu His Tyr Glu Gly Arg
130                 135                 140

Ala Val Asp Ile Thr Thr Ser Asp Arg Asp Lys Ser Lys Tyr Gly Thr
145                 150                 155                 160

Leu Ser Arg Leu Ala Val Glu Ala Gly Phe Asp Trp Val Tyr Tyr Glu
                165                 170                 175

Ser Lys Ala His Ile His Cys Ser Val Lys Ala Glu Asn Ser Val Ala
            180                 185                 190

Ala Lys Ser Gly Gly Cys Phe Pro Gly Ser Ala Leu Val Ser Leu Gln
        195                 200                 205

Asp Gly Gly Gln Lys Ala Val Lys Asp Leu Asn Pro Gly Asp Lys Val
    210                 215                 220

Leu Ala Ala Asp Ser Ala Gly Asn Leu Val Phe Ser Asp Phe Ile Met
225                 230                 235                 240

Phe Thr Asp Arg Asp Ser Thr Thr Arg Arg Val Phe Tyr Val Ile Glu
                245                 250                 255

Thr Gln Glu Pro Val Glu Lys Ile Thr Leu Thr Ala Ala His Leu Leu
```

```
                    260                 265                 270
Phe Val Leu Asp Asn Ser Thr Glu Asp Leu His Thr Met Thr Ala Ala
            275                 280                 285
Tyr Ala Ser Ser Val Arg Ala Gly Gln Lys Val Met Val Val Asp Asp
            290                 295                 300
Ser Gly Gln Leu Lys Ser Val Ile Val Gln Arg Ile Tyr Thr Glu Glu
305                 310                 315                 320
Gln Arg Gly Ser Phe Ala Pro Val Thr Ala His Gly Thr Ile Val Val
                    325                 330                 335
Asp Arg Ile Leu Ala Ser Cys Tyr Ala Val Ile Glu Asp Gln Gly Leu
                340                 345                 350
Ala His Leu Ala Phe Ala Pro Ala Arg Leu Tyr Tyr Tyr Val Ser Ser
            355                 360                 365
Phe Leu Ser Pro Lys Thr Pro Ala Val Gly Pro Met Arg Leu Tyr Asn
    370                 375                 380
Arg Arg Gly Ser Thr Gly Thr Pro Gly Ser Cys His Gln Met Gly Thr
385                 390                 395                 400
Trp Leu Leu Asp Ser Asn Met Leu His Pro Leu Gly Met Ser Val Asn
                    405                 410                 415
Ser Ser

<210> SEQ ID NO 15
<211> LENGTH: 475
<212> TYPE: PRT
<213> ORGANISM: Homo sapiens
<220> FEATURE:
<221> NAME/KEY: SITE
<222> LOCATION: (463)
<223> OTHER INFORMATION: Xaa=unknown amino acid residue

<400> SEQUENCE: 15

Met Leu Leu Leu Ala Arg Cys Leu Leu Val Leu Val Ser Ser Leu
1               5                   10                  15
Leu Val Cys Ser Gly Leu Ala Cys Gly Pro Gly Arg Gly Phe Gly Lys
                20                  25                  30
Arg Arg His Pro Lys Lys Leu Thr Pro Leu Ala Tyr Lys Gln Phe Ile
            35                  40                  45
Pro Asn Val Ala Glu Lys Thr Leu Gly Ala Ser Gly Arg Tyr Glu Gly
        50                  55                  60
Lys Ile Ser Arg Asn Ser Glu Arg Phe Lys Glu Leu Thr Pro Asn Tyr
65                  70                  75                  80
Asn Pro Asp Ile Ile Phe Lys Asp Glu Glu Asn Thr Gly Ala Asp Arg
                85                  90                  95
Leu Met Thr Gln Arg Cys Lys Asp Lys Leu Asn Ala Leu Ala Ile Ser
            100                 105                 110
Val Met Asn Gln Trp Pro Gly Val Lys Leu Arg Val Thr Glu Gly Trp
        115                 120                 125
Asp Glu Asp Gly His His Ser Glu Glu Ser Leu His Tyr Glu Gly Arg
    130                 135                 140
Ala Val Asp Ile Thr Thr Ser Asp Arg Asp Arg Ser Lys Tyr Gly Met
145                 150                 155                 160
Leu Ala Arg Leu Ala Val Glu Ala Gly Phe Asp Trp Val Tyr Tyr Glu
                165                 170                 175
Ser Lys Ala His Ile His Cys Ser Val Lys Ala Glu Asn Ser Val Ala
            180                 185                 190
```

Ala Lys Ser Gly Gly Cys Phe Pro Gly Ser Ala Thr Val His Leu Glu
        195                 200                 205

Gln Gly Gly Thr Lys Leu Val Lys Asp Leu Ser Pro Gly Asp Arg Val
    210                 215                 220

Leu Ala Ala Asp Asp Gln Gly Arg Leu Leu Tyr Ser Asp Phe Leu Thr
225                 230                 235                 240

Phe Leu Asp Arg Asp Asp Gly Ala Lys Lys Val Phe Tyr Val Ile Glu
                245                 250                 255

Thr Arg Glu Pro Arg Glu Arg Leu Leu Leu Thr Ala Ala His Leu Leu
            260                 265                 270

Phe Val Ala Pro His Asn Asp Ser Ala Thr Gly Glu Pro Glu Ala Ser
        275                 280                 285

Ser Gly Ser Gly Pro Pro Ser Gly Gly Ala Leu Gly Pro Arg Ala Leu
    290                 295                 300

Phe Ala Ser Arg Val Arg Pro Gly Gln Arg Val Tyr Val Val Ala Glu
305                 310                 315                 320

Arg Asp Gly Asp Arg Arg Leu Leu Pro Ala Ala Val His Ser Val Thr
                325                 330                 335

Leu Ser Glu Glu Ala Ala Gly Ala Tyr Ala Pro Leu Thr Ala Gln Gly
            340                 345                 350

Thr Ile Leu Ile Asn Arg Val Leu Ala Ser Cys Tyr Ala Val Ile Glu
        355                 360                 365

Glu His Ser Trp Ala His Arg Ala Phe Ala Pro Phe Arg Leu Ala His
    370                 375                 380

Ala Leu Leu Ala Ala Leu Ala Pro Ala Arg Thr Asp Arg Gly Gly Asp
385                 390                 395                 400

Ser Gly Gly Gly Asp Arg Gly Gly Gly Gly Arg Val Ala Leu Thr
                405                 410                 415

Ala Pro Gly Ala Ala Asp Ala Pro Gly Ala Gly Ala Thr Ala Gly Ile
            420                 425                 430

His Trp Tyr Ser Gln Leu Leu Tyr Gln Ile Gly Thr Trp Leu Leu Asp
        435                 440                 445

Ser Glu Ala Leu His Pro Leu Gly Met Ala Val Lys Ser Ser Xaa Ser
    450                 455                 460

Arg Gly Ala Gly Gly Gly Ala Arg Glu Gly Ala
465                 470                 475

<210> SEQ ID NO 16
<211> LENGTH: 411
<212> TYPE: PRT
<213> ORGANISM: Homo sapiens

<400> SEQUENCE: 16

Met Ser Pro Ala Arg Leu Arg Pro Arg Leu His Phe Cys Leu Val Leu
1               5                   10                  15

Leu Leu Leu Leu Val Val Pro Ala Ala Trp Gly Cys Gly Pro Gly Arg
            20                  25                  30

Val Val Gly Ser Arg Arg Arg Pro Pro Arg Lys Leu Val Pro Leu Ala
        35                  40                  45

Tyr Lys Gln Phe Ser Pro Asn Val Pro Glu Lys Thr Leu Gly Ala Ser
    50                  55                  60

Gly Arg Tyr Glu Gly Lys Ile Ala Arg Ser Ser Glu Arg Phe Lys Glu
65                  70                  75                  80

Leu Thr Pro Asn Tyr Asn Pro Asp Ile Ile Phe Lys Asp Glu Glu Asn
                85                  90                  95

```
Thr Gly Ala Asp Arg Leu Met Thr Gln Arg Cys Lys Asp Arg Leu Asn
            100                 105                 110

Ser Leu Ala Ile Ser Val Met Asn Gln Trp Pro Gly Val Lys Leu Arg
        115                 120                 125

Val Thr Glu Gly Trp Asp Glu Asp Gly His His Ser Glu Glu Ser Leu
    130                 135                 140

His Tyr Glu Gly Arg Ala Val Asp Ile Thr Thr Ser Asp Arg Asp Arg
145                 150                 155                 160

Asn Lys Tyr Gly Leu Leu Ala Arg Leu Ala Val Glu Ala Gly Phe Asp
                165                 170                 175

Trp Val Tyr Tyr Glu Ser Lys Ala His Val His Cys Ser Val Lys Ser
            180                 185                 190

Glu His Ser Ala Ala Lys Thr Gly Gly Cys Phe Pro Ala Gly Ala
        195                 200                 205

Gln Val Arg Leu Glu Ser Gly Ala Arg Val Ala Leu Ser Ala Val Arg
    210                 215                 220

Pro Gly Asp Arg Val Leu Ala Met Gly Glu Asp Gly Ser Pro Thr Phe
225                 230                 235                 240

Ser Asp Val Leu Ile Phe Leu Asp Arg Glu Pro His Arg Leu Arg Ala
                245                 250                 255

Phe Gln Val Ile Glu Thr Gln Asp Pro Pro Arg Arg Leu Ala Leu Thr
            260                 265                 270

Pro Ala His Leu Leu Phe Thr Ala Asp Asn His Thr Glu Pro Ala Ala
        275                 280                 285

Arg Phe Arg Ala Thr Phe Ala Ser His Val Gln Pro Gly Gln Tyr Val
    290                 295                 300

Leu Val Ala Gly Val Pro Gly Leu Gln Pro Ala Arg Val Ala Ala Val
305                 310                 315                 320

Ser Thr His Val Ala Leu Gly Ala Tyr Ala Pro Leu Thr Lys His Gly
                325                 330                 335

Thr Leu Val Val Glu Asp Val Val Ala Ser Cys Phe Ala Ala Val Ala
            340                 345                 350

Asp His His Leu Ala Gln Leu Ala Phe Trp Pro Leu Arg Leu Phe His
        355                 360                 365

Ser Leu Ala Trp Gly Ser Trp Thr Pro Gly Glu Gly Val His Trp Tyr
    370                 375                 380

Pro Gln Leu Leu Tyr Arg Leu Gly Arg Leu Leu Glu Glu Gly Ser
385                 390                 395                 400

Phe His Pro Leu Gly Met Ser Gly Ala Gly Ser
                405                 410

<210> SEQ ID NO 17
<211> LENGTH: 396
<212> TYPE: PRT
<213> ORGANISM: Homo sapiens

<400> SEQUENCE: 17

Met Ala Leu Leu Thr Asn Leu Leu Pro Leu Cys Cys Leu Ala Leu Leu
 1               5                  10                  15

Ala Leu Pro Ala Gln Ser Cys Gly Pro Gly Arg Gly Pro Val Gly Arg
            20                  25                  30

Arg Arg Tyr Ala Arg Lys Gln Leu Val Pro Leu Leu Tyr Lys Gln Phe
        35                  40                  45

Val Pro Gly Val Pro Glu Arg Thr Leu Gly Ala Ser Gly Pro Ala Glu
```

```
            50                  55                  60
Gly Arg Val Ala Arg Gly Ser Glu Arg Phe Arg Asp Leu Val Pro Asn
 65                  70                  75                  80

Tyr Asn Pro Asp Ile Ile Phe Lys Asp Glu Glu Asn Ser Gly Ala Asp
                 85                  90                  95

Arg Leu Met Thr Glu Arg Cys Lys Glu Arg Val Asn Ala Leu Ala Ile
            100                 105                 110

Ala Val Met Asn Met Trp Pro Gly Val Arg Leu Arg Val Thr Glu Gly
        115                 120                 125

Trp Asp Glu Asp Gly His His Ala Gln Asp Ser Leu His Tyr Glu Gly
130                 135                 140

Arg Ala Leu Asp Ile Thr Thr Ser Asp Arg Asp Arg Asn Lys Tyr Gly
145                 150                 155                 160

Leu Leu Ala Arg Leu Ala Val Glu Ala Gly Phe Asp Trp Val Tyr Tyr
                165                 170                 175

Glu Ser Arg Asn His Val His Val Ser Val Lys Ala Asp Asn Ser Leu
            180                 185                 190

Ala Val Arg Ala Gly Gly Cys Phe Pro Gly Asn Ala Thr Val Arg Leu
        195                 200                 205

Trp Ser Gly Glu Arg Lys Gly Leu Arg Glu Leu His Arg Gly Asp Trp
210                 215                 220

Val Leu Ala Ala Asp Ala Ser Gly Arg Val Val Pro Thr Pro Val Leu
225                 230                 235                 240

Leu Phe Leu Asp Arg Asp Leu Gln Arg Ala Ser Phe Val Ala Val
                245                 250                 255

Glu Thr Glu Trp Pro Pro Arg Lys Leu Leu Thr Pro Trp His Leu
            260                 265                 270

Val Phe Ala Ala Arg Gly Pro Ala Pro Ala Pro Gly Asp Phe Ala Pro
        275                 280                 285

Val Phe Ala Arg Arg Leu Arg Ala Gly Asp Ser Val Leu Ala Pro Gly
        290                 295                 300

Gly Asp Ala Leu Arg Pro Ala Arg Val Ala Arg Val Ala Arg Glu Glu
305                 310                 315                 320

Ala Val Gly Val Phe Ala Pro Leu Thr Ala His Gly Thr Leu Leu Val
                325                 330                 335

Asn Asp Val Leu Ala Ser Cys Tyr Ala Val Leu Glu Ser His Gln Trp
            340                 345                 350

Ala His Arg Ala Phe Ala Pro Leu Arg Leu Leu His Ala Leu Gly Ala
        355                 360                 365

Leu Leu Pro Gly Gly Ala Val Gln Pro Thr Gly Met His Trp Tyr Ser
370                 375                 380

Arg Leu Leu Tyr Arg Leu Ala Glu Glu Leu Leu Gly
385                 390                 395

<210> SEQ ID NO 18
<211> LENGTH: 416
<212> TYPE: PRT
<213> ORGANISM: Brachydanio rerio

<400> SEQUENCE: 18

Met Asp Val Arg Leu His Leu Lys Gln Phe Ala Leu Leu Cys Phe Ile
 1               5                  10                  15

Ser Leu Leu Leu Thr Pro Cys Gly Leu Ala Cys Gly Pro Gly Arg Gly
            20                  25                  30
```

```
Tyr Gly Lys Arg Arg His Pro Lys Lys Leu Thr Pro Leu Ala Tyr Lys
         35                  40                  45

Gln Phe Ile Pro Asn Val Ala Glu Lys Thr Leu Gly Ala Ser Gly Lys
 50                  55                  60

Tyr Glu Gly Lys Ile Thr Arg Asn Ser Glu Arg Phe Lys Glu Leu Ile
 65                  70                  75                  80

Pro Asn Tyr Asn Pro Asp Ile Ile Phe Lys Asp Glu Asn Thr Asn
                 85                  90                  95

Ala Asp Arg Leu Met Thr Lys Arg Cys Lys Asp Lys Leu Asn Ser Leu
                100                 105                 110

Ala Ile Ser Val Met Asn His Trp Pro Gly Val Lys Leu Arg Val Thr
             115                 120                 125

Glu Gly Trp Asp Glu Asp Gly His His Leu Glu Glu Ser Leu His Tyr
         130                 135                 140

Glu Gly Arg Ala Val Asp Ile Thr Thr Ser Asp Arg Asp Lys Ser Lys
145                 150                 155                 160

Tyr Gly Met Leu Ser Arg Leu Ala Val Glu Ala Gly Phe Asp Trp Val
                165                 170                 175

Tyr Tyr Glu Ser Lys Ala His Ile His Cys Ser Val Lys Ala Glu Asn
                180                 185                 190

Ser Val Ala Ala Lys Ser Gly Gly Cys Phe Pro Gly Ser Gly Thr Val
             195                 200                 205

Thr Leu Gly Asp Gly Thr Arg Lys Pro Ile Lys Asp Leu Lys Val Gly
         210                 215                 220

Asp Arg Val Leu Ala Ala Asp Glu Lys Gly Asn Val Leu Ile Ser Asp
225                 230                 235                 240

Phe Ile Met Phe Ile Asp His Asp Pro Thr Thr Arg Arg Gln Phe Ile
                245                 250                 255

Val Ile Glu Thr Ser Glu Pro Phe Thr Lys Leu Thr Leu Thr Ala Ala
             260                 265                 270

His Leu Val Phe Val Gly Asn Ser Ser Ala Ala Ser Gly Ile Thr Ala
         275                 280                 285

Thr Phe Ala Ser Asn Val Lys Pro Gly Asp Thr Val Leu Val Trp Glu
 290                 295                 300

Asp Thr Cys Glu Ser Leu Lys Ser Val Thr Val Lys Arg Ile Tyr Thr
305                 310                 315                 320

Glu Glu His Glu Gly Ser Phe Ala Pro Val Thr Ala His Gly Thr Ile
                325                 330                 335

Ile Val Asp Gln Val Leu Ala Ser Cys Tyr Ala Val Ile Glu Asn His
             340                 345                 350

Lys Trp Ala His Trp Ala Phe Ala Pro Val Arg Leu Cys His Lys Leu
         355                 360                 365

Met Thr Trp Leu Phe Pro Ala Arg Glu Ser Asn Val Asn Phe Gln Glu
 370                 375                 380

Asp Gly Ile His Trp Tyr Ser Asn Met Leu Phe His Ile Gly Ser Trp
385                 390                 395                 400

Leu Leu Asp Arg Asp Ser Phe His Pro Leu Gly Ile Leu His Leu Ser
                405                 410                 415

<210> SEQ ID NO 19
<211> LENGTH: 1416
<212> TYPE: DNA
<213> ORGANISM: Drosophila melanogaster
<220> FEATURE:
<221> NAME/KEY: CDS
```

<222> LOCATION: (1)..(1413)

<400> SEQUENCE: 19

```
atg gat aac cac agc tca gtg cct tgg gcc agt gcc gcc agt gtc acc      48
Met Asp Asn His Ser Ser Val Pro Trp Ala Ser Ala Ala Ser Val Thr
 1               5                  10                  15 tgt ctc tcc ctg gga tgc caa atg cca cag ttc cag ttc cag ttc cag      96
Cys Leu Ser Leu Gly Cys Gln Met Pro Gln Phe Gln Phe Gln Phe Gln
             20                  25                  30 ctc caa atc cgc agc gag ctc cat ctc cgc aag ccc gca aga aga acg     144
Leu Gln Ile Arg Ser Glu Leu His Leu Arg Lys Pro Ala Arg Arg Thr
         35                  40                  45 caa acg atg cgc cac att gcg cat acg cag cgt tgc ctc agc agg ctg     192
Gln Thr Met Arg His Ile Ala His Thr Gln Arg Cys Leu Ser Arg Leu
     50                  55                  60 acc tct ctg gtg gcc ctg ctg atc gtc ttg ccg atg gtc ttt agc         240
Thr Ser Leu Val Ala Leu Leu Ile Val Leu Pro Met Val Phe Ser
 65                  70                  75                  80 ccg gct cac agc tgc ggt cct ggc cga gga ttg ggt cgt cat agg gcg     288
Pro Ala His Ser Cys Gly Pro Gly Arg Gly Leu Gly Arg His Arg Ala
                 85                  90                  95 cgc aac ctg tat ccg ctg gtc ctc aag cag aca att ccc aat cta tcc     336
Arg Asn Leu Tyr Pro Leu Val Leu Lys Gln Thr Ile Pro Asn Leu Ser
            100                 105                 110 gag tac acg aac agc gcc tcc gga cct ctg gag ggt gtg atc cgt cgg     384
Glu Tyr Thr Asn Ser Ala Ser Gly Pro Leu Glu Gly Val Ile Arg Arg
        115                 120                 125 gat tcg ccc aaa ttc aag gac ctc gtg ccc aac tac aac agg gac atc     432
Asp Ser Pro Lys Phe Lys Asp Leu Val Pro Asn Tyr Asn Arg Asp Ile
    130                 135                 140 ctt ttc cgt gac gag gaa ggc acc gga gcg gat ggc ttg atg agc aag     480
Leu Phe Arg Asp Glu Glu Gly Thr Gly Ala Asp Gly Leu Met Ser Lys
145                 150                 155                 160 cgc tgc aag gag aag cta aac gtg ctg gcc tac tcg gtg atg aac gaa     528
Arg Cys Lys Glu Lys Leu Asn Val Leu Ala Tyr Ser Val Met Asn Glu
                165                 170                 175 tgg ccc ggc atc cgg ctg ctg gtc acc gag agc tgg gac gag gac tac     576
Trp Pro Gly Ile Arg Leu Leu Val Thr Glu Ser Trp Asp Glu Asp Tyr
            180                 185                 190 cat cac ggc cag gag tcg ctc cac tac gag ggc cga gcg gtg acc att     624
His His Gly Gln Glu Ser Leu His Tyr Glu Gly Arg Ala Val Thr Ile
        195                 200                 205 gcc acc tcc gat cgc gac cag tcc aaa tac ggc atg ctc gct cgc ctg     672
Ala Thr Ser Asp Arg Asp Gln Ser Lys Tyr Gly Met Leu Ala Arg Leu
    210                 215                 220 gcc gtc gag gct gga ttc gat tgg gtc tcc tac gtc agc agg cgc cac     720
Ala Val Glu Ala Gly Phe Asp Trp Val Ser Tyr Val Ser Arg Arg His
225                 230                 235                 240 atc tac tgc tcc gtc aag tca gat tcg tcg atc agt tcc cac gtg cac     768
Ile Tyr Cys Ser Val Lys Ser Asp Ser Ser Ile Ser Ser His Val His
                245                 250                 255 ggc tgc ttc acg ccg gag agc aca gcg ctg ctg gag agt gga gtc cgg     816
Gly Cys Phe Thr Pro Glu Ser Thr Ala Leu Leu Glu Ser Gly Val Arg
            260                 265                 270 aag ccg ctc ggc gag ctc tct atc gga gat cgt gtt ttg agc atg acc     864
Lys Pro Leu Gly Glu Leu Ser Ile Gly Asp Arg Val Leu Ser Met Thr
        275                 280                 285 gcc aac gga cag gcc gtc tac agc gaa gtg atc ctc ttc atg gac cgc     912
Ala Asn Gly Gln Ala Val Tyr Ser Glu Val Ile Leu Phe Met Asp Arg
    290                 295                 300
```

```
aac ctc gag cag atg caa aac ttt gtg cag ctg cac acg gac ggt gga      960
Asn Leu Glu Gln Met Gln Asn Phe Val Gln Leu His Thr Asp Gly Gly
305                 310                 315                 320 gca gtg ctc acg gtg acg ccg gct cac ctg gtt agc gtt tgg cag ccg     1008
Ala Val Leu Thr Val Thr Pro Ala His Leu Val Ser Val Trp Gln Pro
                325                 330                 335 gag agc cag aag ctc acg ttt gtg ttt gcg cat cgc atc gag gag aag     1056
Glu Ser Gln Lys Leu Thr Phe Val Phe Ala His Arg Ile Glu Glu Lys
        340                 345                 350 aac cag gtg ctc gta cgg gat gtg gag acg ggc gag ctg agg ccc cag     1104
Asn Gln Val Leu Val Arg Asp Val Glu Thr Gly Glu Leu Arg Pro Gln
355                 360                 365 cga gtg gtc aag ttg ggc agt gtg cgc agt aag ggc gtg gtc gcg ccg     1152
Arg Val Val Lys Leu Gly Ser Val Arg Ser Lys Gly Val Val Ala Pro
    370                 375                 380 ctg acc cgc gag ggc acc att gtg gtc aac tcg gtg gcc gcc agt tgc     1200
Leu Thr Arg Glu Gly Thr Ile Val Val Asn Ser Val Ala Ala Ser Cys
385                 390                 395                 400 tat gcg gtg atc aac agt cag tcg ctg gcc cac tgg gga ctg gct ccc     1248
Tyr Ala Val Ile Asn Ser Gln Ser Leu Ala His Trp Gly Leu Ala Pro
                405                 410                 415 atg cgc ctg ctg tcc acg ctg gag gcg tgg ctg ccc gcc aag gag cag     1296
Met Arg Leu Leu Ser Thr Leu Glu Ala Trp Leu Pro Ala Lys Glu Gln
            420                 425                 430 ttg cac agt tcg ccg aag gtg gtg agc tcg gcg cag cag cag aat ggc     1344
Leu His Ser Ser Pro Lys Val Val Ser Ser Ala Gln Gln Gln Asn Gly
        435                 440                 445 atc cat tgg tat gcc aat gcg ctc tac aag gtc aag gac tac gtg ctg     1392
Ile His Trp Tyr Ala Asn Ala Leu Tyr Lys Val Lys Asp Tyr Val Leu
450                 455                 460 ccg cag agc tgg cgc cac gat tga                                     1416
Pro Gln Ser Trp Arg His Asp
465                 470
```

<210> SEQ ID NO 20
<211> LENGTH: 471
<212> TYPE: PRT
<213> ORGANISM: Drosophila melanogaster

<400> SEQUENCE: 20

```
Met Asp Asn His Ser Ser Val Pro Trp Ala Ser Ala Ala Ser Val Thr
1               5                   10                  15

Cys Leu Ser Leu Gly Cys Gln Met Pro Gln Phe Gln Phe Gln Phe Gln
            20                  25                  30

Leu Gln Ile Arg Ser Glu Leu His Leu Arg Lys Pro Ala Arg Arg Thr
        35                  40                  45

Gln Thr Met Arg His Ile Ala His Thr Gln Arg Cys Leu Ser Arg Leu
    50                  55                  60

Thr Ser Leu Val Ala Leu Leu Ile Val Leu Pro Met Val Phe Ser
65                  70                  75                  80

Pro Ala His Ser Cys Gly Pro Gly Arg Gly Leu Gly Arg His Arg Ala
                85                  90                  95

Arg Asn Leu Tyr Pro Leu Val Leu Lys Gln Thr Ile Pro Asn Leu Ser
            100                 105                 110

Glu Tyr Thr Asn Ser Ala Ser Gly Pro Leu Glu Gly Val Ile Arg Arg
        115                 120                 125

Asp Ser Pro Lys Phe Lys Asp Leu Val Pro Asn Tyr Asn Arg Asp Ile
    130                 135                 140
```

```
Leu Phe Arg Asp Glu Glu Gly Thr Gly Ala Asp Gly Leu Met Ser Lys
145                 150                 155                 160

Arg Cys Lys Glu Lys Leu Asn Val Leu Ala Tyr Ser Val Met Asn Glu
                165                 170                 175

Trp Pro Gly Ile Arg Leu Leu Val Thr Glu Ser Trp Asp Glu Asp Tyr
            180                 185                 190

His His Gly Gln Glu Ser Leu His Tyr Glu Gly Arg Ala Val Thr Ile
            195                 200                 205

Ala Thr Ser Asp Arg Asp Gln Ser Lys Tyr Gly Met Leu Ala Arg Leu
        210                 215                 220

Ala Val Glu Ala Gly Phe Asp Trp Val Ser Tyr Val Ser Arg Arg His
225                 230                 235                 240

Ile Tyr Cys Ser Val Lys Ser Asp Ser Ser Ile Ser His Ser Val His
                245                 250                 255

Gly Cys Phe Thr Pro Glu Ser Thr Ala Leu Leu Glu Ser Gly Val Arg
            260                 265                 270

Lys Pro Leu Gly Glu Leu Ser Ile Gly Asp Arg Val Leu Ser Met Thr
        275                 280                 285

Ala Asn Gly Gln Ala Val Tyr Ser Glu Val Ile Leu Phe Met Asp Arg
290                 295                 300

Asn Leu Glu Gln Met Gln Asn Phe Val Gln Leu His Thr Asp Gly Gly
305                 310                 315                 320

Ala Val Leu Thr Val Thr Pro Ala His Leu Val Ser Val Trp Gln Pro
                325                 330                 335

Glu Ser Gln Lys Leu Thr Phe Val Phe Ala His Arg Ile Glu Glu Lys
            340                 345                 350

Asn Gln Val Leu Val Arg Asp Val Glu Thr Gly Glu Leu Arg Pro Gln
        355                 360                 365

Arg Val Val Lys Leu Gly Ser Val Arg Ser Lys Gly Val Val Ala Pro
370                 375                 380

Leu Thr Arg Glu Gly Thr Ile Val Val Asn Ser Val Ala Ala Ser Cys
385                 390                 395                 400

Tyr Ala Val Ile Asn Ser Gln Ser Leu Ala His Trp Gly Leu Ala Pro
                405                 410                 415

Met Arg Leu Leu Ser Thr Leu Glu Ala Trp Leu Pro Ala Lys Glu Gln
            420                 425                 430

Leu His Ser Ser Pro Lys Val Val Ser Ser Ala Gln Gln Gln Asn Gly
        435                 440                 445

Ile His Trp Tyr Ala Asn Ala Leu Tyr Lys Val Lys Asp Tyr Val Leu
450                 455                 460

Pro Gln Ser Trp Arg His Asp
465                 470

<210> SEQ ID NO 21
<211> LENGTH: 221
<212> TYPE: PRT
<213> ORGANISM: Unknown Organism
<220> FEATURE:
<223> OTHER INFORMATION: Description of Unknown Organism: Homo sapiens,
      Mus sp., Gallus gallus or Brachydanio rerio
<220> FEATURE:
<221> NAME/KEY: MOD_RES
<222> LOCATION: (7)
<223> OTHER INFORMATION: Any amino acid; preferably Gly, Ala, Val, Leu,
      Ile, Phe, Tyr or Trp
<220> FEATURE:
<221> NAME/KEY: MOD_RES
```

```
-continued

<222> LOCATION: (9)
<223> OTHER INFORMATION: Any amino acid; preferably Arg, His or Lys
<220> FEATURE:
<221> NAME/KEY: MOD_RES
<222> LOCATION: (44)
<223> OTHER INFORMATION: Any amino acid; preferably Gly, Ala, Val, Leu,
      Ile, Ser or Thr
<220> FEATURE:
<221> NAME/KEY: MOD_RES
<222> LOCATION: (85)
<223> OTHER INFORMATION: Any amino acid; preferably Gly, Ala, Val, Leu,
      Ile, Ser or Thr
<220> FEATURE:
<221> NAME/KEY: MOD_RES
<222> LOCATION: (93)
<223> OTHER INFORMATION: Any amino acid; preferably Lys, Arg, His, Asn
      or Gln
<220> FEATURE:
<221> NAME/KEY: MOD_RES
<222> LOCATION: (98)
<223> OTHER INFORMATION: Any amino acid; preferably Lys, Arg or His
<220> FEATURE:
<221> NAME/KEY: MOD_RES
<222> LOCATION: (112)
<223> OTHER INFORMATION: Any amino acid; preferably Ser, Thr, Tyr, Trp
      or Phe
<220> FEATURE:
<221> NAME/KEY: MOD_RES
<222> LOCATION: (132)
<223> OTHER INFORMATION: Any amino acid; preferably Lys, Arg or His
<220> FEATURE:
<221> NAME/KEY: MOD_RES
<222> LOCATION: (137)
<223> OTHER INFORMATION: Any amino acid; preferably Met, Cys, Ser or Thr
<220> FEATURE:
<221> NAME/KEY: MOD_RES
<222> LOCATION: (139)
<223> OTHER INFORMATION: Any amino acid; preferably Gly, Ala, Val, Leu,
      Ile, Ser or Thr
<220> FEATURE:
<221> NAME/KEY: MOD_RES
<222> LOCATION: (181)
<223> OTHER INFORMATION: Any amino acid; preferably Leu, Val, Met, Thr
      or Ser
<220> FEATURE:
<221> NAME/KEY: MOD_RES
<222> LOCATION: (183)
<223> OTHER INFORMATION: Any amino acid; preferably His, Phe, Tyr, Ser,
      Thr, Met or Cys
<220> FEATURE:
<221> NAME/KEY: MOD_RES
<222> LOCATION: (185)
<223> OTHER INFORMATION: Any amino acid; preferably Gln, Asn, Glu, or
      Asp
<220> FEATURE:
<221> NAME/KEY: MOD_RES
<222> LOCATION: (186)
<223> OTHER INFORMATION: Any amino acid; preferably His, Phe, Tyr, Thr,
      Gln, Asn, Glu or Asp
<220> FEATURE:
<221> NAME/KEY: MOD_RES
<222> LOCATION: (189)
<223> OTHER INFORMATION: Any amino acid; preferably Gln, Asn, Glu, Asp,
      Thr, Ser, Met or Cys
<220> FEATURE:
<221> NAME/KEY: MOD_RES
<222> LOCATION: (191)
<223> OTHER INFORMATION: Any amino acid; preferably Ala, Gly, Cys, Leu,
      Val or Met
<220> FEATURE:
<221> NAME/KEY: MOD_RES
<222> LOCATION: (196)
<223> OTHER INFORMATION: Any amino acid; preferably Arg, Lys, Met, Ile,
      Asn, Asp, Glu, Gln, Ser, Thr or Cys
<220> FEATURE:
<221> NAME/KEY: MOD_RES
<222> LOCATION: (200)
<223> OTHER INFORMATION: Any amino acid; preferably Arg, Lys, Met or Ile
<220> FEATURE:
```

```
<221> NAME/KEY: MOD_RES
<222> LOCATION: (206)
<223> OTHER INFORMATION: Any amino acid; preferably Ala, Gly, Cys, Asp,
      Glu, Gln, Asn, Ser, Thr or Met
<220> FEATURE:
<221> NAME/KEY: MOD_RES
<222> LOCATION: (207)
<223> OTHER INFORMATION: Any amino acid; preferably Ala, Gly, Cys, Asp,
      Asn, Glu or Gln
<220> FEATURE:
<221> NAME/KEY: MOD_RES
<222> LOCATION: (209)
<223> OTHER INFORMATION: Any amino acid; preferably Arg, Lys, Met, Ile,
      Asn, Asp, Glu or Gln
<220> FEATURE:
<221> NAME/KEY: MOD_RES
<222> LOCATION: (211)
<223> OTHER INFORMATION: Any amino acid; preferably Leu, Val, Met or Ile
<220> FEATURE:
<221> NAME/KEY: MOD_RES
<222> LOCATION: (212)
<223> OTHER INFORMATION: Any amino acid; preferably Phe, Tyr, Thr, His
      or Trp
<220> FEATURE:
<221> NAME/KEY: MOD_RES
<222> LOCATION: (216)
<223> OTHER INFORMATION: Any amino acid; preferably Ile, Val, Leu or Met
<220> FEATURE:
<221> NAME/KEY: MOD_RES
<222> LOCATION: (217)
<223> OTHER INFORMATION: Any amino acid; preferably Met, Cys, Ile, Leu,
      Val, Thr or Ser
<220> FEATURE:
<221> NAME/KEY: MOD_RES
<222> LOCATION: (219)
<223> OTHER INFORMATION: Any amino acid; preferably Leu, Val, Met, Thr
      or Ser

<400> SEQUENCE: 21

Cys Gly Pro Gly Arg Gly Xaa Gly Xaa Arg Arg His Pro Lys Lys Leu
  1               5                  10                  15

Thr Pro Leu Ala Tyr Lys Gln Phe Ile Pro Asn Val Ala Glu Lys Thr
             20                  25                  30

Leu Gly Ala Ser Gly Arg Tyr Glu Gly Lys Ile Xaa Arg Asn Ser Glu
         35                  40                  45

Arg Phe Lys Glu Leu Thr Pro Asn Tyr Asn Pro Asp Ile Ile Phe Lys
 50                  55                  60

Asp Glu Glu Asn Thr Gly Ala Asp Arg Leu Met Thr Gln Arg Cys Lys
 65                  70                  75                  80

Asp Lys Leu Asn Xaa Leu Ala Ile Ser Val Met Asn Xaa Trp Pro Gly
                 85                  90                  95

Val Xaa Leu Arg Val Thr Glu Gly Trp Asp Glu Asp Gly His His Xaa
            100                 105                 110

Glu Glu Ser Leu His Tyr Glu Gly Arg Ala Val Asp Ile Thr Thr Ser
            115                 120                 125

Asp Arg Asp Xaa Ser Lys Tyr Gly Xaa Leu Xaa Arg Leu Ala Val Glu
130                 135                 140

Ala Gly Phe Asp Trp Val Tyr Tyr Glu Ser Lys Ala His Ile His Cys
145                 150                 155                 160

Ser Val Lys Ala Glu Asn Ser Val Ala Ala Lys Ser Gly Gly Cys Phe
                165                 170                 175

Pro Gly Ser Ala Xaa Val Xaa Leu Xaa Xaa Gly Gly Xaa Lys Xaa Val
            180                 185                 190

Lys Asp Leu Xaa Pro Gly Asp Xaa Val Leu Ala Ala Asp Xaa Xaa Gly
            195                 200                 205
```

```
Xaa Leu Xaa Xaa Ser Asp Phe Xaa Xaa Phe Xaa Asp Arg
    210                 215                 220
```

<210> SEQ ID NO 22
<211> LENGTH: 167
<212> TYPE: PRT
<213> ORGANISM: Unknown Organism
<220> FEATURE:
<223> OTHER INFORMATION: Description of Unknown Organism: Homo sapiens,
      Mus sp., Gallus gallus or Brachydanio rerio
<220> FEATURE:
<221> NAME/KEY: MOD_RES
<222> LOCATION: (7)
<223> OTHER INFORMATION: Any amino acid; preferably Gly, Ala, Val, Leu,
      Ile, Pro, Phe or Tyr
<220> FEATURE:
<221> NAME/KEY: MOD_RES
<222> LOCATION: (8)
<223> OTHER INFORMATION: Any amino acid; preferably Gly, Ala, Val, Leu
      or Ile
<220> FEATURE:
<221> NAME/KEY: MOD_RES
<222> LOCATION: (9)
<223> OTHER INFORMATION: Any amino acid; preferably Gly, Ala, Val, Leu,
      Ile, Lys, His or Arg
<220> FEATURE:
<221> NAME/KEY: MOD_RES
<222> LOCATION: (12)
<223> OTHER INFORMATION: Any amino acid; preferably Lys, Arg or His
<220> FEATURE:
<221> NAME/KEY: MOD_RES
<222> LOCATION: (13)
<223> OTHER INFORMATION: Any amino acid or no residue present;
      preferably Phe, Trp or Tyr
<220> FEATURE:
<221> NAME/KEY: MOD_RES
<222> LOCATION: (14)
<223> OTHER INFORMATION: Any amino acid or no residue present;
      preferably Gly, Ala, Val, Leu or Ile
<220> FEATURE:
<221> NAME/KEY: MOD_RES
<222> LOCATION: (17)
<223> OTHER INFORMATION: Any amino acid; preferably Asn, Gln, His, Arg
      or Lys
<220> FEATURE:
<221> NAME/KEY: MOD_RES
<222> LOCATION: (19)
<223> OTHER INFORMATION: Any amino acid; preferably Gly, Ala, Val, Leu,
      Ile, Ser or Thr
<220> FEATURE:
<221> NAME/KEY: MOD_RES
<222> LOCATION: (22)
<223> OTHER INFORMATION: Any amino acid; preferably Gly, Ala, Val, Leu,
      Ile, Ser or Thr
<220> FEATURE:
<221> NAME/KEY: MOD_RES
<222> LOCATION: (27)
<223> OTHER INFORMATION: Any amino acid; preferably Gly, Ala, Val, Leu,
      Ile, Ser or Thr
<220> FEATURE:
<221> NAME/KEY: MOD_RES
<222> LOCATION: (29)
<223> OTHER INFORMATION: Any amino acid; preferably Ser, Thr, Gln or Asn
<220> FEATURE:
<221> NAME/KEY: MOD_RES
<222> LOCATION: (30)
<223> OTHER INFORMATION: Any amino acid; preferably Met, Cys, Gly, Ala,
      Val, Leu, Ile, Ser or Thr
<220> FEATURE:
<221> NAME/KEY: MOD_RES
<222> LOCATION: (31)
<223> OTHER INFORMATION: Any amino acid; preferably Gly, Ala, Val, Leu,
      Ile or Pro
<220> FEATURE:
<221> NAME/KEY: MOD_RES
<222> LOCATION: (33)
<223> OTHER INFORMATION: Any amino acid; preferably Arg, His or Lys
<220> FEATURE:

```
<221> NAME/KEY: MOD_RES
<222> LOCATION: (40)
<223> OTHER INFORMATION: Any amino acid; preferably Gly, Ala, Val, Leu,
      Ile, Pro, Arg, His or Lys
<220> FEATURE:
<221> NAME/KEY: MOD_RES
<222> LOCATION: (41)
<223> OTHER INFORMATION: Any amino acid; preferably Gly, Ala, Val, Leu,
      Ile, Phe or Tyr
<220> FEATURE:
<221> NAME/KEY: MOD_RES
<222> LOCATION: (44)
<223> OTHER INFORMATION: Any amino acid; preferably Arg, His or Lys
<220> FEATURE:
<221> NAME/KEY: MOD_RES
<222> LOCATION: (45)
<223> OTHER INFORMATION: Any amino acid; preferably Gly, Ala, Val, Leu,
      Ile, Ser or Thr
<220> FEATURE:
<221> NAME/KEY: MOD_RES
<222> LOCATION: (46)
<223> OTHER INFORMATION: Any amino acid; preferably Thr or Ser
<220> FEATURE:
<221> NAME/KEY: MOD_RES
<222> LOCATION: (48)
<223> OTHER INFORMATION: Any amino acid; preferably Gly, Ala, Val, Leu,
      Ile, Asn or Gln
<220> FEATURE:
<221> NAME/KEY: MOD_RES
<222> LOCATION: (53)
<223> OTHER INFORMATION: Any amino acid; preferably Arg, His or Lys
<220> FEATURE:
<221> NAME/KEY: MOD_RES
<222> LOCATION: (54)
<223> OTHER INFORMATION: Any amino acid; preferably Asp or Glu
<220> FEATURE:
<221> NAME/KEY: MOD_RES
<222> LOCATION: (71)
<223> OTHER INFORMATION: Any amino acid; preferably Ser or Thr
<220> FEATURE:
<221> NAME/KEY: MOD_RES
<222> LOCATION: (79)
<223> OTHER INFORMATION: Any amino acid; preferably Glu, Asp, Gln or Asn
<220> FEATURE:
<221> NAME/KEY: MOD_RES
<222> LOCATION: (83)
<223> OTHER INFORMATION: Any amino acid; preferably Glu or Asp
<220> FEATURE:
<221> NAME/KEY: MOD_RES
<222> LOCATION: (84)
<223> OTHER INFORMATION: Any amino acid; preferably Arg, His or Lys
<220> FEATURE:
<221> NAME/KEY: MOD_RES
<222> LOCATION: (85)
<223> OTHER INFORMATION: Any amino acid; preferably Gly, Ala, Val, Leu
      or Ile
<220> FEATURE:
<221> NAME/KEY: MOD_RES
<222> LOCATION: (87)
<223> OTHER INFORMATION: Any amino acid; preferably Gly, Ala, Val, Leu,
      Ile, Thr or Ser
<220> FEATURE:
<221> NAME/KEY: MOD_RES
<222> LOCATION: (95)
<223> OTHER INFORMATION: Any amino acid; preferably Met, Cys, Gln, Asn,
      Arg, Lys or His
<220> FEATURE:
<221> NAME/KEY: MOD_RES
<222> LOCATION: (100)
<223> OTHER INFORMATION: Any amino acid; preferably Arg, His or Lys
<220> FEATURE:
<221> NAME/KEY: MOD_RES
<222> LOCATION: (107)
<223> OTHER INFORMATION: Any amino acid; preferably Trp, Phe, Tyr, Arg,
      His or Lys
<220> FEATURE:
<221> NAME/KEY: MOD_RES
<222> LOCATION: (114)
<223> OTHER INFORMATION: Any amino acid; preferably Gly, Ala, Val, Leu,
```

```
        Ile, Ser, Thr, Tyr or Phe
<220> FEATURE:
<221> NAME/KEY: MOD_RES
<222> LOCATION: (115)
<223> OTHER INFORMATION: Any amino acid; preferably Gln, Asn, Asp or Glu
<220> FEATURE:
<221> NAME/KEY: MOD_RES
<222> LOCATION: (116)
<223> OTHER INFORMATION: Any amino acid; preferably Asp or Glu
<220> FEATURE:
<221> NAME/KEY: MOD_RES
<222> LOCATION: (125)
<223> OTHER INFORMATION: Any amino acid; preferably Gly, Ala, Val, Leu,
        or Ile
<220> FEATURE:
<221> NAME/KEY: MOD_RES
<222> LOCATION: (134)
<223> OTHER INFORMATION: Any amino acid; preferably Arg, His or Lys
<220> FEATURE:
<221> NAME/KEY: MOD_RES
<222> LOCATION: (135)
<223> OTHER INFORMATION: Any amino acid; preferably Asn, Gln, Thr or Ser
<220> FEATURE:
<221> NAME/KEY: MOD_RES
<222> LOCATION: (139)
<223> OTHER INFORMATION: Any amino acid; preferably Gly, Ala, Val, Leu,
        Ile, Ser, Thr, Met or Cys
<220> FEATURE:
<221> NAME/KEY: MOD_RES
<222> LOCATION: (141)
<223> OTHER INFORMATION: Any amino acid; preferably Gly, Ala, Val, Leu,
        Ile, Thr or Ser
<220> FEATURE:
<221> NAME/KEY: MOD_RES
<222> LOCATION: (157)
<223> OTHER INFORMATION: Any amino acid; preferably Arg, His or Lys
<220> FEATURE:
<221> NAME/KEY: MOD_RES
<222> LOCATION: (158)
<223> OTHER INFORMATION: Any amino acid; preferably Asn, Gln, Gly, Ala,
        Val, Leu or Ile
<220> FEATURE:
<221> NAME/KEY: MOD_RES
<222> LOCATION: (160)
<223> OTHER INFORMATION: Any amino acid; preferably Gly, Ala, Val, Leu
        or Ile
<220> FEATURE:
<221> NAME/KEY: MOD_RES
<222> LOCATION: (162)
<223> OTHER INFORMATION: Any amino acid; preferably Gly, Ala, Val, Leu,
        Ile, Ser, Thr or Cys
<220> FEATURE:
<221> NAME/KEY: MOD_RES
<222> LOCATION: (166)
<223> OTHER INFORMATION: Any amino acid; preferably Gly, Ala, Val, Leu,
        Ile, Thr or Ser
<220> FEATURE:
<221> NAME/KEY: MOD_RES
<222> LOCATION: (167)
<223> OTHER INFORMATION: Any amino acid; preferably Asp or Glu

<400> SEQUENCE: 22

Cys Gly Pro Gly Arg Gly Xaa Xaa Xaa Arg Arg Xaa Xaa Xaa Pro Lys
  1               5                  10                  15

Xaa Leu Xaa Pro Leu Xaa Tyr Lys Gln Phe Xaa Pro Xaa Xaa Xaa Glu
                 20                  25                  30

Xaa Thr Leu Gly Ala Ser Gly Xaa Xaa Glu Gly Xaa Xaa Xaa Arg Xaa
             35                  40                  45

Ser Glu Arg Phe Xaa Xaa Leu Thr Pro Asn Tyr Asn Pro Asp Ile Ile
         50                  55                  60

Phe Lys Asp Glu Glu Asn Xaa Gly Ala Asp Arg Leu Met Thr Xaa Arg
 65                  70                  75                  80

Cys Lys Xaa Xaa Xaa Asn Xaa Leu Ala Ile Ser Val Met Asn Xaa Trp
```

-continued

```
                85                  90                  95
Pro Gly Val Xaa Leu Arg Val Thr Glu Gly Xaa Asp Glu Asp Gly His
            100                 105                 110

His Xaa Xaa Xaa Ser Leu His Tyr Glu Gly Arg Ala Xaa Asp Ile Thr
            115                 120                 125

Thr Ser Asp Arg Asp Xaa Xaa Lys Tyr Gly Xaa Leu Xaa Arg Leu Ala
    130                 135                 140

Val Glu Ala Gly Phe Asp Trp Val Tyr Tyr Glu Ser Xaa Xaa His Xaa
145                 150                 155                 160

His Xaa Ser Val Lys Xaa Xaa
                165
```

METHODS OF INHIBITING UNWANTED CELL PROLIFERATION USING HEDGEHOG ANTAGONISTS

RELATED APPLICATIONS

This application additionally claims priority as a continuation-in-part to U.S. application Ser. No. 09/977,864, filed Oct. 15, 2001, which claims priority to U.S. provisional application 60/240,564, filed Oct. 13, 2000, the disclosures of which are hereby incorporated by reference in their entirety.

BACKGROUND OF THE INVENTION

Pattern formation is the activity by which embryonic cells form ordered spatial arrangements of differentiated tissues. The physical complexity of higher organisms arises during embryogenesis through the interplay of cell-intrinsic lineage and cell-extrinsic signaling. Inductive interactions are essential to embryonic patterning in vertebrate development from the earliest establishment of the body plan, to the patterning of the organ systems, to the generation of diverse cell types during tissue differentiation (Davidson, E., (1990) *Development* 108: 365-389; Gurdon, J. B., (1992) *Cell* 68: 185-199; Jessell, T. M. et al., (1992) *Cell* 68: 257-270). The effects of developmental cell interactions are varied. Typically, responding cells are diverted from one route of cell differentiation to another by inducing cells that differ from both the uninduced and induced states of the responding cells (inductions). Sometimes cells induce their neighbors to differentiate like themselves (homeogenetic induction); in other cases a cell inhibits its neighbors from differentiating like itself. Cell interactions in early development may be sequential, such that an initial induction between two cell types leads to a progressive amplification of diversity. Moreover, inductive interactions occur not only in embryos, but in adult cells as well, and can act to establish and maintain morphogenetic patterns as well as induce differentiation (J. B. Gurdon (1992) *Cell* 68:185-199).

Members of the Hedgehog family of signaling molecules mediate many important short- and long-range patterning processes during invertebrate and vertebrate development. In the fly, a single hedgehog gene regulates segmental and imaginal disc patterning. In contrast, in vertebrates, a hedgehog gene family is involved in the control of left-right asymmetry, polarity in the CNS, somites and limb, organogenesis, chondrogenesis and spermatogenesis.

The first hedgehog gene was identified by a genetic screen in the fruit fly *Drosophila melanogaster* (Nüsslein-Volhard, C. and Wieschaus, E. (1980) *Nature* 287, 795-801). This screen identified a number of mutations affecting embryonic and larval development. In 1992 and 1993, the molecular nature of the *Drosophila* hedgehog (hh) gene was reported (C. F., Lee et al. (1992) *Cell* 71, 33-50), and since then, several hedgehog homologues have been isolated from various vertebrate species. While only one hedgehog gene has been found in *Drosophila* and other invertebrates, multiple Hedgehog genes are present in vertebrates.

The vertebrate family of hedgehog genes includes at least four members, e.g., paralogs of the single *Drosophila* hedgehog gene. Exemplary hedgehog genes and proteins are described in PCT publications WO 95/18856 and WO 96/17924. Three of these members, herein referred to as Desert hedgehog (Dhh), Sonic hedgehog (Shh) and India hedgehog (Ihh), apparently exist in all vertebrates, including fish, birds, and mammals. A fourth member, herein referred to as tiggie-winkle hedgehog (Thh), appears specific to fish. Desert hedgehog (Dhh) is expressed principally in the testes, both in mouse embryonic development and in the adult rodent and human; India hedgehog (Ihh) is involved in bone development during embryogenesis and in bone formation in the adult; and Shh, which, as described above, is primarily involved in morphogenic and neuroinductive activities. Given the critical inductive roles of hedgehog polypeptides in the development and maintenance of vertebrate organs, the identification of hedgehog interacting proteins is of paramount significance in both clinical and research contexts.

The various Hedgehog proteins consist of a signal peptide, a highly conserved N-terminal region, and a more divergent C-terminal domain. In addition to signal sequence cleavage in the secretory pathway (Lee, J. J. et al. (1992) *Cell* 71:33-50; Tabata, T. et al. (1992) *Genes Dev.* 2635-2645; Chang, D. E. et al. (1994) *Development* 120:3339-3353), Hedgehog precursor proteins undergo an internal autoproteolytic cleavage which depends on conserved sequences in the C-terminal portion (Lee et al. (1994) *Science* 266:1528-1537; Porter et al. (1995) *Nature* 374:363-366). This autocleavage leads to a 19 kD N-terminal peptide and a C-terminal peptide of 26-28 kD (Lee et al. (1992) supra; Tabata et al. (1992) supra; Chang et al. (1994) supra; Lee et al. (1994) supra; Bumcrot, D. A., et al. (1995) *Mol. Cell. Biol.* 15:2294-2303; Porter et al. (1995) supra; Ekker, S. C. et al. (1995) *Curr. Biol.* 5:944-955; Lai, C. J. et al. (1995) *Development* 121:2349-2360). The N-terminal peptide stays tightly associated with the surface of cells in which it was synthesized, while the C-terminal peptide is freely diffusible both in vitro and in vivo (Porter et al. (1995) *Nature* 374:363; Lee et al. (1994) supra; Bumcrot et al. (1995) supra; Marti, E. et al. (1995) *Development* 121:2537-2547; Roelink, H. et al. (1995) *Cell* 81:445-455). Interestingly, cell surface retention of the N-terminal peptide is dependent on autocleavage, as a truncated form of HH encoded by an RNA which terminates precisely at the normal position of internal cleavage is diffusible in vitro (Porter et al. (1995) supra) and in vivo (Porter, J. A. et al. (1996) *Cell* 86, 21-34). Biochemical studies have shown that the autoproteolytic cleavage of the HH precursor protein proceeds through an internal thioester intermediate that subsequently is cleaved in a nucleophilic substitution. It is likely that the nucleophile is a small lipophilic molecule that becomes covalently bound to the C-terminal end of the N-peptide (Porter et al. (1996) supra), tethering it to the cell surface. The biological implications are profound. As a result of the tethering, a high local concentration of N-terminal Hedgehog peptide is generated on the surface of the Hedgehog producing cells. It is this N-terminal peptide which is both necessary and sufficient for short- and long-range Hedgehog signaling activities in *Drosophila* and vertebrates (Porter et al. (1995) supra: Ekker et al. (1995) supra: Lai et al. (1995) supra; Roelink, H. et al. (1995) *Cell* 81:445-455; Porter et al. (1996) supra: Fietz, M. J. et al. (1995) *Curr. Biol.* 5:643-651; Fan, C.-M. et al. (1995) *Cell* 81:457-465; Marti, E., et al. (1995) *Nature* 375:322-325; Lopez-Martinez et al. (1995) *Curr. Biol* 5:791-795; Ekker, S. C. et al. (1995) *Development* 121:2337-2347; Forbes, A. J. et al. (1996) *Development* 122:1125-1135).

HH has been implicated in short- and long-range patterning processes at various sites during *Drosophila* development. In the establishment of segment polarity in early embryos, it has short-range effects that appear to be directly mediated, while in the patterning of the imaginal discs, it induces long-range effects via the induction of secondary signals.

In vertebrates, several hedgehog genes have been cloned in the past few years. Of these genes, Shh has received most of the experimental attention, as it is expressed in different organizing centers, which are the sources of signals that pattern neighboring tissues. Recent evidence indicates that Shh is involved in these interactions.

The expression of Shh starts shortly after the onset of gastrulation in the presumptive midline mesoderm, the node in the mouse (Chang et al. (1994) supra; Echelard, Y. et al. (1993) Cell 75:1417-1430), the rat (Roelink, H. et al. (1994) Cell 76:761-775) and the chick (Riddle, R. D. et al. (1993) Cell 75:1401-1416), and the shield in the zebrafish (Ekker et al. (1995) supra; Krauss, S. et al. (1993) Cell 75:1431-1444). In chick embryos, the Shh expression pattern in the node develops a left-right asymmetry, which appears to be responsible for the left-right situs of the heart (Levin, M. et al. (1995) Cell 82:803-814).

In the CNS, Shh from the notochord and the Doorplate appears to induce ventral cell fates. When ectopically expressed, Shh leads to a ventralization of large regions of the mid- and hindbrain in mouse (Echelard et al. (1993) supra; Goodrich, L.V. et al. (1996) Genes Dev. 10:301-312), Xenopus (Roelink, H. et al. (1994) supra; Ruiz i Altaba, A. et al. (1995) Mol. Cell. Neurosci. 6:106-121), and zebrafish (Ekker et al. (1995) supra; Krauss et al. (1993) supra; Hammerschmidt, M., et al. (1996) Genes Dev. 10:647-658). In explants of intermediate neuroectoderm at spinal cord levels, Shh protein induces floorplate and motor neuron development with distinct concentration thresholds, floor plate at high and motor neurons at lower concentrations (Roelink et al. (1995) supra; Marti et al. (1995) supra; Tanabe, Y. et al. (1995) Curr. Biol. 5:651-658). Moreover, antibody blocking suggests that Shh produced by the notochord is required for notochord-mediated induction of motor neuron fates (Marti et al. (1995) supra). Thus, high concentrations of Shh on the surface of Shh-producing midline cells appears to account for the contact-mediated induction of Doorplate observed in vitro (Placzek, M. et al. (1993) Development 117:205-218), and the midline positioning of the Doorplate immediately above the notochord in vivo. Lower concentrations of Shh released from the notochord and the Doorplate presumably induce motor neurons at more distant ventrolateral regions in a process that has been shown to be contact-independent in vitro (Yamada, T. et al. (1993) Cell 73:673-686). In explants taken at midbrain and forebrain levels, Shh also induces the appropriate ventrolateral neuronal cell types, dopaminergic (Heynes, M. et al. (1995) Neuron 15:35-44; Wang, M. Z. et al. (1995) Nature Med. 1:1184-1188) and cholinergic (Ericson, J. et al. (1995) Cell 81:747-756) precursors, respectively, indicating that Shh is a common inducer of ventral specification over the entire length of the CNS. These observations raise a question as to how the differential response to Shh is regulated at particular anteroposterior positions.

Shh from the midline also patterns the paraxial regions of the vertebrate embryo, the somites in the trunk (Fan et al. (1995) supra) and the head mesenchyme rostral of the somites (Hammerschmidt et al. (1996) supra). In chick and mouse paraxial mesoderm explants, Shh promotes the expression of sclerotome specific markers like Pax1 and Twist, at the expense of the dermamyotomal marker Pax3. Moreover, filter barrier experiments suggest that Shh mediates the induction of the sclerotome directly rather than by activation of a secondary signaling mechanism (Fan, C.-M. and Tessier-Lavigne, M. (1994) Cell 79, 1175-1186).

Shh also induces myotomal gene expression (Hammerschmidt et al. (1996) supra; Johnson, R. L. et al. (1994) Cell 79:1165-1173; Münsterberg, A. E. et al. (1995) Genes Dev. 9:2911-2922; Weinberg, E. S. et al. (1996) Development 122: 271-280), although recent experiments indicate that members of the WNT family, vertebrate homologues of Drosophila wingless, are required in concert (Münsterberg et al. (1995) supra). Puzzlingly, myotomal induction in chicks requires higher Shh concentrations than the induction of sclerotomal markers (Münsterberg et al. (1995) supra), although the sclerotome originates from somitic cells positioned much closer to the notochord. Similar results were obtained in the zebrafish, where high concentrations of Hedgehog induce myotomal and repress sclerotomal marker gene expression (Hammerschmidt et al. (1996) supra). In contrast to amniotes, however, these observations are consistent with the architecture of the fish embryo, as here, the myotome is the predominant and more axial component of the somites. Thus, modulation of Shh signaling and the acquisition of new signaling factors may have modified the somite structure during vertebrate evolution.

In the vertebrate limb buds, a subset of posterior mesenchymal cells, the "Zone of polarizing activity" (ZPA), regulates anteroposterior digit identity (reviewed in Honig, L. S. (1981) Nature 291:72-73). Ectopic expression of Shh or application of beads soaked in Shh peptide mimics the effect of anterior ZPA grafts, generating a mirror image duplication of digits (Chang et al. (1994) supra; Lopez-Martinez et al. (1995) supra; Riddle et al. (1993) supra) (FIG. 2g). Thus, digit identity appears to depend primarily on Shh concentration, although it is possible that other signals may relay this information over the substantial distances that appear to be required for AP patterning (100-150 µm). Similar to the interaction of HH and DPP in the Drosophila imaginal discs, Shh in the vertebrate limb bud activates the expression of Bmp2 (Francis, P. H. et al. (1994) Development 120:209-218), a dpp homologue. However, unlike DPP in Drosophila, Bmp2 fails to mimic the polarizing effect of Shh upon ectopic application in the chick limb bud (Francis et al. (1994) supra). In addition to anteroposterior patterning, Shh also appears to be involved in the regulation of the proximodistal outgrowth of the limbs by inducing the synthesis of the fibroblast growth factor FGF4 in the posterior apical ectodermal ridge (Laufer, E. et al. (1994) Cell 79:993-1003; Niswander, L. et al. (1994) Nature 371:609-612).

The close relationship between Hedgehog proteins and BMPs is likely to have been conserved at many, but probably not all sites of vertebrate Hedgehog expression. For example, in the chick hindgut, Shh has been shown to induce the expression of Bmp4, another vertebrate dpp homologue (Roberts, D. J. et al. (1995) Development 121:3163-3174). Furthermore, Shh and Bmp2, 4, or 6 show a striking correlation in their expression in epithelial and mesenchymal cells of the stomach, the urogenital system, the lung, the tooth buds and the hair follicles (Bitgood, M. J. and McMahon, A. P. (1995) Dev. Biol. 172:126-138). Further, Ihh, one of the two other mouse Hedgehog genes, is expressed adjacent to Bmp expressing cells in the gut and developing cartilage (Bitgood and McMahon (1995) supra).

Recent evidence suggests a model in which Ihh plays a crucial role in the regulation of chondrogenic development (Roberts et al. (1995) supra). During cartilage formation, chondrocytes proceed from a proliferating state via an intermediate, prehypertrophic state to differentiated hypertrophic chondrocytes. Ihh is expressed in the prehypertrophic chondrocytes and initiates a signaling cascade that leads to the blockage of chondrocyte differentiation. Its direct target is the perichondrium around the Ihh expression domain, which responds by the expression of Gli and Patched (Ptc), conserved transcriptional targets of Hedgehog signals (see below). Most likely, this leads to secondary signaling resulting in the synthesis of parathyroid hormone-related protein (PTHrP) in the periarticular perichondrium. PTHrP itself signals back to the prehypertrophic chondrocytes, blocking their further differentiation. At the same time, PTHrP represses expression of Ihh, thereby forming a negative feedback loop that modulates the rate of chondrocyte differentiation.

Patched was originally identified in *Drosophila* as a segment polarity gene, one of a group of developmental genes that affect cell differentiation within the individual segments that occur in a homologous series along the anterior-posterior axis of the embryo. See Hooper, J. E. et al. (1989) *Cell* 59:751; and Nakano, Y. et al. (1989) *Nature* 341:508. Patterns of expression of the vertebrate homologue of patched suggest its involvement in the development of neural tube, skeleton, limbs, craniofacial structure, and skin.

Genetic and functional studies demonstrate that patched is part of the hedgehog signaling cascade, an evolutionarily conserved pathway that regulates expression of a number of downstream genes. See Perrimon, N. (1995) *Cell* 80:517; and Perrimon, N. (1996) *Cell* 86:513. Patched participates in the constitutive transcriptional repression of the target genes; its effect is opposed by a secreted glycoprotein, encoded by hedgehog, or a vertebrate homologue, which induces transcriptional activation. Genes under control of this pathway include members of the Wnt and TGF-beta families.

Patched proteins possess two large extracellular domains, twelve transmembrane segments, and several cytoplasmic segments. See Hooper, supra; Nakano, supra; Johnson, R. L. et al. (1996) *Science* 272:1668; and Hahn, H. et al. (1996) *Cell* 85:841. The biochemical role of patched in the hedgehog signaling pathway is unclear. Direct interaction with the hedgehog protein has, however, been reported (Chen, Y. et al. (1996) *Cell* 87:553), and patched may participate in a hedgehog receptor complex along with another transmembrane protein encoded by the smoothened gene. See Perrimon, supra; and Chen, supra.

The human homologue of patched was recently cloned and mapped to chromosome 9q22.3. See Johnson, supra; and Hahn, supra. This region has been implicated in basal cell nevus syndrome (BCNS), which is characterized by developmental abnormalities including rib and craniofacial alterations, abnormalities of the hands and feet, and spina bifida.

Sporadic tumors also demonstrated a loss of both functional alleles of patched. Of twelve tumors in which patched mutations were identified with a single strand conformational polymorphism screening assay, nine had chromosomal deletion of the second allele and the other three had inactivating mutations in both alleles (Gailani, supra). The alterations did not occur in the corresponding germline DNA.

Most of the identified mutations resulted in premature stop codons or frame shifts (Lench, N. J., et al., *Hum. Genet.* 1997 October; 100(5-6): 497-502). Several, however, were point mutations leading to amino acid substitutions in either extracellular or cytoplasmic domains. These sites of mutation may indicate functional importance for interaction with extracellular proteins or with cytoplasmic members of the downstream signaling pathway.

The involvement of patched in the inhibition of gene expression and the occurrence of frequent allelic deletions of patched in BCC support a tumor suppressor function for this gene. Its role in the regulation of gene families known to be involved in cell signaling and intercellular communication provides a possible mechanism of tumor suppression.

SUMMARY OF THE INVENTION

The present invention contemplates methods and reagents for antagonizing hedgehog signaling. Antagonism of hedgehog signaling can be used to decrease or inhibit at least one of undesirable proliferation, growth, differentiation, or survival of cells. Such undesirable proliferation, growth, differentiation, or survival of cells may be observed in conditions including many forms of cancer. It is contemplated that an agent which antagonizes hedgehog signaling, and thus inhibits the undesirable proliferation, growth, differentiation, or survival of cells, may be an agent which antagonizes hedgehog signaling by interacting with components of the hedgehog signaling pathway either extracellularly, at the cell surface, or intracellularly.

In certain aspects, the present invention makes available methods and reagents for inhibiting undesirable growth states that occur in cells with an active hedgehog signaling pathway. In one embodiment, the subject methods may be used to inhibit unwanted cell proliferation by determining whether cells overexpress a gli gene, and contacting cells that overexpress a gli gene with an effective amount of a hedgehog antagonist. In preferred embodiments, the unwanted cell proliferation is cancer or benign prostatic hyperplasia.

Another aspect of the present invention makes available methods for determining a treatment protocol comprising obtaining a tissue sample from a patient, and determining levels of gli gene expression in said sample, wherein overexpression of a gli gene indicates that treatment with a hedgehog antagonist is appropriate.

A further aspect of the invention provides methods for stimulating surfactant production in a lung cell comprising contacting said cell with an amount of hedgehog antagonist effective to stimulate surfactant production. Another aspect of the invention provides methods for stimulating lamellated body formation in a lung cell comprising contacting said cell with an amount of hedgehog antagonist effective to stimulate lamellated body formation. In preferred embodiments, the lung cell is present in the lung tissue of a premature infant. A1

In other preferred embodiments, hedgehog antagonists of the invention are selected from a small molecule of less than 2000 daltons, a hedgehog antibody, a patched antibody, a smoothened antibody, a mutant hedgehog protein, an antisense nucleic acid, an RNAi construct, and a ribozyme. In particularly preferred embodiments, the hedgehog antagonist is selected from one of formulae I through XXV. In particularly preferred embodiments the hedgehog antagonist is selected from cyclopamine, compound A, tomatidine, jervine, AY9944, triparanol, compound B, and functionally effective derivatives thereof. In yet another preferred embodiment, the hedgehog antagonist is a hedgehog antibody selected from a polyclonal antibody or a monoclonal antibody. Exemplary monoclonal antibodies are specifically immunoreactive with a vertebrate hedgehog polypeptide. In a preferred embodiment, such specifically immunoreactive monoclonal antibodies do not substantially cross react with either an invertebrate hedgehog polypeptide, or with other non-hedgehog polypeptides. Exemplary hedgehog monoclonal antibodies for use as hedgehog antagonists in the subject methods include 5E1, and antibodies which recognize the same epitope as 5E1. We note that Applicants deposited 5E1 with the ATCC (American Type Tissue Collection P.O. Box 1549 Manassas, Va. 20108) under provisions of the Budapest Treaty on Aug. 13, 2002 (Patent Deposit Designation PTA-4595).

In yet another aspect, the invention provides therapeutic compositions of hedgehog antagonists for use in the subject methods. Exemplary therapeutic compositions include, but are not limited to, hedgehog monoclonal antibodies and hedgehog polyclonal antibodies. Exemplary therapeutic compositions of hedgehog monoclonal antibodies comprise a therapeutically effective amount of 5E1, or an antibody which recognizes the same epitope as 5E1, combined with a pharmaceutically acceptable excipient or carrier. Further exemplary compositions of hedgehog monoclonal antibodies comprise a therapeutically effective amount of an antibody which specifically recognizes a hedgehog epitope and blocks/antagonizes hedgehog signal transduction. The effective amount of said hedgehog antibody is sufficient to antagonize hedgehog signaling. The present invention further contemplates therapeutic compositions comprising combinations of more than one hedgehog antagonist formulated with a pharmaceutically acceptable excipient or carrier. Exemplary therapeutic compositions comprise combinations of two or more hedgehog antibodies formulated with a pharmaceutically acceptable excipient or carrier. Further exemplary compositions comprise combinations of one or more hedgehog antibodies, one or more hedgehog non-antibody antagonists (e.g., small organic molecules), and a pharmaceutically acceptable excipient or carrier.

In another aspect, the invention provides methods of determining the likelihood that a cancer will develop in a tissue, comprising obtaining a tissue sample, and determining levels of gli gene expression in said sample, wherein, overexpression of a gli gene indicates that cancer is more likely to develop. In another embodiment of this aspect, the present invention provides methods of determining the likelihood that a cancer will develop in a tissue, comprising obtaining a tissue sample, and determining levels of hedgehog gene expression in said sample, wherein, overexpression of a hedgehog gene indicates that cancer is more likely to develop.

In still another aspect, the present invention makes available methods and reagents for inhibiting at least one of undesirable proliferation, growth, differentiation or survival of a cell with an active hedgehog signaling pathway. In one embodiment, the subject methods may be used to inhibit at least one of unwanted cell proliferation, growth, differentiation or survival by determining whether cells overexpress a gli gene, and contacting cells that overexpress a gli gene with an effective amount of a hedgehog antagonist. In still another embodiment, the subject methods may be used to inhibit at least one of unwanted cell proliferation, growth, differentiation or survival by determining whether cells overexpress a hedgehog gene, and contacting cells that overexpress a hedgehog gene with an effective amount of a hedgehog antagonist. In preferred embodiments, the unwanted cell proliferation, growth, differentiation or survival is cancer or benign prostatic hyperplasia.

Exemplary forms of cancer which may be treated by the subject methods include, but are not limited to, prostate cancer, bladder cancer, lung cancer (including either small cell or non-small cell cancer), colon cancer, kidney cancer, liver cancer, breast cancer, cervical cancer, endometrial or other uterine cancer, ovarian cancer, testicular cancer, cancer of the penis, cancer of the vagina, cancer of the urethra, gall bladder cancer, esophageal cancer, or pancreatic cancer. Additional exemplary forms of cancer which may be treated by the subject methods include, but are not limited to, cancer of skeletal or smooth muscle, stomach cancer, cancer of the small intestine, cancer of the salivary gland, anal cancer, rectal cancer, tyroid cancer, parathyroid cancer, pituitary cancer, and nasopharyngeal cancer. Further exemplary forms of cancer which can be treated with the hedgehog antagonists of the present invention include cancers comprising hedgehog expressing cells. Still further exemplary forms of cancer which can be treated with the hedgehog antagonists of the present invention include cancers comprising gli expressing cells. In one embodiment, the cancer is not characterized by a mutation in patched-1.

The present invention further contemplates methods for determining the appropriate treatment regimen for a patient with cancer. Without being bound by any particular theory, cancers which express a hedgehog gene or a gli gene, or which overexpress a hedgehog gene or a gli gene in comparison to non-cancerous cells of the same tissue type, may be more amenable to treatment with the hedgehog antagonists of the present invention. Accordingly, methods of determining the expression of a hedgehog gene or a gli gene can be used to determine whether treatment with a hedgehog antagonist is appropriate (i.e., is likely to be effective).

In one embodiment, the method comprises determing the level of the expression of a hedgehog gene wherein the hedgehog gene is selected from Shh, Ihh or Dhh. In another embodiment, the method comprises determining the level of expression of a gli gene wherein the gli gene is gli-1, gli-2 or gli-3.

In another aspect, the present invention provides for the use of one or more hedgehog antagonists in the manufacture of a medicament for treating cancer in a patient.

In another aspect, the present invention provides for the use of one or more hedgehog antagonists in the manufacture of a medicament for decreasing unwanted growth, proliferation, or survivial of a cell.

The invention contemplates the use of any hedgehog antagonist regardless of the mechanism of action of that antagonist. Exemplary hedgehog antagonists include, but are not limited to, polypeptides, antisense oligonucleotides, antibodies, RNAi constructs, small molecules, ribozymes, and the like.

DETAILED DESCRIPTION OF THE INVENTION

I. Overview

Figure 1:
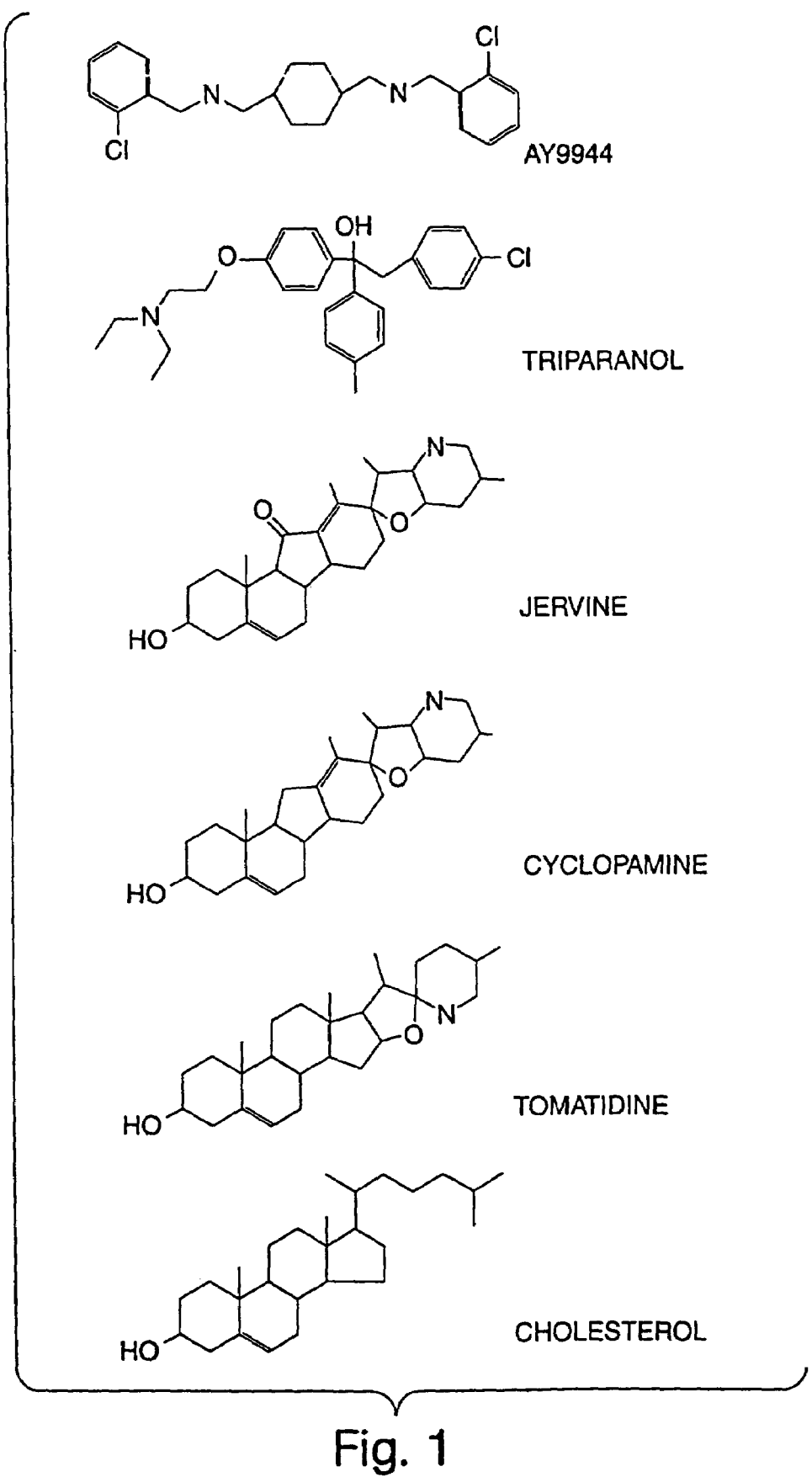
FIG. 1 depicts the chemical structures for AY9944, triparanol, jervine, cyclopamine, tomatidine and cholesterol.

The present invention relates to the discovery that signal transduction pathways regulated by hedgehog, patched (ptc), gli and/or smoothened can be inhibited, at least in part, by hedgehog antagonists. While not wishing to be bound by any theory, in the case of small molecule antagonists, the modulation of a receptor may be the mechanism by which these agents act. For example, the ability of these agents to inhibit proliferation of patched loss-of-function ($ptc^{lof}$) cells may be due to the ability of such molecules to interact with hedgehog, patched, or smoothened, or at least to interfere with the ability of those proteins to activate a hedgehog, ptc, and/or smoothened-mediated signal transduction pathway.

It is, therefore, specifically contemplated that these small molecules which interfere with aspects of hedgehog, ptc, or smoothened signal transduction activity will likewise be capable of changing the role of a cell in tissue development from what would otherwise occur. In preferred embodiments, the cell has a substantially wild-type hedgehog signaling pathway. It is also contemplated that hedgehog antagonists are particularly effective in treating disorders resulting from hyperactivation of the hedgehog pathway, either as a result of mutations in components of the hedgehog signaling pathway or as a result of inappropriate activation of the hedgehog signaling pathway in cell which do not comprise a mutation/lesion in a component of the hedgehog signaling pathway. Therefore, it is desirable to have a method for identifying those cells in which the hedgehog pathway is hyperactive such that antagonist treatment may be efficiently targeted. One of skill in the art will readily recognize, that antagonists for use in the present invention can antagonize hedgehog signaling at any point in the hedgehog signaling pathway. That is, an exemplary antagonist can reduce hedgehog signaling by binding to and antagonizing hedgehog, as for example using a hedgehog antibody. Similarly, an exemplary antagonist can interfere with the interaction between hedgehog and the hedgehog receptor patched. Additionally, one of skill in the art will recognize that exemplary antagonists can interfere with hedgehog signaling by acting intracellularly, as for example using a small molecule antagonist that acts on an intracellular component of the hedgehog signaling pathway. It is contemplated that the hedgehog antagonists of the present invention can be used to antagonize hedgehog signaling in a wild-type cell or in a cell comprising a mutation in a component of the hedgehog signaling pathway.

In certain embodiments, the subject antagonists are organic molecules having a molecular weight less than 2500 amu, more preferably less than 1500 amu, and even more preferably less than 750 amu, and are capable of inhibiting at least some of the biological activities of hedgehog proteins, preferably specifically in target cells.

Thus, the methods of the present invention include the use of small molecules that agonize ptc inhibition of hedgehog signaling in the regulation of repair and/or functional performance of a wide range of cells, tissues and organs having the phenotype of hedgehog gain-of-function and in tissues with wild-type hedgehog activity. For instance, the subject method has therapeutic and cosmetic applications ranging from regulation of neural tissues, bone and cartilage formation and repair, regulation of spermatogenesis, regulation of smooth muscle, regulation of lung, liver and tissue of other organs arising from the primitive gut, regulation of hematopoietic function, regulation of skin and hair growth, etc. Moreover, the subject methods can be performed on cells that are provided in culture (in vitro), or on cells in a whole animal (in vivo). See, for example, PCT publications WO 95/18856 and WO 96/17924 (the specifications of which are expressly incorporated by reference herein).

In another aspect, the present invention provides pharmaceutical preparations comprising, as an active ingredient, a hedgehog antagonist or ptc agonist such as described herein, formulated in an amount sufficient to inhibit, in vivo, proliferation or other biological consequences of hedgehog gain-of-function.

The subject treatments using hedgehog antagonists can be effective for both human and animal subjects. Animal subjects to which the invention is applicable extend to both domestic animals and livestock, raised either as pets or for commercial purposes. Examples are dogs, cats, cattle, horses, sheep, hogs, and goats.

II. Definitions

For convenience, certain terms employed in the specification, examples, and appended claims are collected here.

The phrase "aberrant modification or mutation" of a gene refers to such genetic lesions as, for example, deletions, substitution or addition of nucleotides to a gene, as well as gross chromosomal rearrangements of the gene and/or abnormal methylation of the gene. Likewise, misexpression of a gene refers to aberrant levels of transcription of the gene relative to those levels in a normal cell under similar conditions, as well as non-wild-type splicing of mRNA transcribed from the gene.

The term "adenocarcinoma" as used herein refers to a malignant tumor originating in glandular epithelium.

The term "angiogenesis", as used herein, refers to the formation of blood vessels. Specifically, angiogenesis is a multistep process in which endothelial cells focally degrade and invade through their own basement membrane, migrate through interstitial stroma toward an angiogenic stimulus, proliferate proximal to the migrating tip, organize into blood vessels, and reattach to newly synthesized basement membrane (see Folkman et al., Adv. Cancer Res., Vol. 43, pp. 175-203 (1985)).

"Basal cell carcinomas" exist in a variety of clinical and histological forms such as nodular-ulcerative, superficial, pigmented, morphealike, fibroepithelioma and nevoid syndrome. Basal cell carcinomas are the most common cutaneous neoplasms found in humans. The majority of new cases of nonmelanoma skin cancers fall into this category.

"Benign prostatic hyperplasia", or BPH, is a benign enlargement of the prostate gland that begins normally after age 50 years probably secondary to the effects of male hormones. If significant enlargement occurs, it may pinch off the urethra making urination difficult or impossible.

"Burn wounds" refer to cases where large surface areas of skin have been removed or lost from an individual due to heat and/or chemical agents.

The term "carcinoma" refers to a malignant new growth made up of epithelial cells tending to infiltrate surrounding tissues and to give rise to metastases. Exemplary carcinomas include: "basal cell carcinoma", which is an epithelial tumor of the skin that, while seldom metastasizing, has potentialities for local invasion and destruction; "squamous cell carcinoma", which refers to carcinomas arising from squamous epithelium and having cuboid cells; "carcinosarcoma", which include malignant tumors composed of carcinomatous and sarcomatous tissues; "adenocystic carcinoma", carcinoma marked by cylinders or bands of hyaline or mucinous stroma separated or surrounded by nests or cords of small epithelial cells, occurring in the mammary and salivary glands, and mucous glands of the respiratory tract; "epidermoid carcinoma", which refers to cancerous cells which tend to differentiate in the same way as those of the epidermis; i.e., they tend to form prickle cells and undergo cornification; "nasopharyngeal carcinoma", which refers to a malignant tumor arising in the epithelial lining of the space behind the nose; and "renal cell carcinoma", which pertains to carcinoma of the renal parenchyma composed of tubular cells in varying arrangements. Other carcinomatous epithelial growths are "papillomas", which refers to benign tumors derived from epithelium and having a papillomavirus as a causative agent; and "epidermoidomas", which refers to a cerebral or meningeal tumor formed by inclusion of ectodermal elements at the time of closure of the neural groove.

The "corium" or "dermis" refers to the layer of the skin deep to the epidermis, consisting of a dense bed of vascular connective tissue, and containing the nerves and terminal organs of sensation. The hair roots, and sebaceous and sweat glands are structures of the epidermis which are deeply embedded in the dermis.

"Dental tissue" refers to tissue in the mouth that is similar to epithelial tissue, for example gum tissue. The method of the present invention is useful for treating periodontal disease.

"Dermal skin ulcers" refer to lesions on the skin caused by superficial loss of tissue, usually with inflammation. Dermal skin ulcers that can be treated by the method of the present invention include decubitus ulcers, diabetic ulcers, venous stasis ulcers and arterial ulcers. Decubitus wounds refer to chronic ulcers that result from pressure applied to areas of the skin for extended periods of time. Wounds of this type are often called bedsores or pressure sores. Venous stasis ulcers result from the stagnation of blood or other fluids from defective veins. Arterial ulcers refer to necrotic skin in the area around arteries having poor blood flow.

The term "$ED_{50}$" means the dose of a drug that produces 50% of its maximum response or effect.

An "effective amount" of, e.g., a hedgehog antagonist, with respect to the subject method of treatment, refers to an amount of the antagonist in a preparation which, when applied as part of a desired dosage regimen brings about, e.g., a change in the rate of cell proliferation and/or the state of differentiation of a cell and/or rate of survival of a cell according to clinically acceptable standards for the disorder to be treated or for the cosmetic purpose.

The terms "epithelia", "epithelial" and "epithelium" refer to the cellular covering of internal and external body surfaces (cutaneous, mucous and serous), including the glands and other structures derived therefrom, e.g., corneal, esophageal, epidermal, and hair follicle epithelial cells. Other exemplary epithelial tissue includes: olfactory epithelium, which is the pseudostratified epithelium lining the olfactory region of the nasal cavity, and containing the receptors for the sense of smell; glandular epithelium, which refers to epithelium composed of secreting cells; squamous epithelium, which refers to epithelium composed of flattened plate-like cells. The term epithelium can also refer to transitional epithelium, like that which is characteristically found lining hollow organs that are subject to great mechanical change due to contraction and distention, e.g., tissue which represents a transition between stratified squamous and columnar epithelium.

The term "epithelialization" refers to healing by the growth of epithelial tissue over a denuded surface.

The term "epidermal gland" refers to an aggregation of cells associated with the epidermis and specialized to secrete or excrete materials not related to their ordinary metabolic needs. For example, "sebaceous glands" are holocrine glands in the corium that secrete an oily substance and sebum. The term "sweat glands" refers to glands that secrete sweat, situated in the corium or subcutaneous tissue, opening by a duct on the body surface.

The term "epidermis" refers to the outermost and nonvascular layer of the skin, derived from the embryonic ectoderm, varying in thickness from 0.07-1.4 mm. On the palmar and plantar surfaces it comprises, from within outward, five layers: basal layer composed of columnar cells arranged perpendicularly; prickle-cell or spinous layer composed of flattened polyhedral cells with short processes or spines; granular layer composed of flattened granular cells; clear layer composed of several layers of clear, transparent cells in which the nuclei are indistinct or absent; and horny layer composed of flattened, cornified non-nucleated cells. In the epidermis of the general body surface, the clear layer is usually absent.

"Excisional wounds" include tears, abrasions, cuts, punctures or lacerations in the epithelial layer of the skin and may extend into the dermal layer and even into subcutaneous fat and beyond. Excisional wounds can result from surgical procedures or from accidental penetration of the skin.

The "growth state" of a cell refers to the rate of proliferation of the cell and/or the state of differentiation of the cell. An "altered growth state" is a growth state characterized by an abnormal rate of proliferation, e.g., a cell exhibiting an increased or decreased rate of proliferation relative to a normal cell.

The term "hair" refers to a threadlike structure, especially the specialized epidermal structure composed of keratin and developing from a papilla sunk in the corium, produced only by mammals and characteristic of that group of animals. Also, "hair" may refer to the aggregate of such hairs. A "hair follicle" refers to one of the tubular-invaginations of the epidermis enclosing the hairs, and from which the hairs grow. "Hair follicle epithelial cells" refers to epithelial cells that surround the dermal papilla in the hair follicle, e.g., stem cells, outer root sheath cells, matrix cells, and inner root sheath cells. Such cells may be normal non-malignant cells, or transformed/immortalized cells.

The term "hedgehog" is used to refer generically to any member of the hedgehog family, including sonic, indian, desert and tiggy winkle. The term may be used to indicate protein or gene.

TABLE 1

Guide to hedgehog sequences in Sequence Listing

|  | Nucleotide | Amino Acid |
|---|---|---|
| Chicken Shh | SEQ ID No. 1 | SEQ ID No. 10 |
| Mouse Dhh | SEQ ID No. 2 | SEQ ID No. 11 |
| Mouse Ihh | SEQ ID No. 3 | SEQ ID No. 12 |
| Mouse Shh | SEQ ID No. 4 | SEQ ID No. 13 |
| Zebrafish Shh | SEQ ID No. 5 | SEQ ID No. 14 |
| Human Shh | SEQ ID No. 6 | SEQ ID No. 15 |
| Human Ihh | SEQ ID No. 7 | SEQ ID No. 16 |
| Human Dhh | SEQ ID No. 8 | SEQ ID No. 17 |
| zebrafish Thh | SEQ ID No. 9 | SEQ ID No. 18 |
| Drosophila HH | SEQ ID No. 19 | SEQ ID No. 20 |

The term "hedgehog signaling pathway", "hedgehog pathway" and "hedgehog signal transduction pathway" are all used to refer to the chain of events normally mediated by hedgehog, smoothened, ptc, and gli, among others, and resulting in a changes in gene expression and other phenotypic changes typical of hedgehog activity. The hedgehog pathway can be activated even in the absence of a hedgehog protein by activating a downstream component. For example, overexpression of smoothened will activate the pathway in the absence of hedgehog. gli and ptc gene expression are indicators of an active hedgehog signaling pathway.

The term "hedgehog antagonist" refers to an agent that potentiates or recapitulates the bioactivity of patched, such as to repress transcription of target genes. Preferred hedgehog antagonists can be used to overcome a ptc loss-of-function and/or a smoothened gain-of-function, the latter also being referred to as smoothened antagonists. Other preferred hedgehog antagonists can be used to overcome an inappropriate increase in hedgehog signal transduction, whether said increase in signal transduction is the result in a mutation/lesion in a component of the hedgehog signaling pathway (e.g., ptc, gli1, gli3, smoothened, etc) or whether said increase in signal transduction occurs in the context of a cell which does not comprise a mutation/lesion in a component of the hedgehog signaling pathway (e.g., a wildtype cell with respect to components of the hedgehog signaling pathway). The term 'hedgehog antagonist' as used herein refers not only to any agent that may act by directly inhibiting the normal function of the hedgehog protein, but also to any agent that inhibits the hedgehog signalling pathway, and thus recapitulates the function of ptc. A hedgehog antagonist may be a small molecule, an antibody (including but not restricted to: a diabody, single chain antibody, monoclonal antibody, IgG, IgM, IgA, IgD, IgE, or an antibody fragment comprising at least one pair of variable regions), an antisense nucleic acid, PNA or ribozyme, RNAi construct, or a mutant hedgehog protein that can disrupt or inhibit hedgehog signaling. An antibody may be directed to a protein encoded by any of the genes in the hedgehog pathway, including sonic, indian or desert hedgehog, smoothened, ptc-1, ptc-2, gli-1, gli-2, gli-3, etc. In most cases, the antibody would inhibit the activity of the target protein, but in the case of patched, such an antibody would be an activator of patched. An antisense nucleic acid would likewise decrease production of a protein encoded by any of the genes in the hedgehog pathway, with the exception of patched or other genes encoding negative regulators of the hedgehog signaling pathway.

Such an antagonist is an agent which has one of more of the following properties: (1) it coats, or binds to, a hedgehog on the surface of a hedgehog expressing or sereting cell with sufficient specificity to inhibit a hedgehog-receptor interaction (e.g, a hedgehog-patched interaction); (2) it coats, or binds to, a hedgehog on the surface of a hedgehog-bearing or secreting cell with sufficient specificity to modify, and preferably to inhibit, transduction of a hedgehog-mediated signal; (3) it coats, or binds to, a hedgehog receptor (e.g., patched) in or on cells with sufficient specificity to inhibit the hedgehog-patched interaction; (4) it coats, or binds to, a component of the hedgehog signaling pathway with sufficient specificity to modify, and preferably inhibit, transduction of a hedgehog-mediated signal; (5) it coats, or binds to, an intracellular component of the hedgehog signaling pathway with sufficient specificity to modify, and preferably to inhibit, transduction of a hedgehog-mediated signal. In preferred embodiments, the hedgehog antagonist has two or more of the above cited properties. Moreover, more than one antagonist can be administered. It is further contemplated that when more than one hedgehog antagonist is administered, said agents can inhibit hedgehog signaling through the same mechanism or through differing mechanisms.

The term "hedgehog gain-of-function" refers to an aberrant modification or mutation of a ptc gene, hedgehog gene, or smoothened gene, or a decrease (or loss) in the level of expression of such a gene, which results in a phenotype which resembles contacting a cell with a hedgehog protein, e.g., aberrant activation of a hedgehog pathway. The gain-of-function may include a loss of the ability of the ptc gene product to regulate the level of expression of Ci genes, e.g., Gli1, Gli2, and Gli3. The term 'hedgehog gain-of-function' is also used herein to refer to any similar cellular phenotype (e.g., exhibiting excess proliferation) that occurs due to an alteration anywhere in the hedgehog signal transduction pathway, including, but not limited to, a modification or mutation of hedgehog itself. For example, a tumor cell with an abnormally high proliferation rate due to activation of the hedgehog signalling pathway would have a 'hedgehog gain-of-function' phenotype, even if hedgehog is not mutated in that cell.

As used herein, "immortalized cells" refers to cells that have been altered via chemical and/or recombinant means such that the cells have the ability to grow through an indefinite number of divisions in culture.

"Internal epithelial tissue" refers to tissue inside the body that has characteristics similar to the epidermal layer in the skin. Examples include the lining of the intestine. The method of the present invention is useful for promoting the healing of certain internal wounds, for example wounds resulting from surgery.

The term "keratosis" refers to proliferative skin disorder characterized by hyperplasia of the horny layer of the epidermis. Exemplary keratotic disorders include keratosis follicularis, keratosis palmaris et plantaris, keratosis pharyngea, keratosis pilaris, and actinic keratosis.

"Lamellated bodies" refers to a subcellular structure found in lung cells that are producing surfactants. Lamellated bodies are thought to be the site of lung surfactant biosynthesis. The bodies have a multilayered membranous appearance in an electron micrograph.

The term "$LD_{50}$" means the dose of a drug that is lethal in 50% of test subjects.

The term "nail" refers to the horny cutaneous plate on the dorsal surface of the distal end of a finger or toe.

The term "overexpression" as used in reference to gene expression levels means any level of gene expression in cells of a tissue that is higher than the normal level of expression for that tissue. The normal level of expression for a tissue may be assessed by measuring gene expression in a healthy portion of that tissue.

The term "patched loss-of-function" refers to an aberrant modification or mutation of a ptc gene, or a decreased level of expression of the gene, which results in a phenotype that resembles contacting a cell with a hedgehog protein, e.g., aberrant activation of a hedgehog pathway. The loss-of-function may include a loss of the ability of the ptc gene product to regulate the level of expression of Ci genes, e.g., Gli1, Gli2 and Gli3.

"standard hybridization conditions" refer to salt and temperature conditions substantially equivalent to 0.5×SSC to about 5×SSC and 65° C. for both hybridization and wash. The term "standard hybridization conditions" as used herein is therefore an operational definition and encompasses a range of hybridization conditions. Nevertheless, for the purposes of this present disclosure "high stringency" conditions include hybridizing with plaque screen buffer (0.2% polyvinylpyrrolidone, 0.2% Ficoll 400; 0.2% bovine serum albumin, 50 mM Tris-HCl (pH 7.5); 1 M NaCl; 0.1% sodium pyrophosphate; 1% SDS); 10% dextran sulfate, and 100 ug/ml denatured, sonicated salmon sperm DNA at 65° C. for 12-20 hours, and washing with 75 mM NaCl/7.5 mM sodium citrate (0.5×SSC)/1% SDS at 65° C. "Low stringency" conditions include hybridizing with plaque screen buffer, 10% dextran sulfate and 110 ug/ml denatured, sonicated salmon sperm DNA at 55° C. for 12-20 hours, and washing with 300 mM NaCl/30 mM sodium citrate (2.0×SSC)/1% SDS at 55° C. See also Current Protocols in Molecular Biology, John Wiley & Sons, Inc. New York, Sections 6.3.1-6.3.6, (1989).

A "patient" or "subject" to be treated by the subject method can mean either a human or non-human animal.

The term "prodrug" is intended to encompass compounds that, under physiological conditions, are converted into the therapeutically active agents of the present invention. A common method for making a prodrug is to include selected moieties that are hydrolyzed under physiological conditions to reveal the desired molecule. In other embodiments, the prodrug is converted by an enzymatic activity of the host animal.

As used herein, "proliferating" and "proliferation" refer to cells undergoing mitosis.

Throughout this application, the term "proliferative skin disorder" refers to any disease/disorder of the skin marked by unwanted or aberrant proliferation of cutaneous tissue. These conditions are typically characterized by epidermal cell proliferation or incomplete cell differentiation, and include, for example, X-linked ichthyosis, psoriasis, atopic dermatitis, allergic contact dermatitis, epidermolytic hyperkeratosis, and seborrheic dermatitis. For example, epidermodysplasia is a form of faulty development of the epidermis. Another example is "epidermolysis", which refers to a loosened state of the epidermis with formation of blebs and bullae either spontaneously or at the site of trauma.

As used herein, the term "psoriasis" refers to a hyperproliferative skin disorder that alters the skin's regulatory mechanisms. In particular, lesions are formed which involve primary and secondary alterations in epidermal proliferation, inflammatory responses of the skin, and an expression of regulatory molecules such as lymphokines and inflammatory factors. Psoriatic skin is morphologically characterized by an increased turnover of epidermal cells, thickened epidermis, abnormal keratinization, inflammatory cell infiltrates into the dermis layer and polymorphonuclear leukocyte infiltration into the epidermis layer resulting in an increase in the basal cell cycle. Additionally, hyperkeratotic and parakeratotic cells are present.

The term "skin" refers to the outer protective covering of the body, consisting of the corium and the epidermis, and is understood to include sweat and sebaceous glands, as well as hair follicle structures. Throughout the present application, the adjective "cutaneous" may be used, and should be understood to refer generally to attributes of the skin, as appropriate to the context in which they are used.

The term "small cell carcinoma" refers to a type of malignant neoplasm, commonly of the bronchus. Cells of the tumor have endocrine like characteristics and may secrete one or more of a wide range of hormones, especially regulatory peptides like bombesin.

The term "smoothened gain-of-function" refers to an aberrant modification or mutation of a smo gene, or an increased level of expression of the gene, which results in a phenotype that resembles contacting a cell with a hedgehog protein, e.g., aberrant activation of a hedgehog pathway. While not wishing to be bound by any particular theory, it is noted that ptc may not signal directly into the cell, but rather interact with smoothened, another membrane-bound protein located downstream of ptc in hedgehog signaling (Marigo et al., (1996) *Nature* 384: 177-179). The gene smo is a segment-polarity gene required for the correct patterning of every segment in *Drosophila* (Alcedo et al., (1996) *Cell* 86: 221-232). Human homologs of smo have been identified. See, for example, Stone et al. (1996) *Nature* 384:129-134, and GenBank accession U84401. The smoothened gene encodes an integral membrane protein with characteristics of heterotrimeric G-protein-coupled receptors; i.e., 7-transmembrane regions. This protein shows homology to the *Drosophila* Frizzled (Fz) protein, a member of the wingless pathway. It was originally thought that smo encodes a receptor of the Hh signal. However, this suggestion was subsequently disproved, as evidence for ptc being the Hh receptor was obtained. Cells that express Smo fail to bind Hh, indicating that smo does not interact directly with Hh (Nusse, (1996) *Nature* 384: 119-120). Rather, the binding of Sonic hedgehog (SHH) to its receptor, PTCH, is thought to prevent normal inhibition by PTCH of smoothened (SMO), a seven-span transmembrane protein.

Recently, it has been reported that activating smoothened mutations occur in sporadic basal cell carcinoma, Xie et al. (1998) *Nature* 391: 90-2, and primitive neuroectodermal tumors of the central nervous system, Reifenberger et al. (1998) *Cancer Res* 58: 1798-803.

The term "therapeutic index" refers to the therapeutic index of a drug defined as $LD_{50}/ED_{50}$.

As used herein, "transformed cells" refers to cells that have spontaneously converted to a state of unrestrained growth, i.e., they have acquired the ability to grow through an indefinite number of divisions in culture. Transformed cells may be characterized by such terms as neoplastic, anaplastic and/or hyperplastic, with respect to their loss of growth control.

"Urogenital" refers to the organs and tissues of the urogenital tract, which includes among other tissues, the prostate, ureter, kidney and bladder. A "urogenital cancer" is a cancer of a urogenital tissue.

The term "acylamino" is art-recognized and refers to a moiety that can be represented by the general formula:

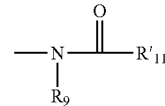

wherein $R_9$ is as defined above, and $R'_{11}$ represents a hydrogen, an alkyl, an alkenyl or —$(CH_2)_m$—$R_8$, where m and $R_8$ are as defined above.

Herein, the term "aliphatic group" refers to a straight-chain, branched-chain, or cyclic aliphatic hydrocarbon group and includes saturated and unsaturated aliphatic groups, such as an alkyl group, an alkenyl group, and an alkynyl group.

The terms "alkenyl" and "alkynyl" refer to unsaturated aliphatic groups analogous in length and possible substitution to the alkyls described above, but that contain at least one double or triple bond respectively.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—(CH$_2$)$_m$—R$_8$, where m and R$_8$ are described above.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., C$_1$-C$_{30}$ for straight chains, C$_3$-C$_{30}$ for branched chains), and more preferably 20 or fewer. Likewise, preferred cycloalkyls have from 3-10 carbon atoms in their ring structure, and more preferably have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF$_3$, —CN and the like. Exemplary substituted alkyls are described below. Cycloalkyls can be further substituted with alkyls, alkenyls, alkoxys, alkylthios, aminoalkyls, carbonyl-substituted alkyls, —CF$_3$, —CN, and the like.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—(CH$_2$)$_m$—R$_8$, wherein m and R$_8$ are defined above. Representative alkylthio groups include methylthio, ethylthio, and the like.

The terms "amine" and "amino" are art-recognized and refer to both unsubstituted and substituted amines, e.g., a moiety that can be represented by the general formula:

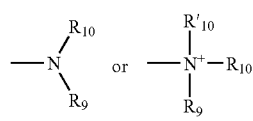

wherein R$_9$, R$_{10}$ and R'10 each independently represent a hydrogen, an alkyl, an alkenyl, —(CH$_2$)$_m$—R$_8$, or R$_9$ and R$_{10}$ taken together with the N atom to which they are attached complete a heterocycle having from 4 to 8 atoms in the ring structure; R$_8$ represents an aryl, a cycloalkyl, a cycloalkenyl, a heterocycle or a polycycle; and m is zero or an integer in the range of 1 to 8. In preferred embodiments, only one of R$_9$ or R$_{10}$ can be a carbonyl, e.g., R$_9$, R$_{10}$ and the nitrogen together do not form an imide. In even more preferred embodiments, R$_9$ and R$_{10}$ (and optionally R'$_{10}$) each independently represent a hydrogen, an alkyl, an alkenyl, or —(CH$_2$)$_m$—R$_8$. Thus, the term "alkylamine" as used herein means an amine group, as defined above, having a substituted or unsubstituted alkyl attached thereto, i.e., at least one of R$_9$ and R$_{10}$ is an alkyl group.

The term "amido" is art-recognized as an amino-substituted carbonyl and includes a moiety that can be represented by the general formula:

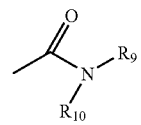

wherein R$_9$, R$_{10}$ are as defined above. Preferred embodiments of the amide will not include imides, which may be unstable.

The term "aralkyl", as used herein, refers to an alkyl group substituted with an aryl group (e.g., an aromatic or heteroaromatic group).

The term "aryl" as used herein includes 5-, 6-, and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphate, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The term "carbocycle", as used herein, refers to an aromatic or non-aromatic ring in which each atom of the ring is carbon.

The term "carbonyl" is art-recognized and includes such moieties as can be represented by the general formula:

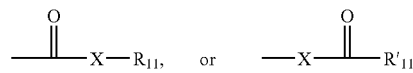

wherein X is a bond or represents an oxygen or a sulfur, and R$_{11}$ represents a hydrogen, an alkyl, an alkenyl, —(CH$_2$)$_m$—R$_8$ or a pharmaceutically acceptable salt, R'$_{11}$ represents a hydrogen, an alkyl, an alkenyl or —(CH$_2$)$_m$—R$_8$, where m and R$_8$ are as defined above. Where X is an oxygen and R$_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiocarbonyl" group. Where X is a sulfur and $R_{11}$ or $R'_{11}$ is not hydrogen, the formula represents a "thioester." Where X is a sulfur and $R_{11}$ is hydrogen, the formula represents a "thiocarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The term "heteroatom" as used herein means an atom of any element other than carbon or hydrogen. Preferred heteroatoms are boron, nitrogen, oxygen, phosphorus, sulfur and selenium.

The terms "heterocyclyl" or "heterocyclic group" refer to 3-to10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The phrase "protecting group" as used herein means temporary substituents that protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_8$, m and $R_8$ being defined above.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

The term "sulfamoyl" is art-recognized and includes a moiety that can be represented by the general formula:

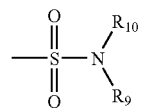

in which $R_9$ and $R_{10}$ are as defined above.

The term "sulfate" is art recognized and includes a moiety that can be represented by the general formula:

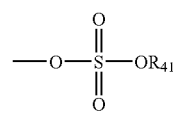

in which $R_{41}$ is as defined above.

The term "sulfonamido" is art recognized and includes a moiety that can be represented by the general formula:

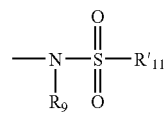

in which $R_9$ and $R'_{11}$ are as defined above.

The term "sulfonate" is art-recognized and includes a moiety that can be represented by the general formula:

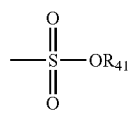

in which $R_{41}$ is an electron pair, hydrogen, alkyl, cycloalkyl, or aryl.

The terms "sulfoxido" or "sulfinyl", as used herein, refers to a moiety that can be represented by the general formula:

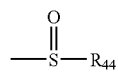

in which $R_{44}$ is selected from the group consisting of hydrogen, alkyl, alkenyl, alkynyl, cycloalkyl, heterocyclyl, aralkyl, or aryl.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g., alkyl, m, n, etc., when it occurs more than once in any structure, is intended to be independent of its definition elsewhere in the same structure.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts may be formed with an appropriate optically active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., the ability to inhibit hedgehog signaling), wherein one or more simple variations of substituents are made which do not adversely affect the efficacy of the compound. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here.

For purposes of this invention, the chemical elements are identified in accordance with the Periodic Table of the Elements, CAS version, Handbook of Chemistry and Physics, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and non-aromatic organic compounds which can be substituted or unsubstituted.

III. Exemplary Compounds and Synthesis Thereof

Hedgehog antagonists of the invention may be essentially any composition that inhibits the activity of the hedgehog signaling pathway, in other words mimicking the effect of patched activity. Hedgehog antagonists may be small molecules (organic or inorganic), antisense nucleotides and PNAs, RNAi constructs, antibodies and altered hedgehog proteins.

Small Molecule Antagonists:

Hedgehog antagonist compounds for certain embodiments of the invention are described in the formulas below and methods of making the compositions are described in detail in the following U.S. patent applications Ser. Nos. 09/663,835, 09/685,244, 09/724,277, 09/687,800, 09/688,018, 60/308,449 and 09/688,076. The exemplary compounds are divided into five parts. For each of the parts, the variable groups and numbers (e.g., $R_1$, L, $Z_2$) are individually and distinctly defined, and are internally consistent but not necessarily consistent from part to part.

Exemplary Compounds Part 1:

As described in further detail below, it is contemplated that the subject methods can be carried out using any of a variety of different steroidal alkaloids which can be readily identified, e.g., by such drug screening assays as described herein. Steroidal alkaloids have a fairly complex nitrogen-containing nucleus. Two exemplary classes of steroidal alkaloids for use in the subject methods are the Solanum type and the Veratrum type. The above notwithstanding, in a preferred embodiment, the methods and compositions of the present invention make use of compounds having a steroidal alkaloid ring system of cyclopamine.

There are more than 50 naturally occurring veratrum alkaloids including veratramine, cyclopamine, cycloposine, jervine, and muldamine occurring in plants of the Veratrum spp. The Zigadenus spp., death camas, also produces several veratrum-type of steroidal alkaloids including zygacine. In general, many of the veratrum alkaloids (e.g., jervine, cyclopamine and cycloposine) consist of a modified steroid skeleton attached spiro to a furanopiperidine. A typical veratrum-type alkaloid may be represented by:

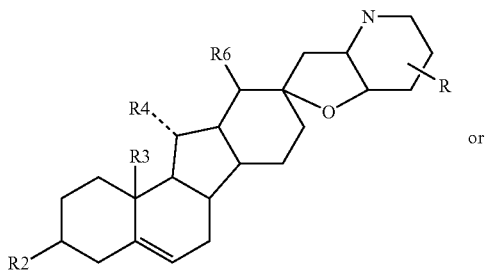

or

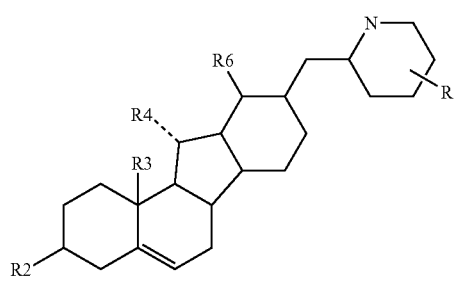

An example of the Solanum type is solanidine. This steroidal alkaloid is the nucleus (i.e., aglycone) for two important glycoalkaloids, solanine and chaconine, found in potatoes. Other plants in the Solanum family including various nightshades, Jerusalem cherries, and tomatoes also contain solanum-type glycoalkaloids. Glycoalkaloids are glycosides of alkaloids. A typical solanum-type alkaloid may be represented by:

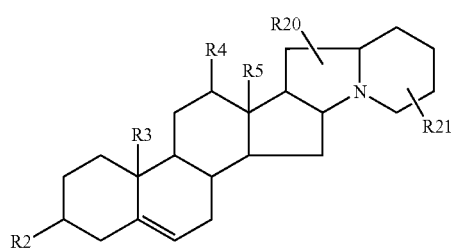

Based on these structures, and the possibility that certain unwanted side effects can be reduced by some manipulation of the structure, a wide range of steroidal alkaloids are contemplated as potential smoothened antagonists for use in the subject method. For example, compounds useful in the subject methods include steroidal alkaloids represented in the general formulas (I), or unsaturated forms thereof and/or seco-, nor- or homo-derivatives thereof:

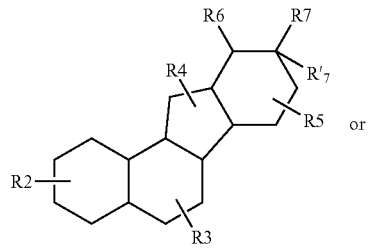

Formula I or

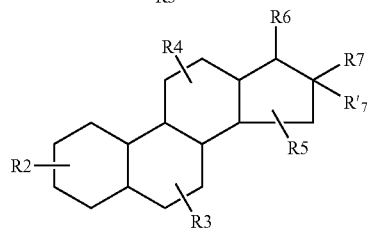

wherein, as valence and stability permit, $R_2$, $R_3$, $R_4$, and $R_5$, represent one or more substitutions to the ring to which each is attached, for each occurrence, independently represent hydrogen, halogens, alkyls, alkenyls, alkynyls, aryls, hydroxyl, =O, =S, alkoxyl, silyloxy, amino, nitro, thiol, amines, imines, amides, phosphoryls, phosphonates, phosphines, carbonyls, carboxyls, carboxamides, anhydrides, silyls, ethers, thioethers, alkylsulfonyls, arylsulfonyls, selenoethers, ketones, aldehydes, esters, sugar (e.g., monosaccharide, disaccharide, polysaccharide, etc.), carbamate (e.g., attached to the steroid at oxygen), carbonate, or —$(CH_2)_m$—$R_8$;

$R_6$, $R_7$, and $R'_7$, are absent or represent, independently, halogens, alkyls, alkenyls, alkynyls, aryls, hydroxyl, =O, =S, alkoxyl, silyloxy, amino, nitro, thiol, amines, imines, amides, phosphoryls, phosphonates, phosphines, carbonyls, carboxyls, carboxamides, anhydrides, silyls, ethers, thioethers, alkylsulfonyls, arylsulfonyls, selenoethers, ketones, aldehydes, esters, or —$(CH_2)_m$—$R_8$, or $R_6$ and $R_7$, or $R_7$ and $R'_7$, taken together form a ring or polycyclic ring, e.g., which is substituted or unsubstituted, with the proviso that at least one of $R_6$, $R_7$, or $R'_7$ is present and includes an amine, e.g., as one of the atoms which makes up the ring;

$R_8$ represents an aryl, a cycloalkyl, a cycloalkenyl, a heterocycle, or a polycycle; and m is an integer in the range 0 to 8 inclusive.

In certain embodiments, $R_2$ represents =O, sugar (e.g., monosaccharide, disaccharide, polysaccharide, etc.), carbamate (e.g., attached to the steroid at oxygen), ester (e.g., attached to the steroid at oxygen), carbonate, or alkoxy. Substituents such as carbamate, ester, carbonate, and alkoxy may be substituted or unsubstituted, e.g., may include additional functional groups such as aryl, aralkyl, heteroaryl, heteroaralkyl, amide, acylamino, carbonyl, ester, carbamate, urea, ketone, sulfonamide, etc.

In certain embodiments, the amine of $R_6$, $R_7$, or $R'_7$ is a tertiary amine.

In particular embodiments, $R_3$, for each occurrence, is an —OH, alkyl, —O-alkyl, —C(O)-alkyl, or —C(O)—$R_8$.

In particular embodiments, $R_4$, for each occurrence, is an absent, or represents —OH, =O, alkyl, —O-alkyl, —C(O)-alkyl, or —C(O)—$R_8$.

In particular embodiments, two of $R_6$, $R_7$, and $R'_7$ taken together form a nitrogen-containing ring, such as a furanopiperidine, such as perhydrofuro[3,2-b]pyridine, a pyranopiperidine, a quinoline, an indole, a pyranopyrrole, a naphthyridine, a thiofuranopiperidine, or a thiopyranopiperidine.

In certain embodiments, the nitrogen-containing ring comprises a tertiary amine, e.g., by having an extraannular substituent on the nitrogen atom, e.g., an alkyl substituted with, for example, aryl, aralkyl, heteroaryl, heteroaralkyl, amide, acylamino, carbonyl, ester, carbamate, urea, ketone, sulfonamide, etc. In certain embodiments, the extraannular substituent of the tertiary amine is a hydrophobic substituent. In certain embodiments, the hydrophobic extraannular substituent includes an aryl, heteroaryl, carbocyclyl, heterocyclyl, or polycyclyl group, such as biotin, a zwitterionic complex of boron, a steroidal polycycle, etc. In certain embodiments, the hydrophobic substituent may consist essentially of a combination of alkyl, amido, acylamino, ketone, ester, ether, halogen, alkenyl, alkynyl, aryl, aralkyl, urea, or similar functional groups, including between 5 and 40 non-hydrogen atoms, more preferably between 5 and 20 non-hydrogen atoms.

In particular embodiments, $R_8$ represents an aryl, a cycloalkyl, a cycloalkenyl, a heterocycle, or a polycycle, and preferably $R_8$ is a piperidine, pyrrolidine, pyridine, pyrimidine, morpholine, thiomorpholine, pyridazine, etc.

In certain preferred embodiments, the definitions outlined above apply, and the subject compounds are represented by general formula Ia or unsaturated forms thereof and/or seco-, nor- or homo-derivatives thereof:

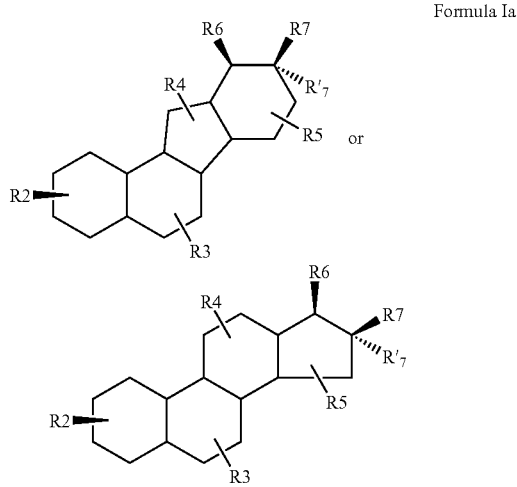

Formula Ia

In certain embodiments, the steroidal alkaloid is represented in the general formula (II), or unsaturated forms thereof and/or seco-, nor- or homo-derivatives thereof:

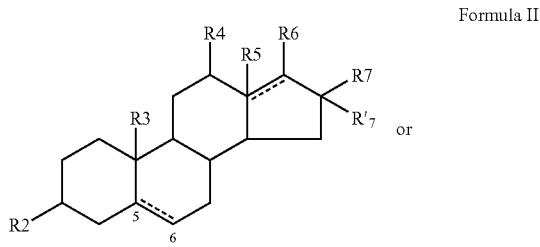

Formula II

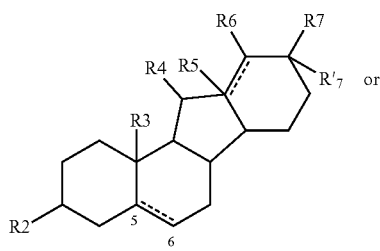

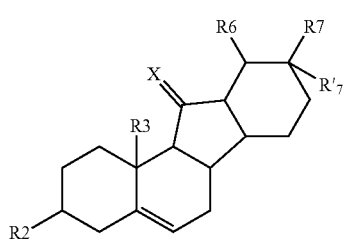

wherein $R_2$, $R_3$, $R_4$, $R_5$, $R_6$, $R_7$, and $R'_7$ are as defined above, and X represents O or S, though preferably O.

In certain embodiments, $R_2$ represents =O, sugar (e.g., monosaccharide, disaccharide, polysaccharide, etc.), carbamate (e.g., attached to the steroid at oxygen), ester (e.g., attached to the steroid at oxygen), carbonate, or alkoxy. Substituents such as carbamate, ester, carbonate, and alkoxy may be substituted or unsubstituted, e.g., may include additional functional groups such as aryl, aralkyl, heteroaryl, heteroaralkyl, amide, acylamino, carbonyl, ester, carbamate, urea, ketone, sulfonamide, etc.

In certain embodiments, the amine of $R_6$, $R_7$, or $R'_7$ is a tertiary amine, e.g., substituted with a substituted or unsubstituted alkyl. In certain embodiments, the amine is part of a bicyclic ring system formed from $R_7$ and $R'_7$, e.g., a furanopiperidine system, and the third substituent is an alkyl substituted with, for example, aryl, aralkyl, heteroaryl, heteroaralkyl, amide, acylamino, carbonyl, ester, carbamate, urea, ketone, sulfonamide, etc. In certain embodiments, the extraannular substituent of the tertiary amine is a hydrophobic substituent. In certain embodiments, the hydrophobic extraannular substituent includes an aryl, heteroaryl, carbocyclyl, heterocyclyl, or polycyclyl group, such as biotin, a zwitterionic complex of boron, a steroidal polycycle, etc. In certain embodiments, the hydrophobic substituent may consist essentially of a combination of alkyl, amido, acylamino, ketone, ester, ether, halogen, alkenyl, alkynyl, aryl, aralkyl, urea, or similar functional groups, including between 5 and 40 non-hydrogen atoms, more preferably between 5 and 20 non-hydrogen atoms.

In certain preferred embodiments, the definitions outlined above apply, and the subject compounds are represented by general formula IIa or unsaturated forms thereof and/or seco-, nor- or homo-derivatives thereof:

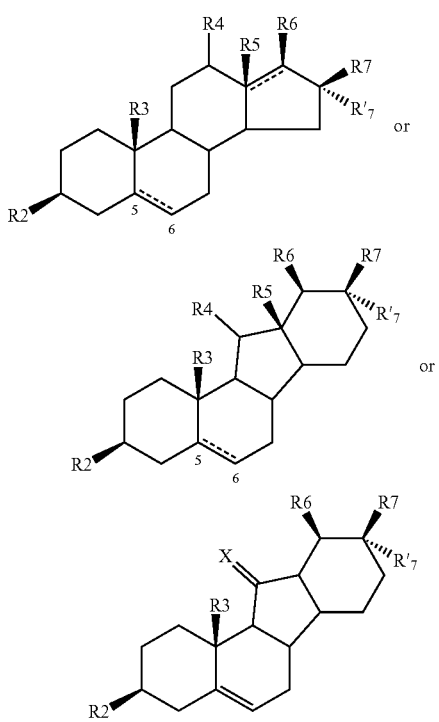

Formula IIa

In certain embodiments, the steroidal alkaloid is represented in the general formula (III), or unsaturated forms thereof and/or seco-, nor- or homo-derivatives thereof:

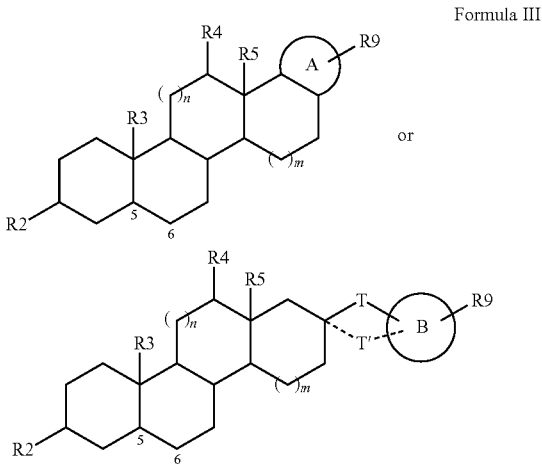

Formula III wherein
$R_2$, $R_3$, $R_4$, $R_5$ and $R_8$ are as defined above;
A and B represent monocyclic or polycyclic groups;
T represents an alkyl, an aminoalkyl, a carboxyl, an ester, an amide, ether or amine linkage of 1-10 bond lengths;
T' is absent, or represents an alkyl, an aminoalkyl, a carboxyl, an ester, an amide, ether or amine linkage of 1-3 bond lengths, wherein if T and T' are present together, than T and T' taken together with the ring A or B form a covalently closed ring of 5-8 ring atoms;
$R_9$ represents one or more substitutions to the ring A or B, which for each occurrence, independently represent halogens, alkyls, alkenyls, alkynyls, aryls, hydroxyl, =O, =S, alkoxyl, silyloxy, amino, nitro, thiol, amines, imines, amides, phosphoryls, phosphonates, phosphines, carbonyls, carboxyls, carboxamides, anhydrides, silyls, ethers, thioethers, alkylsulfonyls, arylsulfonyls, selenoethers, ketones, aldehydes, esters, or $-(CH_2)_m-R_8$; and
n and m are, independently, zero, 1 or 2;
with the proviso that A, or T, T', and B, taken together, include at least one amine.

In certain embodiments, $R_2$ represents =O, sugar (e.g., monosaccharide, disaccharide, polysaccharide, etc.), carbamate (e.g., attached to the steroid at oxygen), ester (e.g., attached to the steroid at oxygen), carbonate, or alkoxy. Substituents such as carbamate, ester, carbonate, and alkoxy may be substituted or unsubstituted, e.g., may include additional functional groups such as aryl, aralkyl, heteroaryl, heteroaralkyl, amide, acylamino, carbonyl, ester, carbamate, urea, ketone, sulfonamide, etc.

In certain embodiments, the amine of A, or T, T', and B, is a tertiary amine, e.g., substituted with a substituted or unsubstituted alkyl, e.g., substituted with aryl, aralkyl, heteroaryl, heteroaralkyl, amide, acylamino, carbonyl, ester, carbamate, urea, ketone, sulfonamide, etc. In certain embodiments, the extraannular substituent of the tertiary amine is a hydrophobic substituent. In certain embodiments, the hydrophobic extraannular substituent includes an aryl, heteroaryl, carbocyclyl, heterocyclyl, or polycyclyl group, such as biotin, a zwitterionic complex of boron, a steroidal polycycle, etc. In certain embodiments, the hydrophobic substituent may consist essentially of a combination of alkyl, amido, acylamino, ketone, ester, ether, halogen, alkenyl, alkynyl, aryl, aralkyl, urea, or similar functional groups, including between 5 and 40 non-hydrogen atoms, more preferably between 5 and 20 non-hydrogen atoms.

In certain preferred embodiments, the definitions outlined above apply, and the subject compounds are represented by general formula IIIa or unsaturated forms thereof and/or seco-, nor- or homo-derivatives thereof:

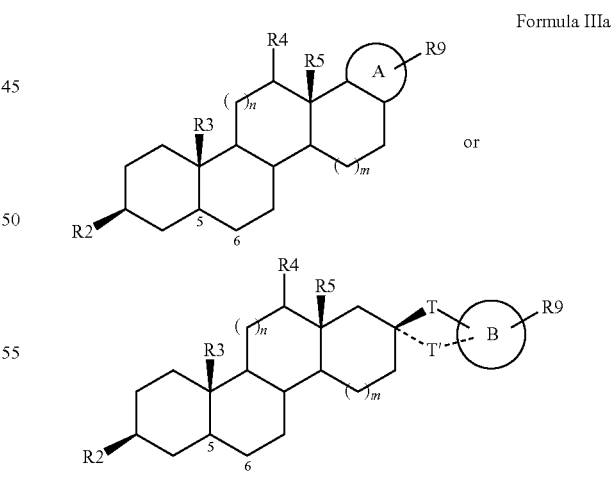

Formula IIIa

For example, the subject methods can utilize smoothened antagonists based on the veratrum-type steroidal alkaloids jervine, cyclopamine, cycloposine, mukiamine or veratramine, e.g., which may be represented in the general formula (IV), or unsaturated forms thereof and/or seco-, nor- or homo-derivatives thereof:

Formula IV

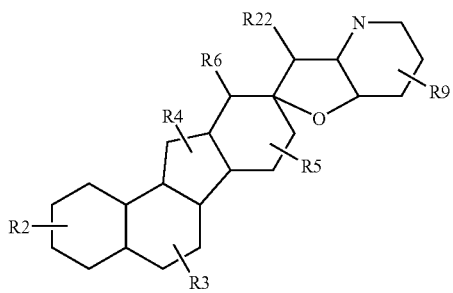

or

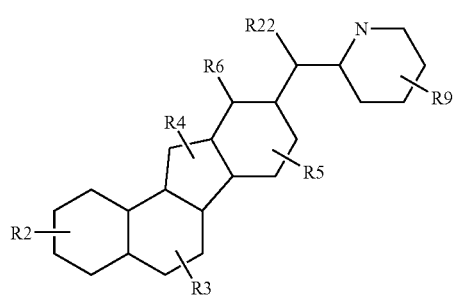

wherein $R_2$, $R_3$, $R_4$, $R_5$, $R_6$ and $R_9$ are as defined above;

$R_{22}$ is absent or represents an alkyl, an alkoxyl or —OH.

In certain embodiments, $R_2$ represents =O, sugar (e.g., monosaccharide, disaccharide, polysaccharide, etc.), carbamate (e.g., attached to the steroid at oxygen), ester (e.g., attached to the steroid at oxygen), carbonate, or alkoxy. Substituents such as carbamate, ester, carbonate, and alkoxy may be substituted or unsubstituted, e.g., may include additional functional groups such as aryl, aralkyl, heteroaryl, heteroaralkyl, amide, acylamino, carbonyl, ester, carbamate, urea, ketone, sulfonamide, etc.

In certain embodiments, $R_9$ includes a substituent on nitrogen, e.g., a substituted or unsubstituted alkyl, e.g., substituted with, for example, aryl, aralkyl, heteroaryl, heteroaralkyl, amide, acylamino, carbonyl, ester, carbamate, urea, ketone, sulfonamide, etc. In certain embodiments, the extraannular substituent (e.g., $R_9$) of the tertiary amine is a hydrophobic substituent. In certain embodiments, the hydrophobic extraannular substituent includes an aryl, heteroaryl, carbocyclyl, heterocyclyl, or polycyclyl group, such as biotin, a zwitterionic complex of boron, a steroidal polycycle, etc. In certain embodiments, the hydrophobic substituent may consist essentially of a combination of alkyl, amido, acylamino, ketone, ester, ether, halogen, alkenyl, alkynyl, aryl, aralkyl, urea, or similar functional groups, including between 5 and 40 non-hydrogen atoms, more preferably between 5 and 20 non-hydrogen atoms.

In certain preferred embodiments, the definitions outlined above apply, and the subject compounds are represented by general formula IVa or unsaturated forms thereof and/or seco-, nor- or homo-derivatives thereof:

Formula IVa

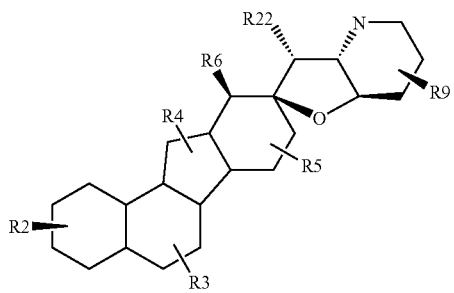

or

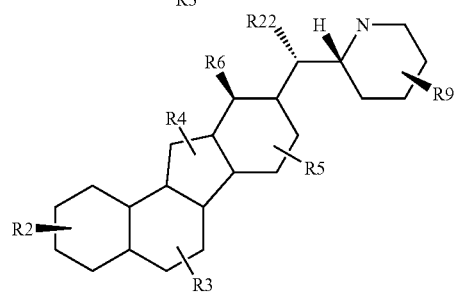

In certain embodiments, the steroidal alkaloid is represented in the general formula (V) or unsaturated forms thereof and/or seco-, nor- or homo-derivatives thereof:

Formula V

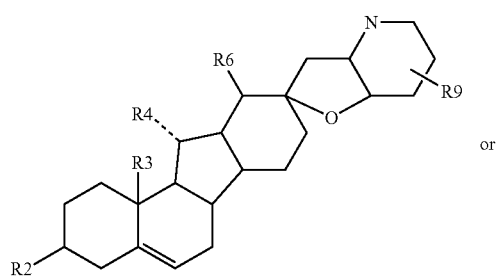

or

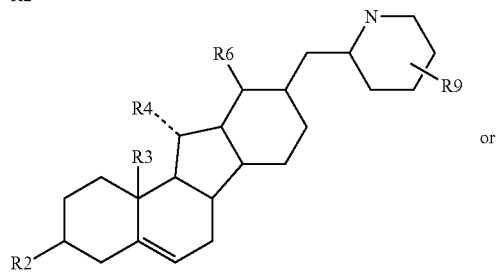

or

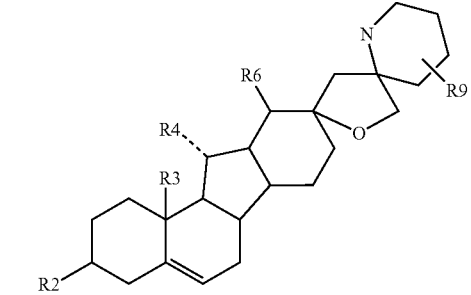

wherein $R_2$, $R_3$, $R_4$, $R_6$ and $R_9$ are as defined above;

In certain embodiments, $R_2$ represents =O, sugar (e.g., monosaccharide, disaccharide, polysaccharide, etc.), carbamate (e.g., attached to the steroid at oxygen), ester (e.g., attached to the steroid at oxygen), carbonate, or alkoxy. Substituents such as carbamate, ester, carbonate, and alkoxy may be substituted or unsubstituted, e.g., may include additional functional groups such as aryl, aralkyl, heteroaryl, heteroaralkyl, amide, acylamino, carbonyl, ester, carbamate, urea, ketone, sulfonamide, etc.

In certain embodiments, $R_9$ includes a substituent on nitrogen, e.g., a substituted or unsubstituted alkyl, e.g., substituted with, for example, aryl, aralkyl, heteroaryl, heteroaralkyl, amide, acylamino, carbonyl, ester, carbamate, urea, ketone, sulfonamide, etc.

In certain embodiments, the extraannular substituent of the tertiary amine (e.g., $R_9$) is a hydrophobic substituent. In certain embodiments, the hydrophobic extraannular substituent includes an aryl, heteroaryl, carbocyclyl, heterocyclyl, or polycyclyl group, such as biotin, a zwitterionic complex of boron, a steroidal polycycle, etc. In certain embodiments, the hydrophobic substituent may consist essentially of a combination of alkyl, amido, acylamino, ketone, ester, ether, halogen, alkenyl, alkynyl, aryl, aralkyl, urea, or similar functional groups, including between 5 and 40 non-hydrogen atoms, more preferably between 5 and 20 non-hydrogen atoms.

In certain preferred embodiments, the definitions outlined above apply, and the subject compounds are represented by general formula Va or unsaturated forms thereof and/or seco-, nor- or homo-derivatives thereof:

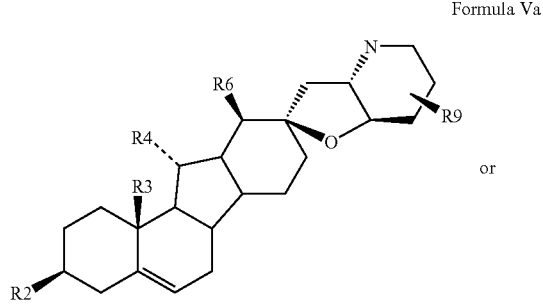

Formula Va

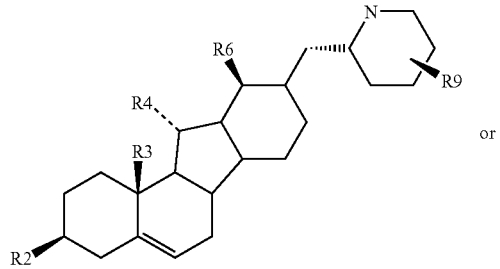

or

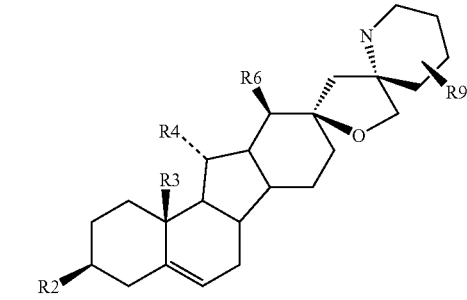

Another class of smoothened antagonists can be based on the veratrum-type steroidal alkaloids resembling verticine and zygacine, e.g., general formula (VI), or unsaturated forms thereof and/or seco-, nor- or homo-derivatives thereof:

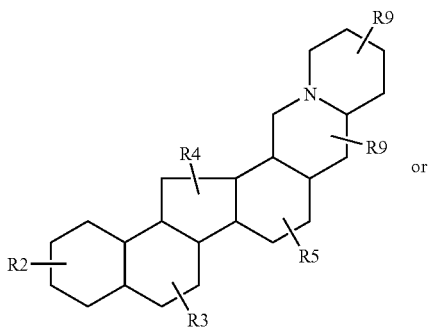

or

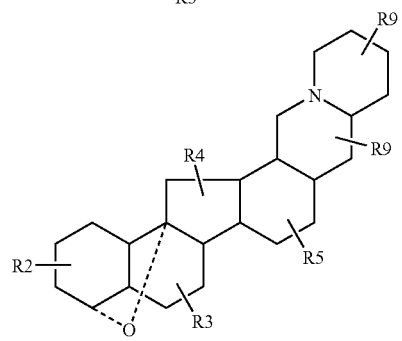

Formula VI wherein $R_2$, $R_3$, $R_4$, $R_5$ and $R_9$ are as defined above;

In certain embodiments, $R_2$ represents =O, sugar (e.g., monosaccharide, disaccharide, polysaccharide, etc.), carbamate (e.g., attached to the steroid at oxygen), ester (e.g., attached to the steroid at oxygen), carbonate, or alkoxy. Substituents such as carbamate, ester, carbonate, and alkoxy may be substituted or unsubstituted, e.g., may include additional functional groups such as aryl, aralkyl, heteroaryl, heteroaralkyl, amide, acylamino, carbonyl, ester, carbamate, urea, ketone, sulfonamide, etc.

In certain preferred embodiments, the definitions outlined above apply, and the subject compounds are represented by general formula VIa or unsaturated forms thereof and/or seco-, nor- or homo-derivatives thereof:

Formula VIa

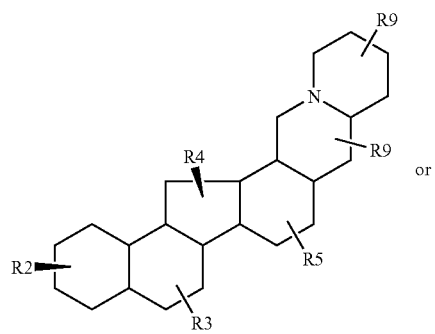

or

-continued

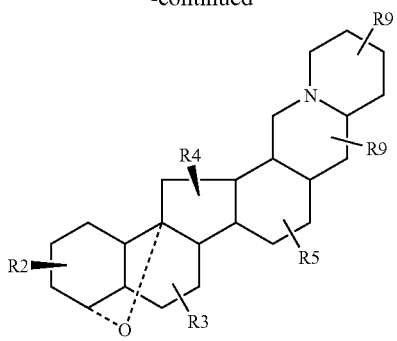

In certain embodiments, the steroidal alkaloid is represented in the general formula (VII) or unsaturated forms thereof and/or seco-, nor- or homo-derivatives thereof:

Formula VII

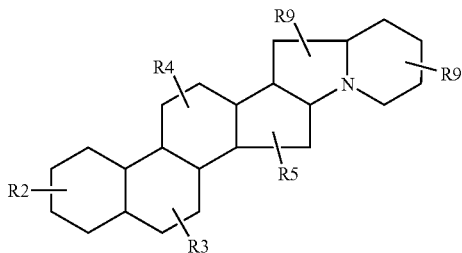

wherein $R_2$, $R_3$, $R_4$, $R_5$ and $R_9$ are as defined above.

In certain embodiments, $R_2$ represents =O, sugar (e.g., monosaccharide, disaccharide, polysaccharide, etc.), carbamate (e.g., attached to the steroid at oxygen), ester (e.g., attached to the steroid at oxygen), carbonate, or alkoxy. Substituents such as carbamate, ester, carbonate, and alkoxy may be substituted or unsubstituted, e.g., may include additional functional groups such as aryl, aralkyl, heteroaryl, heteroaralkyl, amide, acylamino, carbonyl, ester, carbamate, urea, ketone, sulfonamide, etc.

In certain preferred embodiments, the definitions outlined above apply, and the subject compounds are represented by general formula VIIa or unsaturated forms thereof and/or seco-, nor- or homo-derivatives thereof:

Formula VIIa

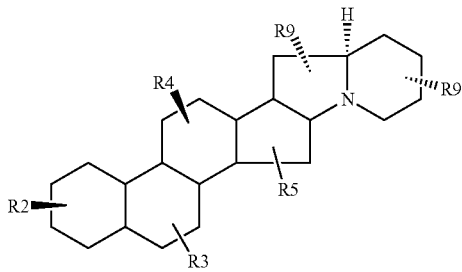

In certain embodiments, the subject antagonists and activators can be chosen on the basis of their selectively for the smoothened pathway. This selectivity can be for the smoothened pathway versus other steroid-mediated pathways (such as testosterone or estrogen mediated activities), as well as selectivity for particular hedgehog/ptc/smoothened pathways, e.g., which isotype specific for ptc (e.g., ptc-1, ptc-2) or hedgehog (e.g., Shh, Ihh, Dhh, etc.). For instance, the subject method may employ steroidal alkaloids which do not substantially interfere with the biological activity of such steroids as aldosterone, androstane, androstene, androstenedione, androsterone, cholecalciferol, cholestane, cholic acid, corticosterone, cortisol, cortisol acetate, cortisone, cortisone acetate, deoxycorticosterone, digitoxigenin, ergocalciferol, ergosterol, estradiol-17-α, estradiol-17-β, estriol, estrane, estrone, hydrocortisone, lanosterol, lithocholic acid, mestranol, β-methasone, prednisone, pregnane, pregnenolone, progesterone, spironolactone, testosterone, triamcinolone and their derivatives, at least so far as those activities are unrelated to ptc related signaling.

In one embodiment, the subject steroidal alkaloid for use in the present method has a kd for members of the nuclear hormone receptor superfamily of greater than 1 μM, and more preferably greater than 1 mM, e.g., it does not bind estrogen, testosterone receptors or the like. Preferably, the subject smoothened antagonist has no estrogenic activity at physiological concentrations (e.g., in the range of 1 ng-1 mg/kg).

In this manner, untoward side effects which may be associated certain members of the steroidal alkaloid class can be reduced. For example, using the drug screening assays described herein, the application of combinatorial and medicinal chemistry techniques to the steroidal alkaloids provides a means for reducing such unwanted negative side effects including personality changes, shortened life spans, cardiovascular diseases and vascular occlusion, organ toxicity, hyperglycemia and diabetes, Cushnoid features, "wasting" syndrome, steroidal glaucoma, hypertension, peptic ulcers, and increased susceptibility to infections. For certain embodiments, it will be beneficial to reduce the teratogenic activity relative to jervine, as for example, in the use of the subject method to selectively inhibit spermatogenesis.

In a preferred embodiment, the subject antagonists are steroidal alkaloids other than spirosolane, tomatidine, jervine, etc.

In particular embodiments, the steroidal alkaloid is chosen for use because it is more selective for one patched isoform over the next, e.g., 10-fold, and more preferably at least 100-or even 1000-fold more selective for one patched pathway (ptc-1, ptc-2) over another. Likewise, the steroidal alkaloid may be chosen for use because it is more selective for one smoothened isoform over the next, e.g., 10-fold, and more preferably at least 100- or even 1000-fold more selective for one wild-type smoothened protein (should various isoforms exist) or for activated smoothened mutants relative to wild-type smoothened. In certain embodiments, the subject method can be carried out conjointly with the administration of growth and/or trophic factors, or compositions that also act on other parts of the hedgehog/smoothened pathway. For instance, it is contemplated that the subject methods can include treatment with an agent that modulates cAMP levels, e.g., increasing or decreasing intracellular levels of cAMP.

In one embodiment, the subject method utilizes a smoothened antagonist, and the conjoint agent elevates cAMP levels in order to enhance the efficacy of the smoothened antagonist.

For example, compounds that may activate adenylate cyclase include forskolin (FK), cholera toxin (CT), pertussis toxin (PT), prostaglandins (e.g., PGE-1 and PGE-2), colforsin and β-adrenergic receptor agonists. β-Adrenergic receptor agonists (sometimes referred to herein as "β-adrenergic agonists") include albuterol, bambuterol, bitolterol, carbuterol, clenbuterol, clorprenaline, denopamine, dioxethedrine, dopexamine, ephedrine, epinephrine, etafedrine, ethylnorepinephrine, fenoterol, formoterol, hexoprenaline, ibopamine, isoetharine, isoproterenol, mabuterol, metaproterenol, methoxyphenamine, norepinephrine, oxyfedrine, pirbuterol, prenalterol, procaterol, propranolol, protokylol, quinterenol, reproterol, rimiterol, ritodrine, salmefamol, soterenol, salmeterol, terbutaline, tretoquinol, tulobuterol, and xamoterol.

Compounds which may inhibit a cAMP phosphodiesterase include anrinone, milrinone, xanthine, methylxanthine, anagrelide, cilostamide, medorinone, indolidan, rolipram, 3-isobutyl-1-methylxanthine (IBMX), chelerythrine, cilostazol, glucocorticoids, griseolic acid, etazolate, caffeine, indomethacin, papverine, MDL 12330A, SQ 22536, GDPssS, clonidine, type III and type IV phosphodiesterase inhibitors, methylxanthines such as pentoxifylline, theophylline, theobromine, pyrrolidinones and phenyl cycloalkane and cycloalkene derivatives (described in PCT publications Nos. WO 92/19594 and WO 92/10190), lisophylline, and fenoxamine.

Analogs of cAMP which may be useful in the present method include dibutyryl-cAMP (db-cAMP), (8-(4)-chlorophenylthio)-cAMP (cpt-cAMP), 8-[(4-bromo-2,3-dioxobutyl)thio]-cAMP, 2-[(4-bromo-2,3-dioxobutyl)thio]-cAMP, 8-bromo-cAMP, dioctanoyl-cAMP, Spadenosine 3':5'-cyclic phosphorothioate, 8-piperidino-cAMP, $N^6$-phenyl-cAMP, 8-methylamino-cAMP, 8-(6-aminohexyl)amino-cAMP, 2'-deoxy-cAMP, $N^6$,2'-O-dibutryl-cAMP, $N^6$,2'-O-disuccinyl-cAMP, $N^6$-monobutyryl-cAMP, 2'-O-monobutyryl-cAMP, 2'-O-monobutryl-8-bromo-cAMP, $N^6$-monobutryl-2'-deoxy-cAMP, and 2'-O-monosuccinyl-cAMP.

Compounds which may reduce the levels or activity of cAMP include prostaglandylinositol cyclic phosphate (cyclic PIP), endothelins (ET)-1 and -3, norepinepurine, K252a, dideoxyadenosine, dynorphins, melatonin, pertussis toxin, staurosporine, $G_i$ agonists, MDL 12330A, SQ 22536, GDPssS and clonidine, beta-blockers, and ligands of G-protein coupled receptors. Additional compounds are disclosed in U.S. Pat. Nos. 5,891,875, 5,260,210, and 5,795,756.

Above-listed compounds useful in the subject methods may be modified to increase the bioavailability, activity, or other pharmacologically relevant property of the compound. For example, forskolin has the formula:

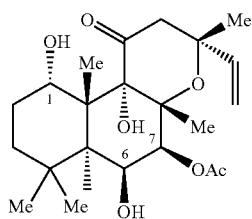

Forskolin

Modifications of forskolin that have been found to increase the hydrophilic character of forskolin without severely attenuating the desired biological activity include acylation of the hydroxyls at C6 and/or C7 (after removal of the acetyl group) with hydrophilic acyl groups. In compounds wherein C6 is acylated with a hydrophilic acyl group, C7 may optionally be deacetylated. Suitable hydrophilic acyl groups include groups having the structure —(CO)(CH$_2$)$_n$X, wherein X is OH or NR$_2$; R is hydrogen, a C$_1$-C$_4$ alkyl group, or two Rs taken together form a ring comprising 3-8 atoms, preferably 5-7 atoms, which may include heteroatoms (e.g., piperazine or morpholine rings); and n is an integer from 1-6, preferably from 1-4, even more preferably from 1-2. Other suitable hydrophilic acyl groups include hydrophilic amino acids or derivatives thereof, such as aspartic acid, glutamic acid, asparagine, glutamine, serine, threonine, tyrosine, etc., including amino acids having a heterocyclic side chain. Forskolin, or other compounds listed above, modified by other possible hydrophilic acyl side chains known to those of skill in the art may be readily synthesized and tested for activity in the present method.

Similarly, variants or derivatives of any of the above-listed compounds may be effective as cAMP antagonists in the subject method, e.g., in order to decrease cAMP levels and potentiate the activity of a smoothened activator. Those skilled in the art will readily be able to synthesize and test such derivatives for suitable activity.

Exemplary Compounds Part II:

Additional steroidal alkaloids are contemplated as potential hedgehog antagonists for use in the subject method. For example, compounds useful in the subject methods include steroidal alkaloids represented in the general formulas (VIII), or unsaturated forms thereof and/or seco-, nor- or homo-derivatives thereof:

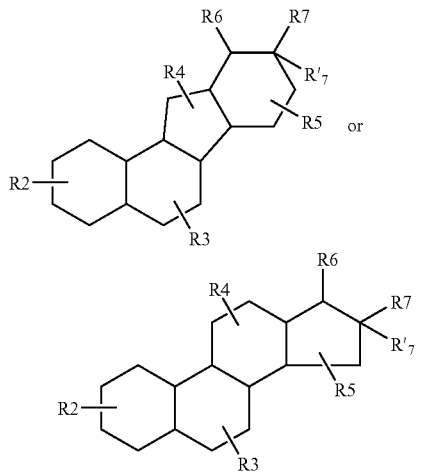

Formula VIII wherein, as valence and stability permit, $R_2$, $R_3$, $R_4$, and $R_5$, represent one or more substitutions to the ring to which each is attached, for each occurrence, independently represent hydrogen, halogens, alkyls, alkenyls, alkynyls, aryls, hydroxyl, =O, =S, alkoxyl, silyloxy, amino, nitro, thiol, amines, imines, amides, phosphoryls, phosphonates, phosphines, carbonyls, carboxyls, carboxamides, anhydrides, silyls, ethers, thioethers, alkylsulfonyls, arylsulfonyls, selenoethers, ketones, aldehydes, esters, sugar (e.g., monosaccharide, disaccharide, polysaccharide, etc.), carbamate (e.g., attached to the steroid at oxygen), carbonate, or —(CH$_2$)$_m$—R$_8$;

$R_6$, $R_7$, and $R'_7$, are absent or represent, independently, halogens, alkyls, alkenyls, alkynyls, aryls, hydroxyl, =O, =S, alkoxyl, silyloxy, amino, nitro, thiol, amines, imines, amides, phosphoryls, phosphonates, phosphines, carbonyls, carboxyls, carboxamides, anhydrides, silyls, ethers, thioethers, alkylsulfonyls, arylsulfonyls, selenoethers, ketones, aldehydes, esters, or —(CH$_2$)$_m$—R$_8$, or $R_6$ and $R_7$, or $R_7$ and $R'_7$, taken together form a ring or polycyclic ring, e.g., which is substituted or unsubstituted, with the proviso that at least one of $R_6$, $R_7$, or $R'_7$ is present and includes a primary or secondary amine;

$R_8$ represents an aryl, a cycloalkyl, a cycloalkenyl, a heterocycle, or a polycycle; and m is an integer in the range 0 to 8 inclusive.

In Preferred Embodiments, $R_2$ and $R_3$, for each occurrence, is an —OH, alkyl, —O-alkyl, —C(O)-alkyl, or —C(O)—$R_8$;

$R_4$, for each occurrence, is an absent, or represents —OH, =O, alkyl, —O-alkyl, —C(O)-alkyl, or —C(O)—$R_8$;

$R_6$, $R_7$, and $R'_7$ each independently represent, hydrogen, alkyls, alkenyls, alkynyls, amines, imines, amides, carbonyls, carboxyls, carboxamides, ethers, thioethers, esters, or —(CH$_2$)$_m$—$R_8$, or $R_7$, and $R'_7$ taken together form a furanopiperidine, such as perhydrofuro[3,2-b]pyridine, a pyranopiperidine, a quinoline, an indole, a pyranopyrrole, a naphthyridine, a thiofuranopiperidine, or a thiopyranopiperidine with the proviso that at least one of $R_6$, $R_7$, or $R'_7$ is present and includes a primary or secondary amine;

$R_8$ represents an aryl, a cycloalkyl, a cycloalkenyl, a heterocycle, or a polycycle, and preferably $R_8$ is a piperidine, pyrimidine, morpholine, thiomorpholine, pyridazine, In certain preferred embodiments, the definitions outlined above apply, and the subject compounds are represented by general formula VIIIa or unsaturated forms thereof and/or seco-, nor- or homo-derivatives thereof:

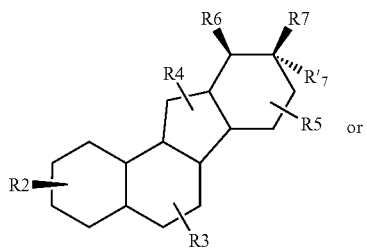

Formula VIIIa

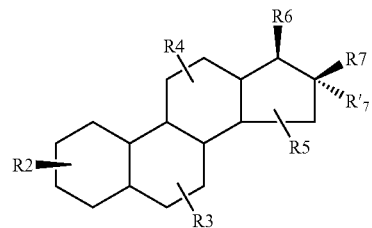

In preferred embodiments, the subject hedgehog antagonists can be represented in one of the following general formulas (IX) or unsaturated forms thereof and/or seco-, nor- or homo-derivatives thereof:

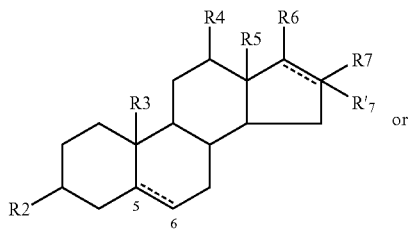

or

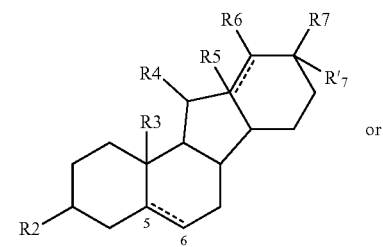

or

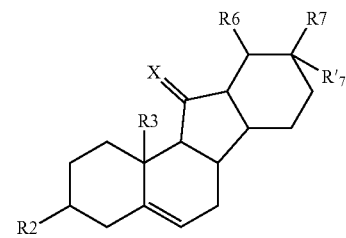

Formula IX wherein $R_2$, $R_3$, $R_4$, $R_5$, $R_6$, $R_7$, and $R'_7$ are as defined above, and X represents O or S, though preferably O.

In certain preferred embodiments, the definitions outlined above apply, and the subject compounds are represented by general formula IXa or unsaturated forms thereof and/or seco-, nor- or homo-derivatives thereof:

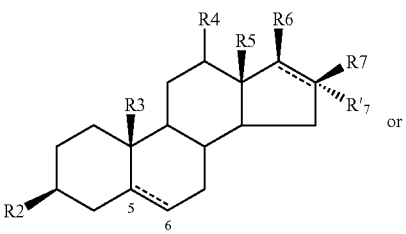

Formula IXa or

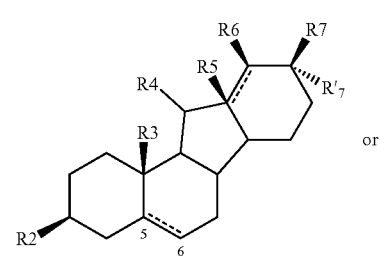

or

-continued

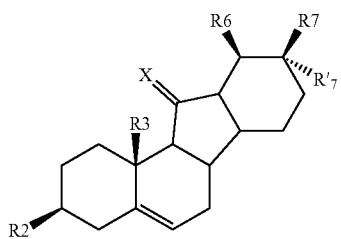

In certain embodiments, the subject hedgehog antagonists are represented by the general formula (X) or unsaturated forms thereof and/or seco-, nor- or homo-derivatives thereof:

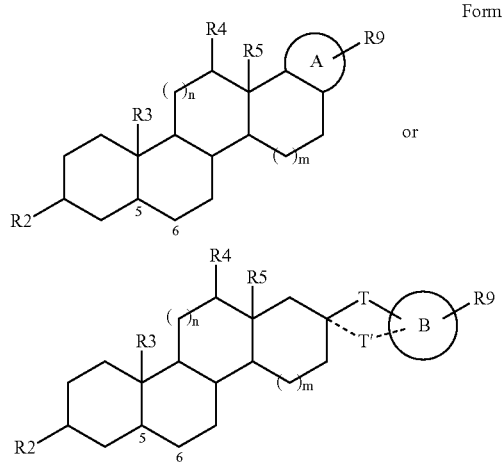

Formula X wherein

R$_2$, R$_3$, R$_4$, R$_5$ and R$_8$ are as defined above;

A and B represent monocyclic or polycyclic groups;

T represents an alkyl, an aminoalkyl, a carboxyl, an ester, an amide, ether or amine linkage of 1-10 bond lengths;

T' is absent, or represents an alkyl, an aminoalkyl, a carboxyl, an ester, an amide, ether or amine linkage of 1-3 bond lengths, wherein if T and T' are present together, than T and T' taken together with the ring A or B form a covalently closed ring of 5-8 ring atoms;

R9 represents one or more substitutions to the ring A or B, which for each occurrence, independently represent halogens, alkyls, alkenyls, alkynyls, aryls, hydroxyl, =O, =S, alkoxyl, silyloxy, amino, nitro, thiol, amines, imines, amides, phosphoryls, phosphonates, phosphines, carbonyls, carboxyls, carboxamides, anhydrides, silyls, ethers, thioethers, alkylsulfonyls, arylsulfonyls, selenoethers, ketones, aldehydes, esters, or —(CH$_2$)$_m$—R$_8$; and n and m are, independently, zero, 1 or 2;

with the proviso that A and R$_9$, or T, T' B and R$_9$, taken together include at least one primary or secondary amine.

In certain preferred embodiments, the definitions outlined above apply, and the subject compounds are represented by general formula Xa or unsaturated forms thereof and/or seco-, nor- or homo-derivatives thereof:

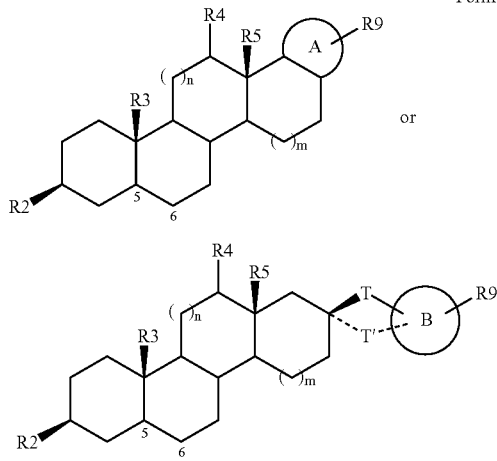

Formula Xa

For example, the subject methods can utilize hedgehog antagonists based on the veratrum-type steroidal alkaloids jervine, cyclopamine, cycloposine, mukiamine or veratramine, e.g., which may be represented in the general formula (XI) or unsaturated forms thereof and/or seco-, nor- or homo-derivatives thereof:

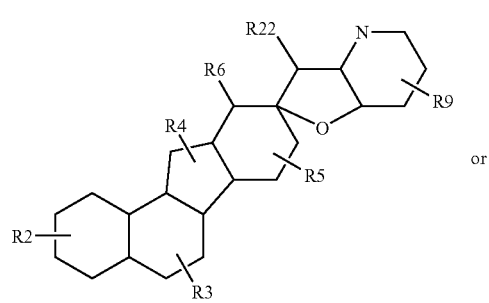

Formula XI

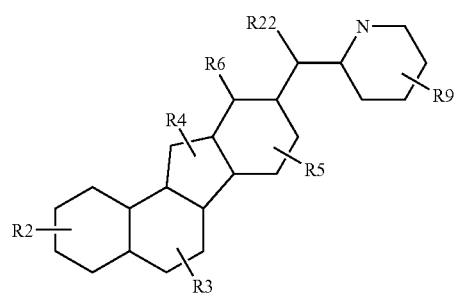

wherein

R$_2$, R$_3$, R$_4$, R$_5$, R$_6$ and R$_9$ are as defined above;

R$_{22}$ is absent or represents an alkyl, an alkoxyl or —OH.

In certain preferred embodiments, the definitions outlined above apply, and the subject compounds are represented by general formula XIa or unsaturated forms thereof and/or seco-, nor- or homo-derivatives thereof:

Formula XIa

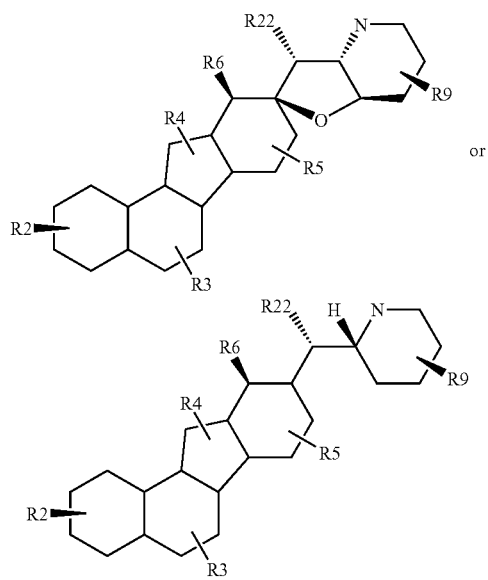

or

In even more preferred embodiments, the subject antagonists are represented in the formulas (XII) or unsaturated forms thereof and/or seco-, nor- or homo-derivatives thereof:

Formula XII

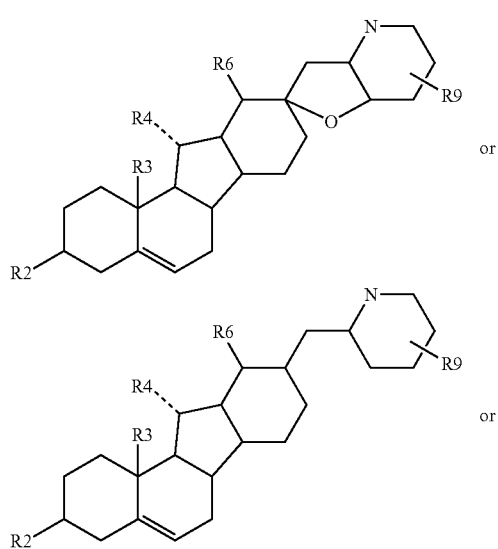

or wherein $R_2$, $R_3$, $R_4$, $R_6$ and $R_9$ are as defined above;

In certain preferred embodiments, the definitions outlined above apply, and the subject compounds are represented by general formula XIIa or unsaturated forms thereof and/or seco-, nor- or homo-derivatives thereof:

Formula XIIa

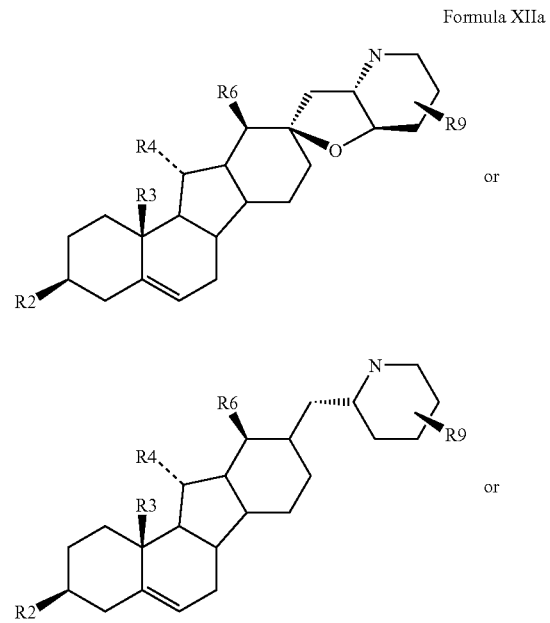

Another class of hedgehog antagonists can be based on the veratrum-type steroidal alkaloids resembling verticine and zygacine, e.g., represented in the general formulas (VI) or unsaturated forms thereof and/or seco-, nor- or homo-derivatives thereof:

Formula XIII

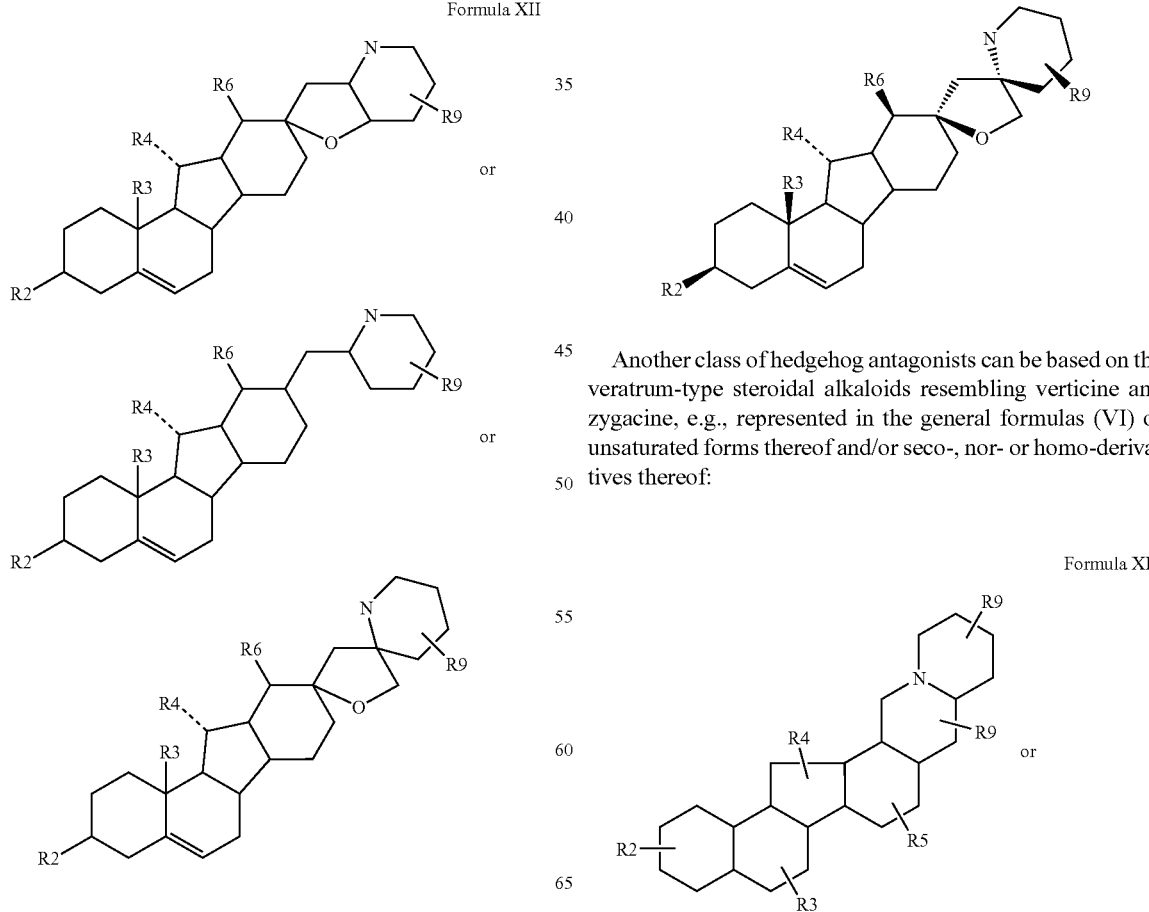

or

-continued

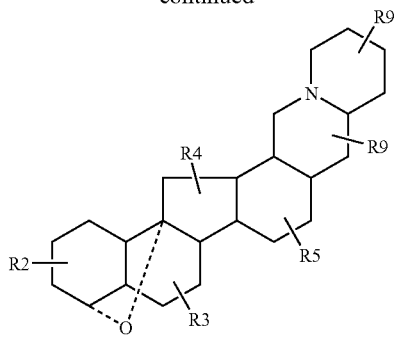

wherein $R_2$, $R_3$, $R_4$, $R_5$ and $R_9$ are as defined above.

In certain preferred embodiments, the definitions outlined above apply, and the subject compounds are represented by general formula XIIa or unsaturated forms thereof and/or seco-, nor- or homo-derivatives thereof:

Formula XIIIa

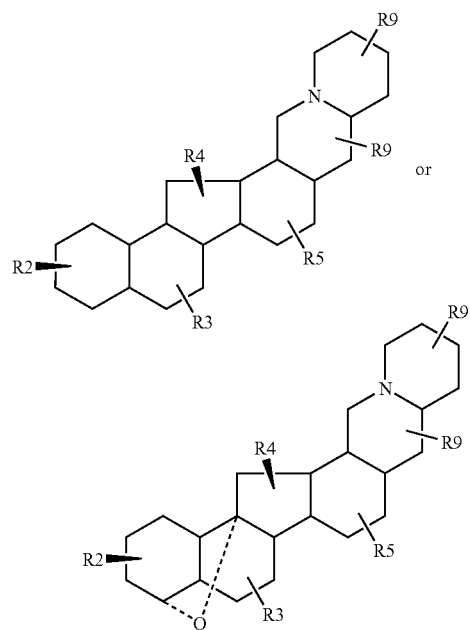

Still another class of potential hedgehog antagonists are based on the solanum-type steroidal alkaloids, e.g., solanidine, which may be represented in the general formula (XIV) or unsaturated forms thereof and/or seco-, nor- or homo-derivatives thereof:

Formula XIV

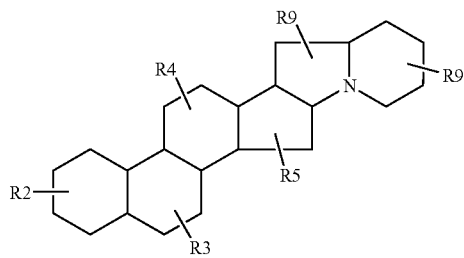

wherein $R_2$, $R_3$, $R_4$, $R_5$ and $R_9$ are as defined above.

In certain preferred embodiments, the definitions outlined above apply, and the subject compounds are represented by general formula XIVa or unsaturated forms thereof and/or seco-, nor- or homo-derivatives thereof:

Formula XIVa

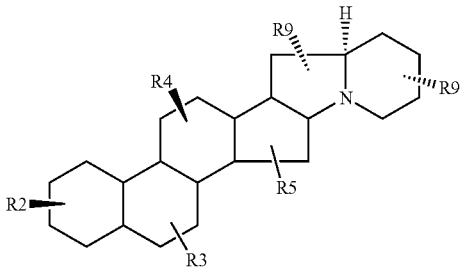

In certain embodiments, the subject antagonists can be chosen on the basis of their selectively for the hedgehog pathway. This selectivity can for the hedgehog pathway versus other steroid-mediated pathways (such as testosterone or estrogen mediated activities), as well as selectivity for particular hedgehog pathways, e.g., which isotype specific for hedgehog (e.g., Shh, Ihh, Dhh) or the patched receptor (e.g., ptc-1, ptc-2). For instance, the subject method may employ steroidal alkaloids which do not substantially interfere with the biological activity of such steroids as aldosterone, androstane, androstene, androstenedione, androsterone, cholecalciferol, cholestane, cholic acid, corticosterone, cortisol, cortisol acetate, cortisone, cortisone acetate, deoxycorticosterone, digitoxigenin, ergocalciferol, ergosterol, estradiol-17-α, estradiol-17-β, estriol, estrane, estrone, hydrocortisone, lanosterol, lithocholic acid, mestranol, β-methasone, prednisone, pregnane, pregnenolone, progesterone, spironolactone, testosterone, triamcinolone and their derivatives, at least so far as those activities are unrelated to ptc related signaling.

In one embodiment, the subject steroidal alkaloid for use in the present method has a $k_d$ for members of the nuclear hormone receptor superfamily of greater than 1 μM, and more preferably greater than 1 mM, e.g., it does not bind estrogen, testosterone receptors or the like. Preferably, the subject hedgehog antagonist has no estrogenic activity at physiological concentrations (e.g., in the range of 1 ng-1 mg/kg).

In this manner, untoward side effects which may be associated certain members of the steroidal alkaloid class can be reduced. For example, using the drug screening assays described herein, the application of combinatorial and medicinal chemistry techniques to the steroidal alkaloids provides a means for reducing such unwanted negative side effects including personality changes, shortened life spans, cardiovascular diseases and vascular occlusion, organ toxicity, hyperglycemia and diabetes, Cushnoid features, "wasting" syndrome, steroidal glaucoma, hypertension, peptic ulcers, and increased susceptibility to infections. For certain embodiments, it will be beneficial to reduce the teratogenic activity relative to jervine, as for example, in the use of the subject method to selectively inhibit spermatogenesis.

In a preferred embodiment, the subject antagonists are steroidal alkaloids other than spirosolane, tomatidine, jervine, etc.

In certain preferred embodiments, the subject inhibitors inhibit a hedgehog signal transduction pathway with an $ED_{50}$ of 1 mM or less, more preferably of 1 μM or less, and even more preferably of 1 nM or less.

In certain embodiments, the subject inhibitors inhibit a hedgehog signal transduction pathway with an $ED_{50}$ of 1 mM or less, more preferably 1 μM or less, and even more preferably 1 nM or less.

In particular embodiments, the steroidal alkaloid is chosen for use because it is more selective for one patched isoform over the next, e.g., 10-fold, and more preferably at least 100- or even 1000-fold more selective for one patched pathway (ptc-1, ptc-2) over another.

Exemplary Compounds Part III:

As described in further detail below, it is contemplated that the subject methods can be carried out using a variety of different small molecules which can be readily identified, for example, by such drug screening assays as described herein. For example, compounds useful in the subject methods include compounds may be represented by general formula (XV):

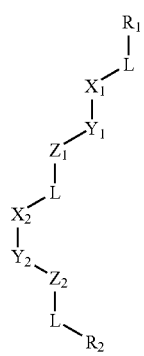

Formula XV wherein, as valence and stability permit, $R_1$ and $R_2$, independently for each occurrence, represent H, lower alkyl, aryl (e.g., substituted or unsubstituted), aralkyl (e.g., substituted or unsubstituted, e.g., —$(CH_2)_n$aryl), or heteroaryl (e.g., substituted or unsubstituted), or heteroaralkyl (e.g., substituted or unsubstituted, e.g., —$(CH_2)_n$heteroaralkyl-);

L, independently for each occurrence, is absent or represents —$(CH_2)_n$-alkyl, -alkenyl-, -alkynyl-, —$(CH_2)_n$alkenyl-, —$(CH_2)_n$alkynyl-, —$(CH_2)_nO(CH_2)_p$—, —$(CH_2)_nNR_2(CH_2)_p$—, —$(CH_2)_nS(CH_2)_p$—, —$(CH_2)_n$alkenyl$(CH_2)_p$—, —$(CH_2)_n$alkynyl$(CH_2)_p$—, —$O(CH_2)_n$—, —$NR_2(CH_2)_n$—, or —$S(CH_2)_n$—;

$X_1$ and $X_2$ can be selected, independently, from —$N(R_8)$—, —O—, —S—, —Se—, —N=N—, —ON=CH—, —$(R_8)$N—$N(R_8)$—, —$ON(R_8)$—, a heterocycle, or a direct bond between L and $Y_1$ or $Y_2$, respectively;

$Y_1$ and $Y_2$ can be selected, independently, from —C(=O)—, —C(=S)—, —$S(O_2)$—, —S(O)—, —C(=NCN)—, —P(=O)$(OR_2)$—, a heteroaromatic group, or a direct bond between $X_1$ and $Z_1$ or $X_2$ and $Z2$, respectively;

$Z_1$ and $Z_2$ can be selected, independently, from —$N(R_8)$—, —O—, —S—, —Se—, —N=N—, —ON=CH—, —$R_8$N—$NR_8$—, —$ONR_8$—, a heterocycle, or a direct bond between $Y_1$ or $Y_2$ respectively, and L;

$R_8$, independently for each occurrence, represents H, lower alkyl, —$(CH_2)_n$aryl (e.g., substituted or unsubstituted), —$(CH_2)_n$heteroaryl (e.g., substituted or unsubstituted), or two $R_8$ taken together may form a 4- to 8-membered ring, e.g., with $X_1$ and $Z_1$ or $X_2$ and $Z_1$, which ring may include one or more carbonyls;

p represents, independently for each occurrence, an integer from 0 to 10, preferably from 0 to 3; and n, individually for each occurrence, represents an integer from 0 to 10, preferably from 0 to 5.

In certain embodiments, $R_1$ represents a substituted or unsubstituted heteroaryl group.

In certain embodiments, $X_1$ and $X_2$ can be selected from —$N(R_8)$—, —O—, —S—, a direct bond, and a heterocycle, $Y_1$ and $Y_2$ can be selected from —C(=O)—, —C(=S)—, and —$S(O_2)$—, and $Z_1$ or $Z_2$ can be selected from —$N(R_8)$—, —O—, —S—, a direct bond, and a heterocycle.

In certain related embodiments, $X_1$—$Y_1$—$Z_1$ or $X_2$—$Y_2$—$Z_2$ taken together represents a urea (N—C(O)—N) or an amide (N—C(O) or C(O)—N).

In certain embodiments, $X_1$ or $X_2$ represents a diazacarbocycle, such as a piperazine.

In certain embodiments, $R_1$ represents a fused cycloalkyl-aryl or cycloalkyl-heteroaryl system, for example:

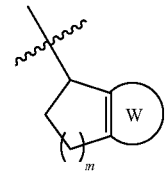

wherein W is a substituted or unsubstituted aryl or heteroaryl ring fused to the cycloalkyl ring and m is an integer from 1-4 inclusive, e.g., from 1-3, or from 1-2. The fused system may be bound to L from any carbon of the fused system, including the position depicted above. In certain embodiments, $R_1$ may represent a tetrahydronaphthyl group, and preferably $Y_1$—$X_1$—L—$R_1$ taken together represent a tetrahydronaphthyl amide group, such as:

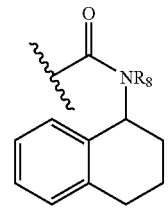

In embodiments wherein $Y_1$ and $Z_1$ are absent and $X_1$ comprises a pyrimidone, compounds useful in the present invention may be represented by general formula (XVI):

Formula XVI

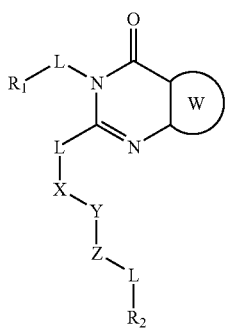

wherein, as valence and stability permit, $R_1$ and $R_2$, independently for each occurrence, represent H, lower alkyl, —$(CH_2)_n$aryl (e.g., substituted or unsubstituted), or —$(CH_2)_n$heteroaryl (e.g., substituted or unsubstituted);

L, independently for each occurrence, is absent or represents —$(CH_2)_n$-alkyl, -alkenyl-, -alkynyl-, —$(CH_2)_n$alkenyl-, —$(CH_2)_n$alkynyl-, —$(CH_2)_nO(CH_2)_p$—, —$(CH_2)_nNR_2(CH_2)_p$—, —$(CH_2)_nS(CH_2)_p$—, —$(CH_2)_n$alkenyl$(CH_2)_p$—, —$(CH_2)_n$alkynyl$(CH_2)_p$—, —$O(CH_2)_n$—, —$NR_2(CH_2)_n$—, or —$S(CH_2)_n$—;

X can be selected from —$N(R_8)$—, —O—, —S—, —Se—, —N=N—, —ON=CH—, —$(R_8)$N—N$(R_8)$—, —ON$(R_8)$—, a heterocycle, or a direct bond between L and Y;

Y can be selected from —C(=O)—, —C(=S)—, —$S(O_2)$—, —S(O)—, —C(=NCN)—, —P(=O)(OR_2)—, a heteroaromatic group, or a direct bond between X and Z;

Z can be selected from —$N(R_8)$—, —O—, —S—, —Se—, —N=N—, —ON=CH—, —$R_8$N—NR$_8$—, —ONR$_8$—, a heterocycle, or a direct bond between Y and L;

$R_8$, independently for each occurrence, represents H, lower alkyl, —$(CH_2)_n$aryl (e.g., substituted or unsubstituted), —$(CH_2)_n$heteroaryl (e.g., substituted or unsubstituted), or two $R_8$ taken together may form a 4- to 8-membered ring, e.g., with X and Z, which ring may include one or more carbonyls;

W represents a substituted or unsubstituted aryl or heteroaryl ring fused to the pyrimidone ring;

p represents, independently for each occurrence, an integer from 0 to 10, preferably from 0 to 3; and n, individually for each occurrence, represents an integer from 0 to 10, preferably from 0 to 5.

In embodiments wherein $Y_1$ and $Z_1$ are absent and $X_1$ comprises a pyrimidone, compounds useful in the present invention may be represented by general formula (XVII):

Formula XVII

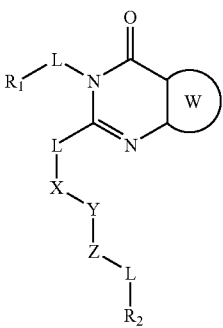

wherein, as valence and stability permit, $R_1$ and $R_2$, independently for each occurrence, represent H, lower alkyl, aryl (e.g., substituted or unsubstituted), aralkyl (e.g., substituted or unsubstituted, e.g., —$(CH_2)_n$aryl), or heteroaryl (e.g., substituted or unsubstituted), or heteroaralkyl (e.g., substituted or unsubstituted, e.g., —$(CH_2)_n$heteroaralkyl-);

L, independently for each occurrence, is absent or represents —$(CH_2)_n$-alkyl, -alkenyl-, -alkynyl-, —$(CH_2)_n$alkenyl-, —$(CH_2)_n$alkynyl-, —$(CH_2)_nO(CH_2)_p$—, —$(CH_2)_nNR_2(CH_2)_p$—, —$(CH_2)_nS(CH_2)_p$—, —$(CH_2)_n$alkenyl$(CH_2)_p$—, —$(CH_2)_n$alkynyl$(CH_2)_p$—, —$O(CH_2)_n$—, —$NR_2(CH_2)_n$—, or —$S(CH_2)_n$—, which may optionally be substituted with a group selected from H, substituted or unsubstituted lower alkyl, alkenyl, or alkynyl, cycloalkylalkyl (e.g., substituted or unsubstituted, e.g., —$(CH_2)_n$cycloalkyl), (e.g., substituted or unsubstituted), aryl (e.g., substituted or unsubstituted), aralkyl (e.g., substituted or unsubstituted, e.g., —$(CH_2)_n$aryl), or heteroaryl (e.g., substituted or unsubstituted), or heteroaralkyl (e.g., substituted or unsubstituted, e.g., —$(CH_2)_n$heteroaralkyl-), preferably from H, lower alkyl, —$(CH_2)_n$aryl (e.g., substituted or unsubstituted), or —$(CH_2)_n$heteroaryl (e.g., substituted or unsubstituted);

X can be selected from —$N(R_8)$—, —O—, —S—, —Se—, —N=N—, —ON=CH—, —$(R_8)$N—N$(R_8)$—, —ON$(R_8)$—, a heterocycle, or a direct bond between L and Y;

Y can be selected from —C(=O)—, —C(=S)—, —$S(O_2)$—, —S(O)—, —C(=NCN)—, —P(=O)(OR_2)—, a heteroaromatic group, or a direct bond between X and Z;

Z can be selected from —$N(R_8)$—, —O—, —S—, —Se—, —N=N—, —ON=CH—, —$R_8$N—NR$_8$—, —ONR$_8$—, a heterocycle, or a direct bond between Y and L;

$R_8$, independently for each occurrence, represents H, lower alkyl, aryl (e.g., substituted or unsubstituted), aralkyl (e.g., substituted or unsubstituted, e.g., —$(CH_2)_n$aryl), or heteroaryl (e.g., substituted or unsubstituted), or heteroaralkyl (e.g., substituted or unsubstituted, e.g., —$(CH_2)_n$heteroaralkyl-), or two $R_8$ taken together may form a 4- to 8-membered ring, e.g., with X and Z, which ring may include one or more carbonyls;

W represents a substituted or unsubstituted aryl or heteroaryl ring fused to the pyrimidone ring;

p represents, independently for each occurrence, an integer from 0 to 10, preferably from 0 to 3; and n, individually for each occurrence, represents an integer from 0 to 10, preferably from 0 to 5.

In certain embodiments, $R_1$ represents a substituted or unsubstituted aryl or heteroaryl group, e.g., a phenyl ring, a pyridine ring, etc. In certain embodiments wherein —$LR_1$ represents a substituted aryl or heteroaryl group, $R_1$ is preferably not substituted with an isopropoxy ($Me_2$CHO—) group. In certain embodiments wherein —$LR_1$ represents a substituted aryl or heteroaryl group, $R_1$ is preferably not substituted with an ether group. In certain embodiments, substituents on $R_1$ (e.g., other than hydrogen) are selected from halogen, cyano, alkyl, alkenyl, alkynyl, aryl, hydroxyl, (unbranched alkyl-O—), silyloxy, amino, nitro, thiol, amino, imino, amido, phosphoryl, phosphonate, phosphine, carbonyl, carboxyl, carboxamide, anhydride, silyl, thioether, alkylsulfonyl, arylsulfonyl, sulfoxide, selenoether, ketone, aldehyde, ester, or —$(CH_2)_m$—$R_8$. In certain embodiments, non-hydrogen substituents are selected from halogen, cyano, alkyl, alkenyl, alkynyl, aryl, nitro, thiol, imino, amido, carbonyl, carboxyl, anhydride, thioether, alkylsulfonyl, arylsulfonyl, ketone, aldehyde, and ester. In certain embodiments, non-hydrogen substituents are selected from halogen, cyano, alkyl, alkenyl, alkynyl, nitro, amido, carboxyl, anhydride, alkylsulfonyl, ketone, aldehyde, and ester.

In certain embodiments, X can be selected from —N($R_8$)—, —O—, —S—, a direct bond, and a heterocycle, Y can be selected from —C(=O)—, —C(=S)—, and —S($O_2$)—, and Z can be selected from —N($R_8$)—, —O—, —S—, a direct bond, and a heterocycle. In certain such embodiments, at least one of Z and X is present.

In certain related embodiments, X—Y—Z taken together represents a urea (NC(O)N) or an amide (NC(O) or C(O)N).

In certain embodiments, W is a substituted or unsubstituted benzene ring.

In certain embodiments, X represents a diazacarbocycle, such as a piperazine, e.g., substituted or unsubstituted.

In certain embodiments, X can be selected from —N($R_8$)—, —O—, —S—, and a direct bond, Y can be selected from —C(=O)—, —C(=S)—, and —S($O_2$)—, and Z can be selected from —N($R_8$)—, —O—, —S—, and a direct bond, such that at least one of X and Z is present.

In certain embodiments $R_8$ represents H, lower alkyl, aralkyl, heteroaralkyl, aryl, or heteroaryl, e.g., H or lower alkyl.

In certain embodiments, X represents —NH—.

In certain embodiments, —L—X— represents -(unbranched lower alkyl)-NH—, e.g., —$CH_2$—NH—, —$CH_2CH_2$—NH—, etc.

In certain embodiments, the subject antagonists can be chosen on the basis of their selectively for the hedgehog pathway. This selectivity can be for the hedgehog pathway versus other pathways, or for selectivity between particular hedgehog pathways, e.g., e.g., ptc-1, ptc-2, etc.

In certain preferred embodiments, the subject inhibitors inhibit hedgehog-mediated signal transduction with an $ED_{50}$ of 1 mM or less, more preferably of 1 µM or less, and even more preferably of 1 nM or less.

In particular embodiments, the small molecule is chosen for use because it is more selective for one patched isoform over the next, e.g., 10 fold, and more preferably at least 100 or even 1000 fold more selective for one patched pathway (ptc-1, ptc-2) over another.

In certain embodiments, a compound which is an antagonist of the hedgehog pathway is chosen to selectively antagonize hedgehog activity over protein kinases other than PKA, such as PKC, e.g., the compound modulates the activity of the hedgehog pathway at least an order of magnitude more strongly than it modulates the activity of another protein kinase, preferably at least two orders of magnitude more strongly, even more preferably at least three orders of magnitude more strongly. Thus, for example, a preferred inhibitor of the hedgehog pathway may inhibit hedgehog activity with a $K_i$ at least an order of magnitude lower than its $K_i$ for inhibition of PKC, preferably at least two orders of magnitude lower, even more preferably at least three orders of magnitude lower. In certain embodiments, the $K_i$ for PKA inhibition is less than 10 nM, preferably less than 1 nM, even more preferably less than 0.1 nM.

In certain embodiments, compounds useful in the present invention may be represented by general formula (IV):

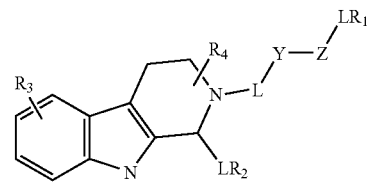

Formula XVIII wherein, as valence and stability permit, $R_1$ and $R_2$, independently for each occurrence, represent H, substituted or unsubstituted lower alkyl, alkenyl, or alkynyl, —($CH_2$)$_n$cycloalkyl (e.g., substituted or unsubstituted), —($CH_2$)$_n$aryl (e.g., substituted or unsubstituted), or —($CH_2$)$_n$heterocyclyl (e.g., substituted or unsubstituted);

L, independently for each occurrence, is absent or represents —($CH_2$)$_n$-alkyl, -alkenyl-, -alkynyl-, —($CH_2$)$_n$alkenyl-, —($CH_2$)$_n$alkynyl-, —($CH_2$)$_n$O($CH_2$)$_p$—, —($CH_2$)$_n$N$R_2$($CH_2$)$_p$—, —($CH_2$)$_n$S($CH_2$)$_p$—, —($CH_2$)$_n$alkenyl($CH_2$)$_p$—, —($CH_2$)$_n$alkynyl($CH_2$)$_p$—, —O($CH_2$)$_n$—, —N$R_2$($CH_2$)$_n$—, or —S($CH_2$)$_n$—;

X and Z, independently, can be selected from —CH—, —N($R_8$)—, —O—, —S—, or —Se—;

Y can be selected from —C(=O)—, —C(=S)—, —S($O_2$)—, —S(O)—, —C(=NCN)—, or —P(=O)(O$R_2$)—;

$R_8$, independently for each occurrence, represents H, substituted or unsubstituted lower alkyl, —($CH_2$)$_n$cycloalkyl (e.g., substituted or unsubstituted), —($CH_2$)$_n$aryl (e.g., substituted or unsubstituted), —($CH_2$)$_n$heterocyclyl (e.g., substituted or unsubstituted), or two $R_8$ taken together may form a 4- to 8-membered ring, e.g., with $X_1$ and $Z_1$ or $X_2$ and $Z_1$, which ring may include one or more carbonyls;

$R_3$ and $R_4$, independently represent from 1-4 substituents on the ring to which they are attached, selected from, independently for each occurrence, hydrogen, halogens, alkyls, alkenyls, alkynyls, aryls, hydroxyl, =O, =S, alkoxyl, silyloxy, amino, nitro, thiol, amines, imines, amides, phosphoryls, phosphonates, phosphines, carbonyls, carboxyls, carboxamides, anhydrides, silyls, ethers, thioethers, alkylsulfonyls, arylsulfonyls, selenoethers, ketones, aldehydes, esters, or —($CH_2$)$_m$—$R_8$;

p represents, independently for each occurrence, an integer from 0 to 10, preferably from 0 to 3; and n, individually for each occurrence, represents an integer from 0 to 10, preferably from 0 to 5.

In certain embodiments, $R_1$ and $R_2$ are independently selected from substituted or unsubstituted aryl, heterocyclyl, branched or unbranched alkyl, or cycloalkyl. In embodiments wherein $R_1$ or $R_2$ is aryl or heterocyclyl, substituents are preferably selected from H, alkyl, acyl, carboxy, ester, amide, cyano, ether, thioether, amino, halogen, nitro, and trihalomethyl.

In certain embodiments, $R_3$ is absent or represents one or two substituents selected from alkyl, acyl, carboxy, ester, amide, cyano, ether, thioether, amino, acyl, halogen, nitro, and trihalomethyl.

In certain embodiments, $R_4$ is absent or represents one or two substituents selected from ether, amino, thioether, alkyl, aryl, (=O), or carbonyl (e.g., carboxy, ester, ketone, aldehyde, etc.).

In certain embodiments, L is absent for each occurrence, or represents —$CH_2$— or —$CH_2CH_2$—.

In certain embodiments, X represents $NR_8$. $R_8$ preferably represents H.

In certain embodiments, Z represents $NR_8$. $R_8$ preferably represents H.

In certain embodiments, Y represents —C(=O)—, —C(=S)—, or —S(O$_2$)—.

Exemplary Compounds Part 4:

As described in further detail below, it is contemplated that the subject methods can be carried out using a variety of different small molecules which can be readily identified, for example, by such drug screening assays as described herein. For example, compounds useful in the subject methods include compounds may be represented by general formula (XVIII):

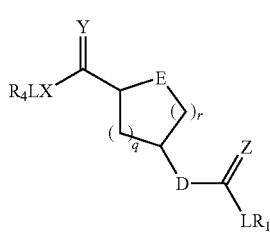

Formula XVIII wherein, as valence and stability permit, $R_1$, $R_2$, $R_3$, and $R_4$, independently for each occurrence, represent H, lower alkyl, —(CH$_2$)$_n$aryl (e.g., substituted or unsubstituted), or —(CH$_2$)$_n$heteroaryl (e.g., substituted or unsubstituted);

L, independently for each occurrence, is absent or represents —(CH$_2$)$_n$—, -alkenyl-, alkynyl-, —(CH$_2$)$_n$alkenyl-, —(CH$_2$)$_n$alkynyl-, —(CH$_2$)$_n$O(CH$_2$)$_p$—, —(CH$_2$)$_n$NR$_8$(CH$_2$)$_p$—, —(CH$_2$)$_n$S(CH$_2$)$_p$—, —(CH$_2$)$_n$alkenyl(CH$_2$)$_p$—, —(CH$_2$)$_n$alkynyl(CH$_2$)$_p$—, —O(CH$_2$)$_n$—, —NR$_8$(CH$_2$)$_n$—, or —S(CH$_2$)$_n$—;

X and D, independently, can be selected from —N(R$_8$)—, —O—, —S—, —(R$_8$)N—N(R$_8$)—, —ON(R$_8$)—, or a direct bond;

Y and Z, independently, can be selected from O or S;

E represents O, S, or NR$_5$, wherein R$_5$ represents LR$_8$ or —(C=O)LR$_8$.

$R_8$, independently for each occurrence, represents H, lower alkyl, —(CH$_2$)$_n$aryl (e.g., substituted or unsubstituted), —(CH$_2$)$_n$heteroaryl (e.g., substituted or unsubstituted), or two $R_8$ taken together may form a 4- to 8-membered ring;

p represents, independently for each occurrence, an integer from 0 to 10, preferably from 0 to 3;

n, individually for each occurrence, represents an integer from 0 to 10, preferably from 0 to 5; and q and r represent, independently for each occurrence, an integer from 0-2.

In certain embodiments, D does not represent N-lower alkyl. In certain embodiments, D represents an aralkyl- or heteroaralkyl-substituted amine.

In certain embodiments, $R_1$ represents a lower alkyl group, such as a branched alkyl, a cycloalkyl, or a cycloalkylalkyl, for example, cyclopropyl, cyclopropylmethyl, neopentyl, cyclobutyl, isobutyl, isopropyl, sec-butyl, cyclobutylmethyl, etc.

In certain embodiments, Y and Z are O.

In certain embodiments, the sum of q and r is less than 4, e.g., is 2 or 3.

In certain embodiments, XLR$_4$, taken together, include a cyclic amine, such as a piperazine, a morpholine, a piperidine, a pyrrolidine, etc.

In certain embodiments, at least one of $R_1$, $R_2$, and $R_3$ includes an aryl or heteroaryl group. In certain related embodiments, at least two of $R_1$, $R_2$, and $R_3$ include an aryl or heteroaryl group. In certain embodiments, $R_1$ is lower alkyl.

In certain embodiments, L attached to $R_1$ represents O, S, or NR$_8$, such as NH.

In certain embodiments, E is NR$_8$. In certain embodiments, E represents an aralkyl- or heteroaralkyl-substituted amine, e.g., including polycyclic $R_8$.

In certain embodiments, X is not NH. In certain embodiments, X is included in a ring, or, taken together with —C(=Y)—, represents a tertiary amide.

In certain embodiments, compounds useful in the present invention may be represented by general formula (XIX):

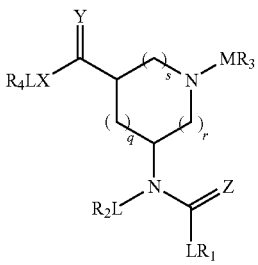

Formula XIX wherein, as valence and stability permit, $R_1$, $R_2$, $R_3$, $R_4$, $R_8$, L, X, Y, Z, n, p, q, and r are as defined above;

M is absent or represents L, —SO$_2$L—, or —(C=O)L—; and s represents, independently for each occurrence, an integer from 0-2.

In certain embodiments, Y and Z are O.

In certain embodiments, $R_1$ represents a lower alkyl group, such as a branched alkyl, a cycloalkyl, or a cycloalkylalkyl, for example, cyclopropyl, cyclopropylmethyl, neopentyl, cyclobutyl, isobutyl, isopropyl, sec-butyl, cyclobutylmethyl, etc.

In certain embodiments, the sum of q, r, and s is less than 5, e.g., is 2, 3, or 4.

In certain embodiments, XLR$_4$, taken together, include a cyclic amine, such as a piperazine, a morpholine, a piperidine, a pyrrolidine, etc.

In certain embodiments, L attached to $R_1$ represents O, S, or NR$_8$, such as NH.

In certain embodiments, at least one of $R_1$, $R_2$, and $R_3$ includes an aryl or heteroaryl group. In certain related embodiments, at least two of $R_1$, $R_2$, and $R_3$ include an aryl or heteroaryl group.

In certain embodiments, M is absent.

In certain embodiments, X is not NH. In certain embodiments, X is included in a ring, or, taken together with —C(=Y)—, represents a tertiary amide.

In certain embodiments, compounds useful in the present invention may be represented by general formula (XX):

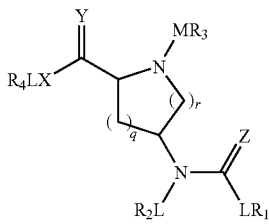

Formula XX wherein, as valence and stability permit, $R_1$, $R_2$, $R_3$, $R_4$, $R_8$, L, M, X, Y, Z, n, p, q, and r are as defined above.

In certain embodiments, Y and Z are O.

In certain embodiments, $R_1$ represents a lower alkyl group, preferably a branched alkyl, a cycloalkyl, or a cycloalkylalkyl, for example, cyclopropyl, cyclopropylmethyl, neopentyl, cyclobutyl, isobutyl, isopropyl, sec-butyl, cyclobutylmethyl, etc.

In certain embodiments, the sum of q and r is less than 4, e.g., is 2 or 3.

In certain embodiments, $XLR_4$, taken together, include a cyclic amine, such as a piperazine, a morpholine, a piperidine, a pyrrolidine, etc.

In certain embodiments, at least one of $R_1$, $R_2$, and $R_3$ includes an aryl or heteroaryl group. In certain related embodiments, at least two of $R_1$, $R_2$, and $R_3$ include an aryl or heteroaryl group. In certain embodiments, $R_1$ is lower alkyl.

In certain embodiments, L attached to $R_1$ represents O, S, or $NR_8$, such as NH.

In certain embodiments, M is absent.

In certain embodiments, X is not NH. In certain embodiments, X is included in a ring, or, taken together with —C(=Y)—, represents a tertiary amide.

In certain embodiments, compounds useful in the present invention may be represented by general formula (XXI):

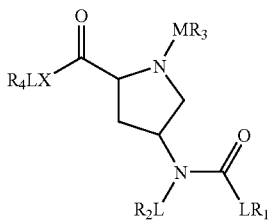

Formula XXI wherein, as valence and stability permit, $R_1$, $R_2$, $R_3$, $R_4$, $R_8$, L, M, X, n, and p are as defined above.

In certain embodiments, $XLR_4$, taken together, include a cyclic amine, such as a piperazine, a morpholine, a piperidine, a pyrrolidine, etc.

In certain embodiments, $R_1$ represents a lower alkyl group, preferably a branched alkyl, a cycloalkyl, or a cycloalkylalkyl, for example, cyclopropyl, cyclopropylmethyl, neopentyl, cyclobutyl, isobutyl, isopropyl, sec-butyl, cyclobutylmethyl, etc.

In certain embodiments, at least one of $R_1$, $R_2$, and $R_3$ includes an aryl or heteroaryl group. In certain related embodiments, at least two of $R_1$, $R_2$, and $R_3$ include an aryl or heteroaryl group. In certain embodiments, $R_1$ is lower alkyl.

In certain embodiments, L attached to $R_1$ represents O, S, or $NR_8$, such as NH.

In certain embodiments, M is absent.

In certain embodiments, X is not NH. In certain embodiments, X is included in a ring, or, taken together with —C(=Y)—, represents a tertiary amide.

In certain embodiments L represents a direct bond for all occurrences.

In certain embodiments, compounds useful in the present invention may be represented by general formula (XXII):

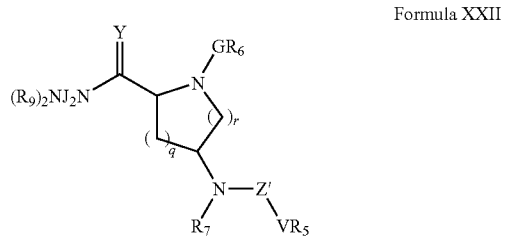

Formula XXII wherein, as valence and stability permit,

Y, n, p, q, and r are as defined above;

Z' represents —C(=O)—, —C(=S)—, —C(=NH)—, $SO_2$, or SO, preferably —C(=O)—, —C(=S)—;

V is absent or represents O, S, or $NR_8$;

G is absent or represents —C(=O)— or —$SO_2$—;

J, independently for each occurrence, represents H or substituted or unsubstituted lower alkyl or alkylene, such as methyl, ethyl, methylene, ethylene, etc., attached to NC(=Y), such that both occurrences of N adjacent to J are linked through at least one occurrence of J, and $R_9$, independently for each occurrence, is absent or represents H or lower alkyl, or two occurrences of J or one occurrence of J taken together with one occurrence of $R_9$, forms a ring of from 5 to 7 members, which ring includes one or both occurrences of N;

$R_5$ represents substituted or unsubstituted alkyl (e.g., branched or unbranched), alkenyl (e.g., branched or unbranched), alkynyl (e.g., branched or unbranched), cycloalkyl, or cycloalkylalkyl;

$R_6$ represents substituted or unsubstituted aryl, aralkyl, heteroaryl, heteroaralkyl, heterocyclyl, heterocyclylalkyl, cycloalkyl, or cycloalkylalkyl, including polycyclic groups; and $R_7$ represents substituted or unsubstituted aryl, aralkyl, heteroaryl, or heteroaralkyl.

In certain embodiments, Y is O. In certain embodiments, Z' represents $SO_2$, —C(=O)—, or —C(=S)—.

In certain embodiments, the sum of q and r is less than 4.

In certain embodiments, $NJ_2N$, taken together, represent a cyclic diamine, such as a piperazine, etc., which may be substituted or unsubstituted, e.g., with one or more substitutents such as oxo, lower alkyl, lower alkyl ether, etc. In certain other embodiments, $NJ_2$ or $NJR_9$ taken together represent a substituted or unsubstituted heterocyclic ring to which the other occurrence of N is attached. In certain embodiments, one or both occurrences of J are substituted with one or more of lower alkyl, lower alkyl ether, lower alkyl thioether, amido, oxo, etc. In certain embodiments, a heterocyclic ring that comprises an occurrence of J has from 5 to 8 members.

In certain embodiments, $R_5$ represents a branched alkyl, cycloalkyl, or cycloalkylalkyl.

In certain embodiments, $R_6$ includes at least one heterocyclic ring, such as a thiophene, furan, oxazole, benzodioxane, benzodioxole, pyrrole, indole, etc.

In certain embodiments, $R_7$ represents a phenyl alkyl, such as a benzyl group, optionally substituted with halogen, hydroxyl, lower alkyl, nitro, cyano, lower alkyl ether (e.g., optionally substituted, such as $CHF_2CF_2O$), or lower alkyl thioether (e.g., optionally substituted, such as $CF_3S$).

In certain embodiments, $R_8$, when it occurs in V, represents H or lower alkyl, preferably H.

In certain embodiments, compounds useful in the present invention may be represented by general formula (XXIII):

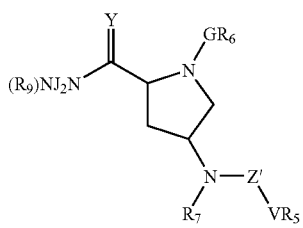

Formula XXIII wherein, as valence and stability permit, $R_5$, $R_6$, $R_7$, $R_8$, $R_9$, $R_{10}$, G, J, V, Y, Z', n, and p are as defined above.

In certain embodiments, Y is O. In certain embodiments, Z' represents $SO_2$, —C(=O)—, or —C(=S)—.

In certain embodiments, $NJ_2N$, taken together, represent a heterocyclic ring, such as a piperazine, etc., which may be substituted or unsubstituted, e.g., with one or more substitutents such as oxo, lower alkyl, lower alkyl ether, etc. In certain other embodiments, $NJ_2$ or $NJR_9$ taken together represent a substituted or unsubstituted heterocyclic ring to which the other occurrence of N is attached. In certain embodiments, one or both occurrences of J are substituted with one or more of lower alkyl, lower alkyl ether, lower alkyl thioether, amido, oxo, etc. In certain embodiments, a heterocyclic ring that comprises an occurrence of J has from 5 to 8 members.

In certain embodiments, $R_5$ represents a branched alkyl, cycloalkyl, or cycloalkylalkyl.

In certain embodiments, $R_6$ includes at least one heterocyclic ring, such as a thiophene, furan, oxazole, benzodioxane, benzodioxole, pyrrole, indole, etc.

In certain embodiments, $R_7$ represents a phenyl alkyl, such as a benzyl group, optionally substituted with halogen, hydroxyl, lower alkyl, nitro, cyano, lower alkyl ether (e.g., optionally substituted, such as $CHF_2CF_2O$), or lower alkyl thioether (e.g., optionally substituted, such as $CF_3S$).

In certain embodiments, $R_8$, when it occurs in V, represents H or lower alkyl, preferably H.

Exemplary Compounds Part 5:

As described in further detail below, it is contemplated that the subject methods can be carried out using a variety of different small molecules which can be readily identified, for example, by such drug screening assays as described herein. For example, compounds useful in the subject methods include compounds may be represented by general formula (XXIV):

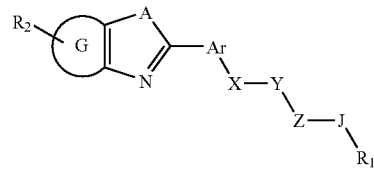

Formula XXIV wherein, as valence and stability permit,

X and Z, independently, represent —N($R_7$)—, —O—, —S—, —($R_7$)N—N($R_7$)—, —ON($R_7$)—, or a direct bond, preferably —N($R_7$)—, —O—, —S—, or a direct bond;

Y represents —C(=O)—, —C(=S)—, —C(=N$R_7$)—, $SO_2$, or SO, preferably —C(=O)—, $SO_2$, or —C(=S)—;

A represents O, S, or $NR_7$, preferably O or NH, and most preferably NH;

G represents a cycloalkyl, heterocyclyl, aryl, or heteroaryl ring fused to the ring to which it is attached, preferably an aryl or heteroaryl ring.

Ar represents a substituted or unsubstituted aryl or heteroaryl ring, such as a substituted or unsubstituted phenyl ring;

$R_1$ represents H or substituted or unsubstituted alkyl, alkenyl, alkynyl, aryl, heteroaryl, heterocyclyl, or cycloalkyl, including polycyclic groups;

$R_2$ represents from 0-4 substituents on the ring to which it is attached, such as halogen, lower alkyl, lower alkenyl, aryl, heteroaryl, carbonyl group (e.g., ester, carboxyl, or formyl), thiocarbonyl (e.g., thioester, thiocarboxylate, or thioformate), ketone, aldehyde, amino, acylamino, amido, amidino, cyano, nitro, azido, sulfonyl, sulfoxido, sulfate, sulfonate, sulfarnoyl, sulfonamido, phosphoryl, phosphonate, phosphinate, J-$R_8$, J—OH, J-lower alkyl, J-lower alkenyl, J—$R_8$, J—SH, J—$NH_2$, protected forms of the above, or any two $R_2$, when occurring more than once in a cyclic or polycyclic structure, can be taken together form a 4- to 8-membered cycloalkyl, aryl, or heteroaryl;

$R_7$, independently for each occurrence, represents H, lower alkyl (e.g., substituted or unsubstituted), J-cycloalkyl (e.g., substituted or unsubstituted), J-heterocyclyl (e.g., substituted or unsubstituted), J-aryl (e.g., substituted or unsubstituted), J-heteroaryl (e.g., substituted or unsubstituted);

$R_8$, independently for each occurrence, represents H, lower alkyl (e.g., substituted or unsubstituted), cycloalkyl (e.g., substituted or unsubstituted), heterocyclyl (e.g., substituted or unsubstituted), aryl (e.g., substituted or unsubstituted), or heteroaryl (e.g., substituted or unsubstituted); and J represents, independently for each occurrence, a chain having from 0-8 (preferably from 0-4) units selected from $CK_2$, NK, O, and S, wherein K represents, independently for each occurrence, H or lower alkyl.

In certain embodiments, at least one of Z and X is not a direct bond. In certain embodiments, X—Y—Z includes an amide, urea, or sulfonamide. In certain embodiments, X is selected from —N($R_8$)—, —O—, —S—, and preferably represents NH.

In certain embodiments, $R_1$ includes an aryl or heteroaryl ring, optionally substituted with from 1-5 substituents, such as nitro, halogen, cyano, lower alkyl, acylamino (e.g., $R_8$—C(=O)NH—), alkoxy, alkylamino, a substituted or unsubstituted cycloalkyl, heterocyclyl, aryl, or heteroaryl fused to the aryl or heteroaryl ring.

In certain embodiments, X and the ring comprising A are disposed on Ar in a meta (i.e., 1,3) relationship.

In certain embodiments, G represents a phenyl or piperidine ring.

In certain embodiments, J is absent.

In certain embodiments, $R_2$ represents from 1-4 substituents selected from halogen, cyano, nitro, alkoxy, amino, acylamino (e.g., $R_8$—C(=O)NH—), a substituted or unsubstituted cycloalkyl, heterocyclyl, aryl, or heteroaryl fused to G, and substituted or unsubstituted lower alkyl.

In certain embodiments, compounds useful in the present invention may be represented by general formula (XXV):

Formula XXV

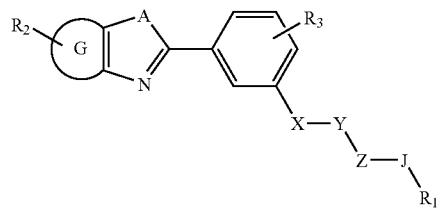

wherein, as valence and stability permit,

X and Z, independently, represent —N($R_7$)—, —O—, —S—, —($R_7$)N—N($R_7$)—, —ON($R_7$)—, or a direct bond, preferably —N($R_7$)—, —O—, —S—, or a direct bond;

Y represents —C(=O)—, —C(=S)—, —C(=N$R_7$)—, $SO_2$, or SO, preferably —C(=O)—, $SO_2$, or —C(=S)—;

A represents O, S, or N$R_7$, preferably O or NH, and most preferably NH;

G represents a cycloalkyl, heterocyclyl, aryl, or heteroaryl ring fused to the ring to which it is attached, preferably an aryl or heteroaryl ring.

$R_1$ represents H or substituted or unsubstituted alkyl, alkenyl, alkynyl, aryl, heteroaryl, heterocyclyl, or cycloalkyl, including polycyclic groups;

$R_2$ represents from 0-4 substituents on the ring to which it is attached, such as halogen, lower alkyl, lower alkenyl, aryl, heteroaryl, carbonyl group (e.g., ester, carboxyl, or formyl), thiocarbonyl (e.g., thioester, thiocarboxylate, or thioformate), ketone, aldehyde, amino, acylamino, amido, amidino, cyano, nitro, azido, sulfonyl, sulfoxido, sulfate, sulfonate, sulfamoyl, sulfonamido, phosphoryl, phosphonate, phosphinate, J-$R_8$, J—OH, J-lower alkyl, J-lower alkenyl, J—$R_8$, J—SH, J—$NH_2$, protected forms of the above, or any two $R_2$, when occurring more than once in a cyclic or polycyclic structure, can be taken together form a 4- to 8-membered cycloalkyl, aryl, or heteroaryl;

$R_3$ represents from 0-4 substituents on the ring to which it is attached, such as halogen, hydroxyl, alkoxy, amino, alkylamino, cyano, nitro, substituted or unsubstituted lower alkyl, and acyl, preferably halogen or substituted or unsubstituted lower alkyl;

$R_7$, independently for each occurrence, represents H, lower alkyl (e.g., substituted or unsubstituted), J-cycloalkyl (e.g., substituted or unsubstituted), J-heterocyclyl (e.g., substituted or unsubstituted), J-aryl (e.g., substituted or unsubstituted), J-heteroaryl (e.g., substituted or unsubstituted);

$R_8$, independently for each occurrence, represents H, lower alkyl (e.g., substituted or unsubstituted), cycloalkyl (e.g., substituted or unsubstituted), heterocyclyl (e.g., substituted or unsubstituted), aryl (e.g., substituted or unsubstituted), or heteroaryl (e.g., substituted or unsubstituted); and J represents, independently for each occurrence, a chain having from 0-8 (preferably from 0-4) units selected from $CK_2$, NK, O, and S, wherein K represents, independently for each occurrence, H or lower alkyl.

In certain embodiments, at least one of Z and X is not a direct bond. In certain embodiments, X—Y—Z includes an amide, urea, or sulfonamide. In certain embodiments, X is selected from —N($R_8$)—, —O—, —S—, and preferably represents NH.

In certain embodiments, $R_1$ includes an aryl or heteroaryl ring, optionally substituted with from 1-5 substituents, such as nitro, halogen, cyano, lower alkyl, acylamino (e.g., $R_8$—C(=O)NH—), alkoxy, alkylamino, a substituted or unsubstituted cycloalkyl, heterocyclyl, aryl, or heteroaryl fused to the aryl or heteroaryl ring.

In certain embodiments, G represents a phenyl or piperidine ring.

In certain embodiments, J is absent.

In certain embodiments, $R_2$ represents from 1-4 substituents selected from halogen, cyano, nitro, alkoxy, amino, acylamino (e.g., $R_8$—C(=O)NH—), a substituted or unsubstituted cycloalkyl, heterocyclyl, aryl, or heteroaryl fused to G, and substituted or unsubstituted lower alkyl.

In certain embodiments, $R_3$ includes a substituent, such as a substituted or unsubstituted alkyl or a halogen, at a position para either to X or to the ring including A.

In certain embodiments, the subject antagonists can be chosen on the basis of their selectivity for the hedgehog pathway. This selectivity can be for the hedgehog pathway versus other pathways, or for selectivity between particular hedgehog pathways, e.g., ptc-1, ptc-2, etc.

In certain preferred embodiments, the subject inhibitors inhibit ptc loss-of-function, hedgehog gain-of-function, or smoothened gain-of-function mediated signal transduction with an $ED_{50}$ of 1 mM or less, more preferably of 1 µM or less, and even more preferably of 1 nM or less. Similarly, in certain preferred embodiments, the subject inhibitors inhibit activity of the hedgehog pathway with a $K_i$ less than 10 nM, preferably less than 1 nM, even more preferably less than 0.1 nM.

In particular embodiments, the small molecule is chosen for use because it is more selective for one patched isoform over the next, e.g., 10-fold, and more preferably at least 100- or even 1000-fold more selective for one patched pathway (ptc-1, ptc-2) over another.

In certain embodiments, a compound which is an antagonist of the hedgehog pathway is chosen to selectively antagonize hedgehog activity over protein kinases other than PKA, such as PKC, e.g., the compound modulates the activity of the hedgehog pathway at least an order of magnitude more strongly than it modulates the activity of another protein kinase, preferably at least two orders of magnitude more strongly, even more preferably at least three orders of magnitude more strongly. Thus, for example, a preferred inhibitor of the hedgehog pathway may inhibit hedgehog activity with a $K_i$ at least an order of magnitude lower than its $K_i$ for inhibition of PKC, preferably at least two orders of magnitude lower, even more preferably at least three orders of magnitude lower. In certain embodiments, the $K_i$ for PKA inhibition is less than 10 nM, preferably less than 1 nM, even more preferably less than 0.1 nM.

Figure 2A:
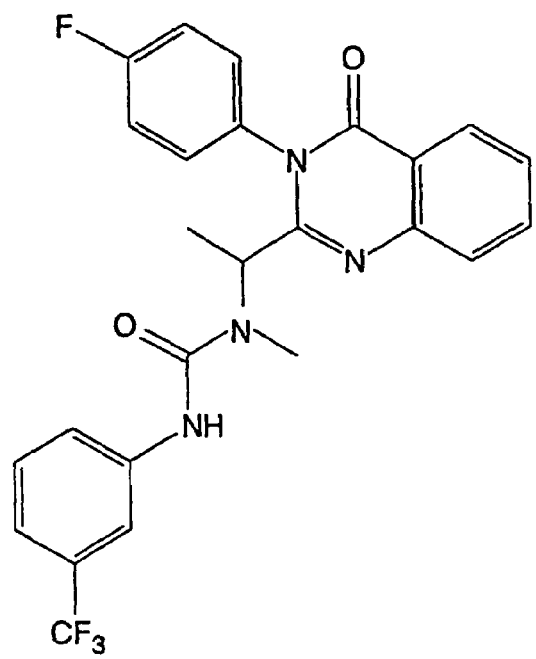
FIG. 2A depicts the chemical structure for compound A.
Figure 2B:
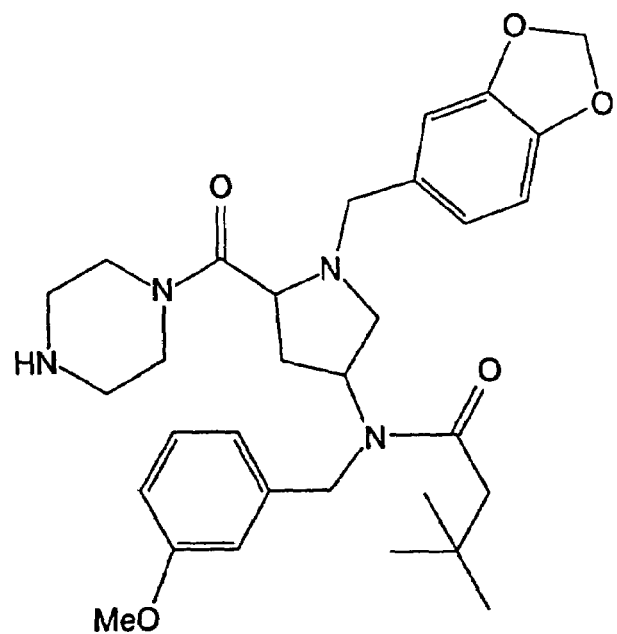
FIG. 2B shows the chemical structure for compound B.
Figure 3:
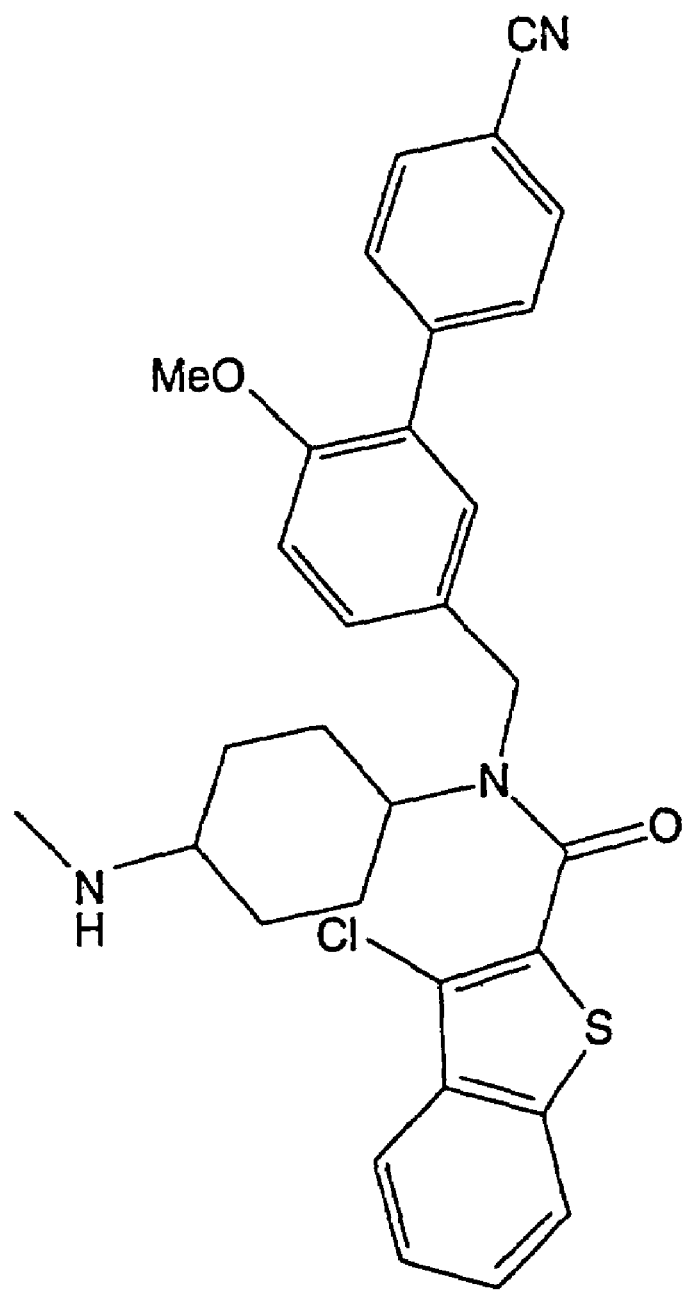
FIG. 3 shows the chemical structure for agonist Z.

In certain preferred embodiments, hedgehog antagonists include AY9944, triparanol, jervine, cyclopamine and tomatidine (see FIG. 1), compound A (see FIG. 2) and compound B (see FIG. 3).

Antagonist Hedgehog Mutants:

It is anticipated that certain mutant forms of a hedgehog protein may act as hedgehog antagonists. While not wishing to be bound to any particular theory, it is well known that mutant forms of protein signaling factors are capable of binding to the appropriate receptor and yet not capable of activating the receptor. Such mutant proteins act as antagonists by displacing the wild-type proteins and blocking the normal receptor activation. Mutant hedgehog proteins may behave similarly. Alternatively, altered hedgehog proteins may bind directly to and inhibit the wild-type forms of hedgehog and so act as antagonists. There are many well known methods for obtaining mutants with a desired activity.

Antagonist forms of hedgehog may be identified by using a hedgehog sensitive screening system. For example, a cell line transfected with a gli-1-lacZ reporter gene construct could be monitored for beta-galactosidase activity. Gli-1 is a reporter for activation of the hedgehog signaling pathway and hedgehog mutants that inhibit gli-1-driven reporter gene expression would be hedgehog antagonists. Any number of reporter genes may be used, including luciferase, green fluorescent protein (and variants including yellow, red, blue and cyan), GUS, and other fluorescent or chromogenic proteins.

Methods for generating large pools of mutant proteins are well known in the art. In one embodiment, the invention contemplates using hedgehog polypeptides generated by combinatorial mutagenesis. Such methods, as are known in the art, are convenient for generating both point and truncation mutants, and can be especially useful for identifying potential variant sequences (e.g., homologs) that are functional in binding to a receptor for hedgehog proteins. The purpose of screening such combinatorial libraries is to generate, for example, novel hedgehog homologs that can act as either agonists or antagonists. To illustrate, hedgehog homologs can be engineered by the present method to provide more efficient binding to a cognate receptor, such as patched, yet still retain at least a portion of an activity associated with hedgehog. Thus, combinatorially derived homologs can be generated to have an increased potency relative to a naturally occurring form of the protein. Likewise, hedgehog homologs can be generated by the present combinatorial approach to act as antagonists, in that they are able to mimic, for example, binding to other extracellular matrix components (such as receptors), yet not induce any biological response, thereby inhibiting the action of authentic hedgehog or hedgehog agonists. Moreover, manipulation of certain domains of hedgehog by the present method can provide domains more suitable for use in fusion proteins, such as one that incorporates portions of other proteins which are derived from the extracellular matrix and/or which bind extracellular matrix components.

To further illustrate the state of the art of combinatorial mutagenesis, it is noted that the review article of Gallop et al. (1994) J Med Chem 37:1233 describes the general state of the art of combinatorial libraries as of the earlier 1990's. In particular, Gallop et al state at page 1239 "[s]creening the analog libraries aids in determining the minimum size of the active sequence and in identifying those residues critical for binding and intolerant of substitution". In addition, the Ladner et al. PCT publication WO90/02809, the Goeddel et al. U.S. Pat. No. 5,223,408, and the Markland et al. PCT publication WO92/15679 illustrate specific techniques which one skilled in the art could utilize to generate libraries of hedgehog variants which can be rapidly screened to identify variants/fragments which retained a particular activity of the hedgehog polypeptides. These techniques are exemplary of the art and demonstrate that large libraries of related variants/truncants can be generated and assayed to isolate particular variants without undue experimentation. Gustin et al. (1993) Virology 193:653, and Bass et al. (1990) Proteins: Structure, Function and Genetics 8:309-314 also describe other exemplary techniques from the art which can be adapted as means for generating mutagenic variants of hedgehog polypeptides.

Indeed, it is plain from the combinatorial mutagenesis art that large scale mutagenesis of hedgehog proteins, without any preconceived ideas of which residues were critical to the biological function, can generate wide arrays of variants having equivalent biological activity. Indeed, it is the ability of combinatorial techniques to screen billions of different variants by high throughout analysis that removes any requirement of a priori understanding or knowledge of critical residues.

To illustrate, the amino acid sequences for a population of hedgehog homologs or other related proteins are aligned, preferably to promote the highest homology possible. Such a population of variants can include, for example, hedgehog homologs from one or more species. Amino acids that appear at each position of the aligned sequences are selected to create a degenerate set of combinatorial sequences. In a preferred embodiment, the variegated library of hedgehog variants is generated by combinatorial mutagenesis at the nucleic acid level, and is encoded by a variegated gene library. For instance, a mixture of synthetic oligonucleotides can be enzymatically ligated into gene sequences such that the degenerate set of potential hedgehog sequences are expressible as individual polypeptides, or alternatively, as a set of larger fusion proteins (e.g., for phage display) containing the set of hedgehog sequences therein.

As illustrated in PCT publication WO 95/18856, to analyze the sequences of a population of variants, the amino acid sequences of interest can be aligned relative to sequence homology. The presence or absence of amino acids from an aligned sequence of a particular variant is relative to a chosen consensus length of a reference sequence, which can be real or artificial.

In an illustrative embodiment, alignment of exons 1, 2 and a portion of exon 3 encoded sequences (e.g., the N-terminal approximately 221 residues of the mature protein) of each of the Shh clones produces a degenerate set of Shh polypeptides represented by the general formula:

C-G-P-G-R-G-X(1)-G-X(2)-R-R-H-P-K-K-L-T-P-L-A-Y-K-Q-F-I-P-N-V-A-E-K-T-L-G-A-S-G-R-Y-E-G-K-I-X(3)-R-N-S-E-R-F-K-E-L-T-P-N-Y-N-P-D-I-I-F-K-D-E-E-N-T-G-A-D-R-L-M-T-Q-R-C-K-D-K-L-N-X(4)-L-A-I-S-V-M-N-X(5)-W-P-G-V-X(6)-L-R-V-T-E-G-W-D-E-D-G-H-H-X(7)-E-E-S-L-H-Y-E-G-R-A-V-D-I-T-T-S-D-R-D-X(8)-S-K-Y-G-X(9)-L-X(10)-R-L-A-V-E-A-G-F-D-W-V-Y-Y-E-S-K-A-H-I-H-C-S-V-K-A-E-N-S-V-A-A-K-S-G-G-C-F-P-G-S-A-X(1)-V-X(12)-L-X(13)-X(14)-G-G-X(15)-K-X-(16)-V-K-D-L-X(17)-P-G-D-X(18)-V-L-A-A-D-X(19)-X(20)-G-X(21)-L-X(22)-X(23)-S-D-F-X(24)-X(25)-F-X(26)-D-R (SEQ ID No: 21 wherein each of the degenerate positions "X" can be an amino acid which occurs in that position in one of the human, mouse, chicken or zebrafish Shh clones, or, to expand the library, each X can also be selected from amongst amino acid residue which would be conservative substitutions for the amino acids which appear naturally in each of those positions. For instance, Xaa(1) represents Gly, Ala, Val, Leu, Ile, Phe, Tyr or Trp ; Xaa(2) represents Arg, His or Lys; Xaa(3) represents Gly, Ala, Val, Leu, Ile, Ser or Thr; Xaa(4) represents Gly, Ala, Val, Leu, Ile, Ser or Thr; Xaa(5) represents Lys, Arg, His, Asn or Gln; Xaa(6) represents Lys, Arg or His; Xaa(7) represents Ser, Thr, Tyr, Trp or Phe; Xaa(8) represents Lys, Arg or His; Xaa(9) represents Met, Cys, Ser or Thr; Xaa(10) represents Gly, Ala, Val, Leu, Ile, Ser or Thr; Xaa(11) represents Leu, Val, Met, Thr or Ser; Xaa(12) represents His, Phe, Tyr, Ser, Thr, Met or Cys; Xaa(13) represents Gln, Asn, Glu, or Asp; Xaa(14) represents His, Phe, Tyr, Thr, Gln, Asn, Glu or Asp; Xaa(15) represents Gln, Asn, Glu, Asp, Thr, Ser, Met or Cys; Xaa(16) represents Ala, Gly, Cys, Leu, Val or Met; Xaa(17) represents Arg, Lys, Met, Ile, Asn, Asp, Glu, Gln, Ser, Thr or Cys; Xaa(18) represents Arg, Lys, Met or Ile; Xaa(19) represents Ala, Gly, Cys, Asp, Glu, Gln, Asn, Ser, Thr or Met; Xaa(20) represents Ala, Gly, Cys, Asp, Asn, Glu or Gln; Xaa(21) represents Arg, Lys, Met, Ile, Asn, Asp, Glu or Gln; Xaa(22) represent Leu, Val, Met or Ile; Xaa(23) represents Phe, Tyr, Thr, His or Trp; Xaa(24) represents Ile, Val, Leu or Met; .Xaa(25) represents Met, Cys, Ile, Leu, Val, Thr or Ser; Xaa(26) represents Leu, Val, Met, Thr or Ser. In an even more expansive library, each X can be selected from any amino acid.

In similar fashion, alignment of each of the human, mouse, chicken and zebrafish hedgehog clones, can provide a degenerate polypeptide sequence represented by the general formula:

C-G-P-G-R-G-X(1)-X(2)-X(3)-R-R-X(4)-X(5)-X(6)-P-K-X(7)-L-X(8)-P-L-X(9)-Y-K-Q-F-X(10)-P-X(11)-X(12)-X(13)-E-X(14)-T-L-G-A-S-G-X(15)-X(16)-E-G-X(17)-X(18)-X(19)-R-X(20)-S-E-R-F-X(21)-X(22)-L-T-P-N-Y-N-P-D-I-I-F-K-D-E-E-N-X(23)-G-A-D-R-L-M-T-X(24)-R-C-K-X(25)-X(26)-X(27)-N-X(28)-L-A-I-S-V-M-N-X(29)-W-P-G-V-X(30)-L-R-V-T-E-G-X(31)-D-E-D-G-H-H-X(32)-X(33)-X(34)-S-L-H-Y-E-G-R-A-X(35)-D-I-T-T-S-D-R-D-X(36)-X(37)-K-Y-G-X(38)-L-X(39)-R-L-A-V-E-A-G-F-D-W-V-Y-Y-E-S-X(40)-X(41)-H-X(42)-H-X(43)-S-V-K-X(44)-X(45) (SEQ IDNo:22)

wherein, as above, each of the degenerate positions "X" can be an amino acid which occurs in a corresponding position in one of the wild-type clones, and may also include amino acid residue which would be conservative substitutions, or each X can be any amino acid residue. In an exemplary embodiment, Xaa(1) represents Gly, Ala, Val, Leu, Ile, Pro, Phe or Tyr; Xaa(2) represents Gly, Ala, Val, Leu or Le; Xaa(3) represents Gly, Ala, Val, Leu, Ile, Lys, His or Arg; Xaa(4) represents Lys, Arg or His; Xaa(5) represents Phe, Trp, Tyr or an amino acid gap; Xaa(6) represents Gly, Ala, Val, Leu, Ile or an amino acid gap; Xaa(7) represents Asn, Gln, His, Arg or Lys; Xaa(8) represents Gly, Ala, Val, Leu, Ile, Ser or Thr; Xaa(9) represents Gly, Ala, Val, Leu, Ile, Ser or Thr; Xaa(10) represents Gly, Ala, Val, Leu, Ile, Ser or Thr; Xaa(11) represents Ser, Thr, Gln or Asn; Xaa(12) represents Met, Cys, Gly, Ala, Val, Leu, Ile, Ser or Thr; Xaa(13) represents Gly, Ala, Val, Leu, Be or Pro; Xaa(14) represents Arg, His or Lys; Xaa(15) represents Gly, Ala, Val, Leu, Ile, Pro, Arg, His or Lys; Xaa(16) represents Gly, Ala, Val, Leu, Ile, Phe or Tyr; Xaa(17) represents Arg, His or Lys; Xaa(18) represents Gly, Ala, Val, Leu, Ile, Ser or Thr; Xaa(19) represents Thr or Ser; Xaa(20) represents Gly, Ala, Val, Leu, Ile, Asn or Gln; Xaa(21) represents Arg, His or Lys; Xaa(22) represents Asp or Glu; Xaa(23) represents Ser or Thr; Xaa(24) represents Glu, Asp, Gln or Asn; Xaa(25) represents Glu or Asp; Xaa(26) represents Arg, His or Lys; Xaa(27) represents Gly, Ala, Val, Leu or Ile; Xaa(28) represents Gly, Ala, Val, Leu, Ile, Thr or Ser; Xaa(29) represents Met, Cys, Gln, Asn, Arg, Lys or His; Xaa(30) represents Arg, His or Lys; Xaa(31) represents Trp, Phe, Tyr, Arg, His or Lys; Xaa(32) represents Gly, Ala, Val, Leu, Ile, Ser, Thr, Tyr or Phe; Xaa(33) represents Gln, Asn, Asp or Glu; Xaa(34) represents Asp or Glu; Xaa(35) represents Gly, Ala, Val, Leu, Ile; Xaa(36) represents Arg, His or Lys; Xaa(37) represents Asn, Gln, Thr or Ser; Xaa(38) represents Gly, Ala, Val, Leu, Ile, Ser, Thr, Met or Cys; Xaa(39) represents Gly, Ala, Val, Leu, Ile, Thr or Ser; Xaa(40) represents Arg, His or Lys; Xaa(41) represents Asn, Gln, Gly, Ala, Val, Leu or Ile; Xaa (42) represents Gly, Ala, Val, Leu or Ile; Xaa(43) represents Gly, Ala, Val, Leu, Ile, Ser, Thr or Cys; Xaa(44) represents Gly, Ala, Val, Leu, Ile, Thr or Ser; and Xaa(45) represents Asp or Glu.

There are many ways by which the library of potential hedgehog homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential hedgehog sequences. The synthesis of degenerate oligonucleotides is well known in the art (see for example, Narang, S A (1983) Tetrahedron 39:3; Itakura et al. (1981) Recombinant DNA, Proc 3rd Cleveland Sympos. Macromolecules, ed. A G Walton, Amsterdam: Elsevier pp273-289; Itakura et al. (1984) Annu. Rev. Biochem. 53:323; Itakura et al. (1984) Science 198: 1056; Ike et al. (1983) Nucleic Acid Res. 11:477. Such techniques have been employed in the directed evolution of other proteins (see, for example, Scott et al. (1990) Science 249: 386-390; Roberts et al. (1992) PNAS 89:2429-2433; Devlin et al. (1990) *Science* 249: 404-406; Cwirla et al. (1990) PNAS 87: 6378-6382; as well as U.S. Pat. Nos. 5,223,409, 5,198, 346, and 5,096,815).

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis of hedgehog homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate hedgehog sequences created by combinatorial mutagenesis techniques.

In yet another screening assay, the candidate hedgehog gene products are displayed on the surface of a cell or viral particle, and the ability of particular cells or viral particles to associate with a hedgehog-binding moiety (such as the patched protein or other hedgehog receptor) via this gene product is detected in a "panning assay". Such panning steps can be carried out on cells cultured from embryos. For instance, the gene library can be cloned into the gene for a surface membrane protein of a bacterial cell, and the resulting fusion protein detected by panning (Ladner et al., WO 88/06630; Fuchs et al. (1991) Bio/Technology 9:1370-1371; and Goward et al. (1992) TIBS 18:136-140). In a similar fashion, fluorescently labeled molecules that bind hedgehog can be used to score for potentially functional hedgehog homologs. Cells can be visually inspected and separated under a fluorescence microscope, or, where the morphology of the cell permits, separated by a fluorescence-activated cell sorter.

In an alternate embodiment, the gene library is expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at very high concentrations, large number of phage can be screened at one time. Second, since each infectious phage displays the combinatorial gene product on its surface, if a particular phage is recovered from an affinity matrix in low yield, the phage can be amplified by another round of infection. The group of almost identical *E. coli* filamentous phages M13, fd, and f1 are most often used in phage display libraries, as either of the phage gIII or gVIII coat proteins can be used to generate fusion proteins without disrupting the ultimate packaging of the viral particle (Ladner et al. PCT publication WO 90/02909; Garrard et al., PCT publication WO 92/09690; Marks et al. (1992) J. Biol. Chem. 267:16007-16010; Griffths et al. (1993) EMBO J 12:725-734; Clackson et al. (1991) Nature 352:624-628; and Barbas et al. (1992) PNAS 89:4457-4461).

In an illustrative embodiment, the recombinant phage antibody system (RPAS, Pharamacia Catalog number 27-9400-01) can be easily modified for use in expressing and screening hedgehog combinatorial libraries. For instance, the pCANTAB 5-phagemid of the RPAS kit contains the gene that encodes the phage gIII coat protein. The hedgehog combinatorial gene library can be cloned into the phagemid adjacent to the gIII signal sequence such that it will be expressed as a gIII fusion protein. After ligation, the phagemid is used to transform competent *E. coli* TG1 cells. Transformed cells are subsequently infected with M13KO7 helper phage to rescue the phagemid and its candidate hedgehog gene insert. The resulting recombinant phage contain phagemid DNA encoding a specific candidate hedgehog, and display one or more copies of the corresponding fusion coat protein. The phage-displayed candidate hedgehog proteins that are capable of binding a hedgehog receptor are selected or enriched by panning. For instance, the phage library can be applied to cells that express the patched protein and unbound phage washed away from the cells. The bound phage is then isolated, and if the recombinant phage express at least one copy of the wild type gIII coat protein, they will retain their ability to infect *E. coli*. Thus, successive rounds of reinfection of *E. coli*, and panning will greatly enrich for hedgehog homologs, which can then be screened for further biological activities in order to differentiate agonists and antagonists.

Combinatorial mutagenesis has a potential to generate very large libraries of mutant proteins, e.g., in the order of $10^{26}$ molecules. Combinatorial libraries of this size may be technically challenging to screen even with high throughput screening assays such as phage display. To overcome this problem, a new technique has been developed recently, recursive ensemble mutagenesis (REM), which allows one to avoid the very high proportion of non-functional proteins in a random library and simply enhances the frequency of functional proteins, thus decreasing the complexity required to achieve a useful sampling of sequence space. REM is an algorithm that enhances the frequency of functional mutants in a library when an appropriate selection or screening method is employed (Arkin and Yourvan, 1992, PNAS USA 89:7811-7815; Yourvan et al., 1992, Parallel Problem Solving from Nature, 2., In Maenner and Manderick, eds., Elsevir Publishing Co., Amsterdam, pp. 401-410; Delgrave et al., 1993, Protein Engineering 6(3):327-331).

Antibody Antagonists:

It is anticipated that antibodies can act as hedgehog antagonists. Antibodies can have extraordinary affinity and specificity for particular epitopes. Antibodies that bind to any protein in the hedgehog signaling pathway may have the capacity to act as antagonists. Antibodies that bind to hedgehog, smoothened or gli-1 may act by simply sterically hindering the proper protein-protein interactions or occupying active sites. Antibodies that bind to patched proteins may act as antagonists if they cause hyperactivation of the patched protein, for example stimulating patched association with smoothened. Proteins with extracellular domains are readily bound by exogenously supplied antibodies.

One aspect of the present invention are methods and compositions comprising hedgehog antibodies which antibodies are hedgehog antagonists. Preferred antibodies are specifically immunoreactive with a vertebrate hedgehog protein. For example, by using immunogens derived from hedgehog protein, monoclonal or polyclonal antibodies can be made using standard protocols (See, for example, Antibodies: A laboratory manual ed. by Harlow and Lane (Cold Spring Harbor Press: 1988)). A mammal, such as a mouse, a hamster or rabbit can be immunized with an immunogenic form of the peptide (e.g., a vertebrate hedgehog polypeptide or an antigenic fragment which is capable of eliciting an antibody response). Techniques for conferring immunogenicity on a protein or peptide include conjugation to carriers or other techniques well known in the art. An immunogenic portion of a hedgehog protein can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of a hedgehog protein of a vertebrate organism. In yet a further preferred embodiment the present invention provides, for example, antibodies which are immunospecific for discrete hedgehog family member, e.g. Shh versus Dhh versus Ihh. Antibodies which are immunospecific for hedgehog, or for a specific hedgehog family member do not substantially cross-react with non-homolgous protein. By not substantially cross react is meant that the antibody has a binding affinity for a non-homologous protein which is at least one order of magnitude, more preferably at least 2 orders of magnitude, and even more preferably at least 3 orders of magnitude less than the binding affinity of the antibody for the protein or proteins for which the antibody is immunospecific. In one embodiment, the antibody does not substantially cross-react with an invertebrate hedgehog protein.

The term antibody as used herein is intended to include fragments thereof which are also specifically reactive with one or more of the vertebrate hedgehog polypeptides. Antibodies can be fragmented using conventional techniques and the fragments screened for utility in the same manner as described above for whole antibodies. For example, F(ab)2 fragments can be generated by treating antibody with pepsin. The resulting F(ab)2 fragment can be treated to reduce disulfide bridges to produce Fab fragments. The antibody of the present invention is further intended to include bispecific and chimeric molecules having affinity for a hedgehog protein conferred by at least one CDR region of the antibody.

Both monoclonal and polyclonal antibodies immunoreactive with hedgehog polypeptides can be used as hedgehog antagonists. Although not all hedgehog antibodies function as hedgehog antagonists, antibodies with hedgehog antagonist activity can be identified in much the same way as other hedgehog antagonists. For example, candidate antibodies can be administered to cells expressing a hedgehog reporter gene, and antibodies that cause decreased reporter gene expression are antagonists.

In one variation, antibodies of the invention can be single chain antibodies (scFv), comprising variable antigen binding domains linked by a polypeptide linker. Single chain antibodies are expressed as a single polypeptide chain and can be expressed in bacteria and as part of a phage display library. In this way, phage that express the appropriate scFv will have hedgehog antagonist activity. The nucleic acid encoding the single chain antibody can then be recovered from the phage and used to produce large quantities of the scFv. Construction and screening of scFv libraries is extensively described in various publications (U.S. Pat. Nos. 5,258,498; 5,482,858; 5,091,513; 4,946,778; 5,969,108; 5,871,907; 5,223,409; 5,225,539).

An illustrative example of a hedgehog antibody which functions as a hedgehog antagonist is 5E1. 5E1 was deposited with the ATCC on Aug. 13, 2002. As noted in the Examples provided herein, 5E1 functions in vitro and in vivo as a hedgehog antagonist. The invention specifically contemplates the use of 5E1, or an antibody which recognizes the same epitope as 5E1 in the subject methods.

The technology for producing monoclonal antibodies is well known. The preferred antibody homologs contemplated herein can be expressed from intact or truncated genomic or cDNA or from synthetic DNAs in prokaryotic or eukaryotic host cells. The dimeric proteins can be isolated from the culture media and/or refolded and dimerized in vitro to form biologically active compositions. Heterodimers can be formed in vitro by combining separate, distinct polypeptide chains. Alternatively, heterodimers can be formed in a single cell by co-expressing nucleic acids encoding separate, distinct polypeptide chains. See, for example, WO93/09229, or U.S. Pat. No. 5,411,941, for several exemplary recombinant heterodimer protein production protocols. Currently preferred host cells include, without limitation, prokaryotes including E. coli, or eukaryotes including yeast, Saccharomyces, insect cells, or mammalian cells, such as CHO, COS or BSC cells. One of ordinary skill in the art will appreciate that other host cells can be used to advantage. For example, anti-hedgehog antibodies may be identified by immunoprecipitation of 1251-labeled cell lysates from hedgehog -expressing cells. Anti-hedgehog antibodies may also be identified by flow cytometry, e.g., by measuring fluorescent staining of cells incubated with an antibody believed to recognize hedgehog protein. The lymphocytes used in the production of hybridoma cells typically are isolated from immunized mammals whose sera have already tested positive for the presence of anti-hedgehog antibodies using such screening assays.

Typically, the immortal cell line (e.g., a myeloma cell line) is derived from the same mammalian species as the lymphocytes. Preferred immortal cell lines are mouse myeloma cell lines that are sensitive to culture medium containing hypoxanthine, arninopterin and thymidine ("HAT medium"). Typically, HAT-sensitive mouse myeloma cells are fused to mouse splenocytes using 1500 molecular weight polyethylene glycol ("PEG 1500"). Hybridoma cells resulting from the fusion are then selected using HAT medium, which kills unfused and unproductively fused myeloma cells (unfused splenocytes die after several days because they are not transformed). Hybridomas producing a desired antibody are detected by screening the hybridoma culture supernatants. For example, hybridomas prepared to produce anti-hedgehog or patched antibodies may be screened by testing the hybridoma culture supernatant for secreted antibodies having the ability to bind to a recombinant hedgehog or patched expressing cell line.

To produce antibody homologs that are intact immunoglobulins, hybridoma cells that tested positive in such screening assays were cultured in a nutrient medium under conditions and for a time sufficient to allow the hybridoma cells to secrete the monoclonal antibodies into the culture medium. Tissue culture techniques and culture media suitable for hybridoma cells are well known. The conditioned hybridoma culture supernatant may be collected and the anti-hedgehog or patched antibodies optionally further purified by well-known methods.

Alternatively, the desired antibody may be produced by injecting the hybridoma cells into the peritoneal cavity of an unimmunized mouse. The hybridoma cells proliferate in the peritoneal cavity, secreting the antibody which accumulates as ascites fluid. The antibody may be harvested by withdrawing the ascites fluid from the peritoneal cavity with a syringe. Several anti-hedgehog or patched monoclonal antibodies have been previously described. These anti-hedgehog or patched monoclonal antibodies and others will be useful in the methods of treatment according to the present invention.

Fully human monoclonal antibody homologs against hedgehog or patched are another preferred binding agent which may block or coat hedgehog ligands in the method of the invention. In their intact form these may be prepared using in vitro-primed human splenocytes, as described by Boerner et al., 1991, J. Immunol., 147, 86-95. Alternatively, they may be prepared by repertoire cloning as described by Persson et al., 1991, Proc. Nat. Acad. Sci. USA, 88: 2432-2436 or by Huang and Stollar, 1991, J. Immunol. Methods 141, 227-236. U.S. Pat. No. 5,798,230 (Aug. 25, 1998, "Process for the preparation of human monoclonal antibodies and their use") who describe preparation of human monoclonal antibodies from human B cells. According to this process, human antibody-producing B cells are immortalized by infection with an Epstein-Barr virus, or a derivative thereof, that expresses Epstein-Barr virus nuclear antigen 2 (EBNA2). EBNA2 function, which is required for immortalization, is subsequently shut off, which results in an increase in antibody production.

In yet another method for producing fully human antibodies, U.S. Pat. No. 5,789,650 (Aug. 4, 1998, "Transgenic non-human animals for producing heterologous antibodies") describes transgenic non-human animals capable of producing heterologous antibodies and transgenic non-human animals having inactivated endogenous immunoglobulin genes. Endogenous immunoglobulin genes are suppressed by antisense polynucleotides and/or by antiserum directed against endogenous immunoglobulins. Heterologous antibodies are encoded by immunoglobulin genes not normally found in the genome of that species of non-human animal. One or more transgenes containing sequences of unrearranged heterologous human immunoglobulin heavy chains are introduced into a non-human animal thereby forming a transgenic animal capable of functionally rearranging transgenic immunoglobulin sequences and producing a repertoire of antibodies of various isotypes encoded by human immunoglobulin genes. Such heterologous human antibodies are produced in B-cells which are thereafter immortalized, e.g., by fusing with an immortalizing cell line such as a myeloma or by manipulating such B-cells by other techniques to perpetuate a cell line capable of producing a monoclonal heterologous, fully human antibody homolog.

Large nonimmunized human phage display libraries may also be used to isolate high affinity antibodies that can be developed as human therapeutics using standard phage technology (Vaughan et al, 1996).

Yet another preferred binding agent which may block or coat hedgehog ligands in the method of the invention is a humanized recombinant antibody homolog having anti-hedgehog or patched specificity. Following the early methods for the preparation of true "chimeric antibodies" (where the entire constant and entire variable regions are derived from different sources), a new approach was described in EP 0239400 (Winter et al.) whereby antibodies are altered by substitution (within a given variable region) of their complementarity determining regions (CDRs) for one species with those from another. This process may be used, for example, to substitute the CDRs from human heavy and light chain Ig variable region domains with alternative CDRs from murine variable region domains. These altered Ig variable regions may subsequently be combined with human Ig constant regions to create antibodies which are totally human in composition except for the substituted murine CDRs. Such CDR-substituted antibodies would be predicted to be less likely to elicit an immune response in humans compared to true chimeric antibodies because the CDR-substituted antibodies contain considerably less non-human components. The process for humanizing monoclonal antibodies via CDR "grafting" has been termed "reshaping". (Riechmann et al., 1988, Nature 332, 323-327; Verhoeyen et al., 1988, Science 239, 1534-1536).

Typically, complementarity determining regions (CDRs) of a murine antibody are transplanted onto the corresponding regions in a human antibody, since it is the CDRs (three in antibody heavy chains, three in light chains) that are the regions of the mouse antibody which bind to a specific antigen. Transplantation of CDRs is achieved by genetic engineering whereby CDR DNA sequences are determined by cloning of murine heavy and light chain variable (V) region gene segments, and are then transferred to corresponding human V regions by site directed mutagenesis. In the final stage of the process, human constant region gene segments of the desired isotype (usually gamma I for CH and kappa for CL) are added and the humanized heavy and light chain genes are co-expressed in mammalian cells to produce soluble humanized antibody.

The transfer of these CDRs to a human antibody confers on this antibody the antigen binding properties of the original murine antibody. The six CDRs in the murine antibody are mounted structurally on a V region "framework" region. The reason that CDR-grafting is successful is that framework regions between mouse and human antibodies may have very similar 3-D structures with similar points of attachment for CDRS, such that CDRs can be interchanged. Such humanized antibody homologs may be prepared, as exemplified in Jones et al., 1986, Nature 321, 522-525; Riechmann, 1988, Nature 332, 323-327; Queen et al., 1989, Proc. Nat. Acad. Sci. USA 86, 10029; and Orlandi et al., 1989, Proc. Nat. Acad. Sci. USA 86, 3833.

Nonetheless, certain amino acids within framework regions are thought to interact with CDRs and to influence overall antigen binding affinity. The direct transfer of CDRs from a murine antibody to produce a recombinant humanized antibody without any modifications of the human V region frameworks often results in a partial or complete loss of binding affinity. In a number of cases, it appears to be critical to alter residues in the framework regions of the acceptor antibody in order to obtain binding activity.

Queen et al., 1989 (supra) and WO 90/07861 (Protein Design Labs) have described the preparation of a humanized antibody that contains modified residues in the framework regions of the acceptor antibody by combining the CDRs of a murine MAb (anti-Tac) with human immunoglobulin framework and constant regions. They have demonstrated one solution to the problem of the loss of binding affinity that often results from direct CDR transfer without any modifications of the human V region framework residues; their solution involves two key steps. First, the human V framework regions are chosen by computer analysts for optimal protein sequence homology to the V region framework of the original murine antibody, in this case, the anti-Tac MAb. In the second step, the tertiary structure of the murine V region is modelled by computer in order to visualize framework amino acid residues which are likely to interact with the murine CDRs and these murine amino acid residues are then superimposed on the homologous human framework. See also U.S. Pat. Nos. 5,693,762; 5,693,761; 5,585,089; and 5,530,101 (Protein Design Labs).

One may use a different approach (Tempest et al.,1991, Biotechnology 9, 266-271) and utilize, as standard, the V region frameworks derived from NEWM and REI heavy and light chains respectively for CDR-grafting without radical introduction of mouse residues. An advantage of using the Tempest et al., approach to construct NEWM and REI based humanized antibodies is that the 3-dimensional structures of NEWM and REI variable regions are known from x-ray crystallography and thus specific interactions between CDRs and V region framework residues can be modeled.

Regardless of the approach taken, the examples of the initial humanized antibody homologs prepared to date have shown that it is not a straightforward process. However, even acknowledging that such framework changes may be necessary, it is not possible to predict, on the basis of the available prior art, which, if any, framework residues will need to be altered to obtain functional humanized recombinant antibodies of the desired specificity. Results thus far indicate that changes necessary to preserve specificity and/or affinity are for the most part unique to a given antibody and cannot be predicted based on the humanization of a different antibody.

Antisense, Ribozyme and Triplex Techniques:

Another aspect of the invention relates to the use of the isolated nucleic acid in "antisense" therapy. As used herein, "antisense" therapy refers to administration or in situ generation of oligonucleotide molecules or their derivatives which specifically hybridize (e.g., bind) under cellular conditions, with the cellular mRNA and/or genomic DNA encoding one or more of the subject hedgehog pathway proteins so as to inhibit expression of that protein, e.g., by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy that relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes a hedgehog signaling protein. Alternatively, the antisense construct is an oligonucleotide probe that is generated ex vivo and which, when introduced into the cell causes inhibition of expression by hybridizing with the mRNA and/or genomic sequences of a hedgehog signaling gene. Such oligonucleotide probes are preferably modified oligonucleotides that are resistant to endogenous nucleases, e.g., exonucleases and/or endonucleases, and are therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) BioTechniques 6:958-976; and Stein et al. (1988) Cancer Res 48:2659-2668. With respect to antisense DNA, oligodeoxyribonucleotides derived from the translation initiation site, e.g., between the −10 and +10 regions of the hedgehog signaling gene nucleotide sequence of interest, are preferred.

Antisense approaches involve the design of oligonucleotides (either DNA or RNA) that are complementary to mRNA encoding a hedgehog signaling protein. The antisense oligonucleotides will bind to the mRNA transcripts and prevent translation. Absolute complementarity, although preferred, is not required. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the mRNA, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well. (Wagner, R. 1994. Nature 372:333). Therefore, oligonucleotides complementary to either the 5' or 3' untranslated, non-coding regions of a gene could be used in an antisense approach to inhibit translation of that mRNA. Oligonucleotides complementary to the 5' untranslated region of the mRNA should include the complement of the AUG start codon. Antisense oligonucleotides complementary to mRNA coding regions are less efficient inhibitors of translation but could also be used in accordance with the invention. Whether designed to hybridize to the 5', 3' or coding region of mRNA, antisense nucleic acids should be at least six nucleotides in length, and are preferably less that about 100 and more preferably less than about 50, 25, 17 or 10 nucleotides in length.

Regardless of the choice of target sequence, it is preferred that in vitro studies are first performed to quantitate the ability of the antisense oligonucleotide to quantitate the ability of the antisense oligonucleotide to inhibit gene expression. It is preferred that these studies utilize controls that distinguish between antisense gene inhibition and nonspecific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors), or agents facilitating transport across the cell membrane (see, e.g., Letsinger et al., 1989, Proc. Natl. Acad. Sci. U.S.A. 86:6553-6556; Lemaitre et al., 1987, Proc. Natl. Acad. Sci. 84:648-652; PCT Publication No. W088/09810, published Dec. 15, 1988) or the blood- brain barrier (see, e.g., PCT Publication No. W089/10134, published Apr. 25, 1988), hybridization-triggered cleavage agents. (See, e.g., Krol et al., 1988, BioTechniques 6:958-976) or intercalating agents. (See, e.g., Zon, 1988, Pharm. Res. 5:539-549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5- bromouracil, 5-chlorouracil, 5-iodouracil, hypoxanthine, xanthine, 4-acetylcytosine, 5-(carboxyhydroxytriethyl) uracil, 5-carboxymethylaminomethyl-2-thiouridine, 5- carboxymethylaminomethyluracil, dihydrouracil, beta-D-galactosylqueosine, inosine, N6- isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil; beta-D- mannosylqueosine, 5'-methoxycarboxymethyluracil, 5-methoxyuracil, 2-methylthio-N6- isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including but not limited to arabinose, 2-fluoroarabinose, xylulose, and hexose.

The antisense oligonucleotide can also contain a neutral peptide-like backbone. Such molecules are termed peptide nucleic acid (PNA)-oligomers and are described, e.g., in Perry-O'Keefe et al. (1996) Proc. Natl. Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet a further embodiment, the antisense oligonucleotide is an -anomeric oligonucleotide. An -anomeric oligonucleotide forms specific double-stranded hybrids with complementary RNA in which, contrary to the usual -units, the strands run parallel to each other (Gautier et al., 1987, Nucl. Acids Res. 15:6625-6641). The oligonucleotide is a 2'-0-methylribonucleotide (Inoue et al., 1987, Nucl. Acids Res. 15:6131-6148), or a chimeric RNA-DNA analogue (Inoue et al., 1987, FEBS Lett. 215:327-330).

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448-7451), etc.

While antisense nucleotides complementary to the coding region of an mRNA sequence can be used, those complementary to the transcribed untranslated region and to the region comprising the initiating methionine are most preferred.

The antisense molecules can be delivered to cells that express hedgehog signaling genes in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

However, it may be difficult to achieve intracellular concentrations of the antisense sufficient to suppress translation on endogenous mRNAs in certain instances. Therefore a preferred approach utilizes a recombinant DNA construct in which the antisense oligonucleotide is placed under the control of a strong pol m or pol II promoter. The use of such a construct to transfect target cells in the patient will result in the transcription of sufficient amounts of single stranded RNAs that will form complementary base pairs with the endogenous hedgehog signaling transcripts and thereby prevent translation. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290:304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al, 1982, Nature 296:3942), etc. Any type of plasmid, cosmid, YAC or viral vector can be used to prepare the recombinant DNA construct that can be introduced directly into the tissue site. Alternatively, viral vectors can be used which selectively infect the desired tissue, in which case administration may be accomplished by another route (e.g., systematically).

Ribozyme molecules designed to catalytically cleave hedgehog signaling mRNA transcripts can also be used to prevent translation of mRNA (See, e.g., PCT International Publication WO90/11364, published Oct. 4, 1990; Sarver et al., 1990, Science 247:1222-1225 and U.S. Pat. No. 5,093, 246). While ribozymes that cleave mRNA at site-specific recognition sequences can be used to destroy particular mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585-591.

The ribozymes of the present invention also include RNA endoribonucleases (hereinafter "Cech-type ribozymes") such as the one which occurs naturally in Tetrahymena thermophila (known as the IVS, or L-19 IVS RNA) and which has been extensively described by Thomas Cech and collaborators (Zaug, et al., 1984, Science, 224:574-578; Zaug and Cech, 1986, Science, 231:470-475; Zaug, et al., 1986, Nature, 324:429-433; published International patent application No. WO88/04300 by University Patents Inc.; Been and Cech, 1986, Cell, 47:207-216). The Cech-type ribozymes have an eight base pair active site that hybridizes to a target RNA sequence whereafter cleavage of the target RNA takes place. The invention encompasses those Cech-type ribozymes that target eight base-pair active site sequences.

As in the antisense approach, the ribozymes can be composed of modified oligonucleotides (e.g., for improved stability, targeting, etc.) and should be delivered to cells that express hedgehog signaling genes in vivo. A preferred method of delivery involves using a DNA construct "encoding" the ribozyme under the control of a strong constitutive pol III or pol II promoter, so that transfected cells will produce sufficient quantities of the ribozyme to destroy targeted messages and inhibit translation. Because ribozymes unlike antisense molecules, are catalytic, a lower intracellular concentration is required for efficiency.

Alternatively, endogenous hedgehog signaling gene expression can be reduced by targeting deoxyribonucleotide sequences complementary to the regulatory region of the gene (i.e., the promoter and/or enhancers) to form triple helical structures that prevent transcription of the gene in target cells in the body. (See generally, Helene, C. 1991, Anticancer Drug Des., 6(6):569-84; Helene, C., et al., 1992, Ann. N.Y. Acad. Sci., 660:27-36; and Maher, L. J., 1992, Bioassays 14(12):807-15).

Nucleic acid molecules to be used in triple helix formation for the inhibition of transcription are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

Antisense RNA and DNA, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

RNAi

RNAi constructs comprise double stranded RNA that can specifically block expression of a target gene. Accordingly, RNAi constructs can act as antagonists by specifically blocking expression of a particular gene. "RNA interference" or "RNAi" is a term initially applied to a phenomenon observed in plants and worms where double-stranded RNA (dsRNA) blocks gene expression in a specific and post-transcriptional manner. Without being bound by theory, RNAi appears to involve mRNA degradation, however the biochemical mechanisms are currently an active area of research. Despite some mystery regarding the mechanism of action, RNAi provides a useful method of inhibiting gene expression in vitro or in vivo.

As used herein, the term "dsRNA" refers to siRNA molecules, or other RNA molecules including a double stranded feature and able to be processed to siRNA in cells, such as hairpin RNA moieties.

The term "loss-of-function," as it refers to genes inhibited by the subject RNAi method, refers to a diminishment in the level of expression of a gene when compared to the level in the absence of RNAi constructs.

As used herein, the phrase "mediates RNAi" refers to (indicates) the ability to distinguish which RNAs are to be degraded by the RNAi process, e.g., degradation occurs in a sequence-specific manner rather than by a sequence-independent dsRNA response, e.g., a PKR response.

As used herein, the term "RNAi construct" is a generic term used throughout the specification to include small interfering RNAs (siRNAs), hairpin RNAs, and other RNA species which can be cleaved in vivo to form siRNAs. RNAi constructs herein also include expression vectors (also referred to as RNAi expression vectors) capable of giving rise to transcripts which form dsRNAs or hairpin RNAs in cells, and/or transcripts which can produce siRNAs in vivo.

"RNAi expression vector" (also referred to herein as a "dsRNA-encoding plasmid") refers to replicable nucleic acid constructs used to express (transcribe) RNA which produces siRNA moieties in the cell in which the construct is expressed. Such vectors include a transcriptional unit comprising an assembly of (1) genetic element(s) having a regulatory role in gene expression, for example, promoters, operators, or enhancers, operatively linked to (2) a "coding" sequence which is transcribed to produce a double-stranded RNA (two RNA moieties that anneal in the cell to form an siRNA, or a single hairpin RNA which can be processed to an siRNA), and (3) appropriate transcription initiation and termination sequences. The choice of promoter and other regulatory elements generally varies according to the intended host cell. In general, expression vectors of utility in recombinant DNA techniques are often in the form of "plasmids" which refer to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The RNAi constructs contain a nucleotide sequence that hybridizes under physiologic conditions of the cell to the nucleotide sequence of at least a portion of the mRNA transcript for the gene to be inhibited (i.e., the "target" gene). The double-stranded RNA need only be sufficiently similar to natural RNA that it has the ability to mediate RNAi. Thus, the invention has the advantage of being able to tolerate sequence variations that might be expected due to genetic mutation, strain polymorphism or evolutionary divergence. The number of tolerated nucleotide mismatches between the target sequence and the RNAi construct sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition.

Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing).

Production of RNAi constructs can be carried out by chemical synthetic methods or by recombinant nucleic acid techniques. Endogenous RNA polymerase of the treated cell may mediate transcription in vivo, or cloned RNA polymerase can be used for transcription in vitro. The RNAi constructs may include modifications to either the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA may be modified to include at least one of an nitrogen or sulfur heteroatom. Modifications in RNA structure may be tailored to allow specific genetic inhibition while avoiding a general response to dsRNA. Likewise, bases may be modified to block the activity of adenosine deaminase. The RNAi construct may be produced enzymatically or by partial/total organic synthesis, any modified ribonucleotide can be introduced by in vitro enzymatic or organic synthesis.

Methods of chemically modifying RNA molecules can be adapted for modifying RNAi constructs (see, for example, Heidenreich et al. (1997) *Nucleic Acids Res,* 25:776-780; Wilson et al. (1994) *J Mol Recog* 7:89-98; Chen et al. (1995) *Nucleic Acids Res* 23:2661-2668; Hirschbein et al. (1997)

*Antisense Nucleic Acid Drug Dev* 7:55-61). Merely to illustrate, the backbone of an RNAi construct can be modified with phosphorothioates, phosphoramidate, phosphodithioates, chimeric methylphosphonate-phosphodiesters, peptide nucleic acids, 5-propynyl-pyrimidine containing oligomers or sugar modifications (e.g., 2'-substituted ribonucleosides, a-configuration).

The double-stranded structure may be formed by a single self-complementary RNA strand or two complementary RNA strands. RNA duplex formation may be initiated either inside or outside the cell. The RNA may be introduced in an amount which allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for genetic inhibition.

In certain embodiments, the subject RNAi constructs are "small interfering RNAs" or "siRNAs." These nucleic acids are around 19-30 nucleotides in length, and even more preferably 21-23 nucleotides in length, e.g., corresponding in length to the fragments generated by nuclease "dicing" of longer double-stranded RNAs. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group.

The siRNA molecules of the present invention can be obtained using a number of techniques known to those of skill in the art. For example, the siRNA can be chemically synthesized or recombinantly produced using methods known in the art. For example, short sense and antisense RNA oligomers can be synthesized and annealed to form double-stranded RNA structures with 2-nucleotide overhangs at each end (Caplen, et al. (2001) *Proc Natl Acad Sci USA*, 98:9742-9747; Elbashir, et al. (2001) *EMBO J*, 20:6877-88). These double-stranded siRNA structures can then be directly introduced to cells, either by passive uptake or a delivery system of choice, such as described below.

In certain embodiments, the siRNA constructs can be generated by processing of longer double-stranded RNAs, for example, in the presence of the enzyme dicer. In one embodiment, the *Drosophila* in vitro system is used. In this embodiment, dsRNA is combined with a soluble extract derived from *Drosophila* embryo, thereby producing a combination. The combination is maintained under conditions in which the dsRNA is processed to RNA molecules of about 21 to about 23 nucleotides.

The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

In certain preferred embodiments, at least one strand of the siRNA molecules has a 3' overhang from about 1 to about 6 nucleotides in length, though may be from 2 to 4 nucleotides in length. More preferably, the 3' overhangs are 1-3 nucleotides in length. In certain embodiments, one strand having a 3' overhang and the other strand being blunt-ended or also having an overhang. The length of the overhangs may be the same or different for each strand. In order to further enhance the stability of the siRNA, the 3' overhangs can be stabilized against degradation. In one embodiment, the RNA is stabilized by including purine nucleotides, such as adenosine or guanosine nucleotides. Alternatively, substitution of pyrimidine nucleotides by modified analogues, e.g., substitution of uridine nucleotide 3' overhangs by 2'-deoxythyinidine is tolerated and does not affect the efficiency of RNAi. The absence of a 2' hydroxyl significantly enhances the nuclease resistance of the overhang in tissue culture medium and may be beneficial in vivo.

In other embodiments, the RNAi construct is in the form of a long double-stranded RNA. In certain embodiments, the RNAi construct is at least 25, 50, 100, 200, 300 or 400 bases. In certain embodiments, the RNAi construct is 400-800 bases in length. The double-stranded RNAs are digested intracellularly, e.g., to produce siRNA sequences in the cell. However, use of long double-stranded RNAs in vivo is not always practical, presumably because of deleterious effects which may be caused by the sequence-independent dsRNA response. In such embodiments, the use of local delivery systems and/or agents which reduce the effects of interferon or PKR are preferred.

In certain embodiments, the RNAi construct is in the form of a hairpin structure (named as hairpin RNA). The hairpin RNAs can be synthesized exogenously or can be formed by transcribing from RNA polymerase III promoters in vivo. Examples of making and using such hairpin RNAs for gene silencing in mammalian cells are described in, for example, Paddison et al., *Genes Dev*, 2002, 16:948-58; McCaffrey et al., *Nature*, 2002, 418:38-9; McManus et al., *RNA*, 2002, 8:842-50; Yu et al., *Proc Natl Acad Sci U S A*, 2002, 99:6047-52). Preferably, such hairpin RNAs are engineered in cells or in an animal to ensure continuous and stable suppression of a desired gene. It is known in the art that siRNAs can be produced by processing a hairpin RNA in the cell.

In yet other embodiments, a plasmid is used to deliver the double-stranded RNA, e.g., as a transcriptional product. In such embodiments, the plasmid is designed to include a "coding sequence" for each of the sense and antisense strands of the RNAi construct. The coding sequences can be the same sequence, e.g., flanked by inverted promoters, or can be two separate sequences each under transcriptional control of separate promoters. After the coding sequence is transcribed, the complementary RNA transcripts base-pair to form the double-stranded RNA.

PCT application WO01/77350 describes an exemplary vector for bi-directional transcription of a transgene to yield both sense and antisense RNA transcripts of the same transgene in a eukaryotic cell. Accordingly, in certain embodiments, the present invention provides a recombinant vector having the following unique characteristics: it comprises a viral replicon having two overlapping transcription units arranged in an opposing orientation and flanking a transgene for an RNAi construct of interest, wherein the two overlapping transcription units yield both sense and antisense RNA transcripts from the same transgene fragment in a host cell.

RNAi constructs can comprise either long stretches of double stranded RNA identical or substantially identical to the target nucleic acid sequence or short stretches of double stranded RNA identical to substantially identical to only a region of the target nucleic acid sequence. Exemplary methods of making and delivering either long or short RNAi constructs can be found, for example, in WO01/68836 and WO01/75164.

Exemplary RNAi constructs that specifically recognize a particular gene, or a particular family of genes can be selected using methodology outlined in detail above with respect to the selection of antisense oligonucleotide. Similarly, methods of delivery RNAi constructs include the methods for delivery antisense oligonucleotides outlined in detail above.

In general, it is anticipated that any of the foregoing methods that decrease the presence or translation of hedgehog, smoothened or gli-1 mRNA will act as hedgehog antagonists, while methods that decrease the production of patched will have an agonist effect.

In certain embodiments, the subject antagonists can be chosen on the basis of their selectively for the hedgehog pathway. This selectivity can be for the hedgehog pathway versus other pathways, or for selectivity between particular hedgehog pathways, e.g., e.g., ptc-1, ptc-2, etc.

In certain preferred embodiments, the subject inhibitors inhibit hedgehog-mediated signal transduction with an $ED_{50}$ of 1 mM or less, more preferably of 1 µM or less, and even more preferably of 1 nM or less.

In particular embodiments, the small molecule is chosen for use because it is more selective for one patched isoform over the next, e.g., 10 fold, and more preferably at least 100 or even 1000 fold more selective for one patched pathway (ptc-1, ptc-2) over another.

In certain embodiments, a compound which is an antagonist of the hedgehog pathway is chosen to selectively antagonize hedgehog activity over protein kinases other than PKA, such as PKC, e.g., the compound modulates the activity of the hedgehog pathway at least an order of magnitude more strongly than it modulates the activity of another protein kinase, preferably at least two orders of magnitude more strongly, even more preferably at least three orders of magnitude more strongly. Thus, for example, a preferred inhibitor of the hedgehog pathway may inhibit hedgehog activity with a $K_i$ at least an order of magnitude lower than its $K_i$ for inhibition of PKC, preferably at least two orders of magnitude lower, even more preferably at least three orders of magnitude lower. In certain embodiments, the $K_i$ for PKA inhibition is less than 10 nM, preferably less than 1 nM, even more preferably less than 0.1 nM.

IV. Exemplary Applications of Method and Compositions

Another aspect of the present invention relates to methods of modulating a differentiated state, survival, and/or proliferation of a cell.

For example, it is contemplated that the subject method could be used to inhibit angiogenesis. Hedgehog is known to stimulate angiogenesis. Matrigel plugs impregnated with hedgehog protein and inserted into mice evince substantial neovascularization, whereas Matrigel plugs not carrying hedgehog show comparatively little vascularization. Hedgehog protein is also capable of increasing vascularization of the normally avascular mouse cornea. The ptc-1 gene is expressed in normal vascular tissues, including the endothelial cells of the aorta, vascular smooth muscle cells, adventitial fibroblasts of the aorta, the coronary vasculature and cardiomyocytes of the atria and ventricles. These tissues are also sensitive to hedgehog protein. Treatment with exogenous hedgehog causes upregulation of ptc-1 expression. In addition, hedgehog proteins stimulate proliferation of vascular smooth muscle cells in vivo. Hedgehog proteins also cause fibroblasts to increase expression of angiogenic growth factors such as VEGF, bFGF, Ang-1 and Ang-2. Lastly, hedgehog proteins are known to stimulate recovery from ischemic injury and stimulate formation of collateral vessels.

Given that hedgehog promotes angiogenesis, hedgehog antagonists are expected to act as angiogenesis inhibitors, particularly in situations where some level of hedgehog signaling is necessary for angiogenesis.

Angiogenesis is fundamental to many disorders. Persistent, unregulated angiogenesis occurs in a range of disease states, tumor metastases and abnormal growths by endothelial cells. The vasculature created as a result of angiogenic processes supports the pathological damage seen in these conditions. The diverse pathological states created due to unregulated angiogenesis have been grouped together as angiogenic dependent or angiogenic associated diseases. Therapies directed at control of the angiogenic processes could lead to the abrogation or mitigation of these diseases.

Diseases caused by, supported by or associated with angiogenesis include ocular neovascular disease, age-related macular degeneration, diabetic retinopathy, retinopathy of prematurity, corneal graft rejection, neovascular glaucoma, retrolental fibroplasia, epidemnic keratoconjunctivitis, Vitamin A deficiency, contact lens overwear, atopic keratitis, superior limbic keratitis, pterygium keratitis sicca, sjogrens, acne rosacea, phylectenulosis, syphilis, Mycobacteria infections, lipid degeneration, chemical bums, bacterial ulcers, fungal ulcers, Herpes simplex infections, Herpes zoster infections, protozoan infections, Kaposi sarcoma, Mooren ulcer, Terrien's marginal degeneration, mariginal keratolysis, rheumatoid arthritis, systemic lupus, polyarteritis, trauma, Wegeners sarcoidosis, Scleritis, Steven's Johnson disease, periphigoid radial keratotomy, corneal graph rejection, rheumatoid arthritis, osteoarthritis chronic inflammation (e.g., ulcerative colitis or Crohn's disease), hemangioma, Osler-Weber-Rendu disease, and hereditary hemorrhagic telangiectasia.

In addition, angiogenesis plays a critical role in cancer. A tumor cannot expand without a blood supply to provide nutrients and remove cellular wastes. Tumors in which angiogenesis is important include solid tumors such as rhabdomyosarcomas, retinoblastoma, Ewing sarcoma, neuroblastoma, and osteosarcoma, and benign tumors such as acoustic neuroma, neurofibroma, trachoma and pyogenic granulomas. Angiogenic factors have been found associated with several solid tumors. Prevention of angiogenesis could halt the growth of these tumors and the resultant damage to the animal due to the presence of the tumor. Angiogenesis is also associated with blood-born tumors such as leukemias, any of various acute or chronic neoplastic diseases of the bone marrow in which unrestrained proliferation of white blood cells occurs, usually accompanied by anemia, impaired blood clotting, and enlargement of the lymph nodes, liver, and spleen. It is believed that angiogenesis plays a role in the abnormalities in the bone marrow that give rise to leukemia-like tumors.

In addition to tumor growth, angiogenesis is important in metastasis. Initially, angiogenesis is important is in the vascularization of the tumor which allows cancerous cells to enter the blood stream and to circulate throughout the body. After the tumor cells have left the primary site, and have settled into the secondary, metastasis site, angiogenesis must occur before the new tumor can grow and expand. Therefore, prevention of angiogenesis could lead to the prevention of metastasis of tumors and possibly contain the neoplastic growth at the primary site.

Angiogenesis is also involved in normal physiological processes such as reproduction and wound healing. Angiogenesis is an important step in ovulation and also in implantation of the blastula after fertilization. Prevention of angiogenesis could be used to induce amenorrhea, to block ovulation or to prevent implantation by the blastula.

It is anticipated that the invention will be useful for the treatment and/or prevention of respiratory distress syndrome or other disorders resulting from inappropriate lung surface tension. Respiratory distress syndrome results from insufficient surfactant in the alveolae of the lungs. The lungs of vertebrates contain surfactant, a complex mixture of lipids and protein that causes surface tension to rise during lung inflation and decrease during lung deflation. During lung deflation, surfactant decreases such that there are no surface forces that would otherwise promote alveolar collapse. Aerated alveoli that have not collapsed during expiration permit continuous oxygen and carbon dioxide transport between blood and alveolar gas and require much less force to inflate during the subsequent inspiration. During inflation, lung surfactant increases surface tension as the alveolar surface area increases. A rising surface tension in expanding alveoli opposes over-inflation in those airspaces and tends to divert inspired air to less well-aerated alveoli, thereby facilitating even lung aeration.

Respiratory distress syndrome is particularly prevalent among premature infants. Lung surfactant is normally synthesized at a very low rate until the last six weeks of fetal life. Human infants born more than six weeks before the normal term of a pregnancy have a high risk of being born with inadequate amounts of lung surfactant and inadequate rates of surfactant synthesis. The more prematurely an infant is born, the more severe the surfactant deficiency is likely to be. Severe surfactant deficiency can lead to respiratory failure within a few minutes or hours of birth. The surfactant deficiency produces progressive collapse of alveoli (atelectasis) because of the decreasing ability of the lung to expand despite maximum inspiratory effort. As a result, inadequate amounts of oxygen reach the infant's blood. RDS can occur in adults as well, typically as a consequence of failure in surfactant biosynthesis.

Lung tissue of premature infants shows high activity of the hedgehog signaling pathway. Inhibition of this pathway using hedgehog antagonists increases the formation of lamellated bodies and increases the expression of genes involved in surfactant biosynthesis. Lamellar bodies are subcellular structures associated with surfactant biosynthesis. For these reasons, treatment of premature infants with a hedgehog antagonist should stimulate surfactant biosynthesis and ameliorate RDS. In cases where adult RDS is associated with hedgehog pathway activation, treatment with hedgehog antagonists should also be effective.

It is further contemplated that the use of hedgehog antagonists may be specifically targeted to disorders where the affected tissue and/or cells evince high hedgehog pathway activation. Expression of gli genes is activated by the hedgehog signaling pathway, including gli-1, gli-2 and gli-3. gli-1 expression is most consistently correlated with hedgehog signaling activity across a wide range of tissues and disorders, while gli-3 is somewhat less so. The gli genes encode transcription factors that activate expression of many genes needed to elicit the full effects of hedgehog signaling. However, the Gli-3 transcription factor can also act as a repressor of hedgehog effector genes, and therefore, expression of gli-3 can cause a decreased effect of the hedgehog signaling pathway. Whether Gli-3 acts as a transcriptional activator or repressor depends on post-translational events, and therefore it is expected that methods for detecting the activating form (versus the repressing form) of Gli-3 protein would also be a reliable measure of hedgehog pathway activation. gli-2 gene expression is expected to provide a reliable marker for hedgehog pathway activation. The gli-1 gene is strongly expressed in a wide array of cancers, hyperplasias and immature lungs, and serves as a marker for the relative activation of the hedgehog pathway. In addition, tissues, such as immature lung, that have high gli gene expression are strongly affected by hedgehog inhibitors. Accordingly, it is contemplated that the detection of gli gene expression may be used as a powerful predictive tool to identify tissues and disorders that will particularly benefit from treatment with a hedgehog antagonist.

In preferred embodiments, gli-1 expression levels are detected, either by direct detection of the transcript or by detection of protein levels or activity. Transcripts may be detected using any of a wide range of techniques that depend primarily on hybridization of probes to the gli-1 transcripts or to cDNAs synthesized therefrom. Well known techniques include Northern blotting, reverse-transcriptase PCR and microarray analysis of transcript levels. Methods for detecting Gli protein levels include Western blotting, immunoprecipitation, two-dimensional polyacrylamide gel electrophoresis (2D SDS-PAGE) (preferably compared against a standard wherein the position of the Gli proteins has been determined), and mass spectroscopy. Mass spectroscopy may be coupled with a series of purification steps to allow high-throughput identification of many different protein levels in a particular sample. Mass spectroscopy and 2D SDS-PAGE can also be used to identify post-transcriptional modifications to proteins including proteolytic events, ubiquitination, phosphorylation, lipid modification etc. Gli activity may also be assessed by analyzing binding to substrate DNA or in vitro transcriptional activation of target promoters. Gel shift assays, DNA footprinting assays and DNA-protein crosslinking assays are all methods that may be used to assess the presence of a protein capable of binding to Gli binding sites on DNA. (*J Mol Med* 1999 June; 77(6):459-68; *Cell* 2000 February 18; 100(4):423-34; *Development* 2000; 127(19):4293-4301)

In preferred embodiments, gli transcript levels are measured and diseased or disordered tissues showing abnormally high gli levels are treated with a hedgehog antagonist. Premature lung tissue, lung cancers (e.g., adenocarcinomas, broncho-alveolar adenocarcinomas, small cell carcinomas), breast cancers (e.g., inferior ductal carcinomas, inferior lobular carcinomas, tubular carcinomas), prostate cancers (e.g., adenocarcinomas), and benign prostatic hyperplasias all show strongly elevated gli-1 expression levels in certain cases. Accordingly, gli-1 expression levels are a powerful diagnostic device to determine which of these tissues should be treated with a hedgehog antagonist. In addition, there is substantial correlative evidence that cancers of urothelial cells (e.g., bladder cancer, other urogenital cancers) will also have elevated gli-1 levels in certain cases. For example, it is known that loss of heterozygosity on chromosome 9q22 is common in bladder cancers. The ptc-1 gene is located at this position and ptc-1 loss of function is probably a partial cause of hyperproliferation, as in many other cancer types. Accordingly, such cancers would also show high gli expression and would be particularly amenable to treatment with a hedgehog antagonist.

Expression of ptc-1 and ptc-2 is also activated by the hedgehog signaling pathway, but these genes are inferior to the gli genes as markers of hedgehog pathway activation. In certain tissues only one of ptc-1 or ptc-2 is expressed although the hedgehog pathway is highly active. For example, in testicular development, indian hedgehog plays an important role and the hedgehog pathway is activated, but only ptc-2 is expressed. Accordingly, these genes are individually unreliable as markers for hedgehog pathway activation, although simultaneous measurement of both genes is contemplated as a useful indicator for tissues to be treated with a hedgehog antagonist.

It is anticipated that any degree of gli overexpression may be useful in determining that a hedgehog antagonist will be an effective therapeutic. In preferred embodiments, gli should be expressed at a level at least twice as high as normal. In particularly preferred embodiments, expression is four, six, eight or ten times as high as normal.

For instance, it is contemplated by the invention that, in light of the findings of an apparently broad involvement of hedgehog, ptc, and smoothened in the formation of ordered spatial arrangements of differentiated tissues in vertebrates, the subject method could be used as part of a process for generating and/or maintaining an array of different vertebrate tissue both in vitro and in vivo. The hedgehog antagonist, whether inductive or anti-inductive with respect to proliferation or differentiation of a given tissue, can be, as appropriate, any of the preparations described above.

For example, the present method is applicable to cell culture techniques wherein it is desirable to reduce the level of hedgehog signaling. In vitro neuronal culture systems have proved to be fundamental and indispensable tools for the study of neural development, as well as the identification of neurotrophic factors such as nerve growth factor (NGF), ciliary trophic factors (CNTF), and brain derived neurotrophic factor (BDNF). One use of the present method may be in cultures of neuronal stem cells, such as in the use of such cultures for the generation of new neurons and glia. In such embodiments of the subject method, the cultured cells can be contacted with a hedgehog antagonist of the present invention in order to alter the rate of proliferation of neuronal stem cells in the culture and/or alter the rate of differentiation, or to maintain the integrity of a culture of certain terminally differentiated neuronal cells. In an exemplary embodiment, the subject method can be used to culture, for example, sensory neurons or, alternatively, motor neurons. Such neuronal cultures can be used as convenient assay systems as well as sources of implantable cells for therapeutic treatments.

To further illustrate other uses of the subject hedgehog antagonists, it is noted that intracerebral grafting has emerged as an additional approach to central nervous system therapies. For example, one approach to repairing damaged brain tissues involves the transplantation of cells from fetal or neonatal animals into the adult brain (Dunnett et al. (1987) *J Exp Biol* 123:265-289; and Freund et al. (1985) *J Neurosci* 5:603-616). Fetal neurons from a variety of brain regions can be successfully incorporated into the adult brain, and such grafts can alleviate behavioral defects. For example, movement disorder induced by lesions of dopaminergic projections to the basal ganglia can be prevented by grafts of embryonic dopaminergic neurons. Complex cognitive functions that are impaired after lesions of the neocortex can also be partially restored by grafts of embryonic cortical cells. The subject method can be used to regulate the growth state in the culture, or where fetal tissue is used, especially neuronal stem cells, can be used to regulate the rate of differentiation of the stem cells.

Stem cells useful in the present invention are generally known. For example, several neural crest cells have been identified, some of which are multipotent and likely represent uncommitted neural crest cells, and others of which can generate only one type of cell, such as sensory neurons, and likely represent committed progenitor cells. The role of hedgehog antagonists employed in the present method to culture such stem cells can be to regulate differentiation of the uncommitted progenitor, or to regulate further restriction of the developmental fate of a committed progenitor cell towards becoming a terminally differentiated neuronal cell. For example, the present method can be used in vitro to regulate the differentiation of neural crest cells into glial cells, schwann cells, chromaffin cells, cholinergic sympathetic or parasympathetic neurons, as well as peptidergic and serotonergic neurons. The hedgehog antagonists can be used alone, or can be used in combination with other neurotrophic factors that act to more particularly enhance a particular differentiation fate of the neuronal progenitor cell.

In addition to the implantation of cells cultured in the presence of the subject hedgehog antagonists, yet another aspect of the present invention concerns the therapeutic application of a hedgehog antagonist to regulate the growth state of neurons and other neuronal cells in both the central nervous system and the peripheral nervous system. The ability of ptc, hedgehog, and smoothened to regulate neuronal differentiation during development of the nervous system and also presumably in the adult state indicates that, in certain instances, the subject hedgehog antagonists can be expected to facilitate control of adult neurons with regard to maintenance, functional performance, and aging of normal cells; repair and regeneration processes in chemically or mechanically lesioned cells; and treatment of degeneration in certain pathological conditions. In light of this understanding, the present invention specifically contemplates applications of the subject method to the treatment protocol of (prevention and/or reduction of the severity of) neurological conditions deriving from: (i) acute, subacute, or chronic injury to the nervous system, including traumatic injury, chemical injury, vascular injury and deficits (such as the ischemia resulting from stroke), together with infectious/inflammatory and tumor-induced injury; (ii) aging of the nervous system including Alzheimer's disease; (iii) chronic neurodegenerative diseases of the nervous system, including Parkinson's disease, Huntington's chorea, amyotrophic lateral sclerosis and the like, as well as spinocerebellar degenerations; and (iv) chronic immunological diseases of the nervous system or affecting the nervous system, including multiple sclerosis.

As appropriate, the subject method can also be used in generating nerve prostheses for the repair of central and peripheral nerve damage. In particular, where a crushed or severed axon is intubulated by use of a prosthetic device, hedgehog antagonists can be added to the prosthetic device to regulate the rate of growth and regeneration of the dendritic processes. Exemplary nerve guidance channels are described in U.S. Pat. Nos. 5,092,871 and 4,955,892.

In another embodiment, the subject method can be used in the treatment of neoplastic or hyperplastic transformations such as may occur in the central nervous system. For instance, the hedgehog antagonists can be utilized to cause such transformed cells to become either post-mitotic or apoptotic. The present method may, therefore, be used as part of a treatment for, e.g., malignant gliomas, meningiomas, medulloblastomas, neuroectodermal tumors, and ependymomas.

In a preferred embodiment, the subject method can be used as part of a treatment regimen for malignant medulloblastoma and other primary CNS malignant neuroectodermal tumors.

In certain embodiments, the subject method is used as part of treatment program for medulloblastoma. Medulloblastoma, a primary brain tumor, is the most common brain tumor in children. A medulloblastoma is a primitive neuroectodermal tumor arising in the posterior fossa. They account for approximately 25% of all pediatric brain tumors (Miller). Histologically, they are small round cell tumors commonly arranged in true rosettes, but may display some differentiation to astrocytes, ependymal cells or neurons (Rorke; Kleihues). PNET's may arise in other areas of the brain including the pineal gland (pineoblastoma) and cerebrum. Those arising in the supratentorial region generally fare worse than their PF counterparts.

Medulloblastoma/PNET's are known to recur anywhere in the CNS after resection, and can even metastasize to bone.

Pretreatment evaluation should therefore include an examination of the spinal cord to exclude the possibility of "dropped metastases". Gadolinium-enhanced MRI has largely replaced myelography for this purpose, and CSF cytology is obtained postoperatively as a routine procedure.

In other embodiments, the subject method is used as part of treatment program for ependymomas. Ependymomas account for approximately 10% of the pediatric brain tumors in children. Grossly, they are tumors that arise from the ependymal lining of the ventricles and microscopically form rosettes, canals, and perivascular rosettes. In the CHOP series of 51 children reported with ependymomas, 3/4 were histologically benign. Approximately 2/3 arose from the region of the 4th ventricle. One third presented in the supratentorial region. Age at presentation peaks between birth and 4 years, as demonstrated by SEER data as well as data from CHOP. The median age is about 5 years. Because so many children with this disease are babies, they often require multimodal therapy.

Yet another aspect of the present invention concerns the observation in the art that ptc, hedgehog, and/or smoothened are involved in morphogenic signals involved in other vertebrate organogenic pathways in addition to neuronal differentiation as described above, having apparent roles in other endodermal patterning, as well as both mesodermal and endodermal differentiation processes. Thus, it is contemplated by the invention that compositions comprising hedgehog antagonists can also be utilized for both cell culture and therapeutic methods involving generation and maintenance of non-neuronal tissue.

In one embodiment, the present invention makes use of the discovery that ptc, hedgehog, and smoothened are apparently involved in controlling the development of stem cells responsible for formation of the digestive tract, liver, lungs, and other organs which derive from the primitive gut. Shh serves as an inductive signal from the endoderm to the mesoderm, which is critical to gut morphogenesis. Therefore, for example, hedgehog antagonists of the instant method can be employed for regulating the development and maintenance of an artificial liver that can have multiple metabolic functions of a normal liver. In an exemplary embodiment, the subject method can be used to regulate the proliferation and differentiation of digestive tube stem cells to form hepatocyte cultures which can be used to populate extracellular matrices, or which can be encapsulated in biocompatible polymers, to form both implantable and extracorporeal artificial livers.

In another embodiment, therapeutic compositions of hedgehog antagonists can be utilized in conjunction with transplantation of such artificial livers, as well as embryonic liver structures, to regulate uptake of intraperitoneal implantation, vascularization, and in vivo differentiation and maintenance of the engrafted liver tissue.

In yet another embodiment, the subject method can be employed therapeutically to regulate such organs after physical, chemical or pathological insult. For instance, therapeutic compositions comprising hedgehog antagonists can be utilized in liver repair subsequent to a partial hepatectomy.

The generation of the pancreas and small intestine from the embryonic gut depends on intercellular signalling between the endodermal and mesodermal cells of the gut. In particular, the differentiation of intestinal mesoderm into smooth muscle has been suggested to depend on signals from adjacent endodermal cells. One candidate mediator of endodermally derived signals in the embryonic hindgut is Sonic hedgehog. See, for example, Apelqvist et al. (1997) *Curr Biol* 7:801-4. The Shh gene is expressed throughout the embryonic gut endoderm with the exception of the pancreatic bud endoderm, which instead expresses high levels of the homeodomain protein Ipf1/Pdx1 (insulin promoter factor 1/pancreatic and duodenal homeobox 1), an essential regulator of early pancreatic development. Apelqvist et al., supra, have examined whether the differential expression of Shh in the embryonic gut tube controls the differentiation of the surrounding mesoderm into specialised mesoderm derivatives of the small intestine and pancreas. To test this, they used the promoter of the Ipf1/Pdx1 gene to selectively express Shh in the developing pancreatic epithelium. In Ipf1/Pdx1-Shh transgenic mice, the pancreatic mesoderm developed into smooth muscle and interstitial cells of Cajal, characteristic of the intestine, rather than into pancreatic mesenchyme and spleen. Also, pancreatic explants exposed to Shh underwent a similar program of intestinal differentiation. These results provide evidence that the differential expression of endodermally derived Shh controls the fate of adjacent mesoderm at different regions of the gut tube.

In the context of the present invention, it is contemplated therefore that the subject hedgehog antagonists can be used to control or regulate the proliferation and/or differentiation of pancreatic tissue both in vivo and in vitro.

In another embodiment, hedgehog antagonists are used to generate endodermal tissue from non-endodermal stem cells including mesenchymal stem cells and stem cells derived from mesodermal tissues. Exemplary mesodermal tissues from which stem cells may be isolated include skeletal muscle, cardiac muscle, kidney, bone, cartilage, and fat.

There are a wide variety of pathological cell proliferative and differentiative conditions for which the inhibitors of the present invention may provide therapeutic benefits, with the general strategy being, for example, the correction of aberrant insulin expression, or modulation of differentiation. More generally, however, the present invention relates to a method of inducing and/or maintaining a differentiated state, enhancing survival and/or affecting proliferation of pancreatic cells, by contacting the cells with the subject inhibitors. For instance, it is contemplated by the invention that, in light of the apparent involvement of ptc, hedgehog, and smoothened in the formation of ordered spatial arrangements of pancreatic tissues, the subject method could be used as part of a technique to generate and/or maintain such tissue both in vitro and in vivo. For instance, modulation of the function of hedgehog can be employed in both cell culture and therapeutic methods involving generation and maintenance of β-cells and possibly also for non-pancreatic tissue, such as in controlling the development and maintenance of tissue from the digestive tract, spleen, lungs, urogenital organs (e.g., bladder), and other organs which derive from the primitive gut.

In an exemplary embodiment, the present method can be used in the treatment of hyperplastic and neoplastic disorders effecting pancreatic tissue, particularly those characterized by aberrant proliferation of pancreatic cells. For instance, pancreatic cancers are marked by abnormal proliferation of pancreatic cells, which can result in alterations of insulin secretory capacity of the pancreas. For instance, certain pancreatic hyperplasias, such as pancreatic carcinomas, can result in hypoinsulinemia due to dysfunction of β-cells or decreased islet cell mass.

Moreover, manipulation of hedgehog signaling properties at different points may be useful as part of a strategy for reshaping/repairing pancreatic tissue both in vivo and in vitro. In one embodiment, the present invention makes use of the apparent involvement of ptc, hedgehog, and smoothened in regulating the development of pancreatic tissue. In general, the subject method can be employed therapeutically to regulate the pancreas after physical, chemical or pathological insult. In yet another embodiment, the subject method can be applied to cell culture techniques, and in particular, may be employed to enhance the initial generation of prosthetic pancreatic tissue devices. Manipulation of proliferation and differentiation of pancreatic tissue, for example, by altering hedgehog activity, can provide a means for more carefully controlling the characteristics of a cultured tissue. In an exemplary embodiment, the subject method can be used to augment production of prosthetic devices which require β-islet cells, such as may be used in the encapsulation devices described in, for example, the Aebischer et al. U.S. Pat. No. 4,892,538, the Aebischer et al. U.S. Pat. No. 5,106,627, the Lim U.S. Pat. No. 4,391,909, and the Sefton U.S. Pat. No. 4,353,888. Early progenitor cells to the pancreatic islets are multipotential, and apparently coactivate all the islet-specific genes from the time they first appear. As development proceeds, expression of islet-specific hormones, such as insulin, becomes restricted to the pattern of expression characteristic of mature islet cells. The phenotype of mature islet cells, however, is not stable in culture, as reappearance of embryonal traits in mature β-cells can be observed. By utilizing the subject hedgehog antagonists, the differentiation path or proliferative index of the cells can be regulated.

Furthermore, manipulation of the differentiative state of pancreatic tissue can be utilized in conjunction with transplantation of artificial pancreas. For instance, manipulation of hedgehog function to affect tissue differentiation can be utilized as a means of maintaining graft viability.

Bellusci et al. (1997) *Development* 124:53 report that Sonic hedgehog regulates lung mesenchymal cell proliferation in vivo. Accordingly, the present method can be used to regulate regeneration of lung tissue, e.g., in the treatment of emphysema.

Fujita et al. (1997) *Biochem Biophys Res Commun* 238:658 reported that Sonic hedgehog is expressed in human lung squamous carcinoma and adenocarcinoma cells. The expression of Sonic hedgehog was also detected in the human lung squamous carcinoma tissues, but not in the normal lung tissue of the same patient. They also observed that Sonic hedgehog stimulates the incorporation of BrdU into the carcinoma cells and stimulates their cell growth, while anti-Shh-N inhibited their cell growth. These results suggest that a ptc, hedgehog, and/or smoothened is involved in the cell growth of such transformed lung tissue and therefore indicates that the subject method can be used as part of a treatment of lung carcinoma and adenocarcinomas, and other proliferative disorders involving the lung epithelia.

Many other tumors may, based on evidence such as involvement of the hedgehog pathway in these tumors, or detected expression of hedgehog or its receptor in these tissues during development, be affected by treatment with the subject compounds. Such tumors include, but are by no means limited to, tumors related to Gorlin's syndrome (e.g., medulloblastoma, meningioma, etc.), tumors evidenced in ptc knock-out mice (e.g., hemangioma, rhabdomyosarcoma, etc.), tumors resulting from gli-1 amplification (e.g., glioblastoma, sarcoma, etc.), tumors connected with TRC8, a ptc homolog (e.g., renal carcinoma, thyroid carcinoma, etc.), Ext-1-related tumors (e.g., bone cancer, etc.), Shh-induced tumors (e.g., lung cancer, chondrosarcomas, etc.), and other tumors (e.g., breast cancer, urogenital cancer (e.g., kidney, bladder, ureter, prostate, etc.), adrenal cancer, gastrointestinal cancer (e.g., stomach, intestine, etc.), etc.).

Exemplary forms of cancer which may be treated by the subject methods include, but are not limited to, prostate cancer, bladder cancer, lung cancer (including either small cell or non-small cell cancer), colon cancer, kidney cancer, liver cancer, breast cancer, cervical cancer, endometrial or other uterine cancer, ovarian cancer, testicular cancer, cancer of the penis, cancer of the vagina, cancer of the urethra, gall bladder cancer, esophageal cancer, or pancreatic cancer. Additional exemplary forms of cancer which may be treated by the subject methods include, but are not limited to, cancer of skeletal or smooth muscle, stomach cancer, cancer of the small intestine, cancer of the salivary gland, anal cancer, rectal cancer, tyroid cancer, parathyroid cancer, pituitary cancer, and nasopharyngeal cancer. Further exemplary forms of cancer which can be treated with the hedgehog antagonists of the present invention include cancers comprising hedgehog expressing cells. Still further exemplary forms of cancer which can be treated with the hedgehog antagonists of the present invention include cancers comprising gli expressing cells. In one embodiment, the cancer is not characterized by a mutation in patched-1.

In still another embodiment of the present invention, compositions comprising hedgehog antagonists can be used in the in vitro generation of skeletal tissue, such as from skeletogenic stem cells, as well as the in vivo treatment of skeletal tissue deficiencies. The present invention particularly contemplates the use of hedgehog antagonists to regulate the rate of chondrogenesis and/or osteogenesis. By "skeletal tissue deficiency", it is meant a deficiency in bone or other skeletal connective tissue at any site where it is desired to restore the bone or connective tissue, no matter how the deficiency originated, e.g., whether as a result of surgical intervention, removal of tumor, ulceration, implant, fracture, or other traumatic or degenerative conditions.

For instance, the method of the present invention can be used as part of a regimen for restoring cartilage function to a connective tissue. Such methods are useful in, for example, the repair of defects or lesions in cartilage tissue which is the result of degenerative wear such as that which results in arthritis, as well as other mechanical derangements which may be caused by trauma to the tissue, such as a displacement of torn meniscus tissue, meniscectomy, a Taxation of a joint by a torn ligament, malignment of joints, bone fracture, or by hereditary disease. The present reparative method is also useful for remodeling cartilage matrix, such as in plastic or reconstructive surgery, as well as periodontal surgery. The present method may also be applied to improving a previous reparative procedure, for example, following surgical repair of a meniscus, ligament, or cartilage. Furthermore, it may prevent the onset or exacerbation of degenerative disease if applied early enough after trauma.

In one embodiment of the present invention, the subject method comprises treating the afflicted connective tissue with a therapeutically sufficient amount of a hedgehog antagonist, particularly an antagonist selective for Indian hedgehog signal transduction, to regulate a cartilage repair response in the connective tissue by managing the rate of differentiation and/or proliferation of chondrocytes embedded in the tissue. Such connective tissues as articular cartilage, interarticular cartilage (menisci), costal cartilage (connecting the true ribs and the sternum), ligaments, and tendons are particularly amenable to treatment in reconstructive and/or regenerative therapies using the subject method. As used herein, regenerative therapies include treatment of degenerative states which have progressed to the point of which impairment of the tissue is obviously manifest, as well as preventive treatments of tissue where degeneration is in its earliest stages or imminent.

In an illustrative embodiment, the subject method can be used as part of a therapeutic intervention in the treatment of cartilage of a diarthroidal joint, such as a knee, an ankle, an elbow, a hip, a wrist, a knuckle of either a finger or toe, or a tempomandibular joint. The treatment can be directed to the meniscus of the joint, to the articular cartilage of the joint, or both. To further illustrate, the subject method can be used to treat a degenerative disorder of a knee, such as which might be the result of traumatic injury (e.g., a sports injury or excessive wear) or osteoarthritis. The subject antagonists may be administered as an injection into the joint with, for instance, an arthroscopic needle. In some instances, the injected agent can be in the form of a hydrogel or other slow release vehicle described above in order to permit a more extended and regular contact of the agent with the treated tissue.

The present invention further contemplates the use of the subject method in the field of cartilage transplantation and prosthetic device therapies. However, problems arise, for instance, because the characteristics of cartilage and fibrocartilage varies between different tissue: such as between articular, meniscal cartilage, ligaments, and tendons, between the two ends of the same ligament or tendon, and between the superficial and deep parts of the tissue. The zonal arrangement of these tissues may reflect a gradual change in mechanical properties, and failure occurs when implanted tissue, which has not differentiated under those conditions, lacks the ability to appropriately respond. For instance, when meniscal cartilage is used to repair anterior cruciate ligaments, the tissue undergoes a metaplasia to pure fibrous tissue. By regulating the rate of chondrogenesis, the subject method can be used to particularly address this problem, by helping to adaptively control the implanted cells in the new environment and effectively resemble hypertrophic chondrocytes of an earlier developmental stage of the tissue.

In similar fashion, the subject method can be applied to enhancing both the generation of prosthetic cartilage devices and to their implantation. The need for improved treatment has motivated research aimed at creating new cartilage that is based on collagen-glycosaminoglycan templates (Stone et al. (1990) *Clin Orthop Relat Red* 252:129), isolated chondrocytes (Grande et al. (1989) *J Orthop Res* 7:208; and Takigawa et al. (1987) *Bone Miner* 2:449), and chondrocytes attached to natural or synthetic polymers (Walitani et al. (1989) *J Bone Jt Surg* 71B:74; Vacanti et al. (1991) *Plast Reconstr Surg* 88:753; von Schroeder et al. (1991) *J Biomed Mater Res* 25:329; Freed et al. (1993) *J Biomed Mater Res* 27:11; and the Vacanti et al. U.S. Pat. No. 5,041,138). For example, chondrocytes can be grown in culture on biodegradable, biocompatible highly porous scaffolds formed from polymers such as polyglycolic acid, polylactic acid, agarose gel, or other polymers that degrade over time as function of hydrolysis of the polymer backbone into innocuous monomers. The matrices are designed to allow adequate nutrient and gas exchange to the cells until engraftment occurs. The cells can be cultured in vitro until adequate cell volume and density has developed for the cells to be implanted. One advantage of the matrices is that they can be cast or molded into a desired shape on an individual basis, so that the final product closely resembles the patient's own ear or nose (by way of example), or flexible matrices can be used which allow for manipulation at the time of implantation, as in a joint.

In one embodiment of the subject method, the implants are contacted with a hedgehog antagonist during certain stages of the culturing process in order to manage the rate of differentiation of chondrocytes and the formation of hypertrophic chrondrocytes in the culture.

In another embodiment, the implanted device is treated with a hedgehog antagonist in order to actively remodel the implanted matrix and to make it more suitable for its intended function. As set out above with respect to tissue transplants, the artificial transplants suffer from the same deficiency of not being derived in a setting which is comparable to the actual mechanical environment in which the matrix is implanted. The ability to regulate the chondrocytes in the matrix by the subject method can allow the implant to acquire characteristics similar to the tissue for which it is intended to replace.

In yet another embodiment, the subject method is used to enhance attachment of prosthetic devices. To illustrate, the subject method can be used in the implantation of a periodontal prosthesis, wherein the treatment of the surrounding connective tissue stimulates formation of periodontal ligament about the prosthesis.

In still further embodiments, the subject method can be employed as part of a regimen for the generation of bone (osteogenesis) at a site in the animal where such skeletal tissue is deficient. India hedgehog is particularly associated with the hypertrophic chondrocytes that are ultimately replaced by osteoblasts. For instance, administration of a hedgehog antagonists of the present invention can be employed as part of a method for regulating the rate of bone loss in a subject. For example, preparations comprising hedgehog antagonists can be employed, for example, to control endochondral ossification in the formation of a "model" for ossification.

In yet another embodiment of the present invention, a hedgehog antagonist can be used to regulate spermatogenesis. The hedgehog proteins, particularly Dhh, have been shown to be involved in the differentiation and/or proliferation and maintenance of testicular germ cells. Dhh expression is initiated in Sertoli cell precursors shortly after the activation of Sry (testicular determining gene) and persists in the testis into the adult. Males are viable but infertile, owing to a complete absence of mature sperm. Examination of the developing testis in different genetic backgrounds suggests that Dhh regulates both early and late stages of spermatogenesis. Bitgood et al. (1996) *Curr Biol* 6:298. In a preferred embodiment, the hedgehog antagonist can be used as a contraceptive. In similar fashion, hedgehog antagonists of the subject method are potentially useful for modulating normal ovarian function.

The subject method also has wide applicability to the treatment or prophylaxis of disorders afflicting epithelial tissue, as well as in cosmetic uses. In general, the method can be characterized as including a step of administering to an animal an amount of a hedgehog antagonist effective to alter the growth state of a treated epithelial tissue. The mode of administration and dosage regimens will vary depending on the epithelial tissue(s) that is to be treated. For example, topical formulations will be preferred where the treated tissue is epidermal tissue, such as dermal or mucosal tissues.

A method that "promotes the healing of a wound" results in the wound healing more quickly as a result of the treatment than a similar wound heals in the absence of the treatment. "Promotion of wound healing" can also mean that the method regulates the proliferation and/or growth of, inter alia, keratinocytes, or that the wound heals with less scarring, less wound contraction, less collagen deposition and more superficial surface area. In certain instances, "promotion of wound healing" can also mean that certain methods of wound healing have improved success rates, (e.g., the take rates of skin grafts,) when used together with the method of the present invention.

Despite significant progress in reconstructive surgical techniques, scarring can be an important obstacle in regaining normal function and appearance of healed skin. This is particularly true when pathologic scarring such as keloids or hypertrophic scars of the hands or face causes functional disability or physical deformity. In the severest circumstances, such scarring may precipitate psychosocial distress and a life of economic deprivation. Wound repair includes the stages of hemostasis, inflammation, proliferation, and remodeling. The proliferative stage involves multiplication of fibroblasts and endothelial and epithelial cells. Through the use of the subject method, the rate of proliferation of epithelial cells in and proximal to the wound can be controlled in order to accelerate closure of the wound and/or minimize the formation of scar tissue.

The present treatment can also be effective as part of a therapeutic regimen for treating oral and paraoral ulcers, e.g., resulting from radiation and/or chemotherapy. Such ulcers commonly develop within days after chemotherapy or radiation therapy. These ulcers usually begin as small, painful irregularly shaped lesions usually covered by a delicate gray necrotic membrane and surrounded by inflammatory tissue. In many instances, lack of treatment results in proliferation of tissue around the periphery of the lesion on an inflammatory basis. For instance, the epithelium bordering the ulcer usually demonstrates proliferative activity, resulting in loss of continuity of surface epithelium. These lesions, because of their size and loss of epithelial integrity, dispose the body to potential secondary infection. Routine ingestion of food and water becomes a very painful event and, if the ulcers proliferate throughout the alimentary canal, diarrhea usually is evident with all its complicating factors. According to the present invention, a treatment for such ulcers that includes application of a hedgehog antagonist can reduce the abnormal proliferation and differentiation of the affected epithelium, helping to reduce the severity of subsequent inflammatory events.

The subject method and compositions can also be used to treat wounds resulting from dermatological diseases, such as lesions resulting from autoimmune disorders such as psoriasis. Atopic dermitits refers to skin trauma resulting from allergies associated with an immune response caused by allergens such as pollens, foods, dander, insect venoms and plant toxins.

In other embodiments, antiproliferative preparations of hedgehog antagonists can be used to inhibit lens epithelial cell proliferation to prevent post-operative complications of extracapsular cataract extraction. Cataract is an intractable eye disease and various studies on a treatment of cataract have been made. But at present, the treatment of cataract is attained by surgical operations. Cataract surgery has been applied for a long time and various operative methods have been examined. Extracapsular lens extraction has become the method of choice for removing cataracts. The major medical advantages of this technique over intracapsular extraction are lower incidence of aphakic cystoid macular edema and retinal detachment. Extracapsular extraction is also required for implantation of posterior chamber-type intraocular lenses, which are now considered to be the lenses of choice in most cases.

However, a disadvantage of extracapsular cataract extraction is the high incidence of posterior lens capsule opacification, often called after-cataract, which can occur in up to 50% of cases within three years after surgery. After-cataract is caused by proliferation of equatorial and anterior capsule lens epithelial cells that remain after extracapsular lens extraction. These cells proliferate to cause Sommerling rings, and along with fibroblasts, which also deposit and occur on the posterior capsule, cause opacification of the posterior capsule, which interferes with vision. Prevention of after-cataract would be preferable to treatment. To inhibit secondary cataract formation, the subject method provides a means for inhibiting proliferation of the remaining lens epithelial cells. For example, such cells can be induced to remain quiescent by instilling a solution containing a hedgehog antagonist preparation into the anterior chamber of the eye after lens removal. Furthermore, the solution can be osmotically balanced to provide minimal effective dosage when instilled into the anterior chamber of the eye, thereby inhibiting subcapsular epithelial growth with some specificity.

The subject method can also be used in the treatment of comeopathies marked by corneal epithelial cell proliferation, as for example in ocular epithelial disorders such as epithelial downgrowth or squamous cell carcinomas of the ocular surface.

Levine et al. (1997) *J Neurosci* 17:6277 show that hedgehog proteins can regulate mitogenesis and photoreceptor differentiation in the vertebrate retina, and Ihh is a candidate factor from the pigmented epithelium to promote retinal progenitor proliferation and photoreceptor differentiation. Likewise, Jensen et al. (1997) *Development* 124:363 demonstrated that treatment of cultures of perinatal mouse retinal cells with the amino-terminal fragment of Sonic hedgehog protein results in an increase in the proportion of cells that incorporate bromodeoxyuridine, in total cell numbers, and in rod photoreceptors, amacrine cells and Muller glial cells, suggesting that Sonic hedgehog promotes the proliferation of retinal precursor cells. Thus, the subject method can be used in the treatment of proliferative diseases of retinal cells and regulate photoreceptor differentiation.

Yet another aspect of the present invention relates to the use of the subject method to control hair growth. Hair is basically composed of keratin, a tough and insoluble protein; its chief strength lies in its disulfide bond of cystine. Each individual hair comprises a cylindrical shaft and a root, and is contained in a follicle, a flask-like depression in the skin. The bottom of the follicle contains a finger-like projection termed the papilla, which consists of connective tissue from which hair grows, and through which blood vessels supply the cells with nourishment. The shaft is the part that extends outwards from the skin surface, whilst the root has been described as the buried part of the hair. The base of the root expands into the hair bulb, which rests upon the papilla. Cells from which the hair is produced grow in the bulb of the follicle; they are extruded in the form of fibers as the cells proliferate in the follicle. Hair "growth" refers to the formation and elongation of the hair fiber by the dividing cells.

As is well known in the art, the common hair cycle is divided into three stages: anagen, catagen and telogen. During the active phase (anagen), the epidermal stem cells of the dermal papilla divide rapidly. Daughter cells move upward and differentiate to form the concentric layers of the hair itself. The transitional stage, catagen, is marked by the cessation of mitosis of the stem cells in the follicle. The resting stage is known as telogen, where the hair is retained within the scalp for several weeks before an emerging new hair developing below it dislodges the telogen-phase shaft from its follicle. From this model it has become clear that the larger the pool of dividing stem cells that differentiate into hair cells, the more hair growth occurs. Accordingly, methods for increasing or reducing hair growth can be carried out by potentiating or inhibiting, respectively, the proliferation of these stem cells.

In certain embodiments, the subject method can be employed as a way of reducing the growth of human hair as opposed to its conventional removal by cutting, shaving, or depilation. For instance, the present method can be used in the treatment of trichosis characterized by abnormally rapid or dense growth of hair, e.g., hypertrichosis. In an exemplary embodiment, hedgehog antagonists can be used to manage hirsutism, a disorder marked by abnormal hairiness. The subject method can also provide a process for extending the duration of depilation.

Moreover, because a hedgehog antagonist will often be cytostatic to epithelial cells, rather than cytotoxic, such agents can be used to protect hair follicle cells from cytotoxic agents that require progression into S-phase of the cell-cycle for efficacy, e.g., radiation-induced death. Treatment by the subject method can provide protection by causing the hair follicle cells to become quiescent, e.g., by inhibiting the cells from entering S phase, and thereby preventing the follicle cells from undergoing mitotic catastrophe or programmed cell death. For instance, hedgehog antagonists can be used for patients undergoing chemo- or radiation-therapies that ordinarily result in hair loss. By inhibiting cell-cycle progression during such therapies, the subject treatment can protect hair follicle cells from death, which might otherwise result from activation of cell death programs. After the therapy has concluded, the instant method can also be removed with concomitant relief of the inhibition of follicle cell proliferation.

The subject method can also be used in the treatment of folliculitis, such as folliculitis decalvans, folliculitis ulerythematosa reticulata or keloid folliculitis. For example, a cosmetic preparation of a hedgehog antagonist can be applied topically in the treatment of pseudofolliculitis, a chronic disorder occurring most often in the submandibular region of the neck and associated with shaving, the characteristic lesions of which are erythematous papules and pustules containing buried hairs.

In another aspect of the invention, the subject method can be used to induce differentiation and/or inhibit proliferation of epithelially derived tissue. Such forms of these molecules can provide a basis for differentiation therapy for the treatment of hyperplastic and/or neoplastic conditions involving epithelial tissue. For example, such preparations can be used for the treatment of cutaneous diseases in which there is abnormal proliferation or growth of cells of the skin.

For instance, the pharmaceutical preparations of the invention are intended for the treatment of hyperplastic epidermal conditions, such as keratosis, as well as for the treatment of neoplastic epidermal conditions such as those characterized by a high proliferation rate for various skin cancers, as for example squamous cell carcinoma. The subject method can also be used in the treatment of autoimmune diseases affecting the skin, in particular, of dermatological diseases involving morbid proliferation and/or keratinization of the epidermis, as for example, caused by psoriasis or atopic dermatosis.

Many common diseases of the skin, such as psoriasis, squamous cell carcinoma, keratoacanthoma and actinic keratosis are characterized by localized abnormal proliferation and growth. For example, in psoriasis, which is characterized by scaly, red, elevated plaques on the skin, the keratinocytes are known to proliferate much more rapidly than normal and to differentiate less completely.

In one embodiment, the preparations of the present invention are suitable for the treatment of dermatological ailments linked to keratinization disorders causing abnormal proliferation of skin cells, which disorders may be marked by either inflammatory or non-inflammatory components. To illustrate, therapeutic preparations of a hedgehog antagonist, e.g., which promotes quiescence or differentiation can be used to treat varying forms of psoriasis, be they cutaneous, mucosal or ungual. Psoriasis, as described above, is typically characterized by epidermal keratinocytes that display marked proliferative activation and differentiation along a "regenerative" pathway. Treatment with an antiproliferative embodiment of the subject method can be used to reverse the pathological epidermal activation and can provide a basis for sustained remission of the disease.

A variety of other keratotic lesions are also candidates for treatment with the subject method. Actinic keratoses, for example, are superficial inflammatory premalignant tumors arising on sun-exposed and irradiated skin. The lesions are erythematous to brown with variable scaling. Current therapies include excisional and cryosurgery. These treatments are painful, however, and often produce cosmetically unacceptable scarring. Accordingly, treatment of keratosis, such as actinic keratosis, can include application, preferably topical, of a hedgehog antagonist composition in amounts sufficient to inhibit hyperproliferation of epidermal/epidermoid cells of the lesion.

Acne represents yet another dermatologic ailment which may be treated by the subject method. Acne vulgaris, for instance, is a multifactor disease most commonly occurring in teenagers and young adults, and is characterized by the appearance of inflammatory and noninflammatory lesions on the face and upper trunk. The basic defect which gives rise to acne vulgaris is hypercomification of the duct of a hyperactive sebaceous gland. Hypercomification blocks the normal mobility of skin and follicle microorganisms, and in so doing, stimulates the release of lipases by *Propinobacterium acnes* and *Staphylococcus epidennidis* bacteria and *Pitrosporum ovale*, a yeast. Treatment with an antiproliferative hedgehog antagonist, particularly topical preparations, may be useful for preventing the transitional features of the ducts, e.g., hypercomification, which lead to lesion formation. The subject treatment may further include, for example, antibiotics, retinoids and antiandrogens.

The present invention also provides a method for treating various forms of dermatitis. Dermatitis is a descriptive term referring to poorly demarcated lesions that are either pruritic, erythematous, scaly, blistered, weeping, fissured or crusted. These lesions arise from any of a wide variety of causes. The most common types of dermatitis are atopic, contact and diaper dermatitis. For instance, seborrheic dermatitis is a chronic, usually pruritic, dermatitis with erythema, dry, moist, or greasy scaling, and yellow-crusted patches on various areas, especially the scalp, with exfoliation of an excessive amount of dry scales. The subject method can also be used in the treatment of stasis dermatitis, an often chronic, usually eczematous dermatitis. Actinic dermatitis is dermatitis that due to exposure to actinic radiation such as that from the sun, ultraviolet waves, or x- or gamma-radiation. According to the present invention, the subject method can be used in the treatment and/or prevention of certain symptoms of dermatitis caused by unwanted proliferation of epithelial cells. Such therapies for these various forms of dermatitis can also include topical and systemic corticosteroids, antipruritics, and antibiotics.

Ailments that may be treated by the subject method are disorders specific to non-humans, such as mange.

In still another embodiment, the subject method can be used in the treatment of human cancers, such as tumors of epithelial tissues such as the skin. For example, hedgehog antagonists can be employed in the subject method as part of a treatment for human carcinomas, adenocarcinomas, sarcomas and the like. Exemplary forms of cancer which may be treated by the subject methods include, but are not limited to, prostate cancer, bladder cancer, lung cancer (including either small cell or non-small cell cancer), colon cancer, kidney cancer, liver cancer, breast cancer, cervical cancer, endometrial or other uterine cancer, ovarian cancer, testicular cancer, cancer of the penis, cancer of the vagina, cancer of the urethra, gall bladder cancer, esophageal cancer, or pancreatic cancer. Additional exemplary forms of cancer which may be treated by the subject methods include, but are not limited to, cancer of skeletal or smooth muscle, stomach cancer, cancer of the small intestine, cancer of the salivary gland, anal cancer, rectal cancer, tyroid cancer, parathyroid cancer, pituitary cancer, and nasopharyngeal cancer. Further exemplary forms of cancer which can be treated with the hedgehog antagonists of the present invention include cancers comprising hedgehog expressing cells. Still further exemplary forms of cancer which can be treated with the hedgehog antagonists of the present invention include cancers comprising gli expressing cells. In one embodiment, the cancer is not characterized by a mutation in patched-1.

In another aspect, the present invention provides pharmaceutical preparations comprising hedgehog antagonists. The hedgehog antagonists for use in the subject method may be conveniently formulated for administration with a biologically acceptable medium, such as water, buffered saline, polyol (for example, glycerol, propylene glycol, liquid polyethylene glycol and the like) or suitable mixtures thereof. The optimum concentration of the active ingredient(s) in the chosen medium can be determined empirically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the hedgehog antagonist, its use in the pharmaceutical preparation of the invention is contemplated. Suitable vehicles and their formulation inclusive of other proteins are described, for example, in the book *Remington's Pharmaceutical Sciences* (Remington's Pharmaceutical Sciences. Mack Publishing Company, Easton, Pa., USA 1985). These vehicles include injectable "deposit formulations".

Pharmaceutical formulations of the present invention can also include veterinary compositions, e.g., pharmaceutical preparations of the hedgehog antagonists suitable for veterinary uses, e.g., for the treatment of livestock or domestic animals, e.g., dogs.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a hedgehog antagonist at a particular target site.

The preparations of the present invention may be given orally, parenterally, topically, or rectally. They are, of course, given by forms suitable for each administration route. For example, they are administered in tablets or capsule form, by injection, inhalation, eye lotion, ointment, suppository, controlled release patch, etc. administration by injection, infusion or inhalation; topical by lotion or ointment; and rectal by suppositories. Oral and topical administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracistemally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms such as described below or by other conventional methods known to those of skill in the art.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular hedgehog antagonist employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable and/or sterile carriers and can also be administered in conjunction with other antimicrobial agents such as penicillins, cephalosporins, aminoglycosides and glycopeptides. Conjunctive therapy thus includes sequential, simultaneous and separate administration of the active compound in a way that the therapeutic effects of the first administered one is not entirely disappeared when the subsequent is administered.

V. Pharmacogenomics

The ability to rapidly assess gene expression in patients promises to radically change the means by which a physician selects an appropriate pharmaceutical for treating a particular disease. Gene expression profiles of diseased tissue can be obtained and therapeutic measures can be selected based on the gene expression profile. This methodology is particularly effective when the molecular mechanism of action for a given therapeutic is known. In other words, if an anti-tumor agent acts by inhibiting a particular oncoprotein, it is desirable to know whether a particular cancer expresses that oncogene before attempting to treat the cancer with the anti-tumor agent. As expression profiling becomes faster, cheaper and more reliable, such information may become a routine part of treatment selection, minimizing fruitless treatment protocols and allowing the more rapid application of appropriate therapeutics.

In addition, if a pool of patients suffering from a certain type of disorder can be segregated into subgroups based on gene expression profiles, drugs can be re-tested for their ability to affect these defined subgroups of patients. Thus drugs that appeared useless in the patient group as a whole may now be found to be useful for patient subgroups. This type of screening may allow the resurrection of failed compounds, the identification of new compounds and the identification of new uses for well-known compounds.

The expression of a particular gene can be assessed in many ways. The level of gene transcript or the level of encoded protein may be determined. The presence of a protein may be determined directly, through methods such as antibody binding, mass spectroscopy and two-dimensional gel electrophoresis, or indirectly, by detecting an activity of the protein, be it a biochemical activity or an effect on the levels of another protein or expression of one or more genes.

Methods for measuring levels of gene transcripts are well known in the art and depend for the most part on hybridization of a single stranded probe to the transcript in question (or a cDNA thereof). Such methods include Northern blotting, using a labeled probe, or PCR amplification of the cDNA (also known as RT-PCR). mRNAs and cDNAs may be labeled according to various methods and hybridized to an oligonucleotide array. Such arrays may contain ordered probes corresponding to one or more genes, and in preferred embodiments, the array contains probes corresponding to all the genes in the genome of the organism from which the RNA was obtained.

A number of methodologies are currently used for the measurement of gene expression. The most sensitive of these methodologies utilizes the polymerase chain reaction (PCR) technique, the details of which are provided in U.S. Pat. No. 4,683,195, U.S. Pat. No. 4,683,202, and U.S. Pat. No. 4,965,188, all to Mullis et al., all of which are specifically incorporated herein by reference. The details of PCR technology, thus, are not included herein. Recently, additional technologies for the amplification of nucleic acids have been described, most of which are based upon isothermal amplification strategies as opposed to the temperature cycling required for PCR. These strategies include, for example, Strand Displacement Amplification (SDA)(U.S. Pat. Nos. 5,455,166 and 5,457,027 both to Walker; Walker et al. (1992) PNAS 89:392; each of which is specifically incorporated herein by reference) and Nucleic Acid Sequence-Based Amplification (NASBA)(U.S. Pat. No. 5,130,238 to Malek et al.; European Patent 525882 to Kievits et al.; both specifically incorporated herein by reference). Each of these amplification technologies are similar in that they employ the use of short, deoxyribonucleic acid primers to define the region of amplification, regardless of the enzymes or specific conditions used.

Until recently, RNA amplification required a separate, additional step and the use of non-thermostable reverse transcriptase enzymes to generate a cDNA capable of being amplified by a thermostable DNA polymerase, such as Taq. The discovery of a recombinant thermostable enzyme (rTth) capable of coupling reverse transcription of the RNA with DNA amplification in a single enzyme:single reaction procedure greatly simplified and enhanced RNA amplification (see, Myers & Gelfand (1991) Biochemistry 30:7661-7666; U.S. Pat. No. 5,407,800 to Gelfand and Myers, both incorporated herein by reference).

In gene expression analysis with microarrays, an array of "probe" oligonucleotides is contacted with a nucleic acid sample of interest, i.e., target, such as polyA mRNA from a particular tissue type. Contact is carried out under hybridization conditions and unbound nucleic acid is then removed. The resultant pattern of hybridized nucleic acid provides information regarding the genetic profile of the sample tested. Gene expression analysis finds use in a variety of applications, including: the identification of novel expression of genes, the correlation of gene expression to a particular phenotype, screening for disease predisposition, identifying the effect of a particular agent on cellular gene expression, such as in toxicity testing; among other applications. Detailed methods for analyzing transcript levels are described in the following patents: U.S. Pat. No. 5,082,830 and WO 97/27317.

Other references of interest include: Schena et al., Science (1995) 467-470; Schena et al., P.N.A.S. U.S.A. (1996) 93: 10614-10616; Pietu et al., Genome Res. (June 1996) 6: 492-503; Zhao et al., Gene (Apr. 24, 1995) 156: 207-213; Soares, Curr. Opin. Biotechnol. (October 1997) 8: 542-546; Raval, J. Pharmacol Toxicol Methods (November 1994) 32: 125-127; Chalifour et al., Anal. Biochem (Feb. 1, 1994) 216: 299-304; Stolz & Tuan, Mol. Biotechnol. (December 19960 6: 225-230; Hong et al., Bioscience Reports (1982) 2: 907; and McGraw, Anal. Biochem. (1984) 143: 298.

VI. Pharmaceutical Compositions

While it is possible for a compound of the present invention to be administered alone, it is preferable to administer the compound as a pharmaceutical formulation (composition). The hedgehog antagonists according to the invention may be formulated for administration in any convenient way for use in human or veterinary medicine. In certain embodiments, the compound included in the pharmaceutical preparation may be active itself, or may be a prodrug, e.g., capable of being converted to an active compound in a physiological setting.

Thus, another aspect of the present invention provides pharmaceutically acceptable compositions comprising a therapeutically effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam. However, in certain embodiments the subject compounds may be simply dissolved or suspended in sterile water. In certain embodiments, the pharmaceutical preparation is non-pyrogenic, i.e., does not elevate the body temperature of a patient.

The phrase "therapeutically effective amount" as used herein means that amount of a compound, material, or composition comprising a compound of the present invention which is effective for producing some desired therapeutic effect by overcoming a hedgehog gain-of-function phenotype in at least a sub-population of cells in an animal and thereby blocking the biological consequences of that pathway in the treated cells, at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject antagonists from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the present hedgehog antagonists may contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like. (See, for example, Berge et al. (1977) "Pharmaceutical Salts", *J. Pharm. Sci.* 66:1-19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound that produces a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

It is known that sterols, such as cholesterol, will form complexes with cyclodextrins. Thus, in preferred embodiments, where the inhibitor is a steroidal alkaloid, it may be formulated with cyclodextrins, such as $\alpha$-, $\beta$- and $\gamma$-cyclodextrin, dimethyl-$\beta$ cyclodextrin and 2-hydroxypropyl-$\beta$-cyclodextrin.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active hedgehog antagonist.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the hedgehog antagonists in the proper medium. Absorption enhancers can also be used to increase the flux of the hedgehog antagonists across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., San Francisco, U.S.A., 1969 or "Livestock Feeds and Feeding" O and B books, Corvallis, Oreg., U.S.A., 1977).

In any of the foregoing embodiment, the invention contemplates that the pharmaceutical preparations may be non-pyrogenic.

The pharmaceutical preparations for use in the methods of the present invention may comprises combinations of two or more hedgehog antagonists. For example, two hedgehog antibodies may be combined with a pharmaceutically acceptable carrier or excipient. The two antibodies may act additively or synergistically. In another example, one or more hedgehog antibodies may be combined with one or more non-antibody hedgehog antagonists (e.g., one or more small organic molecules), and with a pharmaceutically acceptable carrier or excipients. Said combination of hedgehog antagonists may act additively or synergistically.

EXAMPLES

The invention now being generally described, it will be more readily understood by reference to the following examples, which are included merely for purposes of illustration of certain aspects and embodiments of the present invention, and are not intended to limit the invention.

Example 1

Hedgehog, Lung Development and Surfactant Production

Respiratory distress syndrome results from insufficient surfactant in the alveolae of the lungs. The lungs of vertebrates contain surfactant, a complex mixture of lipids and protein that causes surface tension to rise during lung inflation and decrease during lung deflation. During lung deflation, surfactant decreases such that there are no surface forces that would otherwise promote alveolar collapse. Aerated alveoli that have not collapsed during expiration permit continuous oxygen and carbon dioxide transport between blood and alveolar gas and require much less force to inflate during the subsequent inspiration. During inflation, lung surfactant increases surface tension as the alveolar surface area increases. A rising surface tension in expanding alveoli opposes over-inflation in those airspaces and tends to divert inspired air to less well-aerated alveoli, thereby facilitating even lung aeration.

Respiratory distress syndrome is particularly prevalent among premature infants. Lung surfactant is normally synthesized at a very low rate until the last six weeks of fetal life. Human infants born more than six weeks before the normal term of a pregnancy have a high risk of being born with inadequate amounts of lung surfactant and inadequate rates of surfactant synthesis. The more prematurely an infant is born, the more severe the surfactant deficiency is likely to be. Severe surfactant deficiency can lead to respiratory failure within a few minutes or hours of birth. The surfactant deficiency produces progressive collapse of alveoli (atelectasis) because of the decreasing ability of the lung to expand despite maximum inspiratory effort. As a result, inadequate amounts of oxygen reach the infant's blood. RDS can occur in adults as well, typically as a consequence of failure in surfactant biosynthesis.

The role of the hedgehog signaling pathway in lung maturation and surfactant production was investigated, with the finding that inhibition of the hedgehog signaling pathway stimulated surfactant production.

Figure 4:
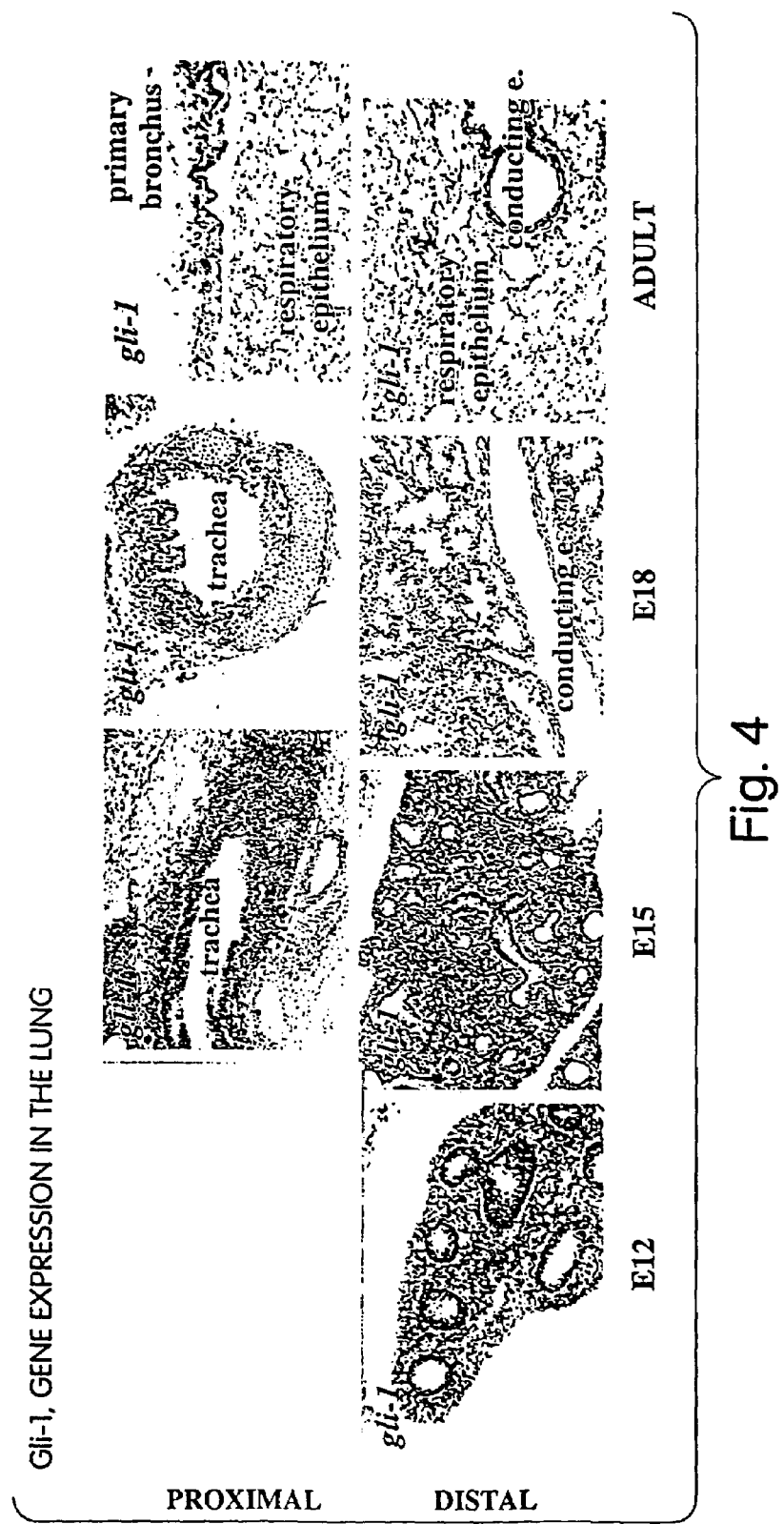
FIG. 4 depicts gli-1 gene expression in embryonic and adult mouse lung.

The expression of a hedgehog-regulated gene, Gli-1, was assessed in embryonic mouse lung tissue. Gli-1 was strongly expressed in the embryonic lung, however this expression decreases during lung maturation (FIG. 4). Note that the decline in hedgehog signaling towards the end of embryogenesis correlates with the maturation of the distal lung epithelium into respiratory pneumocytes. Gli-1, a transcription factor indicative of hedgehog signaling, continues to be expressed in the conducting, but not respiratory airways in the adult.

METHODS: Sections of paraformaldehyde-fixed, paraffin-embedded tissue were cleared, re-hydrated, digested with proteinase K, acetylated and hybridized with [33P]-labeled sonic hedgehog and gli-1 RNA probes over night, respectively. After high stringency post-hybridization washes, slides were dipped in photo-emulsion, incubated for up to three weeks, developed, and imaged using dark field illumination. Dark-field signals were filled in with artificial color (red) and superimposed with bright-field images.

Figure 5:
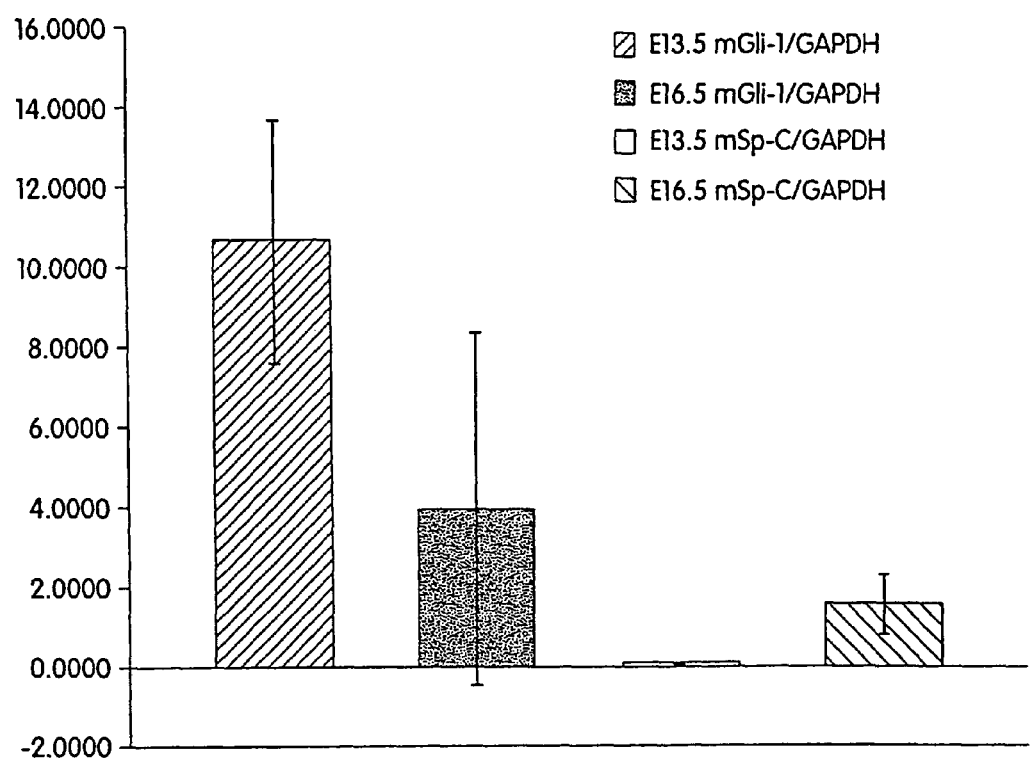
FIG. 5 shows the inverse relationship between gli-1 expression and the expression of markers of lung maturation. Between E13.5 and E16.5, the expression of gli-1 decreases while the expression of the maturation marker, surfactant type C (Sp-C), increases.

To further correlate the decrease in gli-1 expression with lung maturation, expression of gli-1 was compared to expression of the lung maturation marker, surfactant type C (Sp-C) (FIG. 5). This analysis demonstrates that as expression of gli-1 decreases between E13.5-E16.5, the expression of Sp-C increases.

METHODS: E13.5 and E16.5 mouse lung explants were dissected and analyzed by Quantatative Real-Time PCR (Q-RT-PCR). Briefly, total ribonucleic acid (RNA) is isolated from the tissue and subjected to reverse transcription to generate DNA. This DNA is amplified in a polymerase chain reaction using gene-specific primers as well as primers for the ubiquitously expressed housekeeping gene GAPDH. The two primer sets are labeled with different fluorophores, allowing for quantification of both signals in the same reaction tube in a real-time PCR machine (TaqMan). When calculating the expression levels of gli-1 and Sp-C, the specific signal is normalized to the GAPDH signal, which serves as a measure of the total DNA used in the reaction.

As Gli-1 expression is a marker for hedgehog signaling, it appears that the hedgehog signaling pathway is active in immature lung tissue. Accordingly, it was hypothesized that inhibition of the hedgehog signaling pathway would permit more rapid lung maturation and, particularly, stimulate surfactant production.

Figure 6:
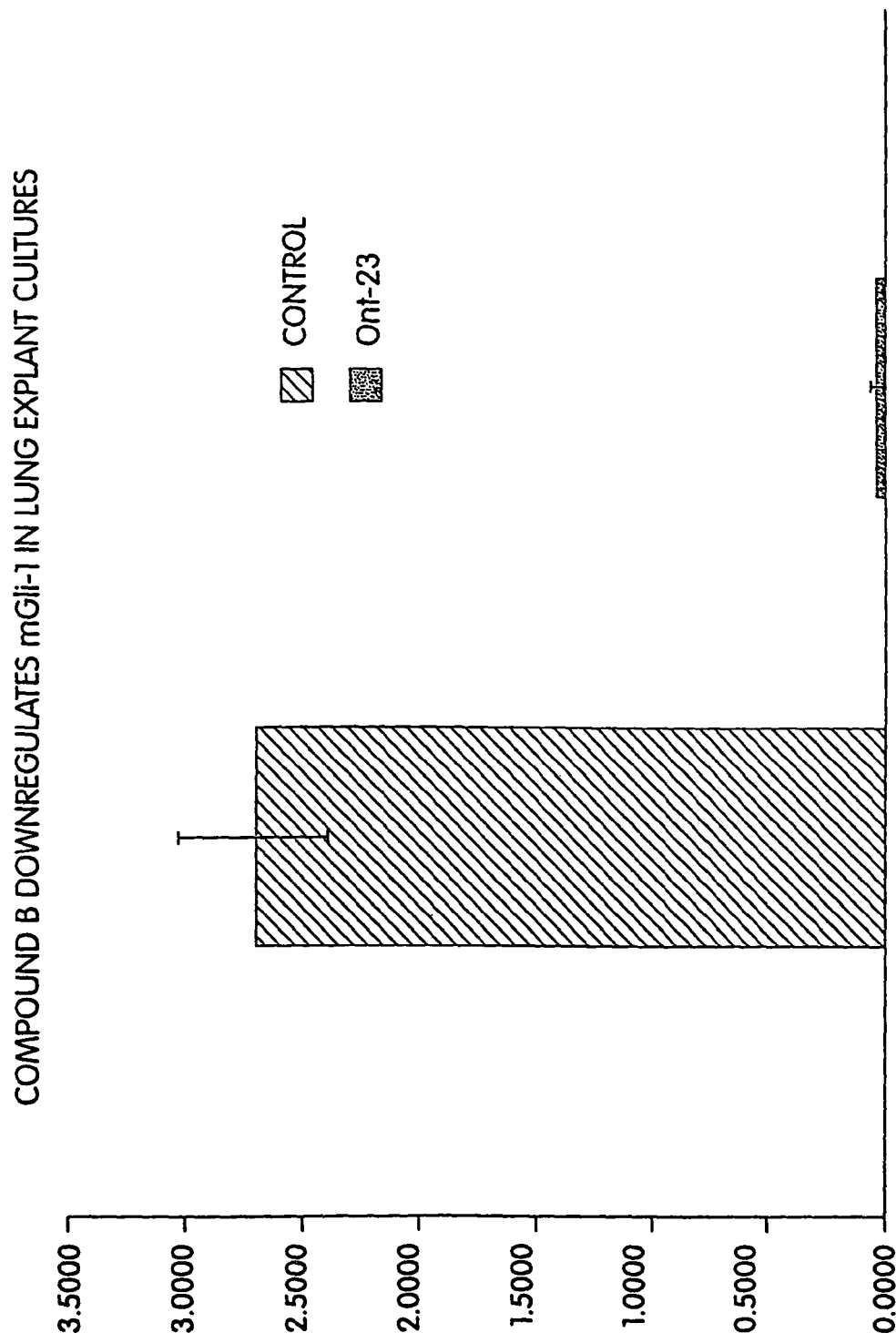
FIG. 6 shows the effect of compound B treatment of embryonic mouse lungs on gli-1 expression.

Treatment of embryonic mouse lungs with hedgehog antagonist compound B downregulates Gli-1 expression (FIG. 6). METHODS: E13.5 embryonic mouse lungs were dissected. Explants were grown exposed to the air-liquid interface in lung explant medium (DMEM based, additives optimized for the culture of mouse lungs) for 67 hrs. They were then processed for quantitative real-time PCR (Q-RT-PCR). Briefly, total ribonucleic acid (RNA) is isolated from the tissue and subjected to reverse transcription to generate DNA. This DNA is amplified in a polymerase chain reaction using gene-specific primers as well as primers for the ubiquitously expressed housekeeping gene GAPDH. The two primer sets are labeled with different fluorophores, allowing for quantification of both signals in the same reaction tube in a real-time PCR machine (TaqMan). When calculating the expression level of gli-1, the specific signal is normalized to the GAPDH signal, which serves as a measure of the total DNA used in the reaction.

Figure 7:
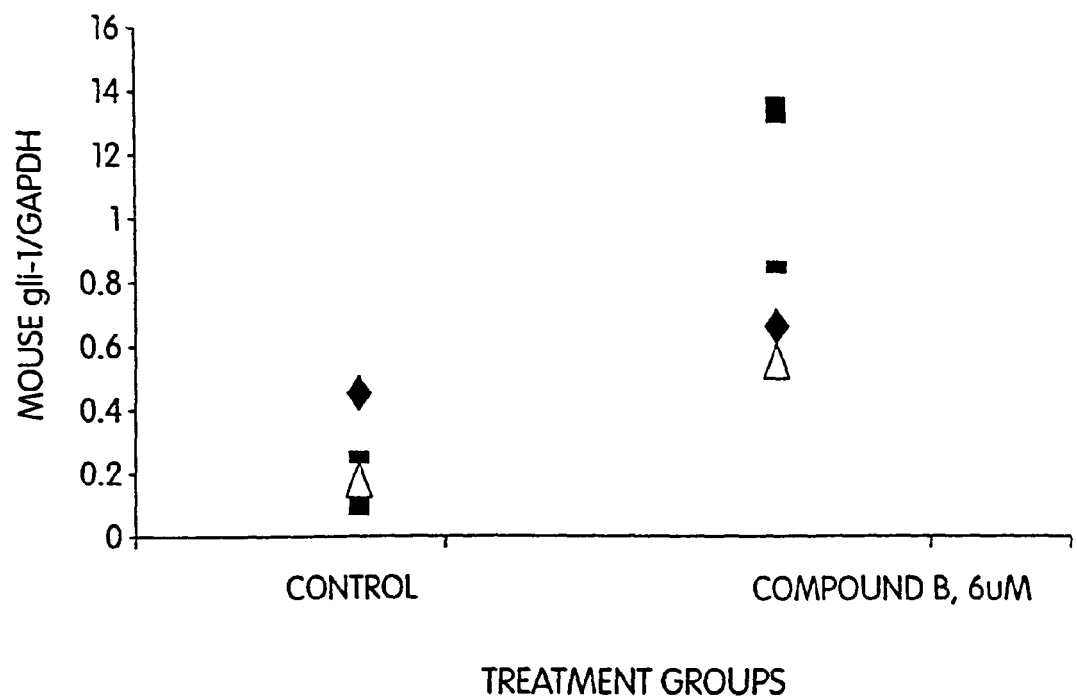
FIG. 7 shows compound B treatment increases surfactant type C production in embryonic mouse lungs.

Compound B treatment increases surfactant type C production in embryonic mouse lungs (FIG. 7). Surfactant production is a measure of lung maturity, and the inability to produce surfactant is the primary cause of adult and infant respiratory distress syndrome. The increase in surfactant type C production was assessed by measuring expression of Sp-C, which encodes a protein critical for the production of surfactant.

METHODS: E13.5 old embryonic mouse lungs were dissected. Explants were grown submerged in lung explant medium (DMEM based, additives optimized for the culture of mouse lungs) for 50 hrs. They were then processed for Q-RT-PCR. Briefly, total ribonucleic acid (RNA) is isolated from the tissue and subjected to reverse transcription to generate DNA. This DNA is amplified in a polymerase chain reaction using gene-specific primers as well as primers for the ubiquitously expressed housekeeping gene GAPDH. The two primer sets are labeled with different fluorophores, allowing for quantification of both signals in the same reaction tube in a real-time PCR machine (TaqMan). When calculating the expression level of Sp-C, the specific signal is normalized to the GAPDH signal, which serves as a measure of the total DNA used in the reaction.

Figure 8:
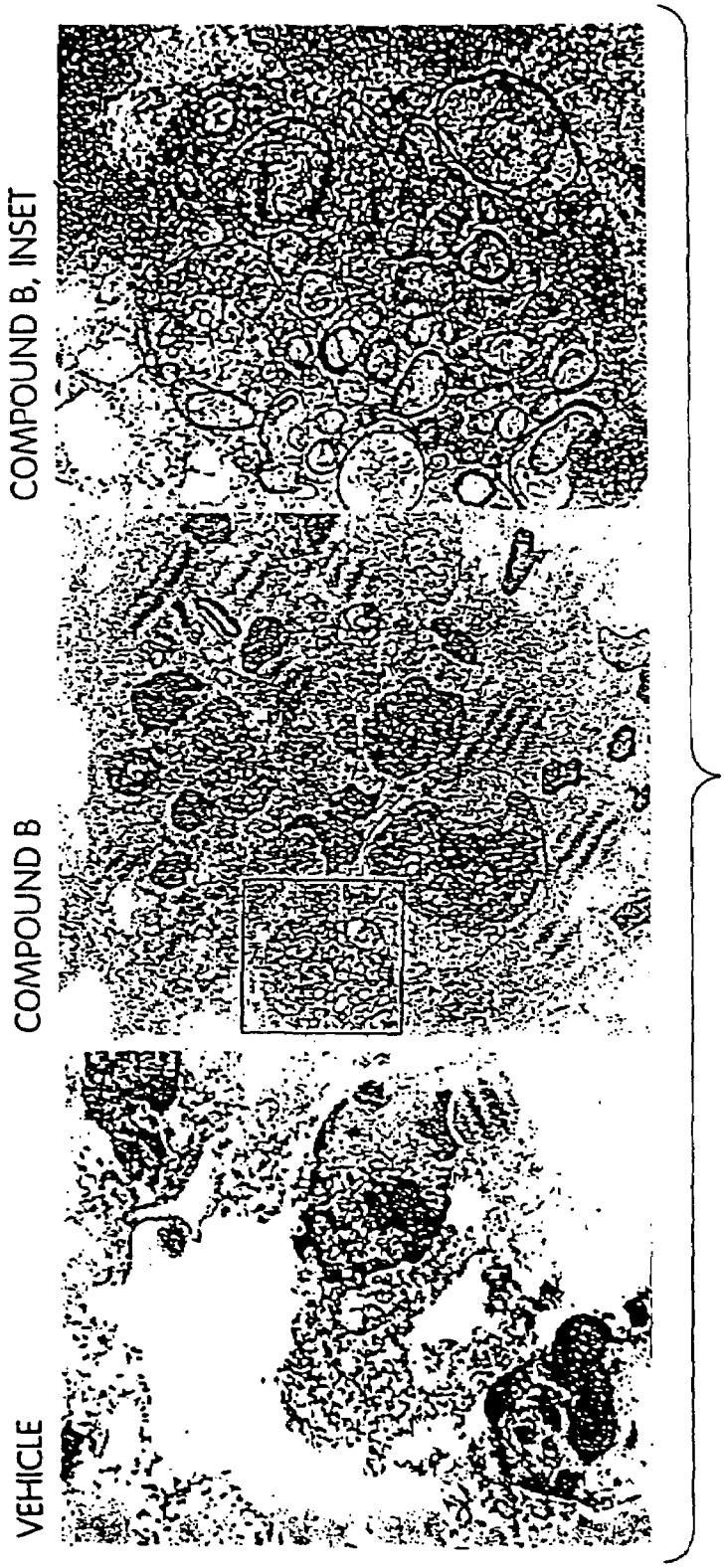
FIG. 8 shows that type II pneumocytes in compound B-treated lungs differentiate prematurely, as evidenced by the presence of surfactant producing lamellated bodies.

Lamellated bodies are subcellular structures found in surfactin-producing lung cells and are thought to be a site of surfactin production. Type II pneumocytes in compound B-treated lungs differentiate prematurely, as evidenced by the presence of surfactant producing lamellated bodies. No such structures could be observed in the vehicle-treated controls (FIG. 8). METHODS: E13.5 old embryonic mouse lungs were dissected. Explants were grown exposed to the air-liquid interface in lung explant medium (DMEM based, additives optimized for the culture of mouse lungs) for 67 hrs. They were then processed for transmission electron microscopy and photographed at a magnification of 62,000.

Figure 9:
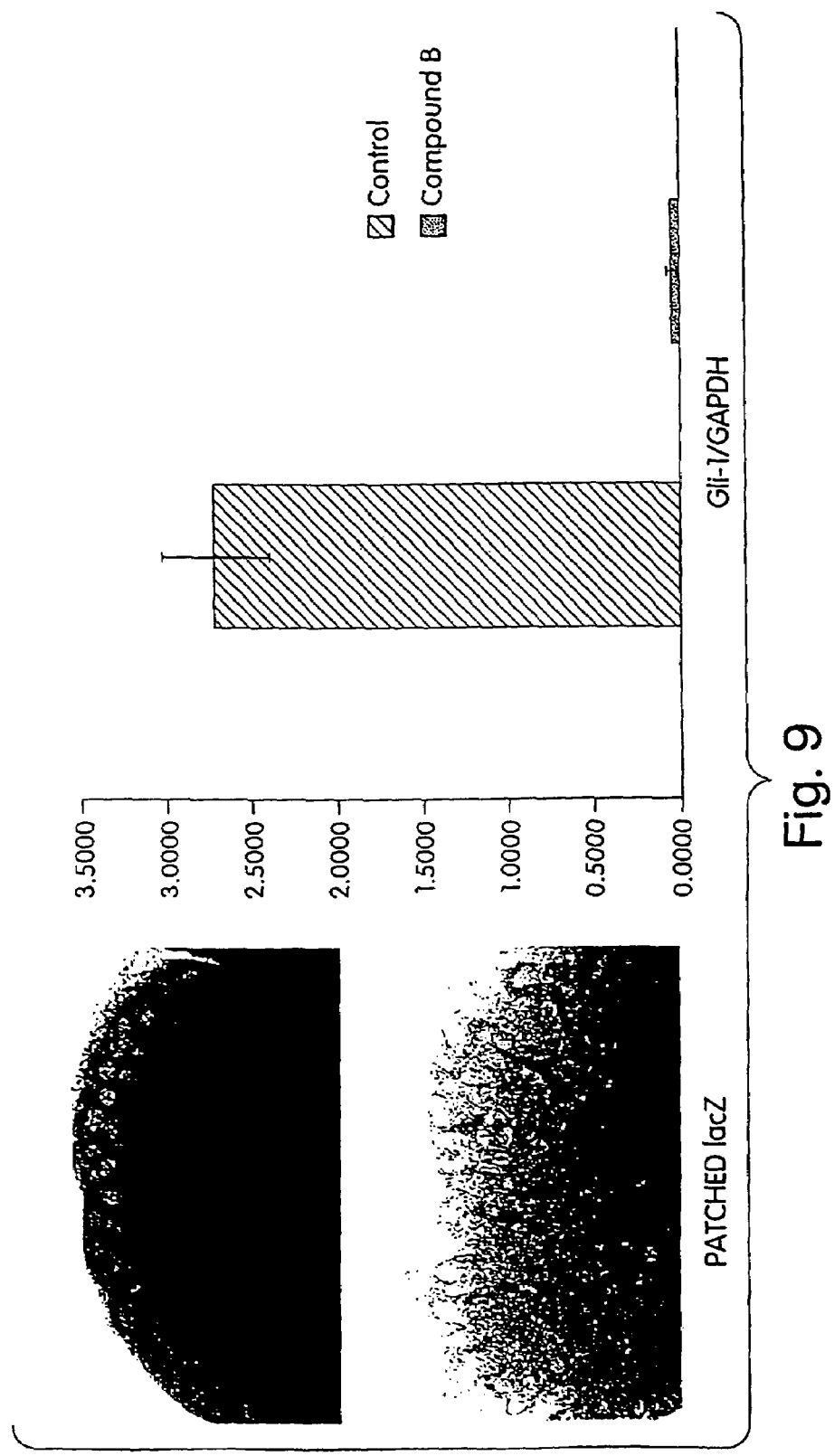
FIG. 9 shows that treatment of embryonic lung cultures with compound B decreases expression of gli-1.
Figure 10:
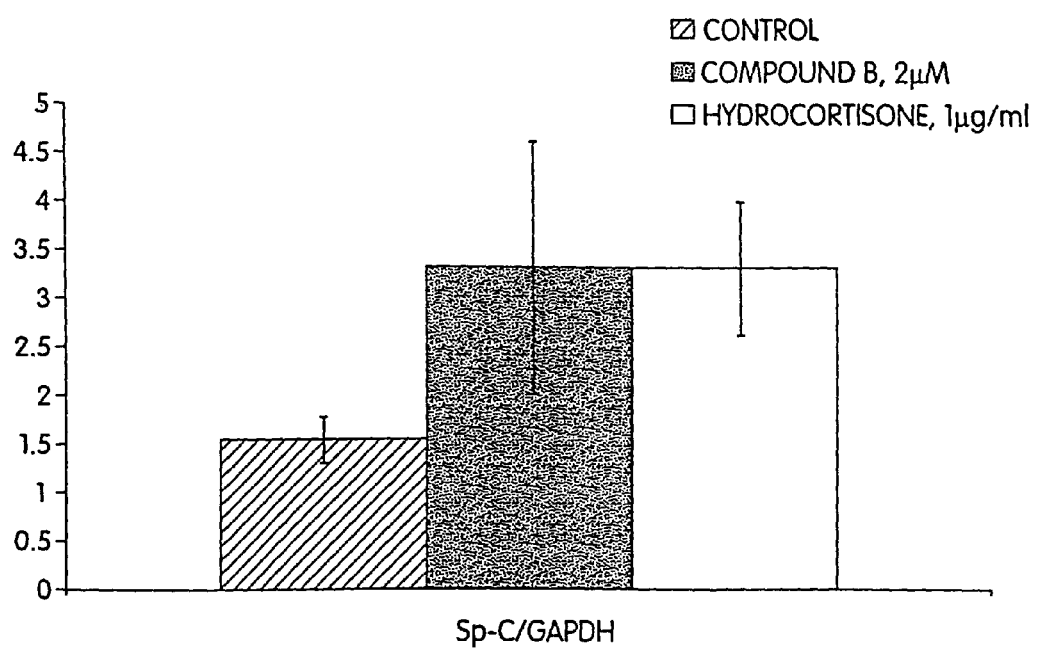
FIG. 10 shows that treatment of embryonic lung cultures with compound B increases expression of the maturation marker Sp-C. The induction of Sp-C observed following treatment is comparable to that observed following treatment with known lung maturation factor hydrocortisone.

FIGS. 9 and 10 show similar results as obtained above upon treatment of embryonic lung cultures with Compound B (FIG. 9-10). The increase in Sp-C expression observed following Compound B treatment is comparable to that observed when embryonic lung explants are treated with the steroid hormone hydrocortisone. Steroids are known to increase lung maturation and surfactant production in animals, including humans.

Figure 11:
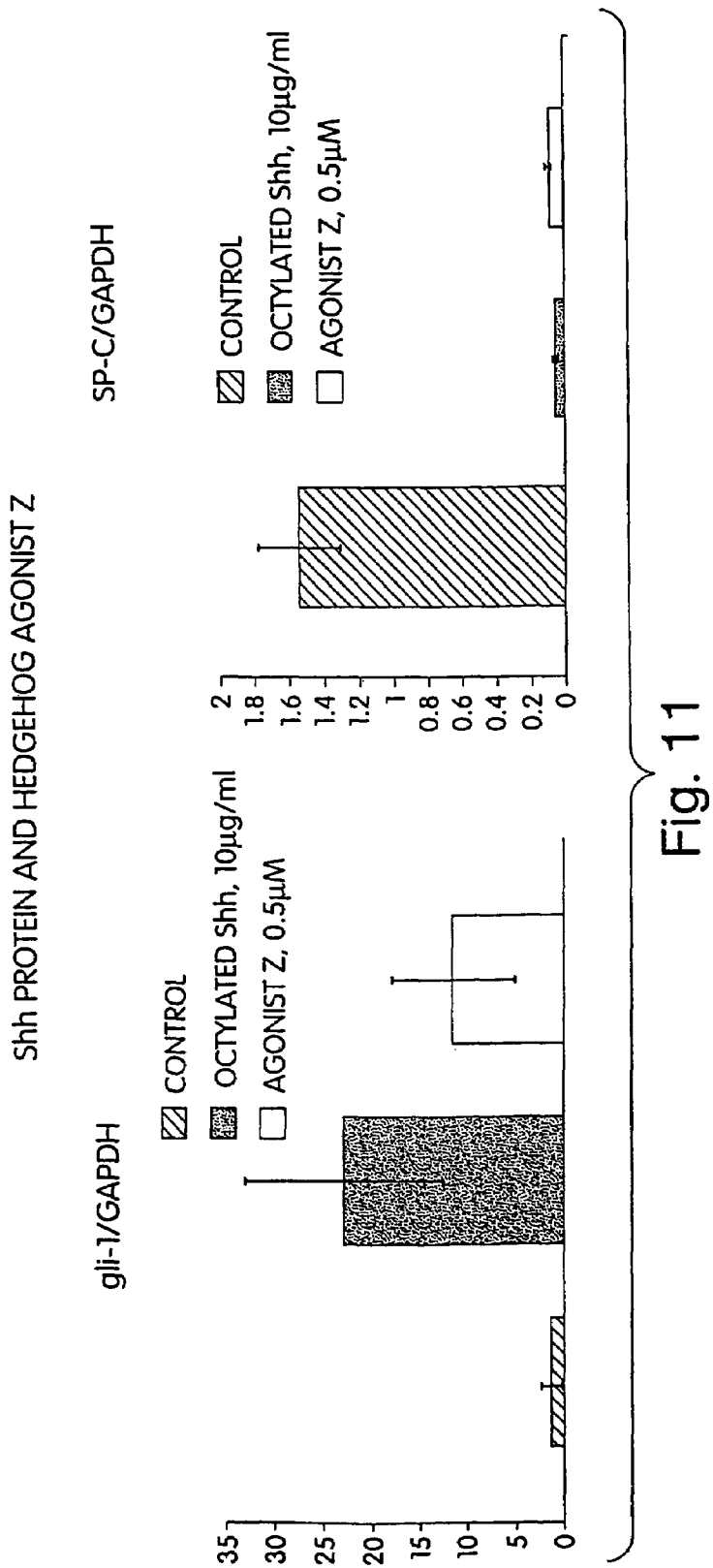
FIG. 11 shows that treatment of embryonic lung cultures with hedgehog agonists has the opposite effect. Treatment with either sonic hedgehog or with agonist Z increases gli-1 expression and decreases Sp-C expression.
Figure 12:
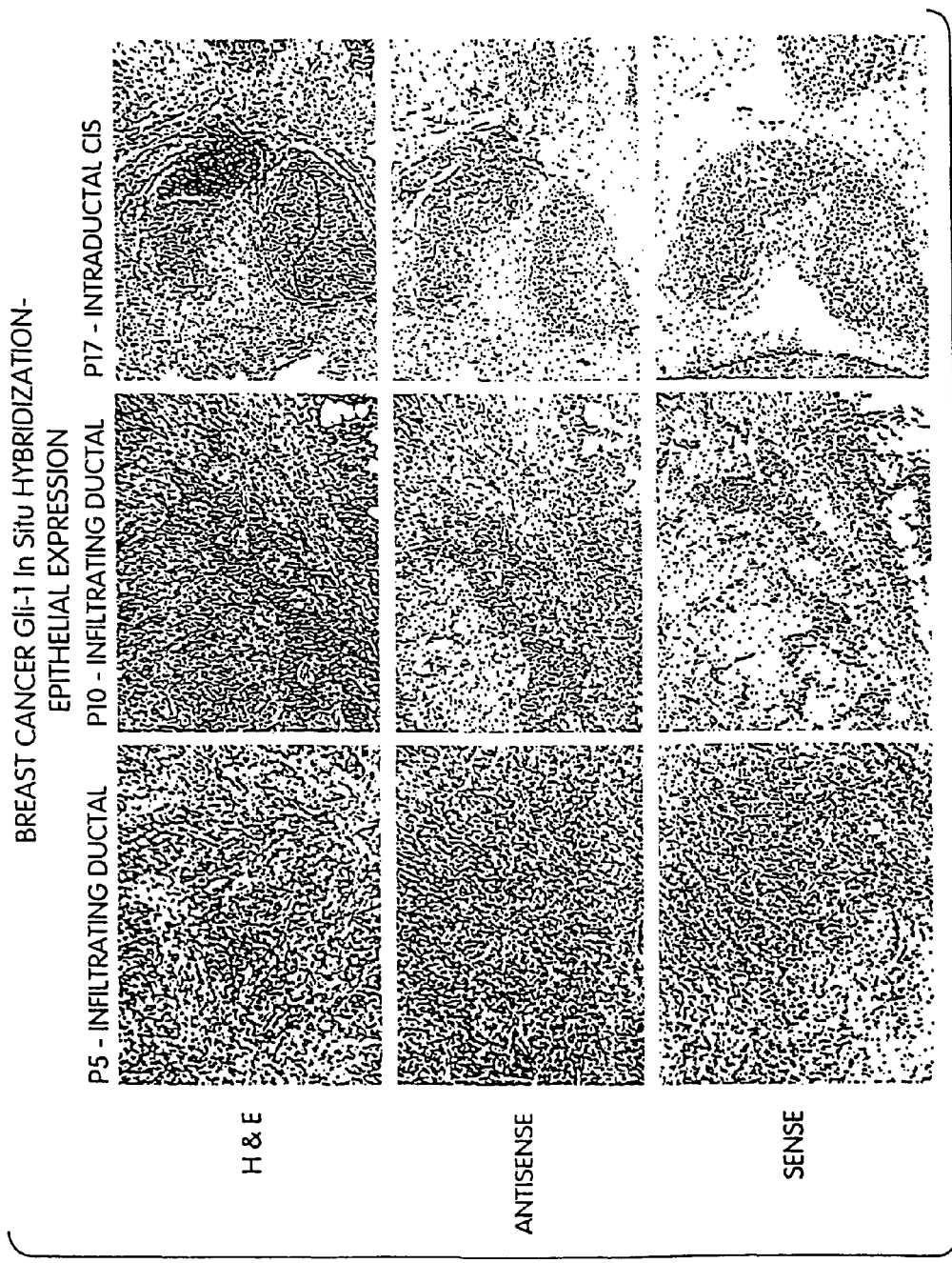
FIG. 12 illustrates gli-1 expression in breast cancer tissue as visualized by in situ hybridization.
Figure 13:
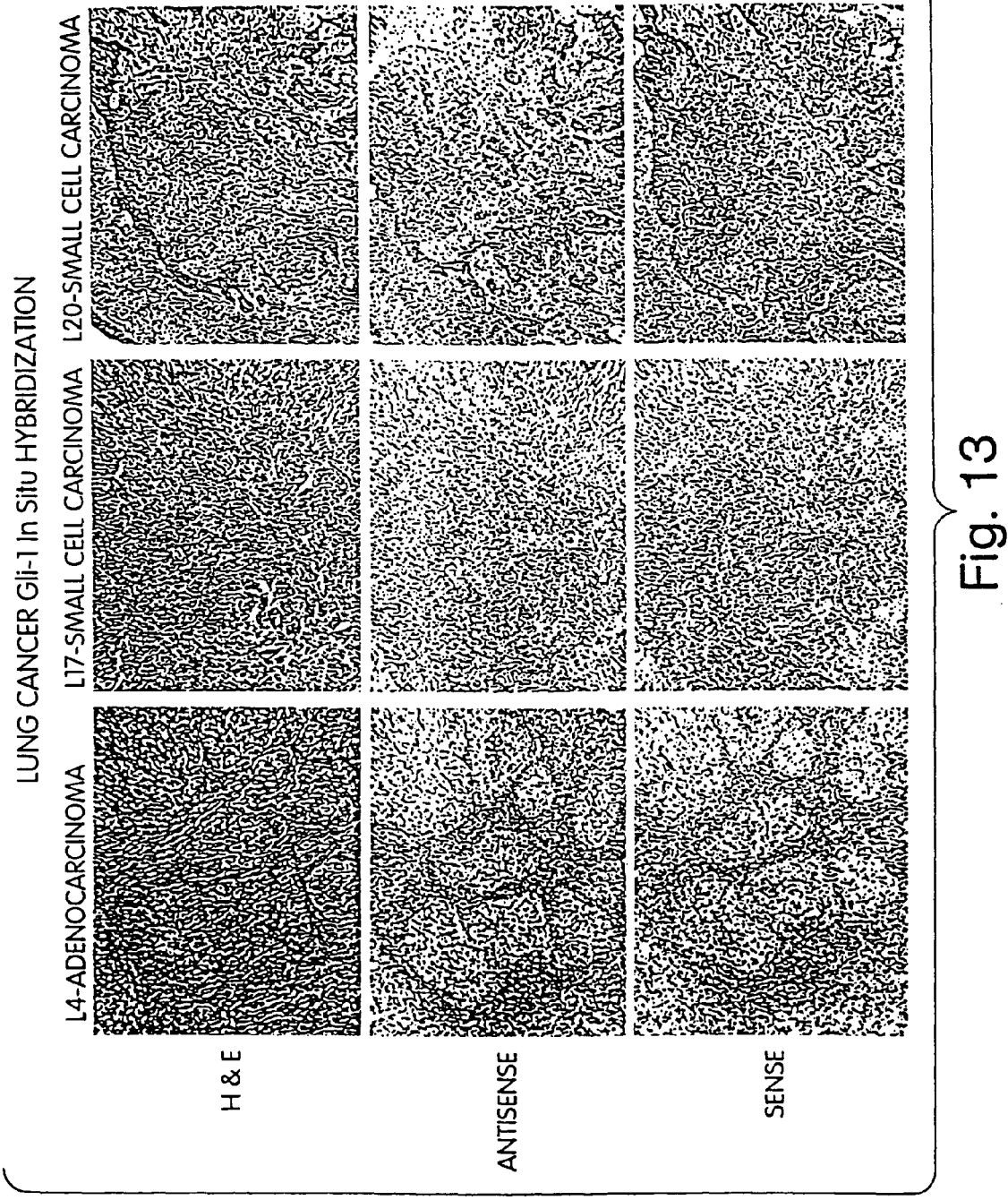
FIG. 13 shows gli-1 expression in lung cancer visualized by in situ hybridization
Figure 14:
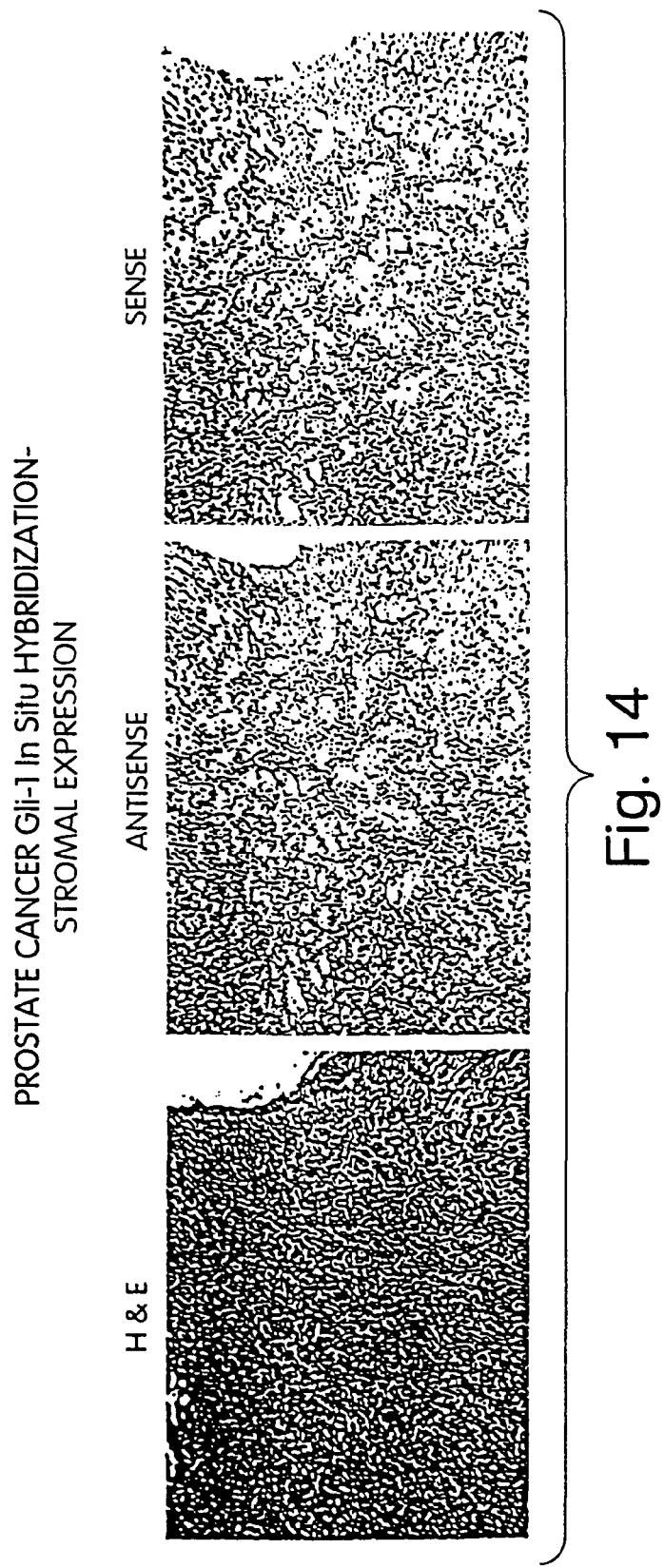
FIG. 14 illustrates gli-1 expression in prostate cancer as visualized by in situ hybridization
Figure 15:
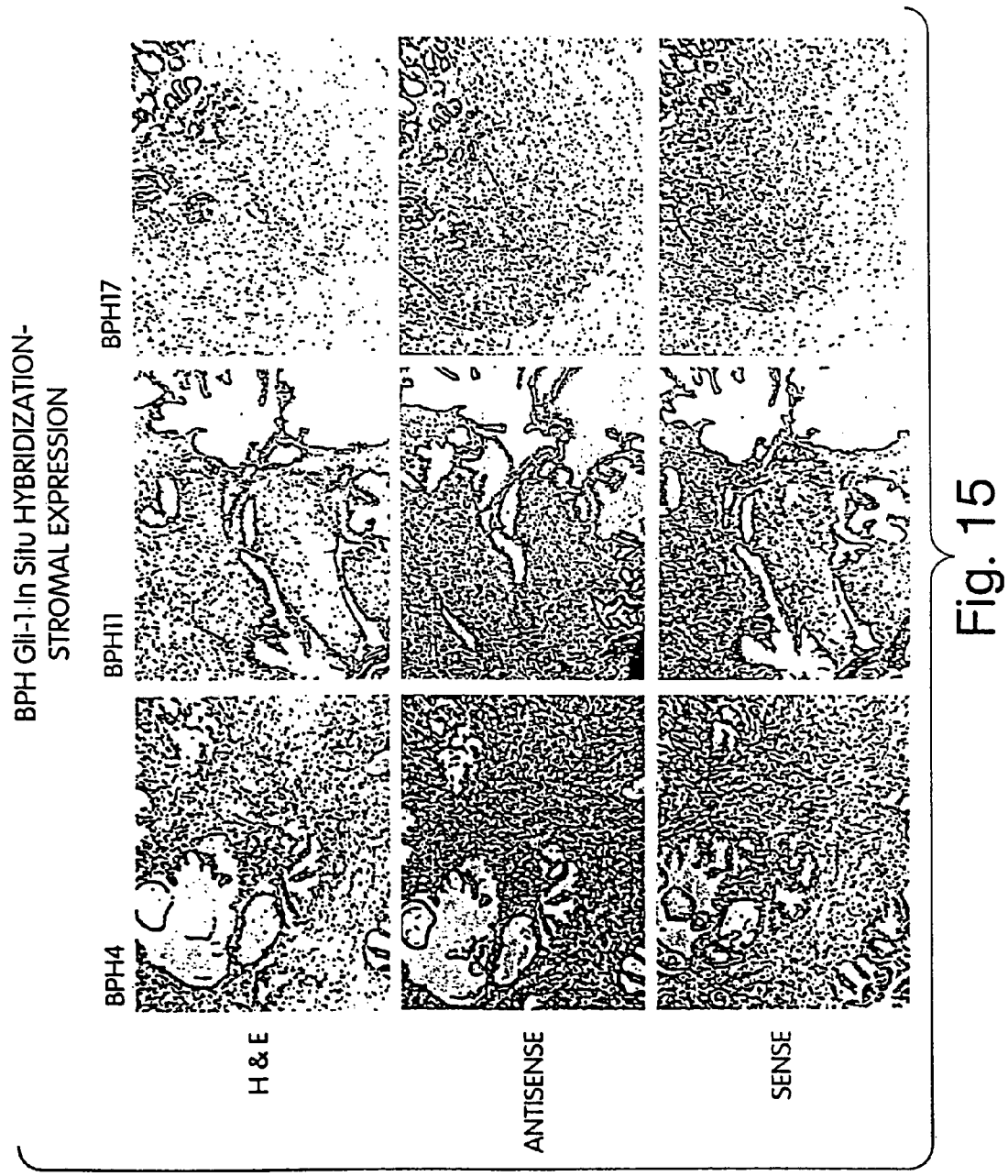
FIG. 15 depicts gli-1 expression in benign prostatic hyperplasia as visualized by in situ hybridization

The specificity of the effects of hedgehog antagonists on lung maturation is demonstrated by examining the effects of agonists of hedgehog signaling on lung maturation. Treatment of embryonic lung cultures with either a lipid modified sonic hedgehog or with a hedgehog agonist compound result in increased expression of gli-1 and decreased expression of Sp-C (FIG. 11).

In summary, these results demonstrate that hedgehog inhibitors can stimulate maturation and surfactin production in immature lung tissue. The hedgehog signaling pathway is active in immature lung tissues, where surfactins are not produced in substantial levels, while the hedgehog pathway is relatively inactive in the adult respiratory airway, where surfactins are produced. Treatment of immature lung tissue with antagonists of the hedgehog signaling pathway causes rapid maturation and the increased presence of molecular and cytological markers associated with surfactin production. Opposite results obtained upon the treatment of lung explants with hedgehog antagonists and agonists demonstrate the specificity of these results.

Example 2

Gli-1 Expression in Human Tumors

Hedgehog Pathway Activation in Human Tumors

Hedgehog signaling plays a causative role in the generation of basal cell carcinoma (BCC). Hedgehog signaling was analyzed to determine whether this pathway is active in other human tumors, more specifically prostate, lung and breast cancer, as well as benign prostate hyperplasia. Hedgehog proteins are known proliferative agents for a variety of cell types. Since hedgehogs have a known proliferative effect on a variety of cell types, hedgehog antagonists may be valuable therapeutics for cancers in which high level hedgehog signaling is present.

The question of hedgehog activation in the tumor types was addressed by conducting radioactive in situ hybridization experiments with gli-1, a known transcriptional effector gene of hedgehog signaling.

Briefly, sections of paraformaldehyde-fixed, paraffin-embedded tissue were cleared, re-hydrated, digested with proteinase K, acetylated and hybridized with [33P]-labeled RNA probes over night. After high stringency post-hybridization washes, slides were dipped in photo-emulsion, incubated for up to three weeks, developed, and imaged using dark field illumination. Dark-field signals were filled in with artificial color (red) and superimposed with bright-field images. Gli-1 expression was graded on a scale from "−" to "+" through "++++". Gli-1 expression was rated "−" when expression was no higher in hyperproliferative cells than in other non-proliferative cells present in the slide. Ratings of "+" through "++++" were given for increased expression levels, with any cell rated "++" or above considered to have substantially increased gli-1 expression. When the signal was not interpretable, a sample is indicated as "ND".

The data for these experiments are summarized in table 1-4 below. In brief, 8 out of 18 breast cancer samples showed substantially increased gli-1 expression. 7 out of 11 lung cancer samples, 11 of 19 benign prostatic hypertrophy samples (BPH), and 6 of 15 prostate cancer samples all showed strong gli-1 expression.

TABLE 1

Results of Gli-1 in situ hybridization in breast cancer tissue

| Tissue | Diagnosis | Sample Number | Age/Sex | Signal |
|---|---|---|---|---|
| Breast | Inf Ductal Carcinoma | 1 | 93F | ND |
| Breast | Inf Ductal Carcinoma | 2 | 37F | +++ |
| Breast | Inf Ductal Carcinoma | 3 | 54F | + |
| Breast | Inf Ductal Carcinoma | 4 | 39F | ++ |
| Breast | Inf Ductal Carcinoma | 5 | 73F | +++ |

TABLE 1-continued

Results of Gli-1 in situ hybridization in breast cancer tissue

| Tissue | Diagnosis | Sample Number | Age/Sex | Signal |
|---|---|---|---|---|
| Breast | Inf Ductal Carcinoma | 6 | 65F | ++++ |
| Breast | Inf Ductal Carcinoma | 7 | 58F | ND |
| Breast | Inf Ductal Carcinoma | 8 | 48F | + |
| Breast | Inf Ductal Carcinoma | 9 | 27F | ++ |
| Breast | Inf Ductal Carcinoma | 10 | NA | +++ |
| Breast | Inf Ductal Carcinoma | 11 | 34F | + |
| Breast | Inf Lobular Carcinoma | 12 | 46F | + |
| Breast | Inf Lobular Carcinoma | 13 | F | − |
| Breast | Inf Lobular Carcinoma | 14 | 56F | + |
| Breast | Inf Lobular Carcinoma | 15 | 70F | − |
| Breast | Intraductal Carcinoma | 16 | 40F | +++ |
| Breast | Intraductal Carcinoma | 17 | 55F | +++ |
| Breast | Medullary Carcinoma | 18 | NA | + |
| Breast | Tubular Carcinoma | 19 | 75F | − |
| Breast | Tubular Carcinoma | 20 | 60F | − |

TABLE 2

Results of Gli-1 in situ hybridization in lung cancer tissue

| Tissue | Diagnosis | Sample Number | Age/Sex | Signal |
|---|---|---|---|---|
| Lung | Adenocarcinoma | 1 | 54F | +++++ |
| Lung | Adenocarcinoma | 2 | 61M | ND |
| Lung | Adenocarcinoma | 3 | 61F | ++++ |
| Lung | Adenocarcinoma | 4 | 58F | +++ |
| Lung | Adenocarcinoma | 5 | 77M | ND |
| Lung | Adenocarcinoma | 6 | 65M | ++ |
| Lung | Adenocarcinoma | 7 | 73M | ND |
| Lung | Adenocarcinoma | 8 | 69M | ND |
| Lung | Adenocarcinoma | 9 | 82M | ND |
| Lung | Adenocarcinoma | 10 | NA | − |
| Lung | Adenocarcinoma | 11 | F | ND |
| Lung | Adenocarcinoma | 12 | 56F | + |
| Lung | Broncho-alveolar adenocar | 13 | 70F | + |
| Lung | Broncho-alveolar adenocar | 14 | 76F | − |
| Lung | Small Cell Carcinoma | 15 | 68M | ++ |
| Lung | Small Cell Carcinoma | 16 | 61M | ND |
| Lung | Small Cell Carcinoma | 17 | 70M | +++++ |
| Lung | Small Cell Carcinoma | 18 | NA | ND |
| Lung | SCC | 19 | 60F | ND |
| Lung | SCC | 20 | 63M | +++++ |

TABLE 3

Results of Gli-1 in situ hybridization in benign prostate hyperplasia

| Tissue | Diagnosis | Sample Number | Age/Sex | Signal |
|---|---|---|---|---|
| Prostate | BPH | 1 | 65M | + |
| Prostate | BPH | 2 | 86M | ++++ |
| Prostate | BPH | 3 | 53M | + |
| Prostate | BPH | 4 | 65M | ++++ |
| Prostate | BPH | 5 | 68M | ++ |
| Prostate | BPH | 6 | 70M | ++ |
| Prostate | BPH | 7 | 54M | − |
| Prostate | BPH | 8 | M | ++ |
| Prostate | BPH | 9 | 69M | − |
| Prostate | BPH | 10 | M | − |
| Prostate | BPH | 11 | 73M | +++ |
| Prostate | BPH | 12 | 53M | ++++ |
| Prostate | BPH | 13 | 84M | − |
| Prostate | BPH | 14 | 67M | − |
| Prostate | BPH | 15 | 66M | ++ |
| Prostate | BPH | 16 | 69M | ++ |
| Prostate | BPH | 17 | 72M | ++++ |
| Prostate | BPH | 18 | M | ++ |

TABLE 3-continued

Results of Gli-1 in situ hybridization in benign prostate hyperplasia

| Tissue | Diagnosis | Sample Number | Age/Sex | Signal |
|---|---|---|---|---|
| Prostate | BPH | 19 | 60M | − |
| Prostate | BPH | 20 | 60M | − |

TABLE 4

Results of Gli-1 in situ hybridization in prostate cancer tissue

| Tissue | Diagnosis | Sample Number | Age/Sex | Signal |
|---|---|---|---|---|
| Prostate | Adenocarcinoma | 1 | 79M | + |
| Prostate | Adenocarcinoma | 2 | 72M | + |
| Prostate | BPH next to Adenocarcinoma | 3 | 81M | ND |
| Prostate | Adenocarcinoma | 4 | 79M | ++ |
| Prostate | Adenocarcinoma | 5 | 81M | ND |
| Prostate | Adenocarcinoma | 6 | 73M | − |
| Prostate | Adenocarcinoma | 7 | 79M | ++ |
| Prostate | Adenocarcinoma | 8 | M | +++ |
| Prostate | Adenocarcinoma | 9 | 69M | ND |
| Prostate | Adenocarcinoma | 10 | 53M | +++ |
| Prostate | Adenocarcinoma | 11 | 65M | + |
| Prostate | Adenocarcinoma | 12 | 60M | ++ |
| Prostate | Adenocarcinoma | 13 | 66M | ND |
| Prostate | Adenocarcinoma | 14 | 66M | + |
| Prostate | Adenocarcinoma | 15 | 92M | − |
| Prostate | Adenocarcinoma | 16 | 80M | − |
| Prostate | Adenocarcinoma | 17 | 78M | ND |
| Prostate | Adenocarcinoma | 18 | 85M | − |
| Prostate | Adenocarcinoma | 19 | 78M | − |
| Prostate | Adenocarcinoma | 20 | 93M | +++ |

In summary, high level Gli-1 expression, i.e., hedgehog signaling activation, can be observed in human prostate cancer and benign prostatic hyperplasia, lung cancer and breast cancer (FIGS. 12-15). Hedgehog pathway activation in these tumor types has never before been described. The presence of an exceptionally active hedgehog pathway in these proliferating cells strongly suggests a causal link between the hedgehog pathway and hyperproliferation in these disorders. It is expected that hedgehog antagonists will be effective as antiproliferative agents in these cancer types.

Example 3

Steroidal Hedgehog Antagonists

Studies were performed to determine the site in the hedgehog signaling pathway at which cyclopamine (an alkaloid steroidal hedgehog antagonist) operates, and therefore better understand the spectrum of tumors caused by Shh pathway-activating lesions that could potentially be treated with this compound. These studies are presented in greater detail in U.S. patent application Beachy et al. entitled "Hedgehog signaling pathways, compositions and uses related thereto" filed Oct. 10, 2000, the contents of which are herein incorporated by reference.

These studies involve the use of mouse embryonic fibroblasts (MEFs) that were generated by trypsin digestion of E8.5 embryos from patched (ptc) +/− matings. The mouse ptc gene was disrupted by homologous recombination in which part of exon 1 and all of exon 2 were replaced with the bacterial lacZ gene (Goodrich et al, (1997) Science 277: 1109). As Ptc protein suppresses Shh signaling, a loss of its function activates the Shh signaling pathway. Shh signaling, through a cascade of events, is mediated by the Gli transcription factors. One of the target genes of Shh signaling is ptc, through Gli-binding sites in the ptc promoter region, and this serves as a feedback mechanism for down regulation of signaling. Thus, in these ptc −/− embryos, the Shh signaling pathway is activated in many tissues, and the lacZ gene product β-galactosidase is expressed in all of those tissues as a report of pathway activation.

These MEFs were obtained to determine whether cyclopamine acts on Ptc or another component of the cascade to inhibit Shh signaling. If the target of cyclopamine is Ptc, then one would expect that when the Shh pathway is activated by the loss of ptc function, it could no longer be inhibited by cyclopamine. The Shh signaling pathway can be activated in these fibroblasts in cell culture, and that the level of β-galactosidase activity does reflect the degree of pathway activation. The MEF line 234 is heterozygous for ptc-lacZ, and thus contains one functional ptc allele capable of maintaining a repressed state of the pathway, but will express lacZ when the pathway is activated by addition of Shh protein.

In contrast, the β-galactosidase activity in MEFs homozygous for ptc-lacZ, (cell line 23-1) is markedly elevated, because in these cells the pathway is constitutively activated by the loss of a functional ptc allele. When these cells are cultured with cyclopamine, β-galactosidase activity is decreased, indicating that when the Shh signaling pathway is unregulated by Ptc repression, it is still sensitive to cyclopamine inhibition. The reduction of β-galactosidase activity appears to result from the specific inhibition of Shh signaling, rather than from cell toxicity because enzymatic activity is normalized to whole protein content of the sample. Also, the reduction of β-galactosidase activity can be obtained with exposure to cyclopamine over a period of time that is shorter than the average cell cycle, and so does not appear to be due solely to an inhibition of cell proliferation.

A final indication that this represents specific inhibition of Shh signaling is that it cannot be achieved with a non-inhibitory, but structurally related compound tomatidine.

Example 4

Lead Compound Discovery/High-throughput Screening Assay

The methodologies described herein can be used to identify a wide assortment of small molecule hedgehog antagonists.

Compounds to be tested are dissolved in DMSO to a concentration of 10 mM, and stored at −20° C. To activate the Hedgehog pathway in the assay cells, an octylated (lipid-modified) form of the N-terminal fragment of the Sonic Hedgehog protein (OCT-SHH) is used. This N-terminal SHH fragment is produced bacterially.

Compounds may be tested in the "Gli-Luc" assay below, using the cell line 10T(s12), wherein the cells contain a Hedgehog-responsive reporter construct utilizing Luciferase as the reporter gene. In this way, Hedgehog pathway signaling activity can be measured via the Gli-Luc response.

10t1/2(s12) cells are plated in a 96-well micro-titer plate (MTP) at 20,000 cells/well in full medium [DMEM with 10% FBS]. Then plates are placed in the incubator for incubation overnight (O/N), at 37° C. and 5% $CO_2$. After 24 h, the medium is replaced with Luciferase-assay medium (DMEM with 5% FBS). Compounds are thawed and diluted in assay medium at 3:1000 (about 300-fold) resulting in a starting concentration of about 30 µM.

Subsequently, 150 µl of each 30 µM sample is added to the first wells (in triplicate). The MTP samples are then diluted at 3-fold dilutions to a total of seven wells, ultimately resulting in a regiment of seven dilutions in triplicate, for each compound. Next, the protein ligand OCT-SHH is diluted in Luciferase-assay medium and added to each well at a final concentration of 0.3 μg/ml. Plates are then returned to the incubator for further incubation O/N, at 37° C. and 5% $CO_2$. After about 24 h, plates are removed from the incubator and the medium is aspirated/discarded. Wells are washed once with assay buffer [PBS+1 mM $Mg^{2+}$ and 1 mM $Ca^{2+}$]. Then 50 μl of assay buffer is added to each well. The Luciferase assay reagent is prepared as described by the vendor (LucLite kit from Packard), and 50 μl is added to each well. Plates are incubated at room temperature (RT) for about 30 minutes after which the signals are read, again at RT, on a Topcount (Packard).

The discovery of compounds that inhibit Shh-induced Gli-transcription exemplifies the utility of the claims in this patent. Activities for these compounds are presented in Table 1 below.

TABLE 1

| Compound | $IC_{50}$ |
|---|---|
| 31 | <10 μM |
| 32 | <5 μM |
| 34 | <5 μM |
| 11 | <5 μM |
| 36 | <5 μM |
| 38 | <5 μM |
| 39 | <5 μM |
| 40 | <10 μM |
| 41 | <10 μM |
| 42 | <5 μM |
| 43 | <10 μM |
| 44 | <1 μM |
| 45 | <5 μM |
| 46 | <0.5 μM |
| 47 | <5 μM |
| 48 | <0.5 μM |
| 49 | <1 μM |
| 50 | <1 μM |
| 51 | <5 μM |
| 52 | <1 μM |
| 53 | <1 μM |
| 54 | <5 μM |
| 55 | <5 μM |
| 56 | <10 μM |
| 57 | <10 μM |
| 58 | <5 μM |
| 59 | <5 μM |
| 60 | <5 μM |
| 61 | <1 μM |
| 62 | <1 μM |
| 63 | <10 μM |
| 64 | <10 μM |
| 65 | <10 μM |
| 66 | <10 μM |
| 67 | <5 μM |
| 68 | <1 μM |
| 69 | <0.5 μM |
| 5 | <0.1 μM |
| 71 | <10 μM |
| 6 | <0.5 μM |
| 73 | <5 μM |
| 74 | <5 μM |
| 75 | <5 μM |

Mouse #456 is a Ptc-knockout heterozygote that received UV irradiation for 6 months. The mouse developed many small BCC lesions, which were blue after X-gal staining. The mouse was sacrificed and the skin was excised with a 2 mm skin punch. Those skin punches were then cultured for 6 days. Comparing to vehicle (DMSO), compound A can decrease the number and size of BCC lesions (blue spots in the picture). This experiment suggests that compound A is able to inhibit murine BCC lesions in mouse #456.

In yet another experiment, E12.5 old ptc-1 (d11) lacZ lungs were harvested and transgenic embryos identified by lacZ detection using tails. Lung explants were grown submerged in mouse explant medium (DMEM based, additives optimized for the culture of mouse lungs) for 48 hrs, fixed in lacZ fixative, rinsed and stained for lacZ O/N at 37° C. Control tissue was untreated, while test tissue was treated with compound A. Strong lacZ expression can be observed in distal and proximal mesenchyme. Treatment with compound A leads to significantly decreased reporter gene expression, as evidenced especially by the weak signal surrounding the distal branching tips of the growing lung epithelium.

Example 5

Bladder Cancer

Cytogenetic and Mutational Data Suggest Hedgehog Activation Plays a Causative Role in Bladder Cancer The cytogenetic and molecular alterations found in bladder cancer are heterogeneous. In establishing the primary, specific mutations in cancers, it is often useful to examine near-diploid cancers, which do not yet have complex, multiple chromosome changes accompanied by hyperdiploidy. Gibas et al., found monosomy of chromosome 9 in 4 out of 9 cases of transitional cell carcinoma of the bladder (Gibas et al. (1984) *Cancer Research* 44:1257-1264). In three of these, the karyotype was near diploid, and in one, monosomy 9 was the only abnormality observed. Therefore, monosomy of chromosome 9 may initiate malignant transformation in a subgroup of such cancers.

More evidence that this change appears as an early event was presented by two other group who reported that deletions of chromosome 9 are the only genetic changes present frequently in superficial papillary tumors (Dalbagni et al. (1993) *Lancet* 342: 469471). In fact, 9q deletions are estimated to occur in approximately 60-70 percent of bladder tumors (Cairns et al. (1992) *Oncogene* 8: 1083-1085; Dalbagni et al., supra). One study reported that deletion of 9q22 occurs in 35% of informative cases (Simoneau et al. 1999). The hedgehog signaling pathway component patched-1 is located on 9q22.

LOH of all other chromosomes is infrequent (less than 10%) in low-grade, non-invasive cancers. Likewise, alteration in bladder-cancer associated oncogenes (ERBB2, EGFR) are also rare in superficial, low-grade tumors (Cairns et al., supra).

On the basis of these cytogenetic findings, the following model for bladder carcinogenesis has been proposed: Initiation occurs by deletion of tumor-suppressor genes on chromosome 9, leading to superficial papillary or occasionally flat tumors, a few of which may then acquire further mutations (e.g., p53) and progress to invasion.

Three groups observed trisomy 7 in a low percentage of bladder cancers (Sandberg, supra; Berger et al. supra; Smeets et al., supra). Shh, which according to our own experiments continues to be expressed in bladder epithelium throughout adult life, localizes to chromosome 7. Berger et al. also observed deletions of 10q24, the locus of su(fu) (Berger et al (1986) *Cancer Genetics and Cytogenetics* 23: 1-24). Likewise, Smeets et al. suggested that 10q loss may be a primary event in the development of bladder cancer (Smeets et al. (1987) *Cancer Genetics and Cytogenetics* 29: 29-41).

This data suggests mechanisms by which the baseline expression of hedgehog signaling present in the adult bladder epithelium may be increased, thus leading to increased proliferation of urothelial cells. This hypothesis is supported by the cytological data, as well as by the finding of McGarvey et al. that described ptc-1, smo and gli-3 expression in normal human urothelium and two transitional cell carcinoma lines (McGarvey et al. (1998) *Oncogene* 17: 1167-1172).

Figure 16:
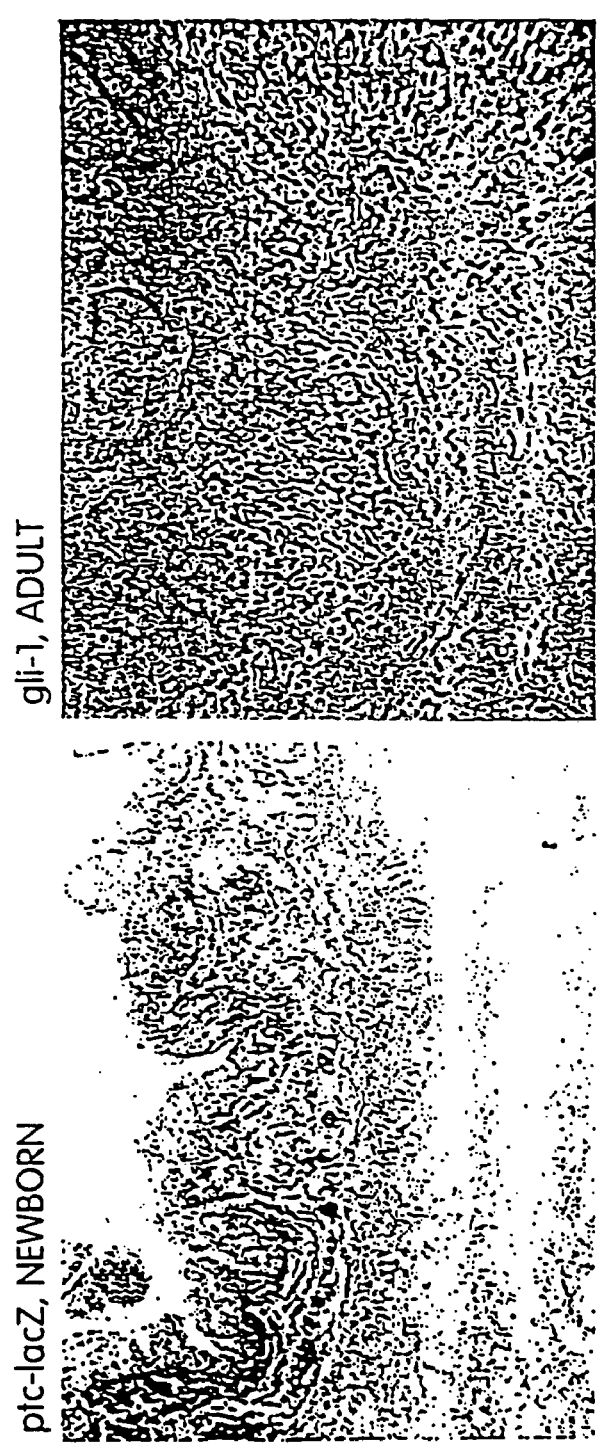
FIG. 16 shows: (A) Ptc-lacZ transgene expression in newborn mouse ptc-1 (d11) lacZ bladder epithelium. LacZ expression can be detected in the proliferating urothelial cells and, more weakly, in adjacent mesenchymal cells. (B) Gli-1 expression in adult mouse bladder epithelium. Gli-1 expression can be detected in the proliferating urothelial cells.

Hedgehog signaling was examined in the mouse bladder, and found to be present in normal bladder. In Ptc-lacZ transgenic newborn mice (ptc-1 (d11) lacZ), LacZ expression can be detected in the proliferating urothelial cells of the bladder epithelium, and more weakly, in adjacent mesenchymal cells (FIG. 16A). Additional in situ hybridization analysis of adult mouse bladder indicates expression of gli-1 in the bladder epithelium, and specifically in the proliferating urothelial cells (FIG. 16B).

METHODS: For lacZ staining, ptc-1 (d11) lacZ bladder was harvested from the transgenic newborn mouse pups identified by lacZ detection using tails. Bladders were fixed in lacZ fixative, rinsed and stained for lacZ O/N at 37° C., then processed for standard histology. Sections were counterstained with eosin. For in situ hybridization, sections of paraformaldehyde-fixed, paraffin-embedded tissue were cleared, re-hydrated, digested with proteinase K, acetylated and hybridized with [33P]-labeled gli-1 RNA probe over night. After high stringency post-hybridization washes, slides were dipped in photo-emulsion, incubated for up to three weeks, developed, and imaged using dark field illumination. Dark-field signals were filled in with artificial color (red) and superimposed with bright-field images.

Hedgehog Signaling in Bladder Cancer

Hedgehog signaling and hedgehog pathway gene expression was analyzed in a human bladder cancer, and in several bladder cancer cell lines. Gene expression in these tissues was measured using Quantitative Real-Time PCR (Q-RT-PCR). These results are summarized in FIGS. 17-19, and demonstrate that hedgehog pathway genes are expressed in bladder cancer cell lines.

Figure 17:
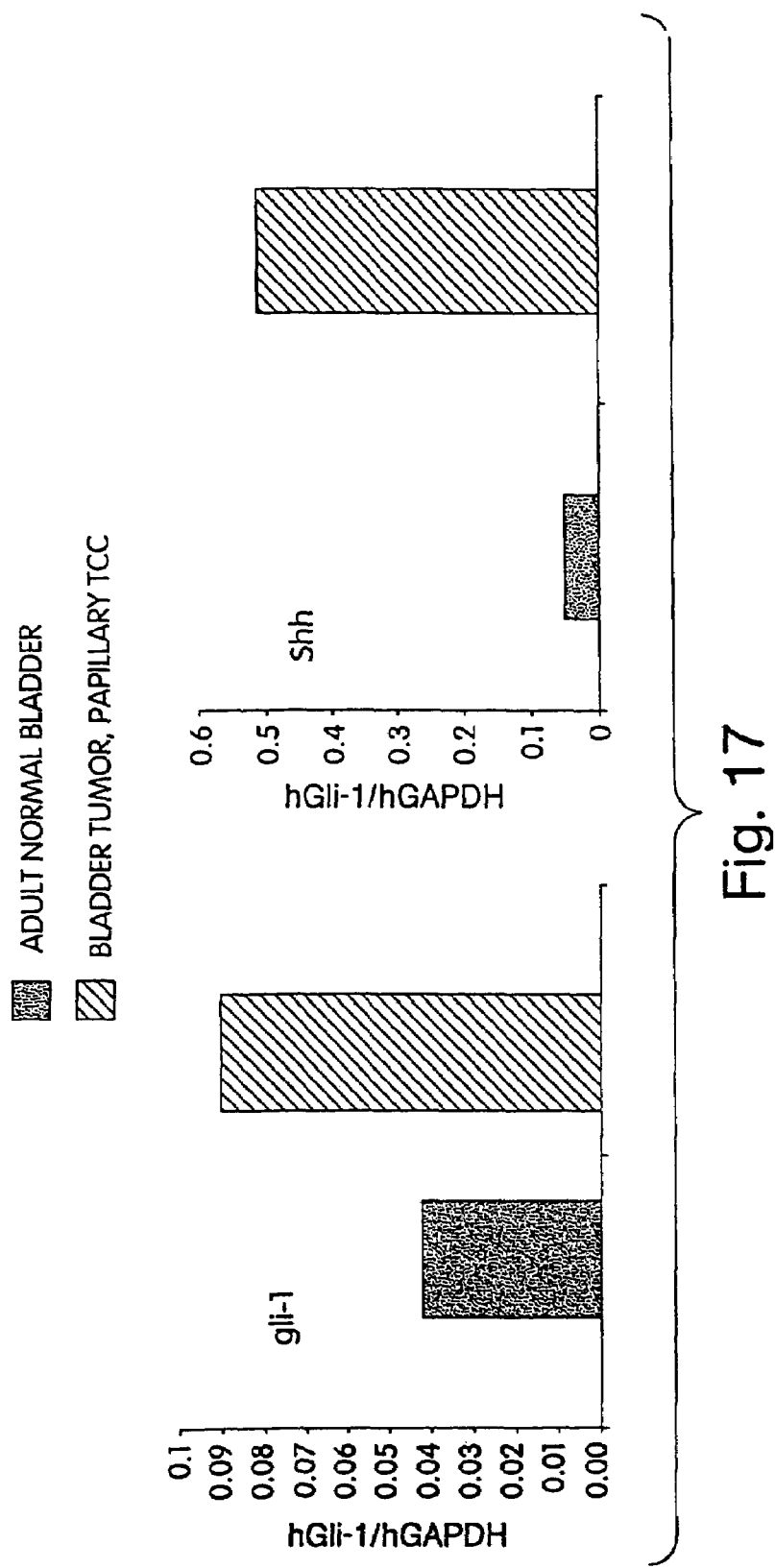
FIG. 17 shows the expression of gli-1 and shh in normal adult bladder and in a commercially available bladder tumor.
Figure 18:
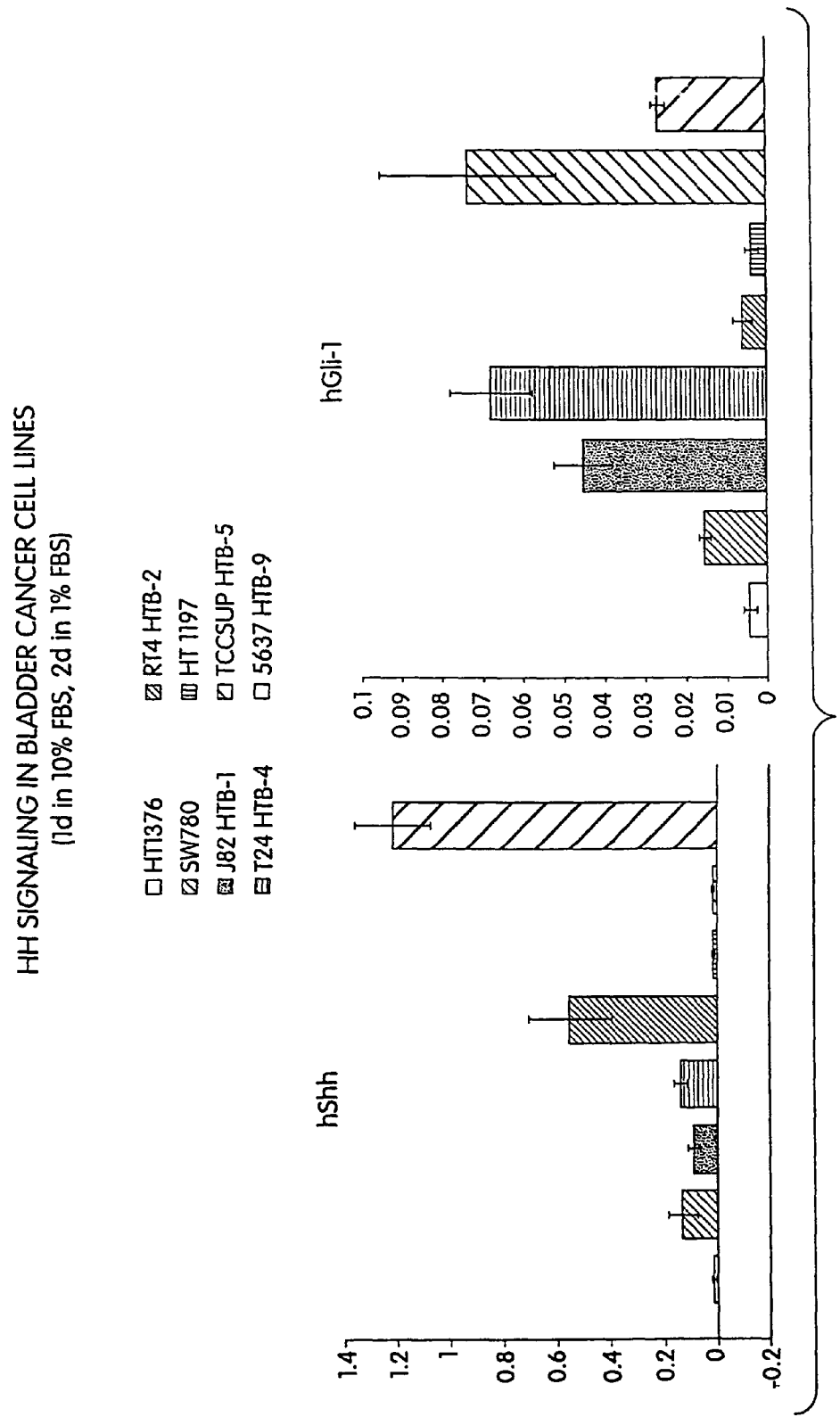
FIG. 18 shows the expression of shh and gli-1 in eight commercially available bladder cancer cell lines. All eight cell lines examined express genes involved in hedgehog signaling.
Figure 19:
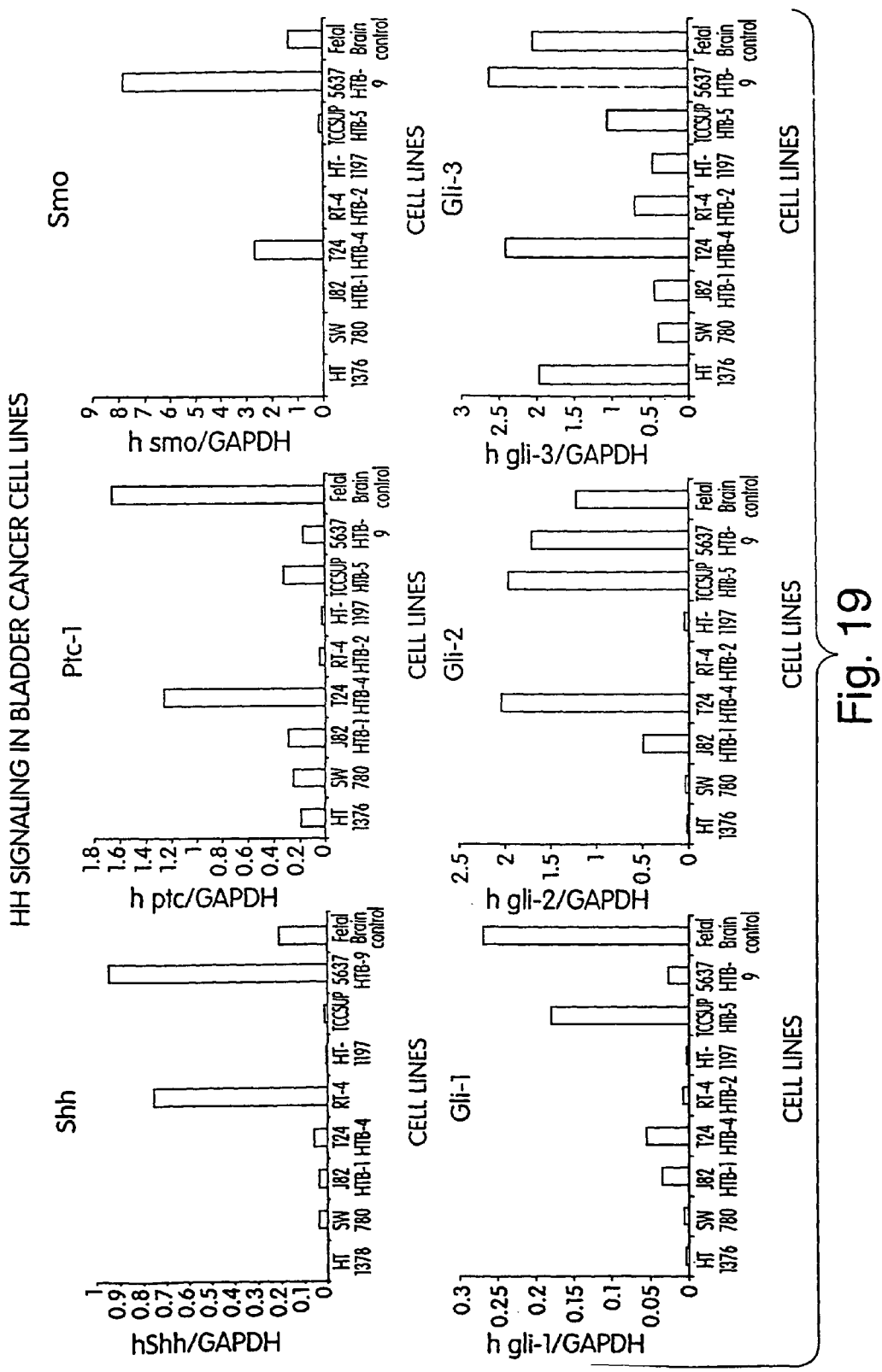
FIG. 19 shows the expression of shh, ptc-1, smo, gli-1, gli-2, and gli-3 in eight commercially available bladder cancer cell lines, as well as in fetal brain.

FIG. 17 demonstrates that shh expression is increased 12-fold and gli-1 expression is increased 2.5 fold in a bladder tumor sample when compared to normal adult bladder. FIG. 18 examines shh and gli-1 expression in eight human bladder cancer cell lines, and FIG. 19 examines expression of shh, ptc-1, smo, gli-1, gli-2, and gli-3 in the same eight human bladder cancer cell lines. These results indicate that components of the hedgehog pathway are expressed in eight out of eight cell lines examined.

METHODS: Experiment 1 (FIG. 17)—evaluation of hedgehog signaling in a bladder tumor. For Quantitative Real-Time Polymerase Chain Reaction (Q-RT-PCR) experiments, commercially available cDNA (Clontech) was amplified using an ABI Prism 7700 Sequence Detection System (TaqMan) from Perkin Elmer and gene-specific primers. The housekeeping gene GAPDH was used to normalize RNA concentration and PCR efficiency, and GAPDH primers were added to the same reactions. Since probes for both genes are labeled with different fluorophores, the specific signal and that of GAPDH can be detected in the same tube. Signal intensities were calculated using the algorithms provided in Sequence Detector v1.7, the software provided by the manufacturer.

Experiment 2 (FIGS. 18-19)—hedgehog signaling in eight bladder cancer cell lines. Bladder cancer cell lines were purchased from ATCC (American Type Culture Collection) and maintained as recommended in the product description. At confluency, cells were rinsed and switched to medium containing 1% serum, a treatment that increases hedgehog signaling. Cells were then grown 2 more days, collected in Trizol (GIBCO-BRL) and RNA isolated according to the manufacturer's protocol. The RNA was then transcribed into first strand cDNA according to standard protocols, and amplified using an ABI Prism 7700 Sequence Detection System (TaqMan) from Perkin Elmer and gene-specific primers. The housekeeping gene GAPDH was used to normalize RNA concentration and PCR efficiency, and GAPDH primers were added to the same reactions. Since probes for both genes are labeled with different fluorophores, the specific signal and that of GAPDH can be detected in the same tube. Signal intensities were calculated using the algorithms provided in Sequence Detector v1.7, the software provided by the manufacturer.

In vitro Assay to Examine Hedgehog Signaling in Bladder Cancer Cell Lines

Figure 20:
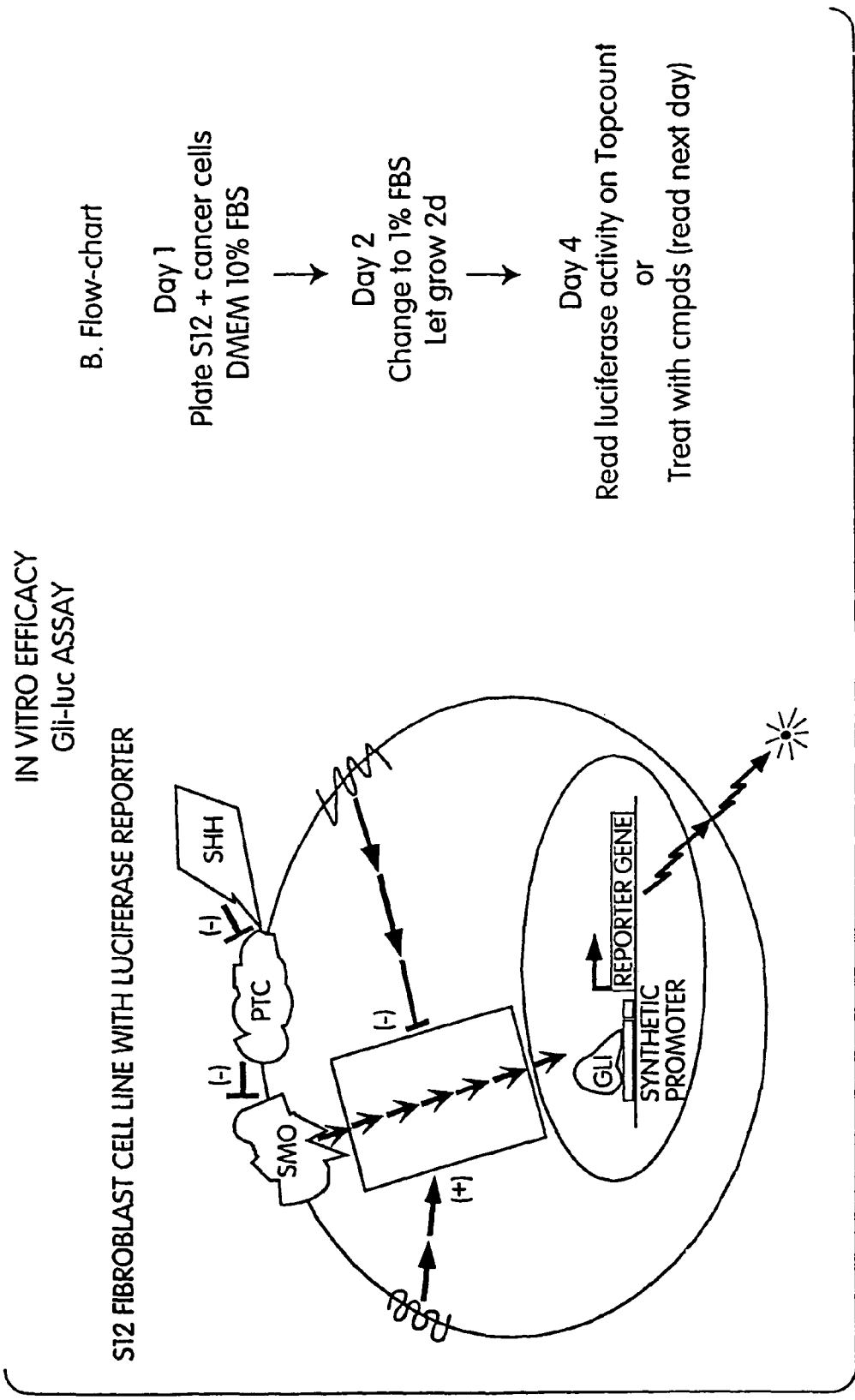
FIG. 20 shows a schematic representation of the gli-Luc assay.

The expression of components of the hedgehog signaling pathway in the eight bladder cancer cell lines examined suggested that hedgehog signaling is active in bladder cancer cells. However the gene expression observed may not be indicative of functional signaling. To assess whether functional hedgehog signaling occurs in bladder cancer cell lines, a gli-Luc in vitro assay was used. This assay is summarized schematically in FIG. 20. Briefly, 10T ½ (S12) fibroblasts expressing a luciferase reporter gene responsive to hedgehog serve as an indicator of hedgehog signaling. When these cells are contacted with functional hedgehog protein, the hedgehog signaling pathway is activated in the S12 cells, and luciferase is expressed. In the experiments presented here, S12 cells are co-cultured with bladder cancer cells. If the bladder cancer cell line secretes functional hedgehog protein, luciferase expression will be activated in the adjacent S12 cells.

Figure 21:
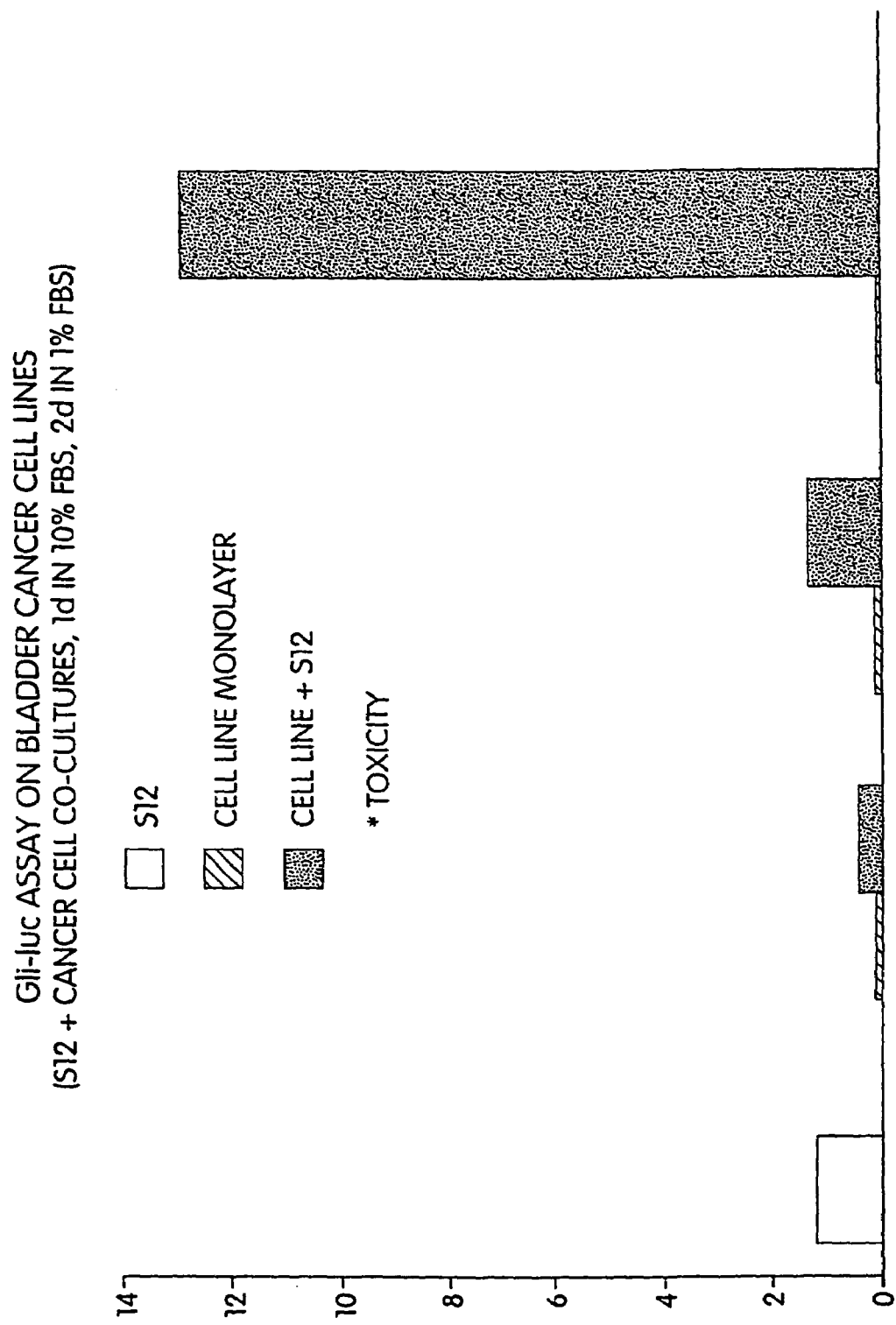
FIG. 21 shows the results of the gli-Luc assay on bladder cancer cell co-cultures. Co-culture of S12 cells with either cell line 5637 or cell line RT4 results in activation of the reporter gene indicating that these cell lines can activate hedgehog signaling.

FIG. 21 shows luciferase induction in S12 cells alone, and in S12 cells co-cultured with three bladder cancer cell lines. Two of the three cell lines examined induced expression of luciferase in S12 cells indicating that these bladder cancer cell lines secrete functional hedgehog protein.

Figure 22:
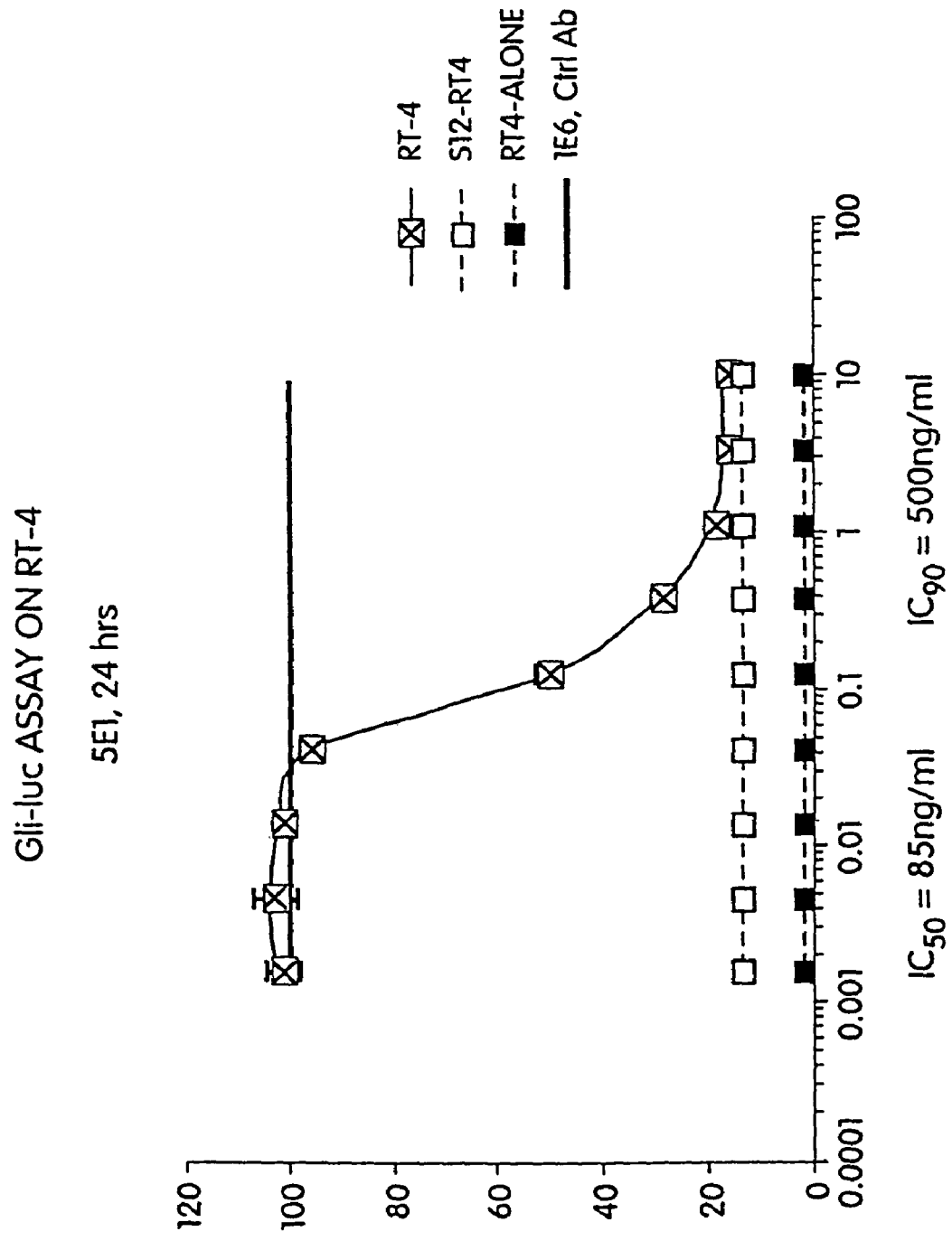
FIG. 22 shows that the Shh antibody 5E1 inhibits activation of the reporter gene in RT-4/S12 co-cultures.

To confirm the specificity of this activation of hedgehog signaling by bladder cancer cell lines, S12/RT-4 co-cultures were treated with the Shh blocking antibody (5E1). FIG. 22 demonstrates that 5E1 treatment of co-cultures inhibits expression of luciferase in S12 cells with an $IC_{50}$ of 85 ng/ml and an $IC_{90}$ of 500 ng/ml. It should be noted that this model also provides a means for evaluating the in vitro efficacy of other hedgehog antagonists including small molecule and polypeptide antagonists.

Hedgehog Signaling in an in vivo Mouse Bladder Tumor Model

Figure 23:
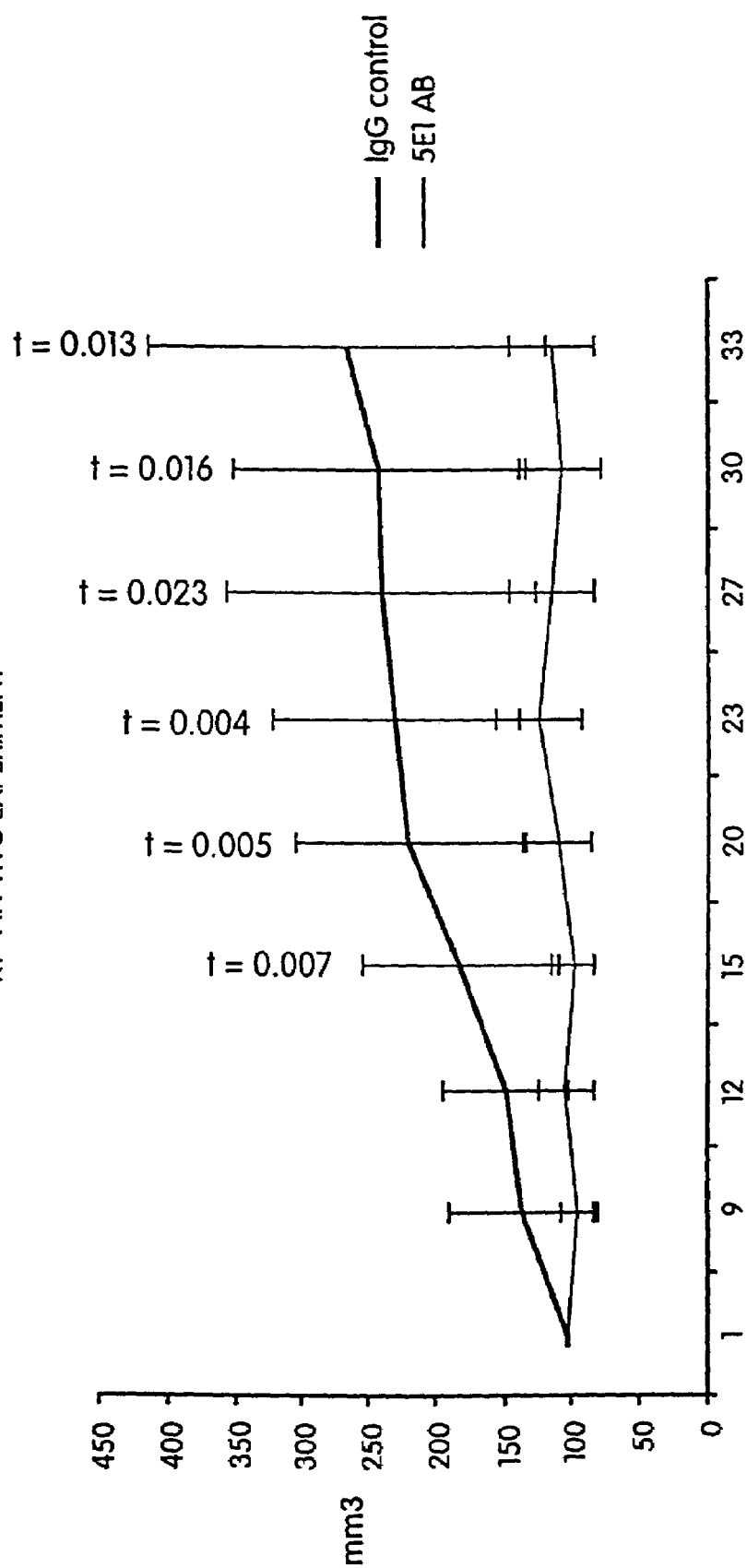
FIG. 23 and 24 show that administration of the Shh antibody 5E1 inhibits tumor growth in vivo in a nude mouse bladder cancer model.
Figure 24:
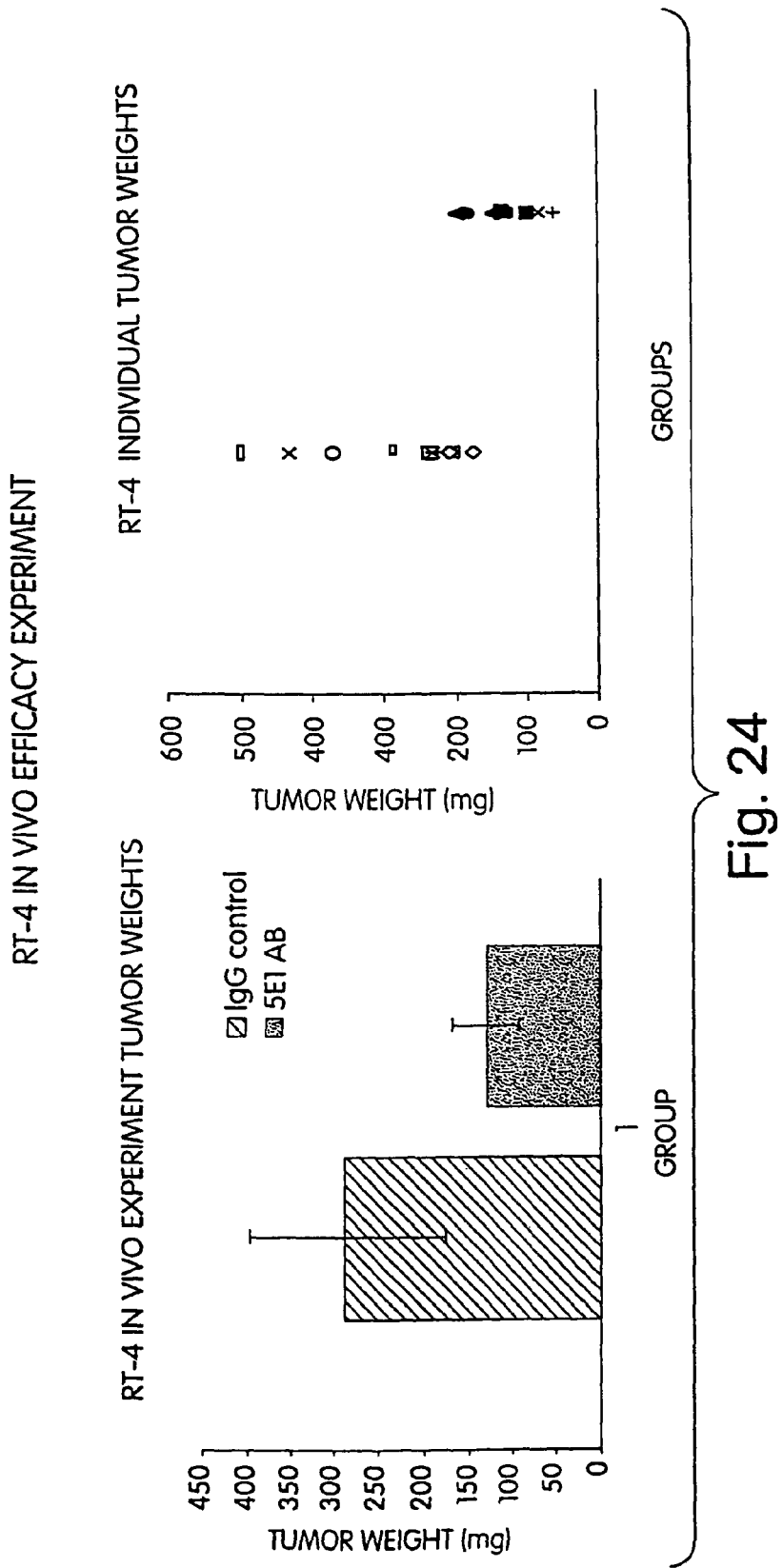

Injection of bladder tumor cells into nude mice induces tumor formation. Based on the ability of the Shh antibody 5E1 to inhibit hedgehog signaling in the in vitro gli-Luc assay described in detail above, the ability of 5E1 to inhibit bladder cell tumor growth in vivo was examined. Briefly, nude mice were injected subcutaneously with $10^7$ RT-4 cells. The mice were divided into two groups and treated with either 5E1 or with a control IgG antibody. FIGS. 23 and 24 show that treatment with 5E1 significantly decreased the size of the tumor in comparison to treatment with the IgG control. It is important to note that due to the procedure used in this particular experiment (injection of tumor cells with Matrigel) the tumors start out with an average size of 100 mm$^3$ due to the Matrigel matrix (=100 μl injection volume). Matrigel is a liquid when kept on wet ice, but solidifies upon injection. Thus, the average tumor size in the 5E1 group at the end of the experiment is roughly equal to that at the beginning of treatment. Results are highly statistically significant (Student's t-test: p=0.017). It should be noted that this model also provides a means for evaluating the in vivo efficacy of other hedgehog antagonists including small molecule and polypeptide antagonists.

Figure 25:
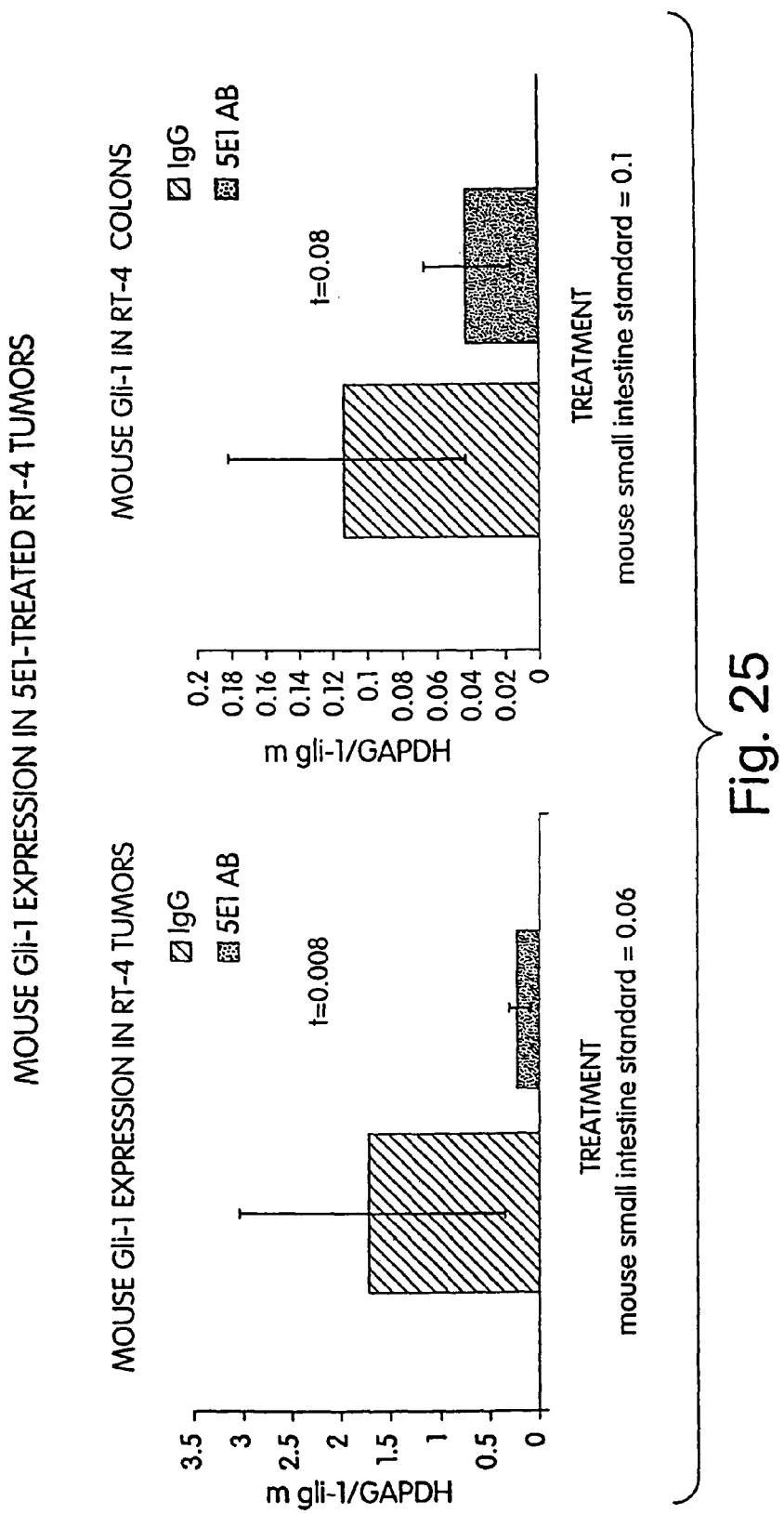
FIG. 25 shows that administration of the Shh antibody 5E1 decreases expression of gli-1 in vivo in a nude mouse bladder cancer model.

In addition to evaluating the effect of 5E1 treatment on tumor size, expression of gli-1 in both the RT-4 tumors and in the surrounding tissue was also evaluated. 5E1 treatment decreased expression of gli-1 in both the RT-4 tumors and in adjacent tissue (FIG. 25). This finding is significant because the in vitro experiments outlined above indicate that these hedgehog-expressing cells can activate hedgehog signaling in adjacent cell. Given the complex nature of cancer progression, it is possible that hedgehog signaling influences cancer both directly and indirectly. The indirect effects may include the induction of proliferative factors, angiogenic factors, or anti-apoptotic factors, to name a few. The induction of such factors may occur within the cancer cells themselves or in adjacent cells. Thus, the demonstration that a hedgehog antagonist 5E1 can inhibit hedgehog signaling in both cancer cells and in surrounding cells has significant implications.

METHODS: Exponentially growing RT-4 cultures were trypsinized, spun down, and resuspended in a small volume of culture medium. The proportion of viable tumor cells was determined by trypan blue exclusion. 107 cells/animal were resuspended in 100 µl Matrigel (a commercially available preparation of basement membrane components) and injected subcutaneously in the right side of the flank of 6-8 week-old athymic male BALB/c nu/nu nude mice. Treatment was begun the day after injection of the cells. Mice were divided into two groups containing 16 animals/group. The control group (IgG control antibody) and the 5E1-treated group were injected 3×/week intraperitoneally with 10 mg/kg antibody. Tumors were measured 2×/week by caliper in 2 dimensions and measurements converted to tumor mass using the formula for a prolate ellipsoid (axb2×/2). As noted above, in this particular example the tumors were injected in combination with Matrigel. Therefore, the tumors have an initial size of 100 mm$^3$ and the inhibition of tumor size observed following 5E1 treatment is nearly a complete inhibition of tumor growth.

Expression of gli-1 was measured using Q-RT-PCR as described throughout the application.

The inhibition of tumor growth by the hedgehog antagonist 5E1 supports the utility of the claimed invention. It is expected that antagonism of hedgehog signaling using a range of agents would have similar effects in decreasing tumor growth, and the efficacy of any candidate compound could be easily assessed using the in vitro and in vivo methods described above.

Example 6

Prostate Cancer

Hedgehog signaling plays an important role in normal prostate development. Sonic hedgehog is required for prostate growth, and expression of Shh is strongly correlated with prostate ductal branching (Podlasek et al. (1999) *Developmental Biology* 209: 28-39). Recent evidence supporting the essential role of shh in proper prostate branching demonstrates that treatment of embryonic prostate with the hedgehog antagonist cyclopamine inhibits growth and branching (W. Bushman, unpublished result). Additionally, the maintenance of low levels of hedgehog signaling in the adult mouse prostate suggests additional roles for hedgehog signaling beyond this early role in the initial growth and branching of the embryonic prostate.

Recent studies have examined the correlation between the expression of components of the hedgehog pathway and prostate cancer. These results show a correlation between increased expression of shh and/or gli-1 and prostate cancer. Additional cytological data supports the idea that mis-regulation of the hedgehog pathway plays a role in prostate cancer. Two studies have described deletions of a fragment of chromosome 10 containing the Su(fu) locus in prostate cancers (Carter et al. (1990) *PNAS* 87: 8751-8755; Li et al. (1997) *Science* 275: 1943-1947). Given the evidence in the literature suggestive of a role for hedgehog signaling in prostate cancer, hedgehog signaling in several prostate cancer cell lines was examined. Additionally, the ability of hedgehog antagonists to decrease activation of hedgehog signaling in prostate tumor cell lines was demonstrated. These results suggest that, like in bladder cancer cells, antagonism of hedgehog signaling has utility in decreasing growth and proliferation of prostate cancer cells.

Hedgehog Signaling in Prostate Cancer

Figure 26:
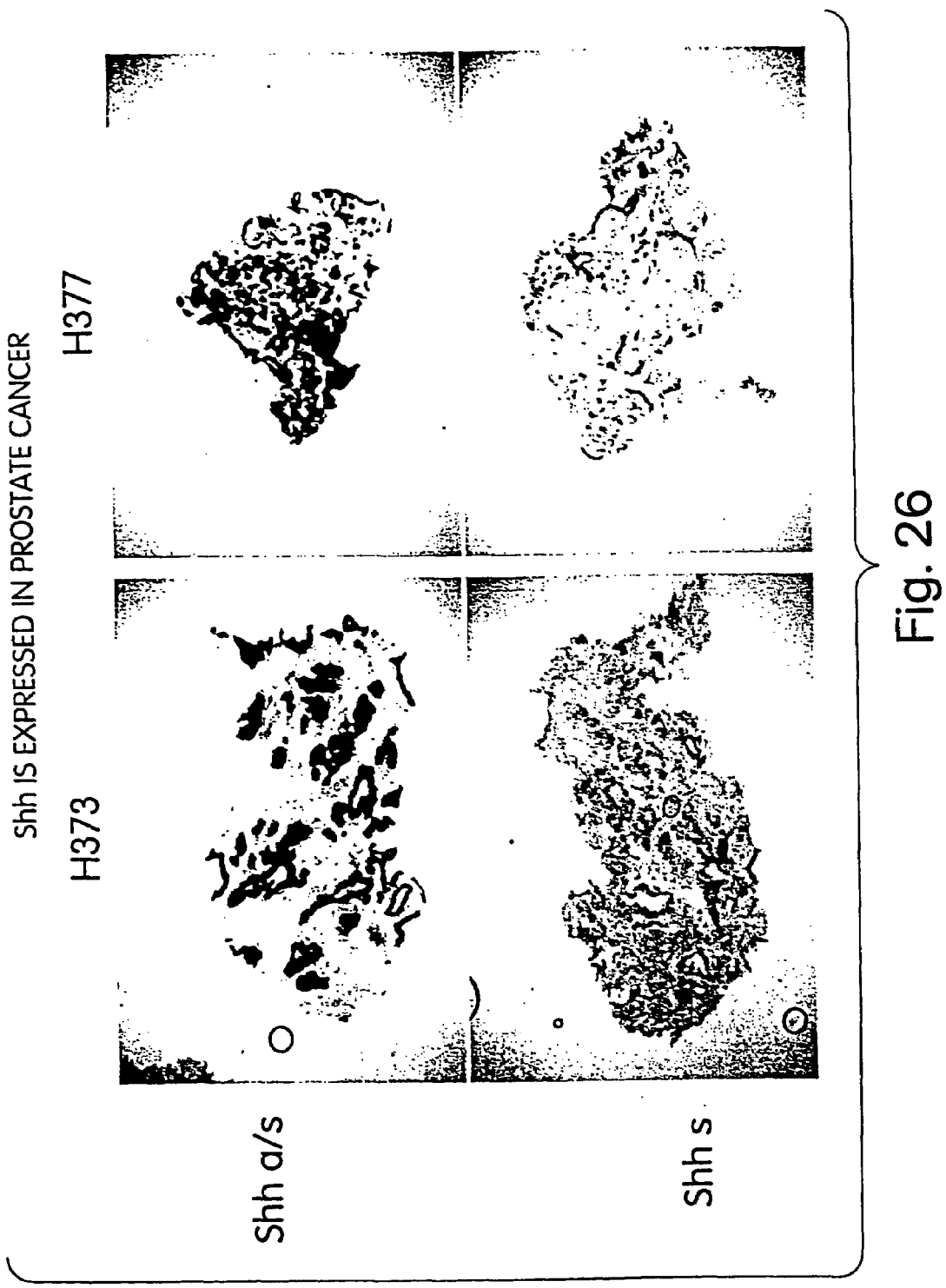
FIG. 26 shows that shh is expressed in prostate cancer samples as visualized by in situ hybridization.
Figure 27:
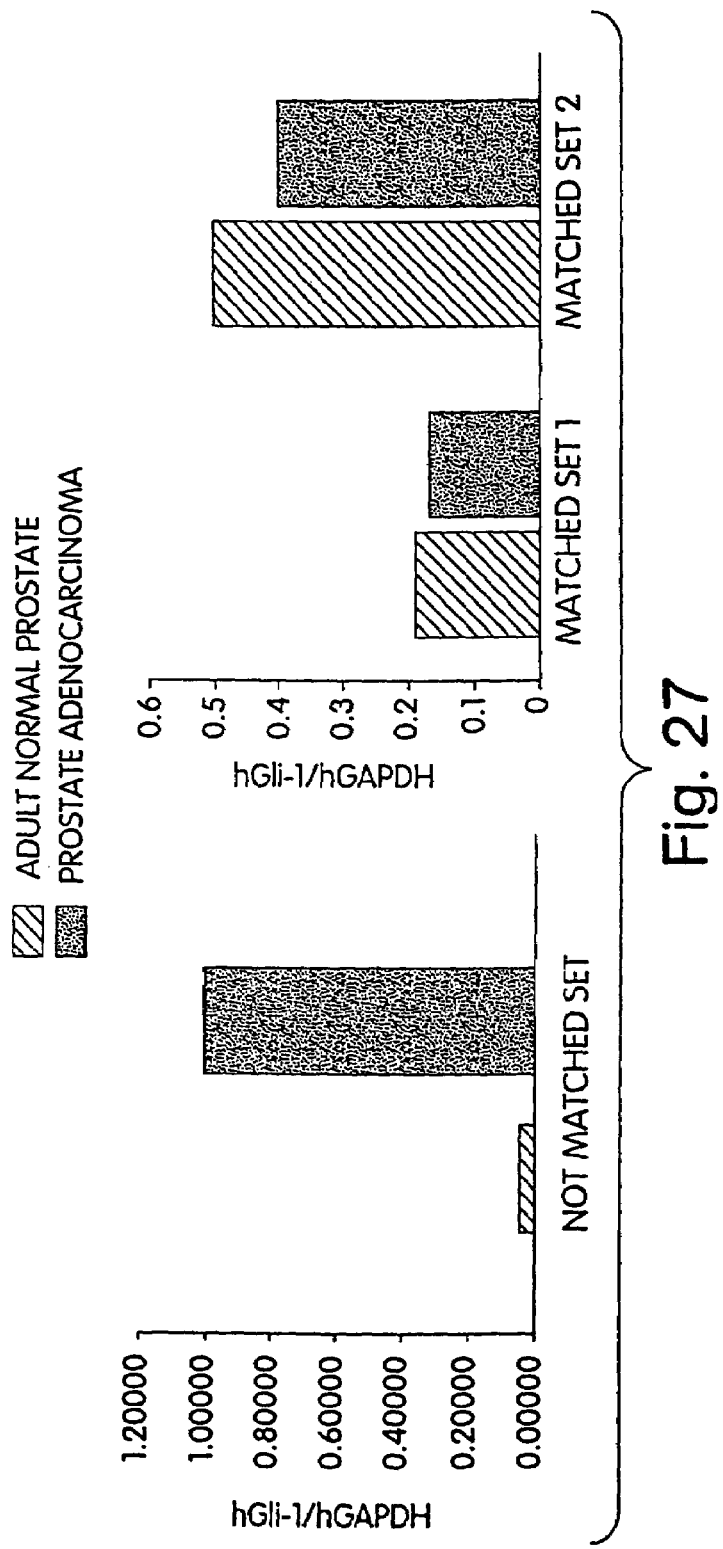
FIG. 27 shows by Q-RT-PCR the expression of gli-1 in normal adult prostate and in a prostate adenocarcinoma.
Figure 28:
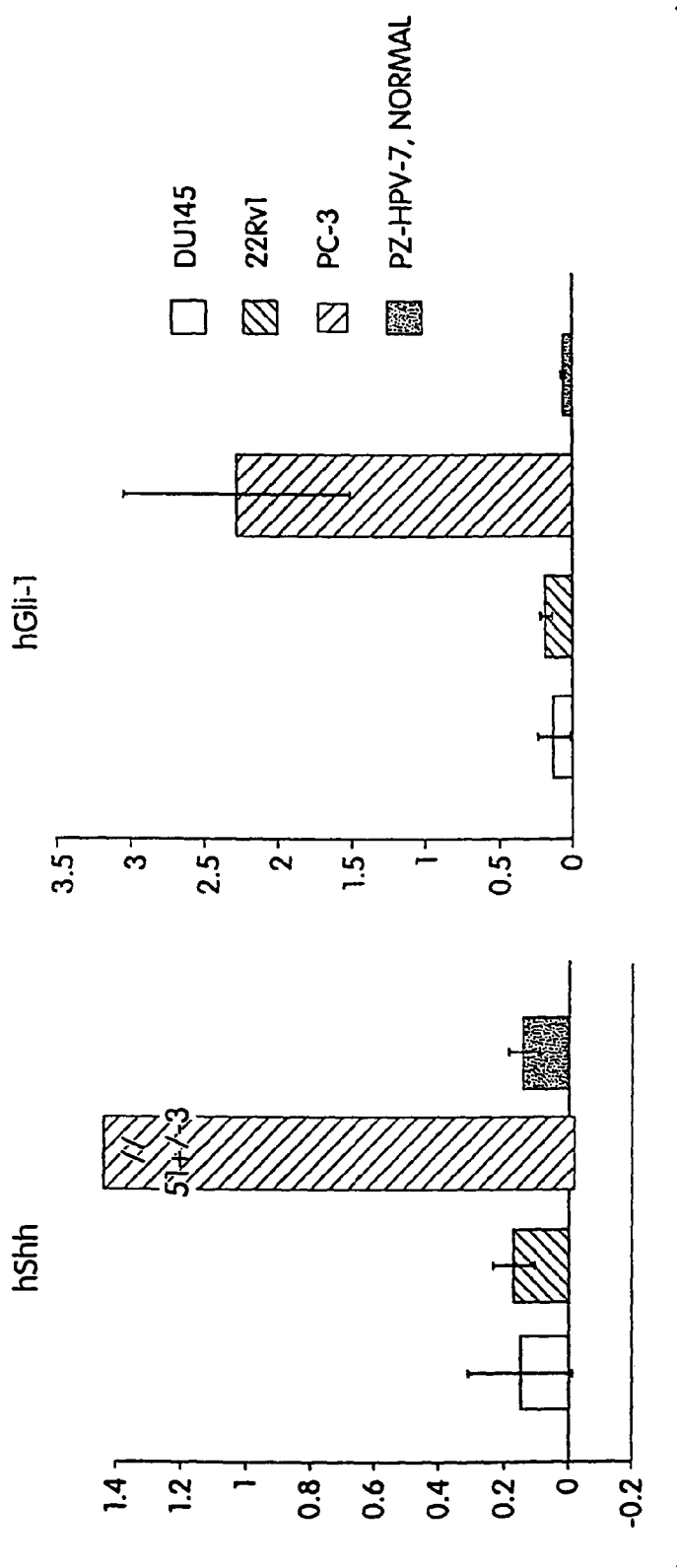
FIG. 28 shows the expression of shh and gli-1 in three prostate cancer cell lines in comparison with expression in a normal prostate cell line.

Expression of shh and gli-1 in both human prostate cancer samples and in commercially available prostate cancer cell lines was examined. FIG. 26 shows in situ hybridization analysis of human prostate cancer samples, and demonstrates the abundant expression of shh. Similarly, FIG. 27 demonstrates high levels of gli-1 expression in prostate cancer cells as measured by Q-RT-PCR. Finally, FIG. 28 examined expression of both shh and gli-1 by Q-RT-PCR in three commercially available prostate cancer cell lines. These results indicate hedgehog signaling occurs in all three commercially available cell lines.

METHODS: In situ hybridization: Paraformaldehyde-fixed tissue is cryo-sectioned into 30 µm sections, digested with proteinase K, hybridized overnight with digoxigenin-labeled RNA probe. After high stringency post-hybridization washes, sections are incubated with an anti-digoxigenin antibody which is labeled with alkaline phosphatase. The signal is visualized by addition of BM purple, a commercially available chromagen solution that reacts with the alkaline phosphatase to form a purple precipitate.

Prostate cancer cell lines were purchased from ATCC (American Type Culture Collection) and maintained as recommended in the product description. At confluency, cells were rinsed and switched to medium containing 1% serum, a treatment that increases hedgehog signaling. Cells were then grown 2 more days, collected in Trizol (GIBCO-BRL) and RNA isolated according to the manufacturer's protocol. The RNA was then transcribed into first strand cDNA according to standard protocols, and amplified using an ABI Prism 7700 Sequence Detection System (TaqMan) from Perkin Elmer and gene-specific primers. The housekeeping gene GAPDH was used to normalize RNA concentration and PCR efficiency, and GAPDH primers were added to the same reactions. Since probes for both genes are labeled with different fluorophores, the specific signal and that of GAPDH can be detected in the same tube. Signal intensities were calculated using the algorithms provided in Sequence Detector v1.7, the software provided by the manufacturer.

In vitro Assay to Examine Hedgehog Signaling in Prostate Cancer Cell Lines

The expression of components of the hedgehog signaling pathway in prostate cancer samples and cell lines suggests that hedgehog signaling is active in prostate cancer. However the gene expression observed may not be indicative of functional signaling. To assess whether functional hedgehog signaling occurs in prostate cancer cell lines, the gli-Luc in vitro assay was employed. This assay was summarized above, and is represented schematically in FIG. 20. Briefly, 10T ½ (S12) fibroblasts expressing a luciferase reporter gene responsive to hedgehog serves as an indicator of hedgehog signaling. When these cells are contacted with functional hedgehog protein, the hedgehog signaling pathway is activated in the S12 cells, and luciferase is expressed. In the experiments presented here, S12 cells are co-cultured with prostate cancer cells. If the prostate cancer cell line secretes functional hedgehog protein, luciferase expression will be activated in the adjacent S12 cells.

Figure 29:
FIG. 29 shows that prostate cancer cell lines induce expression of luciferase when co-cultured with S12 cells in the gli-Luc in vitro assay.

FIG. 29 shows no induction of luciferase in S12 cells cultured alone, or in S12 cells cultured with PZ-HPV-7 (normal) cells. However, luciferase induction is observed when S12 cells are cultured with any of three prostate cancer cell lines: 22Rv1, PC-3, or LNCaP. This result indicates that these prostate cancer cell lines secrete functional hedgehog protein.

Figure 30:
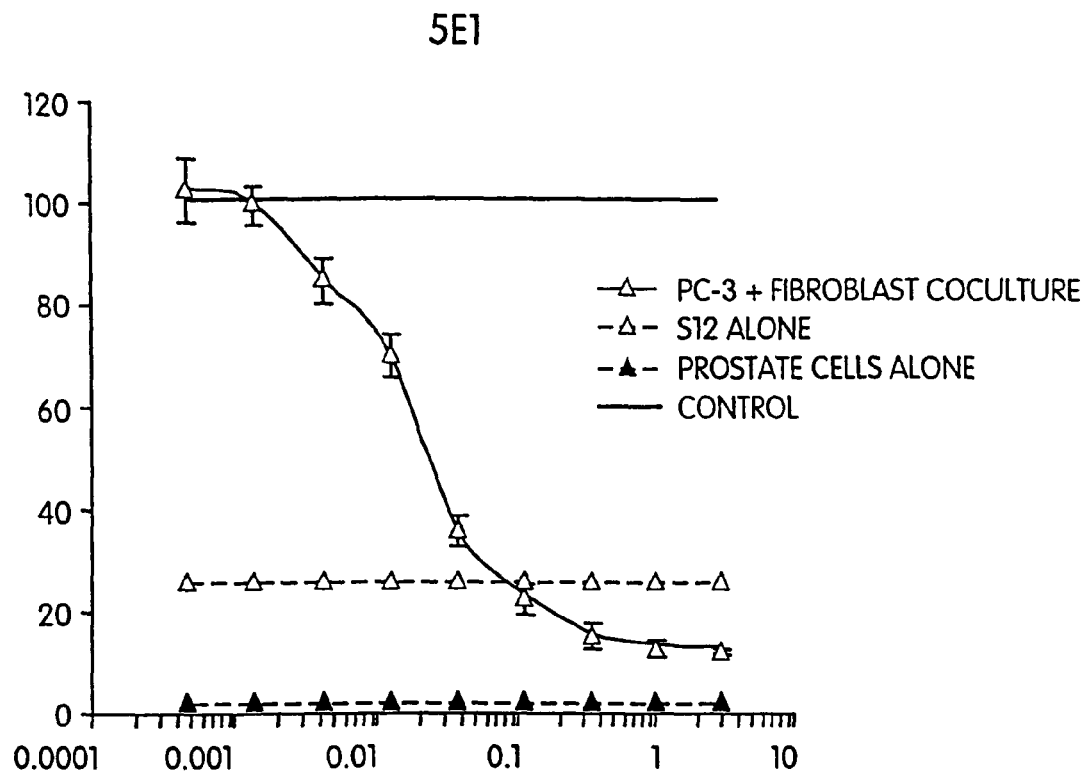
FIG. 30 shows that the antagonizing antibody 5E1 inhibits the induction of luciferase in by prostate cancer cells in the gli-Luc in vitro assay.

To confirm the specificity of this activation of hedgehog signaling by prostate cancer cell lines, S12/prostate cancer co-cultures were treated with the Shh blocking antibody (5E1). FIG. 30 demonstrates that 5E1 treatment of co-cultures inhibits expression of luciferase in S12 cells. METHODS: S12 cultures and co-cultures, and luciferase assays were performed as detailed above.

Example 7

Benign Prostatic Hyperplasia (BPH)

As detailed above, hedgehog signaling appears to have both an important role in early prostate patterning, and a role in maintenance of the adult prostate. Although prostate cancer is one potential affect of misregulation of hedgehog signaling in the adult prostate, another common condition of the prostate that seems to correlate with hedgehog expression is benign prostatic hyperplasia (BPH).

BPH is a disease of the central prostate, and is characterized by increased smooth muscle around the prostatic urethra. Interestingly, shh is expressed in a gradient in the adult prostate with highest expression in the central zone of the prostate. Additionally, shh is involved in smooth muscle differentiation in other tissues including the gut and lung (Apelqvist et al. (1997) Current Biology 7: 801-804; Pepicelli et al. (1998) Current Biology 8: 1083-1086). This evidence identified hedgehog signaling as a good candidate for involvement in the etiology of BPH. Finally, transcription of shh is increased by exposure to dihydro-testosterone (DHT) (Podlasek et al., supra). This is significant because the concentration of 5-alpha-reductase, an enzyme which converts testosterone to DHT, is elevated in BPH stroma (Wilkin et al. (1980) *Acta Endocrinology* 94: 284-288). This data suggests that misregulation of hedgehog signaling may be involved in BPH, and thus that the present invention provides utility for the treatment of BPH.

Hedgehog Signaling in BPH

Figure 31:
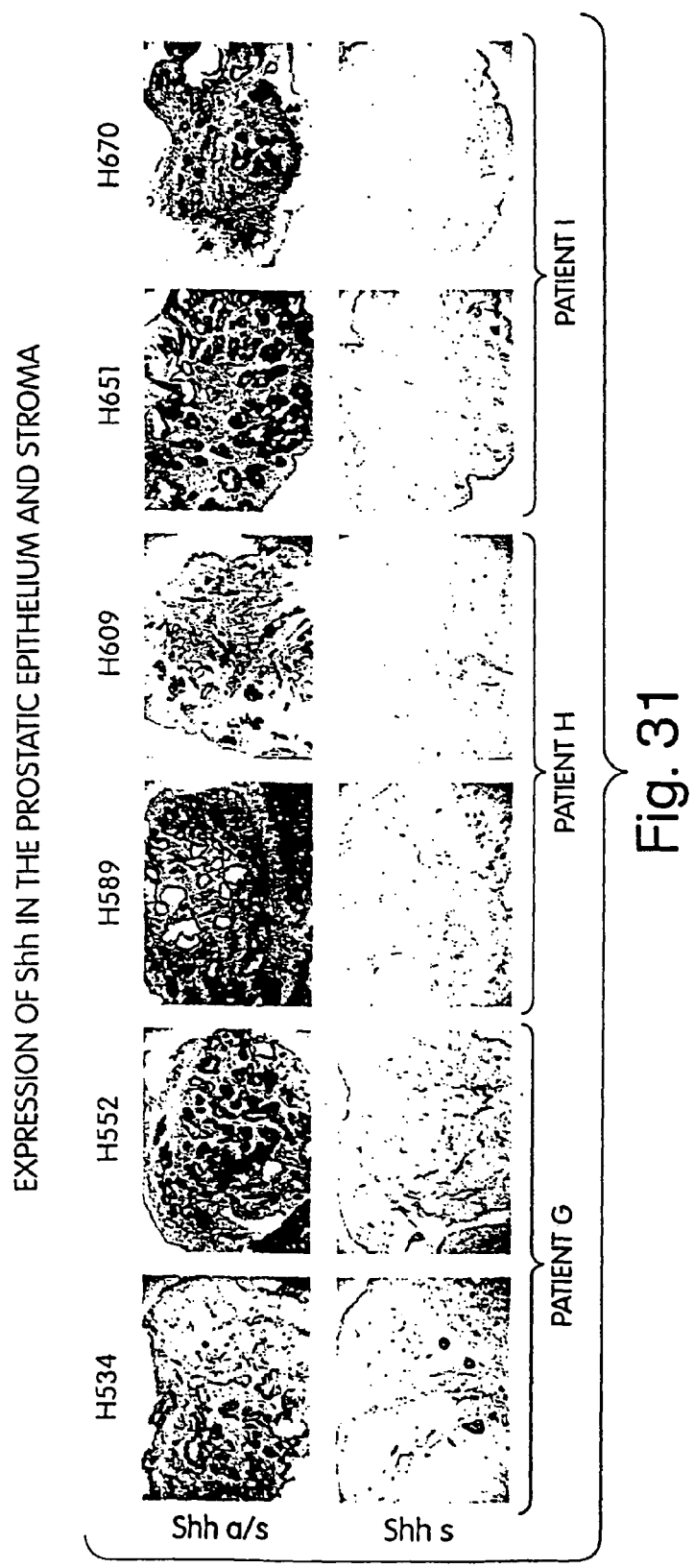
FIG. 31 shows the expression of shh in prostatic epithelium and stroma in human BPH samples.
Figure 32:
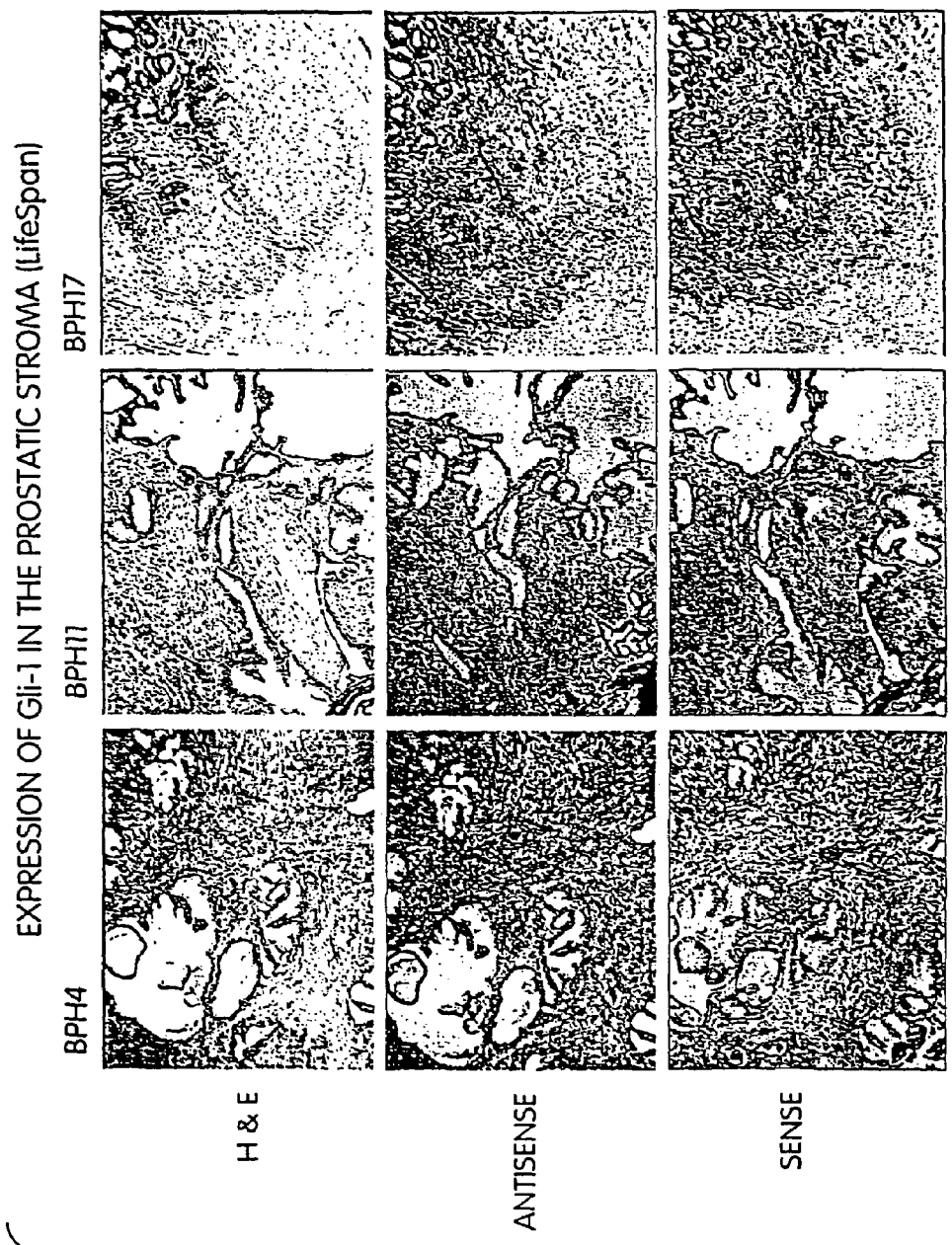
FIG. 32 shows the expression of gli-1 in the prostatic stroma of human BPH samples as measured by radioactive in situ hybridization.
Figure 33:
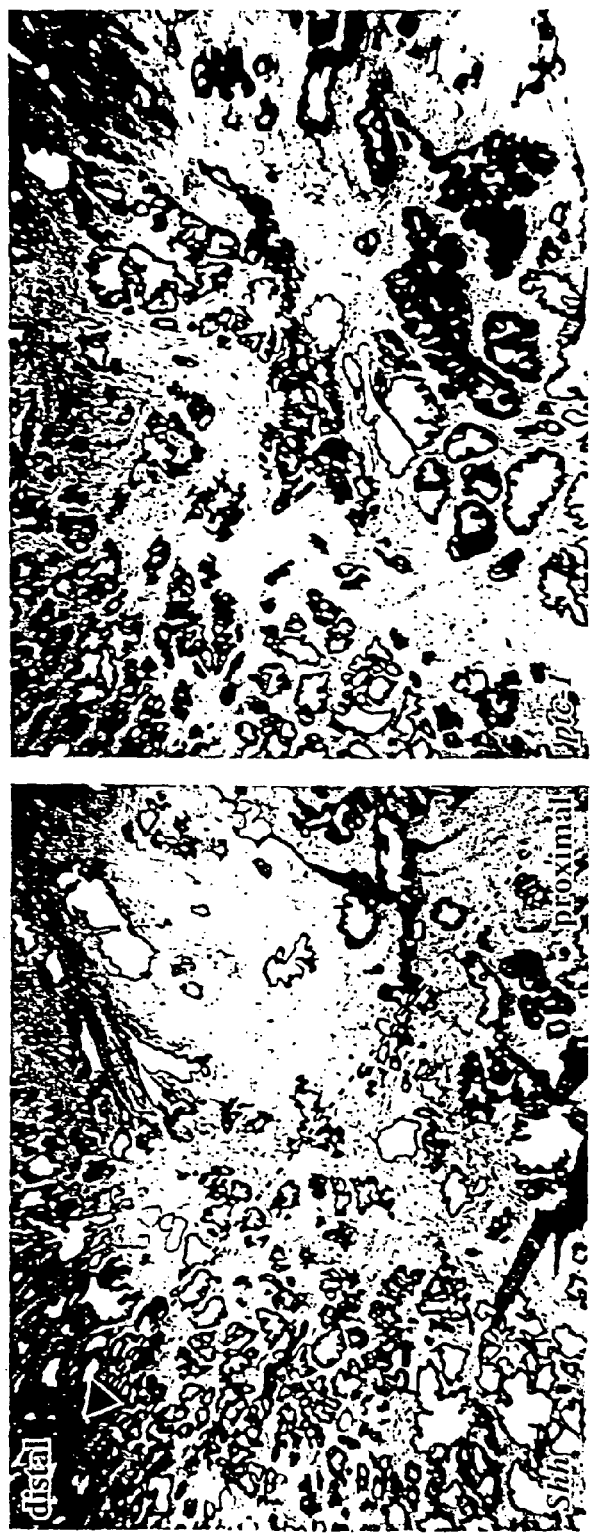
FIG. 33 shows that shh and patched-1 are expressed in a proximo-distal pattern in normal prostate tissue with the highest levels of gene expression occurring in the proximo or central region.

Expression of sonic hedgehog and gli-1 expression in human BPH samples was examined. FIGS. 31 and 32 show in situ hybridization analysis of human BPH samples, and demonstrate that both shh and gli-1 are abundantly expressed in BPH. Furthermore, FIG. 33 demonstrates that shh is not ubiquitously expressed throughout the prostate, but is instead present in a gradient with the highest level of both hedgehog and ptc-1 transcripts present in the proximal central zone of the prostate.

Figure 34:
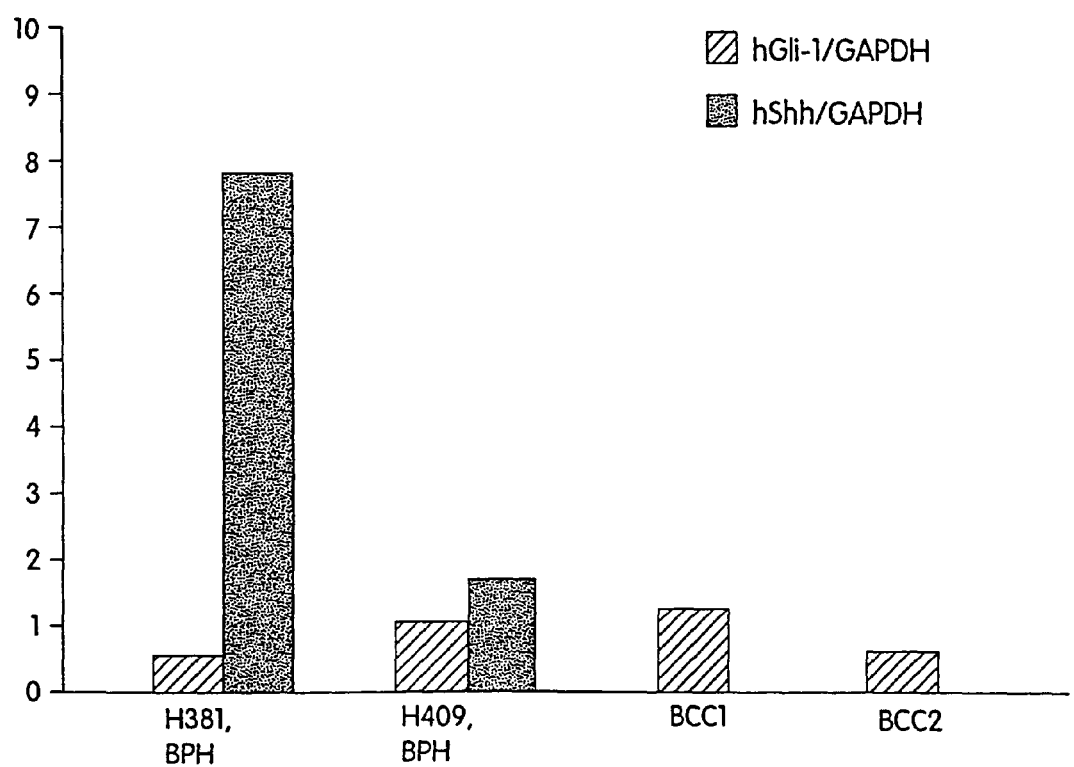
FIG. 34 shows the expression of shh and gli-1 in BPH samples, and compares the levels of gene expression to BCC samples.
Figure 35:
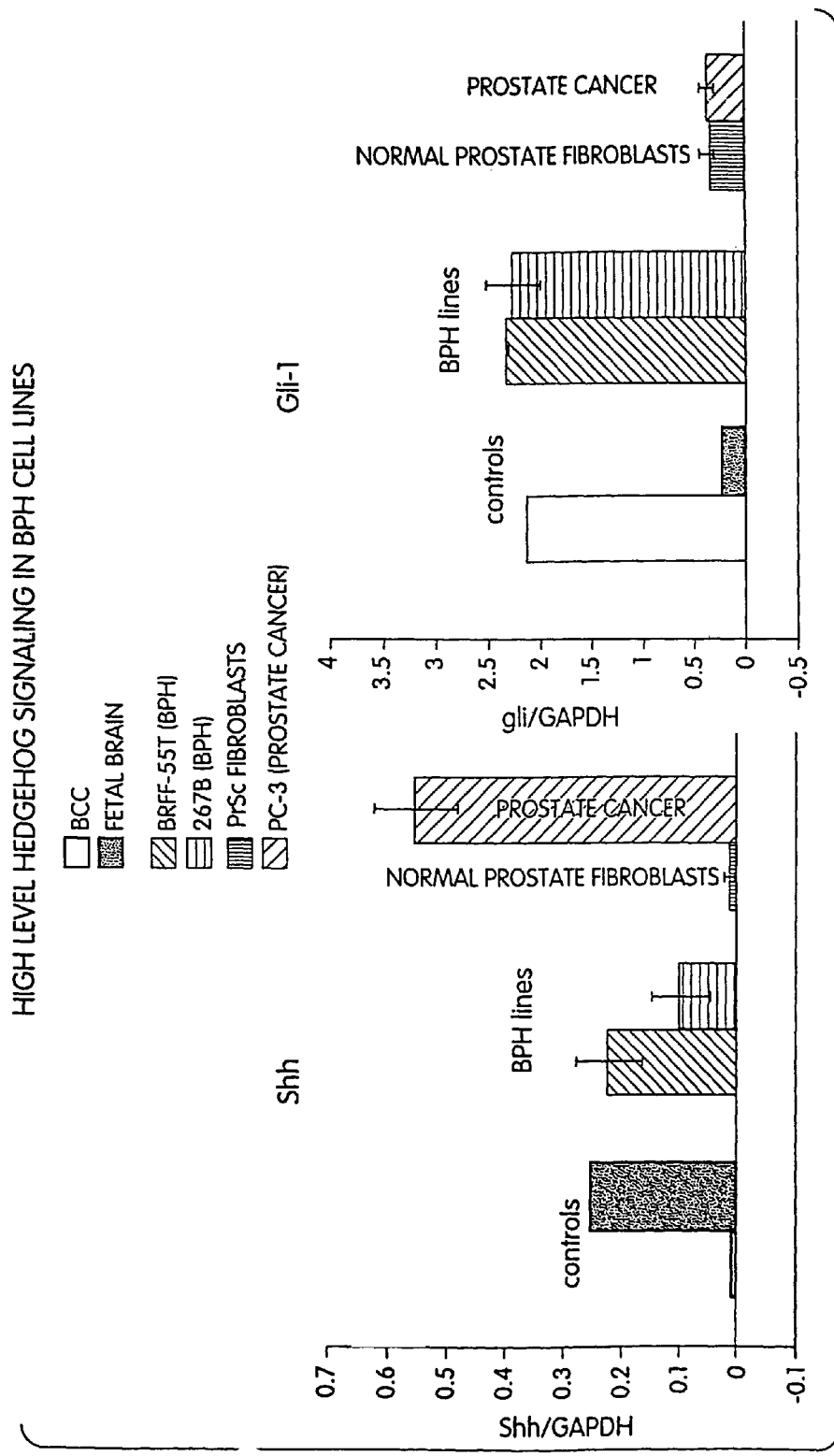
FIG. 35 shows the expression of shh and gli-1 in BPH cell lines, and compares the levels of gene expression to that of BCC samples, normal prostate, and prostate cancer.

Additionally, the expression of shh and gli-1 by Q-RT-PCR was analyzed. FIG. 34 shows that both shh and gli-1 are expressed in BPH samples. Expression of shh and gli-1 in basal cell carcinoma (BCC) samples is provided for comparison. These results demonstrate that gli-1 is expressed in BPH samples at a level similar to that found in a cancer type known to be caused by a hedgehog pathway mutation. Finally, FIG. 35 shows the expression of shh and gli-1 in BPH cell lines, and compares expression to that observed in BCC, prostate cancer cell lines, and normal prostate fibroblasts. Note that gli-1 is expressed at similar levels in both BPH cell lines and in BCC samples. These results are suggestive of a role for hedgehog signaling in BPH and further suggests that antagonism of hedgehog signaling has significant utility in the treatment of BPH.

METHODS: In situ hybridization (FIGS. 31 and 33): Paraformaldehyde-fixed tissue is cryo-sectioned into 30 μm sections, digested with proteinase K, hybridized overnight with digoxigenin-labeled RNA probe. After high stringency post-hybridization washes, sections are incubated with an anti-digoxigenin antibody which is labeled with alkaline phosphatase. The signal is visualized by addition of BM purple, a commercially available chromagen solution that reacts with the alkaline phosphatase to form a purple precipitate.

Radioactive In situ hybridization (FIG. 32): Briefly, 7 mm sections of paraformaldehyde-fixed, paraffin-embedded tissue containing large basal cell islands are cleared, re-hydrated, digested with proteinase K, acetylated and hybridized overnight with $^{33}$P-labeled RNA probes. After high stringency post-hybridization washes, slides were dipped in photo emulsion and incubated in the dark for 14 days at 4° C. After developing, slides were counter-stained with hematoxylin and eosin and imaged using dark-field illumination. Dark-field images were converted to red artificial color and superimposed with bright-field images. Q-RT-PCR: Samples were collected in Trizol (GIBCO-BRL) and RNA isolated according to the manufacturer's protocol. The RNA was then transcribed into first strand cDNA according to standard protocols, and amplified using an ABI Prism 7700 Sequence Detection System (TaqMan) from Perkin Elmer and gene-specific primers. The housekeeping gene GAPDH was used to normalize RNA concentration and PCR efficiency, and GAPDH primers were added to the same reactions. Since probes for both genes are labeled with different fluorophores, the specific signal and that of GAPDH can be detected in the same tube. Signal intensities were calculated using the algorithms provided in Sequence Detector v1.7, the software provided by the manufacturer.

Example 8

Additional Analysis of Hedgehog Expression in Normal and Hyperproliferative Tissue To further access the range of tissues in which the methods and compositions of the present invention may be useful in inhibiting the proliferation, growth, differentiation or survival of cells, hedgehog expression was analyzed in a range of normal and cancerous human tissues. Expression was examined at both the level of hedgehog mRNA using quantitative RT-PCR and at the level of hedgehog protein by immunohistochemistry.

Figure 36:
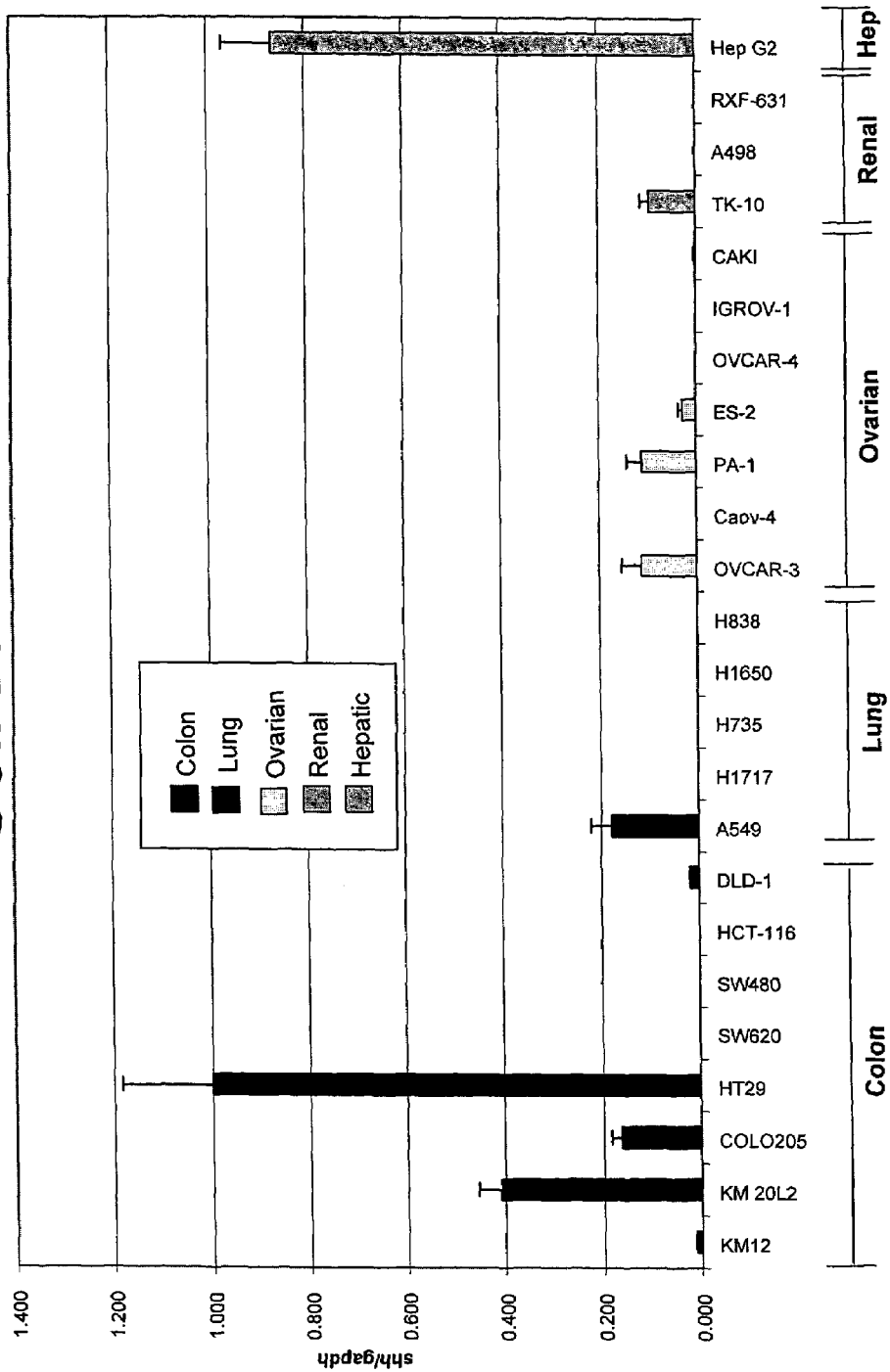
FIG. 36 shows the expression of shh in a variety of colon, lung, ovarian, renal and hepatic human cancer cell lines. Expression of shh is measured using Q-RT-PCR which demonstrates that shh is expressed, to a varying degree, in human cancer cell lines derived from several diverse tissue types.

FIG. 36 presents Q-RT-PCR analysis of Sonic hedgehog (shh) expression in a variety of human cancer cell lines. Shh expression was examined in human colon, lung, ovarian, renal and hepatic cell lines, and these results indicate that shh is expressed, at varying concentrations, in cell lines derived from each of these tissues.

Figure 37:
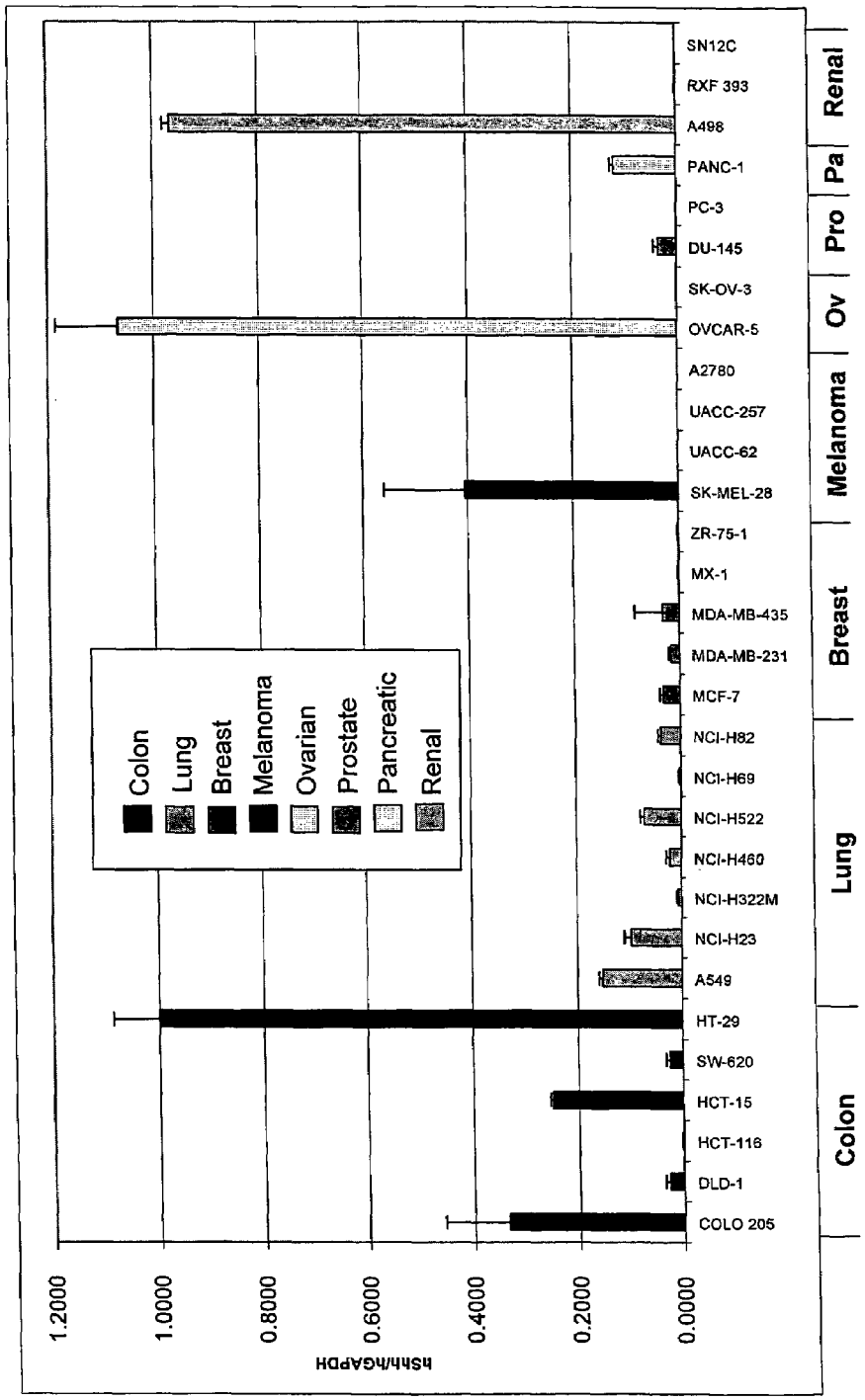
FIG. 37 shows the expression of shh in a variety of passaged tumors derived from colon, lung, breast, melanoma, ovarian, prostate, pancreatic and renal tissue. Expression of shh is measured using Q-RT-PCR which demonstrates that shh is expressed, to a varying degree, in passaged tumors derived from several diverse tissue types.

FIG. 37 presents Q-RT-PCR analysis of shh expression in passaged colon, lung, breast, melanoma, ovarian, prostate, pancreatic and renal tumors. The results demonstrate that shh is expressed, at varying levels, in passaged tumors derived from each of these tissues.

Figure 38:
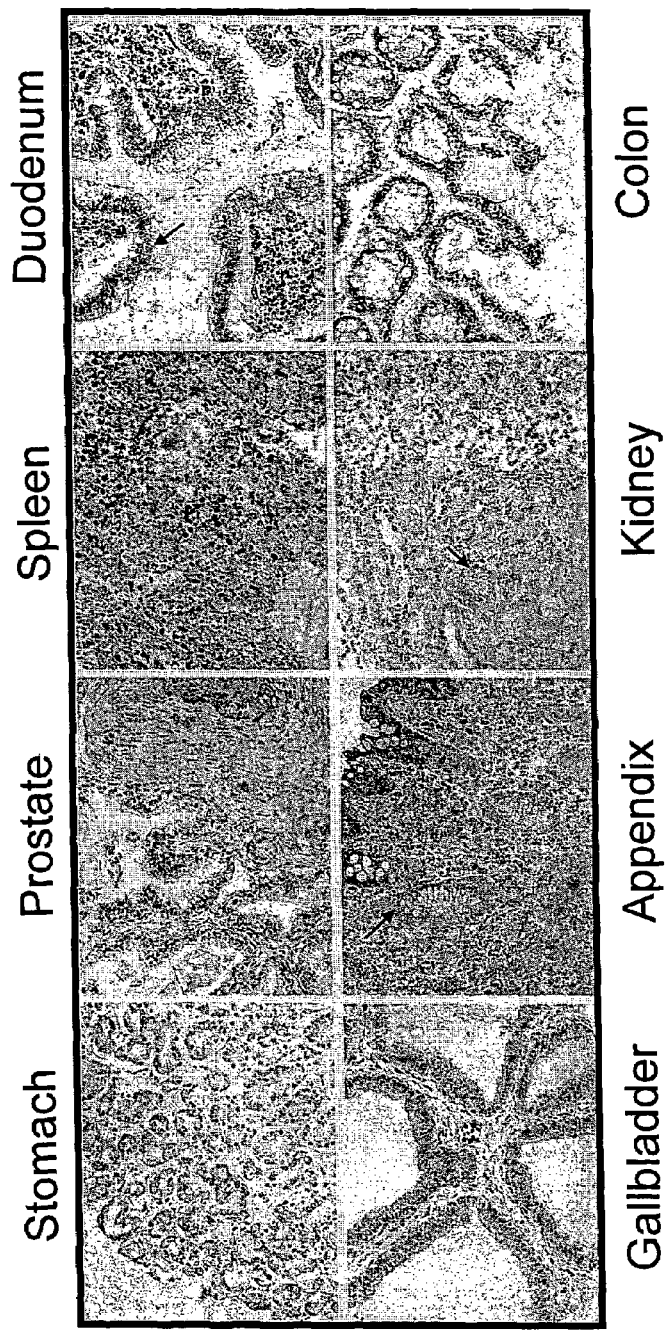
FIG. 38 shows the expression of hedgehog protein in normal human stomach, prostate, spleen, small intestine, large intestine, gall bladder, appendix and kidney tissue. Hedgehog protein expression was examined by immunohistochemistry using a polyclonal anti-hedgehog antibody.

Although the expression of shh RNA in a sample provides evidence that hedgehog signaling may be active in a cell, further information may be gleaned by examining the expression of hedgehog protein in a cell. In order to address this question, immunohistochemistry using a polyclonal anti-hedgehog primary antibody was performed on both normal and cancerous human tissue samples. FIG. 38 shows that hedgehog protein is expressed in normal human tissue harvested from a variety of sources including the stomach, prostate, spleen, small intestine, large intestine, gall bladder, kidney and appendix. It is interesting to note that hedgehog expression is observed in normal adult tissue derived from either the mesoderm or endoderm.

Figure 39:
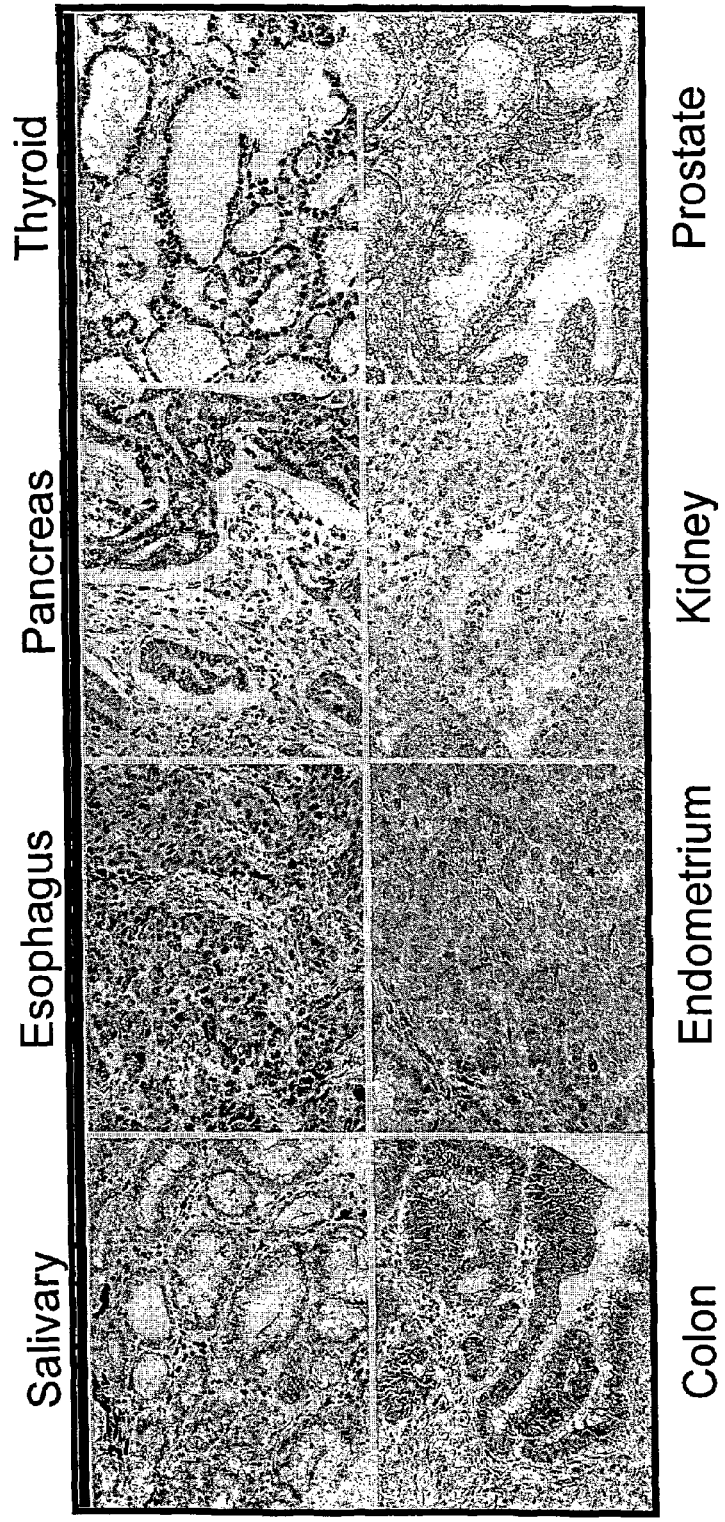
FIG. 39 shows the expression of hedgehog protein in human tumors derived from salivary, esophageal, pancreatic, thyroid, colon, endometrial, kidney and prostate tissue. Hedgehog protein expression was examined by immunohistochemistry using a polyclonal anti-hedgehog antibody.
Figure 40:
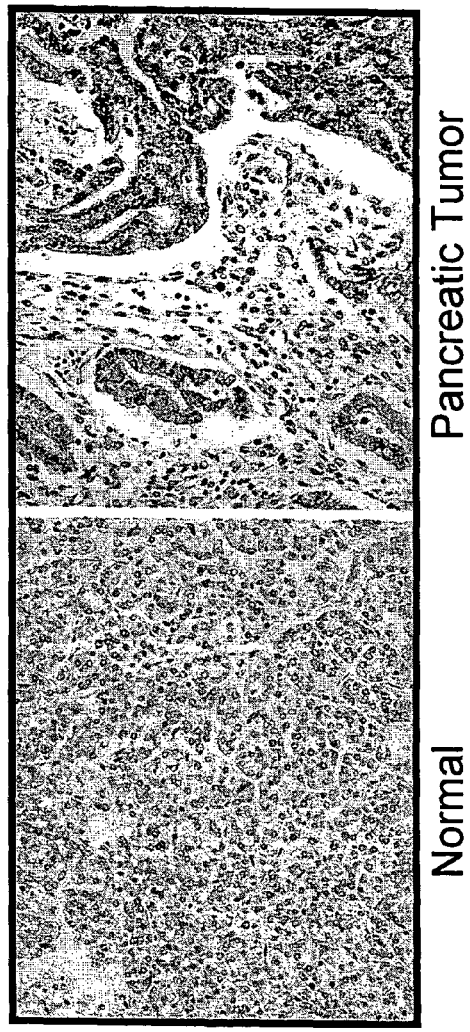
FIG. 40 shows increased expression of hedgehog protein in a sample of pancreatic tumor in comparison to hedgehog protein expression in normal pancreatic tissue. Hedgehog protein expression was measured by immunohistochemistry using a polyclonal anti-hedgehog antibody.

Expression of hedgehog protein was additionally observed in human tumors harvested from a range of tissues. FIGS. 39 and 40 demonstrate that hedgehog protein is detectable by immunohistochemistry in tumors derived from salivary esophageal, pancreatic, thyroid, colon, endometrial, kidney and prostate tissue.

These results indicate that hedgehog is expressed, at both the mRNA and protein level, in a wide range of both normal and hyperproliferative tissues. Further analysis is needed to ascertain, for a given tissue type, the differences in the level of hedgehog expression between normal tissue and hyperproliferative tissue. Such analysis will help provide a better understanding of the mechanistic role of increased hedgehog expression in hyperproliferative conditions including cancer.

METHODS: Q-RT-PCR: Samples were collected in Trizol (GIBCO-BRL) and RNA isolated according to the manufacturer's protocol. The RNA was then transcribed into first strand cDNA according to standard protocols, and amplified using an ABI Prism 7700 Sequence Detection System (TaqMan) from Perkin Elmer and gene-specific primers. The housekeeping gene GAPDH was used to normalize RNA concentration and PCR efficiency, and GAPDH primers were added to the same reactions. Since probes for both genes are labeled with different fluorophores, the specific signal and that of GAPDH can be detected in the same tube. Signal intensities were calculated using the algorithms provided in Sequence Detector v1.7, the software provided by the manufacturer.

Immunohistochemistry: Samples were harvested and processed for immunohistochemistry using standard methods. Samples were incubated overnight with a polyclonal anti-hedgehog primary antibody.

Example 9

Antagonism of Hedgehog Signaling in Colon Cancer

The growth of tumors is a complex process that requires proliferation, angiogenesis, the inhibition of cell death, and many other complex interactions between the cancer cells and the surrounding tissue. An additional mechanism by which hedgehog signaling may influence tumor growth and progression is through the induction of factors that enhance proliferation, angiogenesis, and the inhibition of cell death. For example, sonic hedgehog has been shown to induce VEGF in fibroblasts. Thus, the use of hedgehog antagonists may prevent hedgehog signaling from inducing factors that promote tumor formation, and therefore inhibit tumor formation or progression.

Given the complex interplay which likely exists between tumor cells and the surrounding tissue, we have used two models to analyze the effects of hedgehog antagonists in inhibiting the proliferation, growth, differentiation and survival of hyperproliferative tissues. In the first model, mice are injected with a combination of hedgehog expressing cancer cells and fibroblasts, and the effects of hedgehog antagonists on the growth of this mixed-tumor are examined over time. In the second model, mice are injected with hedgehog expressing cancer cells which have not been previously combined with fibroblast cells. Without wishing to be bound by any particular theory, both models appear to recapitulate at least to some degree the complex interactions which occur during tumor formation. In the mixed tumor model, cancer cells and fibroblast cells interact—much like cancer cells and stromal cells interact during the development of many forms of cancer. In the second model however, it appears that surrounding endogenous cells invade and interact with the injected hedgehog expressing cancer cells similarly recapitulating the interactions which occur in both the mixed-tumor model and during the development of many forms of cancer. Accordingly, results obtained using either model help to address the use of hedgehog antagonists in inhibiting the proliferation, growth, differentiation and survival of hyperproliferative cells.

Model I: Mixed Tumor Model

Figure 41:
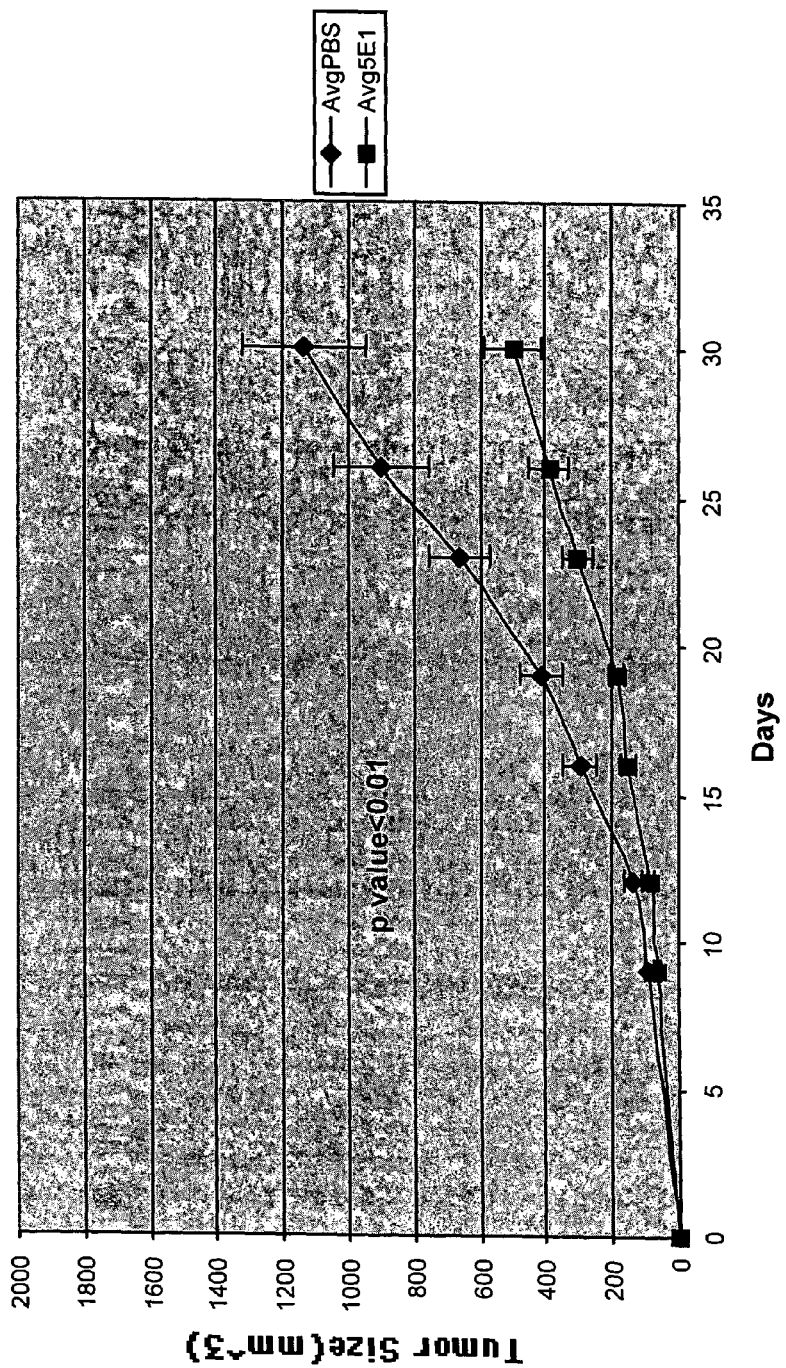
FIG. 41 shows that the Shh blocking antibody 5E1 decreases tumor size when administered to mice injected with a combination of the Shh expressing colon cancer cell line HT-29 and fibroblasts.
Figure 42:
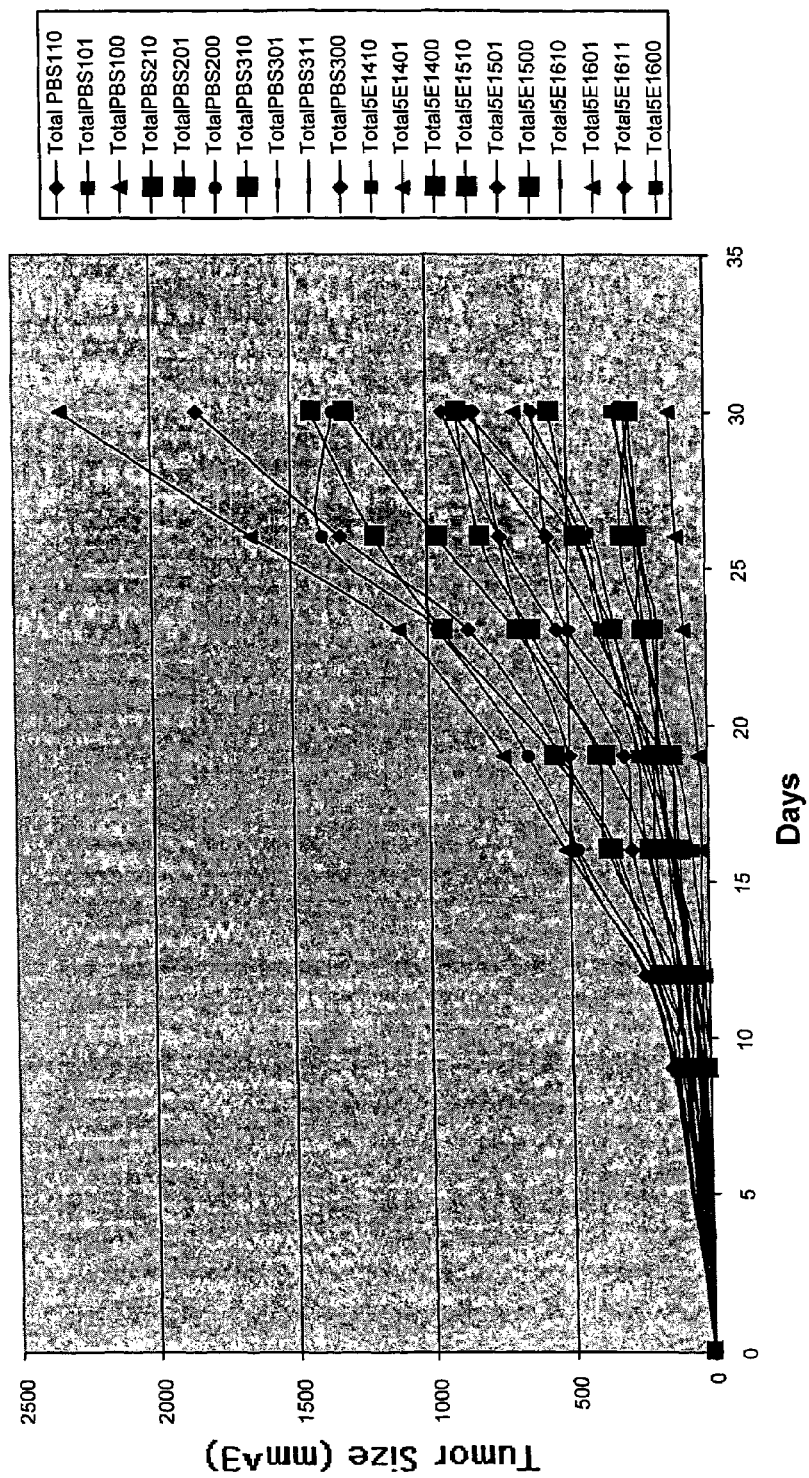
FIG. 42 shows that the Shh blocking antibody 5E1 decreases tumor size when administered to mice injected with a combination of the Shh expressing colon cancer cell line HT-29 and fibroblasts.

To help address this model, the ability of the antagonistic hedgehog antibody 5E1 to inhibit tumor growth in mice injected with a combination of hedgehog expressing colon cancer cells and fibroblasts was investigated. Two experiments were performed to assess the effects of 5E1 treatment on tumor size in mice injected with hedgehog expressing colon cancer cells. In the first experiment, treatment with 5E1, or PBS control, was initiated on the same day as injection with the tumor cells. The results are summarized in FIGS. 41 and 42, and demonstrate that treatment with 5E1 significantly decreases tumor size, weight, and rate of growth in comparison to that of mice treated with PBS (FIGS. 41 and 42). The experiment was performed using two separate colon cancer cell lines with similar affects.

Figure 43:
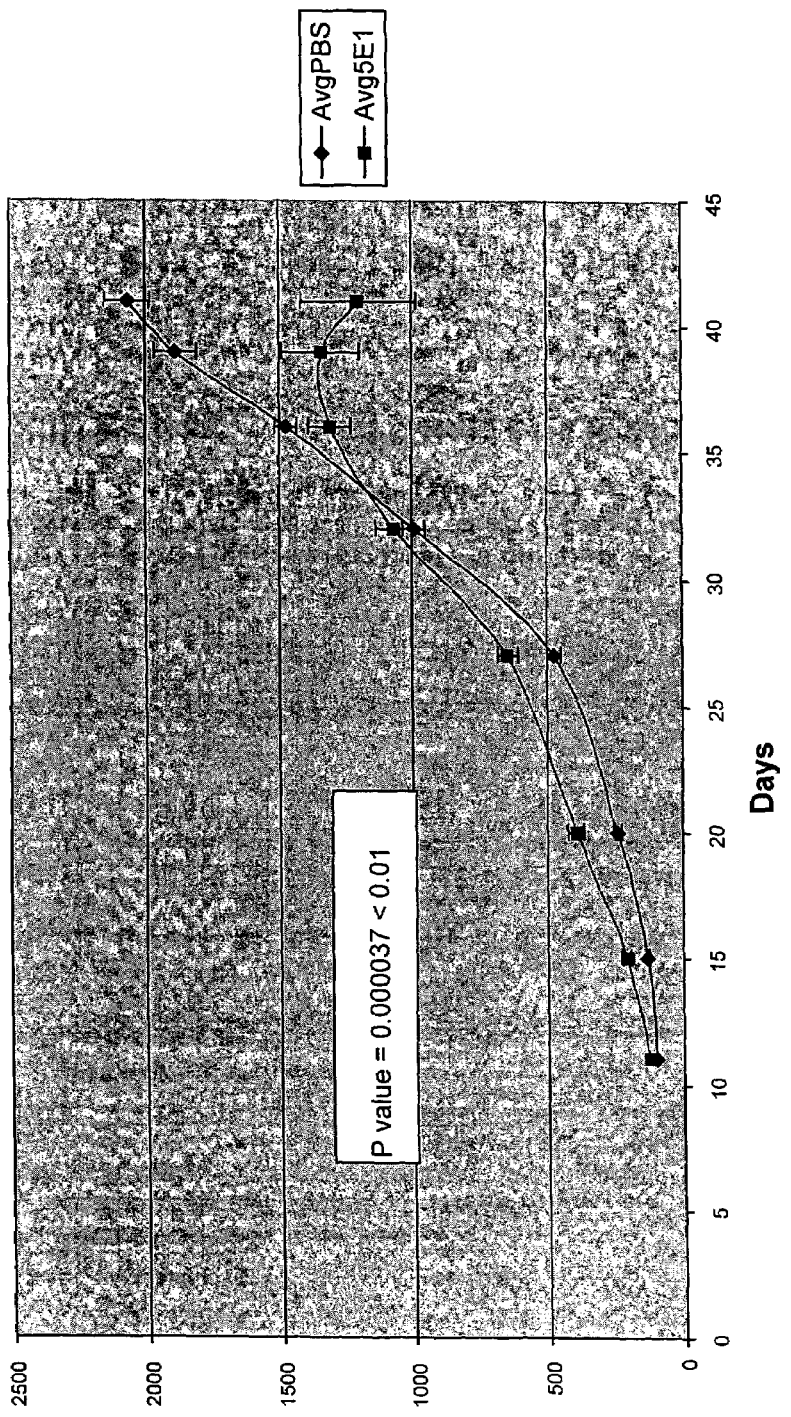
FIG. 43 shows that delayed administration of the Shh blocking antibody 5E1 decreases tumor size when administered to mice injected with a combination of the Shh expressing colon cancer cell line HT-29 and fibroblasts.
Figure 44:
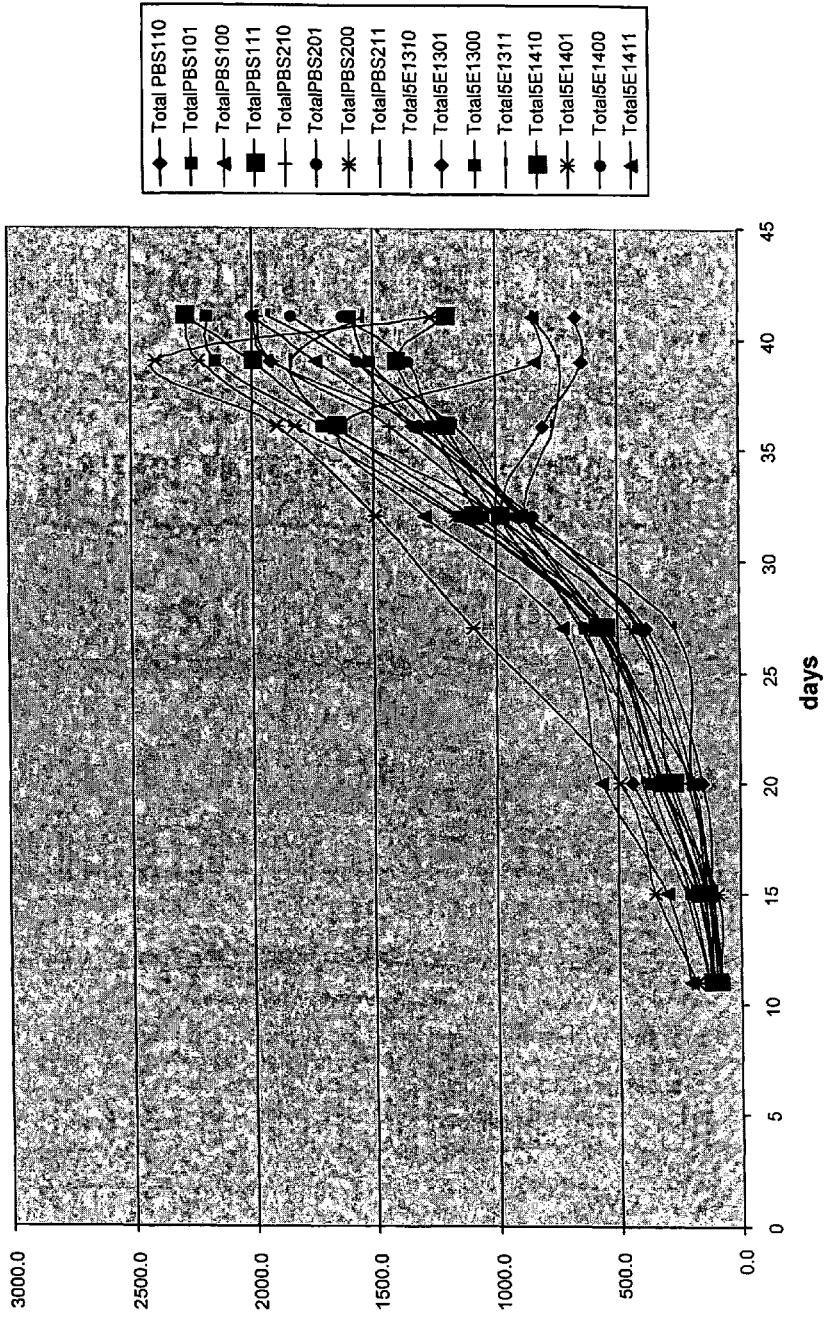
FIG. 44 shows that delayed administration of the Shh blocking antibody 5E1 decreases tumor size when administered to mice injected with a combination of the Shh expressing colon cancer cell line HT-29 and fibroblasts.

In the second experiment, treatment with 5E1 was delayed until the eleventh day of tumor growth. The results are summarized in FIGS. 43 and 44, and demonstrate that treatment with 5E1 significantly decreases the size and rate of growth of the tumor when compared to control mice (FIGS. 43 and 44). The experiment was performed using two separate colon cancer cell lines with similar affects.

Figure 45:
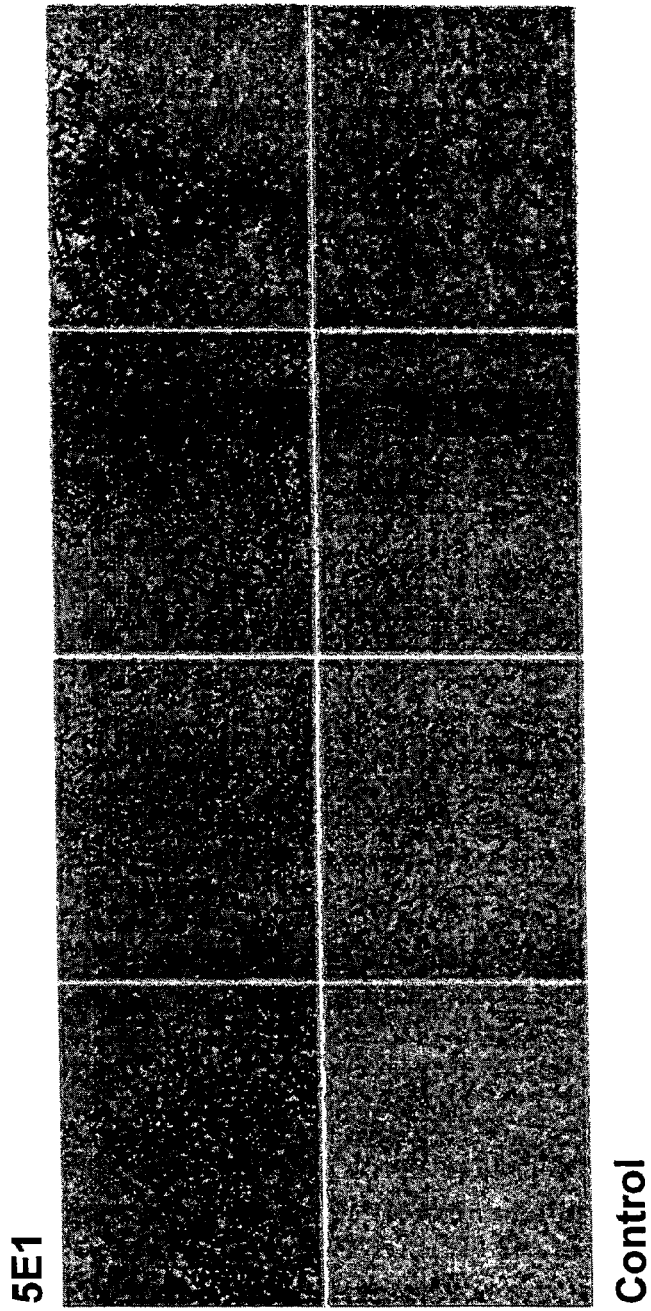
FIG. 45 shows that administration of the Shh blocking antibody 5E1 induces apoptosis in HT-29/fibroblast mixed tumors.

To further understand the mechanism by which administration of a hedgehog antagonist inhibits the growth of tumors in vivo, TUNEL analysis was performed on mixed tumors treated with either 5E1 or with the PBS control. FIG. 45 demonstrates that at least a portion of the cells in the HT-29/fibroblast mixed tumor die apoptotically following administration of the hedgehog antagonist 5E1. This result demonstrates that treatment of these hyperproliferative cells with a hedgehog antagonist inhibits the proliferation, growth and survival of the mixed tumor cells in vivo, and that at least some of this effect is due to the apoptotic death of cells in the mixed tumor following treatment.

These results demonstrate the utility of hedgehog antagonists in the inhibition of proliferation and growth of cancer cells. Additionally, this model provides an in vivo method for easily evaluating the efficacy of candidate hedgehog antagonists.

METHODS: Experiment 1. Twenty nude mice were injected subcutaneously with a combination of $10^6$ HT-29 cells (a Shh expressing colon cancer cell line) and $10^6$ 10T ½ cells (a fibroblast cell line) in a volume of 100 µl. The mice were randomized into two groups. Group A was treated with PBS, and group B was treated with 5E1. The treatments were initiated on the same day as injection of the tumor cells. Treatment was administered IP, 3 times/week over a period of thirty days, and at a dose of 6 mg/kg. Additionally, this experiment was carried out under an identical protocol using another Shh expressing colon cancer cell line (Colo205) with similar results. Experiment 2—delayed administration. Twenty nude mice were injected subcutaneously with a combination of $10^6$ HT-29 cells (a Shh expressing colon cancer cell line) and $10^6$ 10T ½ cells (a fibroblast cell line) in a volume of 100 µl. The mice were randomized into two groups. Group A was treated with PBS, and group B was treated with 5E1. Treatment was initiated after the tumor had grown to day 11. Such tumors had a volume of approximately 90-210 mm$^3$. Treatment was administered IP, 3 times/week over a period of twenty-nine days (until day 40 of total tumor growth), and at a dose of 6 mg/kg. Additionally, this experiment was carried out under an identical protocol using another Shh expressing colon cancer cell line (Colo205) with similar results.

Model II

Figure 46:
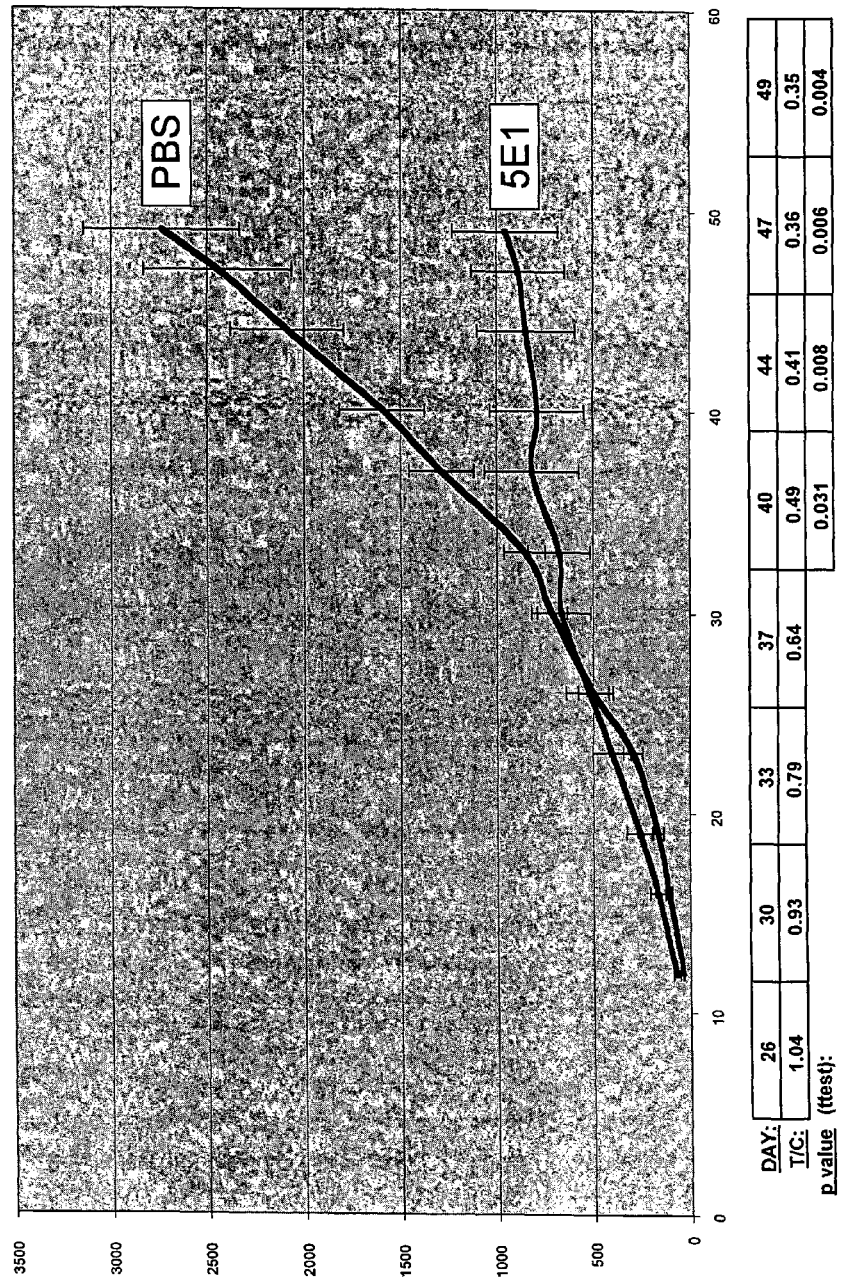
FIG. 46 shows that delayed administration of the Shh blocking antibody 5E1 decreases tumor size when administered to mice injected with the Shh expressing colon cancer cell line HT-29.
Figure 47:
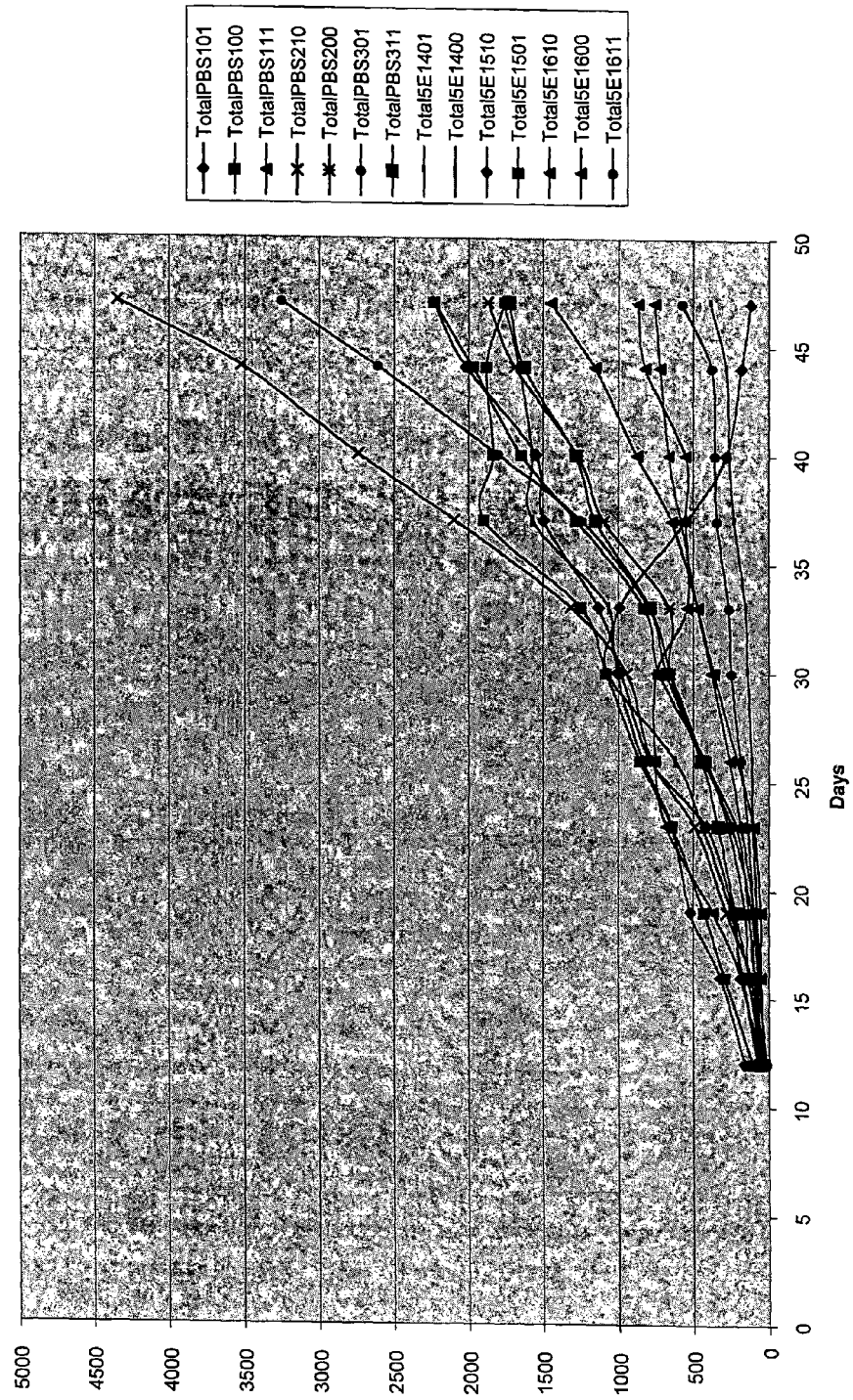
FIG. 47 shows that delayed administration of the Shh blocking antibody 5E1 decreases tumor size when administered to mice injected with the Shh expressing colon cancer cell line HT-29.
Figure 48:
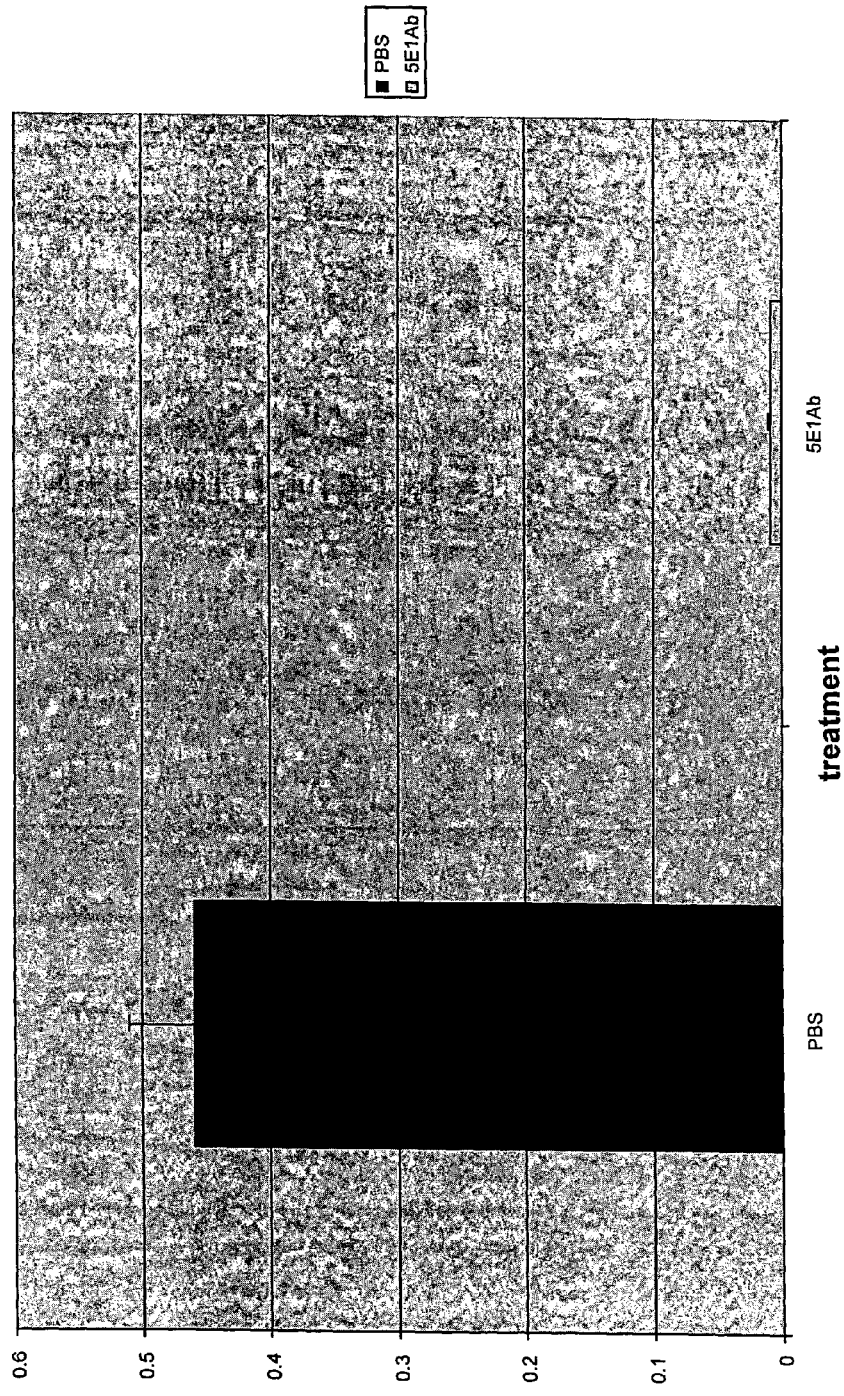
FIG. 48 shows that delayed administration of the Shh blocking antibody 5E1 to mice injected with the Shh expressing colon cancer cell line HT-29 decreases expression of gli-1 mRNA.

Similar experiments were conducted to assess the efficacy of a hedgehog antagonist in decreasing the growth, proliferation and survival of tumors derived from the transplantation of HT-29 cells alone. Hedgehog expressing HT-29 colon cancer cells were injected subcutaneously into nude mice as described in detail above. FIGS. 46 and 47 show that delayed administration of the hedgehog antagonist, 5E1, significantly reduces the growth of such tumors in vivo when compared to tumors treated with the PBS control. Consistant with these results, treatment with 5E1 also significantly reduces the expression of gli-1 in these tumors when compared to tumors treated with the PBS control (FIG. 48).

The results obtained using the two in vivo models described in detail above demonstrate that the antagonism of hedgehog signaling can significantly inhibit the growth, proliferation, and survival of hedgehog expressing tumors.

METHODS: Nude mice were injected subcutaneously with $10^6$ HT-29 cells (a Shh expressing colon cancer cell line) in a volume of 100 µl. The mice were randomized into two groups. Group A was treated with PBS, and group B was treated with 5E1. Treatment was initiated after the tumor had grown to day 11. Treatment was administered IP, 3 times/week over a period of fifty days, and at a dose of 6 mg/kg. Tumor volumes were measured over time. Additionally, expression of gli-1 mRNA was analyzed by Q-RT-PCR in PBS treated versus 5E1 treated tumors.

Example 10

Antagonism of Hedgehog Signaling in Pancreatic Cancer

We had previously demonstrated that hedgehog mRNA and protein are expressed in several pancreatic cancer cell lines, as well as in primary human pancreatic tissue samples. Given the existence of hedgehog expressing pancreatic cancer cell lines, we examined the ability of antagonism of hedgehog signaling to decrease growth, proliferation, and survival of pancreatic cancel cells in xenografts in nude mice. Similar to the results observed with xenografts of hedgehog expressing bladder, prostate and colon cancer cell lines, administration of a hedgehog antagonist decrease the size and survival of tumors generated by xenografts of hedgehog expressing pancreatic cancer cells.

SW1990 Xenograft

SW-1990 is a hedgehog expressing pancreatic ductal adenocarcinoma cell line. To assess the potential efficacy of administration of hedgehog antagonists to treat pancreatic tumors, tumors were generated in nude mice by subcutaneous injection of SW-1990 cells. In these experiments, SW-1990 cells were injected in the absence of fibroblasts. Animals that received the SW-1990 cells were divided into two groups, and immediately began receiving treatment with either the hedgehog blocking antibody 5E1 or PBS. Animals receiving 5E1 received a dose of 2 mg/kg, intraveneously, once per week.

The effects of treatment with the hedgehog antagonist 5E1 were evaluated by measuring tumor volume and weight, as well as by visual inspection of the tumors. Interestingly, tumor volume was variable due to inflammation, and thus visual analysis and tumor weight appear to be a more accurate measure of the effects of hedgehog antagonism on these tumors.

Figure 49:
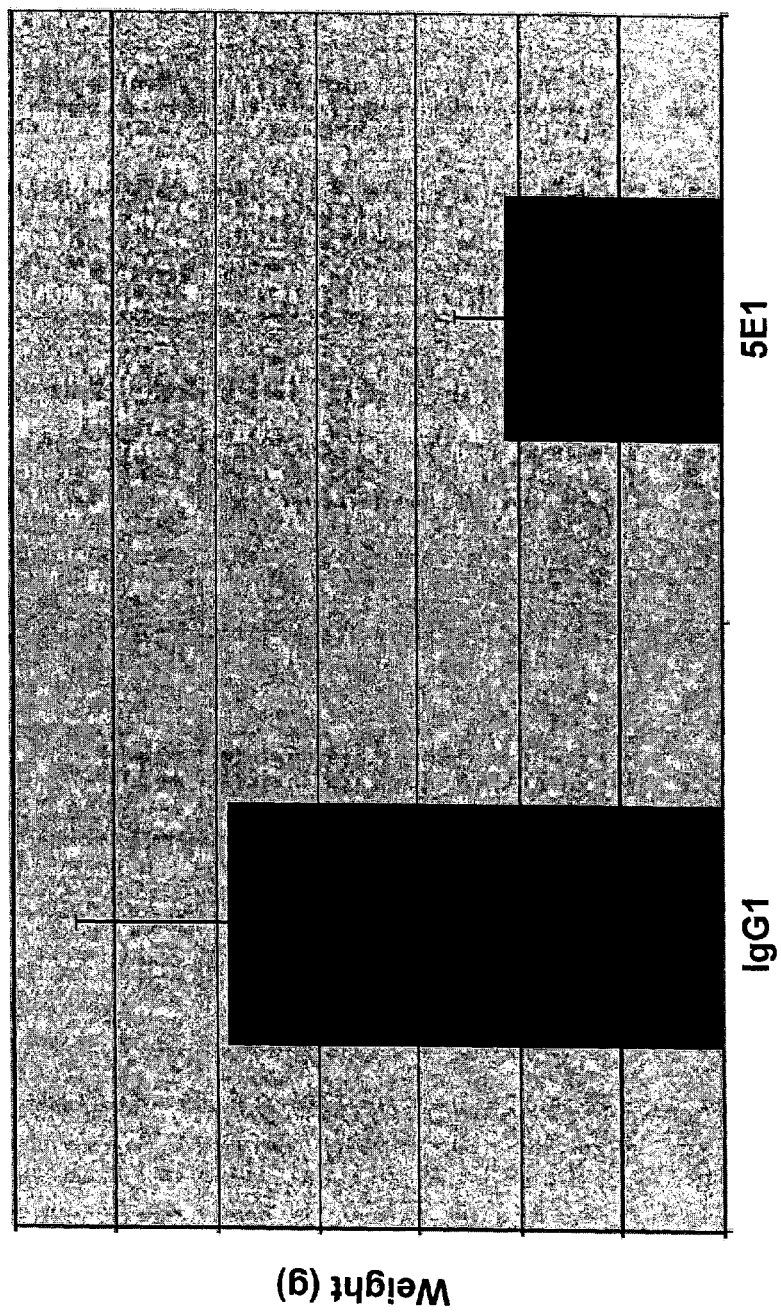
FIG. 49 shows that administration of the Shh blocking antibody 5E1 to mice injected with the hedgehog expressing pancreatic cancer cell line SW1990 decreases tumor weight.
Figure 50:
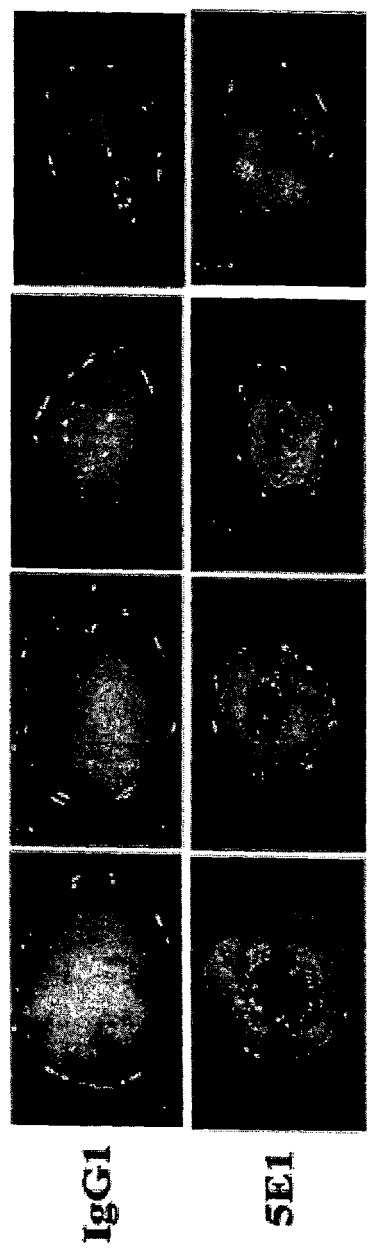
FIG. 50 shows that administration of the Shh blocking antibody 5E1 to mice injected with the hedgehog expressing pancreatic cancer cell line SW1990 decreases tumor size, and results in extensive domains of necrosis within said tumors.
Figure 51:
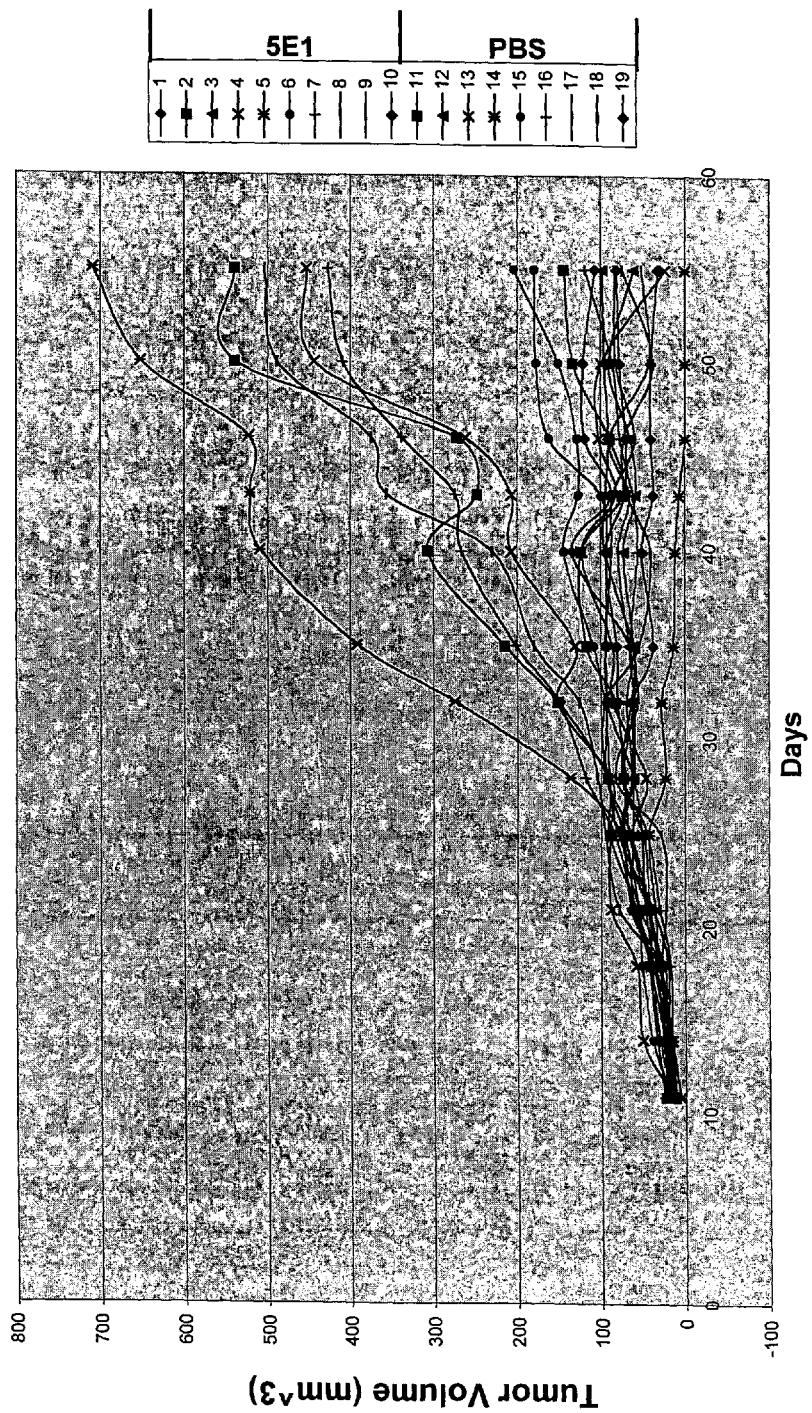
FIG. 51 shows that administration of the Shh blocking antibody 5E1 to mice injected with the hedgehog expressing pancreatic cancer cell line SW1990 decreases tumor volume.

FIG. 49 demonstrates that administration of the blocking antibody 5E1 results in a significant decrease in the weigh of SW1990 xenograft tumors. The effects of 5E1 treatment are most dramatically related through visual inspection of the tumors. FIG. 50 shows that 5E1 treated tumors are smaller than control tumors, and that the 5E1 treated tumors contain extensive regions of necrosis. Although volume of SW1990 xenograft tumors was variable, owing to inflammation, FIG. 51 indicates the overall trend of decreased volume of xenograft tumors following administration of the hedgehog antagonist 5E1.

CF PAC Xenograft

To further confirm the results demonstrating that inhibition of hedgehog signaling has efficacy in inhibiting growth, proliferation and survival of hedgehog expressing pancreatic tumors, similar experiments were conducted with another hedgehog expressing pancreatic tumor cell line, CF PAC. Like SW1990, CF PAC is a hedgehog expressing pancreatic ductal adenocarcinoma cell line. Experiments were performed using similar methods for generating SW1990 xenografts, and for testing the efficacy of the hedgehog antagonist 5E1 in said xenografts. The only difference in the two experiments is that 5E1 treatment was delayed until approximately 11 days following administration of CF-PAC cells The effects of treatment with the hedgehog antagonist 5E1 were evaluated by measuring tumor volume and weight. Interestingly, tumor volume was variable due to inflammation, and thus visual analysis and tumor weight appear to be a more accurate measure of the effects of hedgehog antagonism on these tumors.

Figure 52:
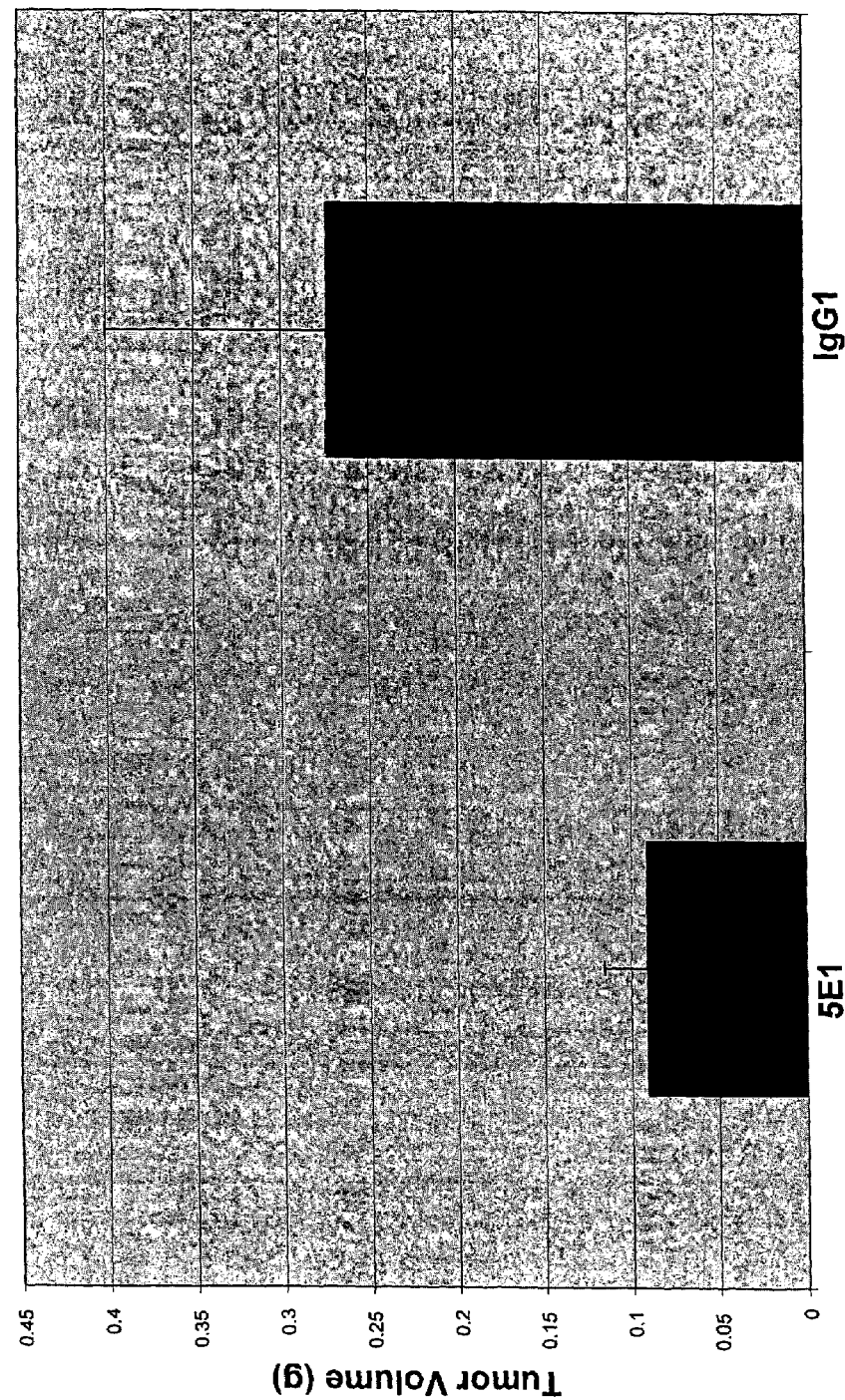
FIG. 52 shows that administration of the Shh blocking antibody 5E1 to mice injected with the hedgehog expressing pancreatic cancer cell line CF PAC decreases tumor weight.
Figure 53:
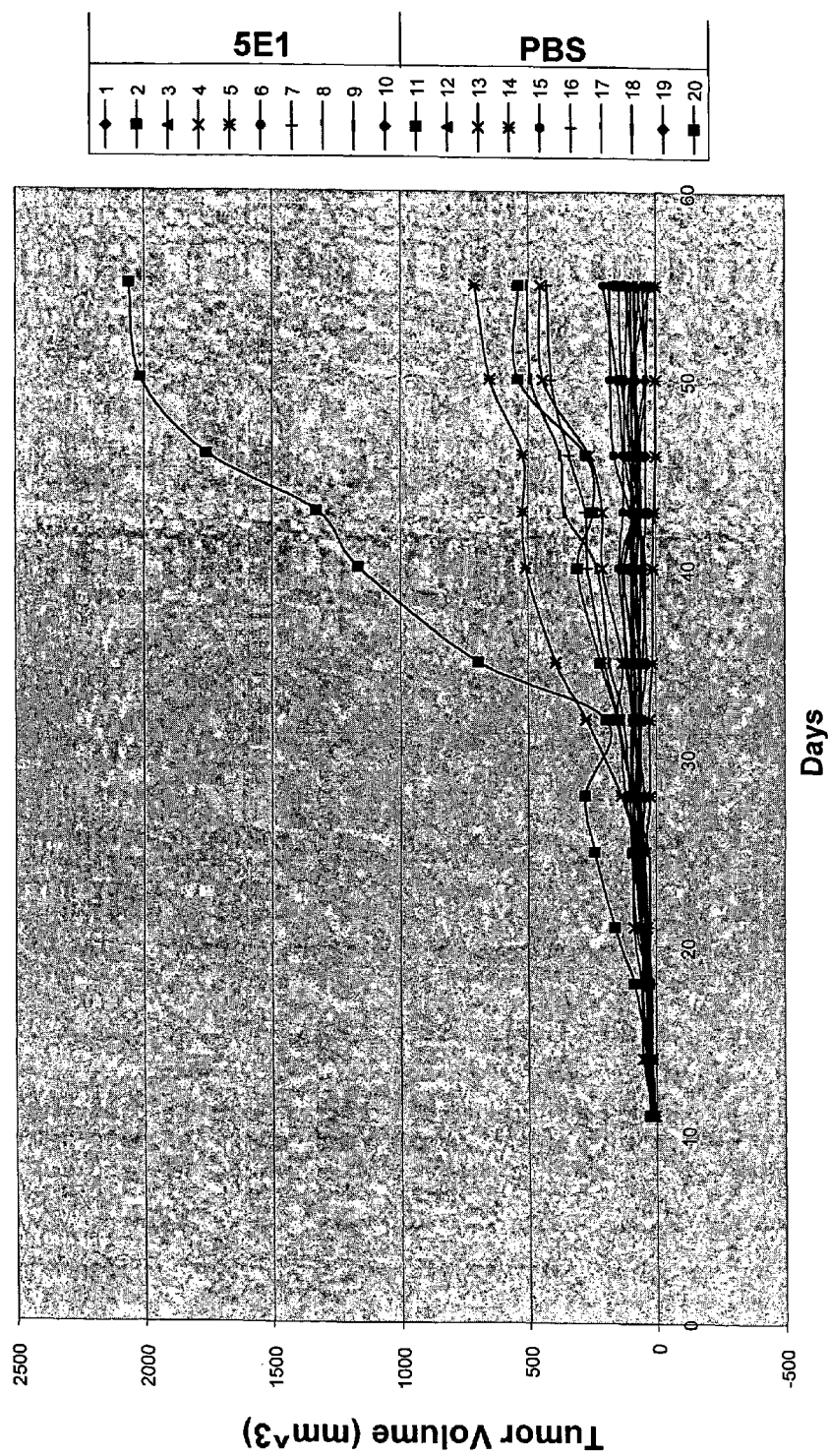
FIG. 53 shows that administration of the Shh blocking antibody 5E1 to mice injected with the hedgehog expressing pancreatic cancer cell line CF PAC decreases tumor volume.

FIG. 52 demonstrates that administration of the blocking antibody 5E1 results in a significant decrease in the weight of CF PAC xenograft tumors. Although the volume of CF PAC xenograft tumors was variable, owing to inflammation, FIG.

Example 11

Non-hedgehog Expressing Cancer Cell Line

Efficacy of antagonism of hedgehog signaling in regulating the growth, proliferation and survival of hyperproliferative cells was examined using a cancer cell line which does not express hedgehog. Without being bound by any particular theory, it is possible that the antagonism of hedgehog signaling is most effective in regulating cell growth, proliferation and survival in cells in which hedgehog signaling is already hyper-activated. Such cells would include, for example, cells comprising a mutation in a component of the hedgehog signaling pathway wherein the mutation results in at least one of gain-of-function of an activator of hedgehog signaling or loss-of-function of a repressor of hedgehog signaling (e.g., patched).

Figure 54:
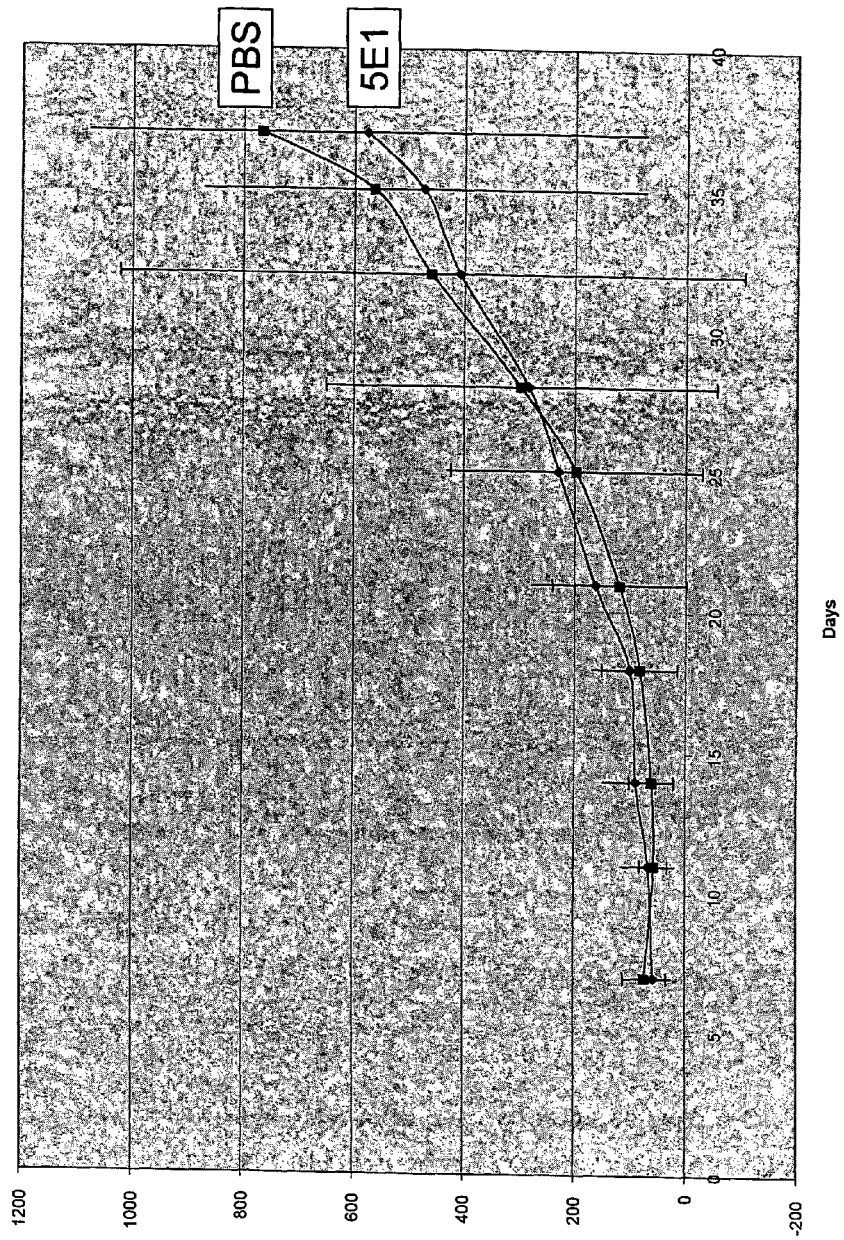
FIG. 54 shows that administration of the Shh blocking antibody 5E1 to mice injected with the non-hedgehog expressing colon cancer cell line SW480 has no effect on tumor volume.

SW-480 is a colon adenocarcinoma cell line which does not express hedgehog. SW-480 cells were administered subcutaneously to nude mice to generate xenografts, as previously described. Approximately seven days after administration of the SW-480 cells, treatment with either 5E1 or PBS control was initiated (delayed administration). In 5E1 treated animals, administration was at a dose of 2 mg/kg, intravenously, once per week. Tumor volumes were measured regularly throughout treatment. FIG. 54 demonstrates that administration of 5E1 appears to have no effect on tumor volume in SW-480 xenografts.

The results of these experiments further underscore that unregulated hedgehog signaling can result in hyper-prolferation and/or inappropriate cell survival. These results demonstrate the uility of inhibition of inappropriate hedgehog signaling as a method of inhibiting inappropriate cell proliferation, growth and survival. Examples of conditions which can be treated by these methods include, but are not limited to, various forms of cancer.

Additionally, the observation that hedgehog antagonism is most effective in regulating cell proliferation, growth and survival in cells which express hedgehog, or cells in which the hedgehog signaling pathway is hyperactivated, suggest diagnostic methods for predicting which conditions and which patients (e.g., which forms of cancer) are most likely to respond to treatment regimens which include a hedgehog antagonist.

Example 12

Drug Screens

The foregoing examples present both in vitro and in vivo models for examining the effects of hedgehog antagonist on cell proliferation. The models provide assays for testing a range of antagonistic agents for the ability to inhibit cell growth and proliferation. Such screens can be used in initial assays to identify lead compounds, and can also be used to evaluate the relative efficacies of candidate compounds.

Antagonistic agents that can be analyzed in this way include small molecules, blocking antibodies, antisense oligonucleotides, and polypeptides. These agents may interfere with hedgehog signaling at any point along the signal transduction pathway. For example, preferred agents may interact with hedgehog, patched-1, or smoothened. Additional preferred agents may interact with an intracellular component of the hedgehog pathway including gli-1, gli-2, or gli-3.

The in vitro and in vivo methods described above are not specific for the cancer cell lines explicitly described herein. Any cell type or cell line could be similarly tested, and these methods could be easily used to assess the ability of hedgehog antagonists to inhibit tumor growth and proliferation in other types of cancer cells. Additionally, the in vitro assay could be employed to analyze hedgehog signaling and the ability of hedgehog antagonists to block hedgehog signaling in other non-cancerous hyperproliferative cell types. For example, hyperproliferative conditions include many other classes of disorders including skin maladies such as psoriasis. The effects of candidate hedgehog antagonists on these cell types can be easily assessed using the methods described here.

All publications, patents and patent applications are herein incorporated by reference in their entirety to the same extent as if each individual publication, patent or patent application was specifically and individually indicated to be incorporated by reference in its entirety.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method of treating a diseased or disordered tissue, comprising
   (a) determining whether said tissue overexpresses a gli-1 gene, and
   (b) contacting said tissue which overexpresses a gli-1 gene with an effective amount of a hedgehog antagonist, which hedgehog antagonist is a hedgehog antibody that binds to Sonic hedgehog protein and inhibits hedgehog signaling;
   wherein the diseased or disordered tissue is tissue exhibiting urogenital cancer, and
   wherein contacting said tissue with said hedgehog antagonist treats the diseased or disordered tissue.

2. A method of claim 1, wherein said cancer is associated with one or more of prostate, ovary, uterus, bladder, and kidney tissues.

3. A method of claim 2, wherein said cancer associated with the prostate is adenocarcinoma.

4. The method of claim 1, wherein said cancer is testicular cancer.

5. The method of claim 1, wherein contacting said tissue with said hedgehog antagonist inhibits at least one of unwanted growth, proliferation or survival of cells of the diseased or disordered tissue.

6. The method of claim 1, wherein said hedgehog antagonist is a humanized antibody that binds to Sonic hedgehog and inhibits hedgehog signaling.

7. The method of claim 1, wherein said hedgehog antagonist is selected from 5E1 or a humanized antibody thereof.

8. The method of claim 7, wherein said hedgehog antagonist is a monoclonal antibody.

9. The method of claim 1, wherein said hedgehog antagonist is a monoclonal antibody.

10. The method of claim 1, wherein said urogenital cancer is associated with one or more of prostate, bladder, kidney, or testicle.

11. The method of claim 1, wherein determining whether said tissue overexpresses a gli-1 gene comprises obtaining a tissue sample from a patient, and determining whether said sample overexpresses said gli-1 gene.

12. The method of claim 11, wherein determining whether said tissue overexpresses a gli-1 gene comprises determining gli-1 transcript expression.

13. The method of claim 11, wherein determining whether said tissue overexpresses a gli-1 gene comprises determining gli-1 protein expression.

14. The method of claim 1, wherein determining whether said tissue overexpresses a gli-1 gene comprises determining gli-1 transcript expression.

15. The method of claim 1, wherein determining whether said tissue overexpresses a gli-1 gene comprises determining gli-1 protein expression.

16. A method of treating a diseased or disordered tissue, comprising
   (a) determining whether said tissue overexpresses a Sonic hedgehog gene, and
   (b) contacting said tissue which overexpresses said Sonic hedgehog gene with an effective amount of a hedgehog antagonist, which hedgehog antagonist is a hedgehog antibody that binds to Sonic hedgehog protein and inhibits hedgehog signaling;
   wherein the diseased or disordered tissue is tissue exhibiting urogenital cancer, and
   wherein contacting said tissue with said hedgehog antagonist treats the diseased or disordered tissue.

17. The method of claim 16, wherein said hedgehog antagonist is a hedgehog antibody selected from 5E1 or a humanized antibody thereof.

18. The method of claim 17, wherein said hedgehog antagonist is a monoclonal antibody.

19. The method of claim 16, wherein said hedgehog antagonist is a monoclonal antibody.

20. The method of claim 16, wherein contacting said tissue with said hedgehog antagonist inhibits at least one of unwanted growth, proliferation or survival of cells of the diseased or disordered tissue.

21. The method of claim 16, wherein said hedgehog antibody is a humanized antibody.

22. The method of claim 16, wherein said hedgehog antibody is selected from 5E1 or a humanized antibody thereof.

23. The method of claim 16, wherein said cancer is testicular cancer.

24. The method of claim 16, wherein said urogenital cancer is associated with one or more of prostate, bladder, kidney, or testicle.

25. The method of claim 16, wherein determining whether said tissue overexpresses a Sonic hedgehog gene comprises obtaining a tissue sample from a patient, and determining whether said sample overexpresses said Sonic hedgehog gene.

26. A method of treating a diseased or disordered tissue in a patient in need thereof, comprising
   (a) determining whether said tissue overexpresses a Sonic hedgehog gene, and (b) contacting said tissue which overexpresses said Sonic hedgehog gene with an effective amount of a hedgehog antibody that binds to Sonic hedgehog protein and antagonizes hedgehog signaling;

wherein the diseased or disordered tissue is tissue exhibiting urogenital cancer, and wherein contacting said tissue with said hedgehog antibody decreases unwanted cell proliferation and treats said diseased or disordered tissue in said patient in need thereof.

27. The method of claim 26, wherein said hedgehog antibody which specifically antagonizes hedgehog signaling is a monoclonal antibody.

28. The method of claim 27, wherein said monoclonal antibody is 5E1 or a monoclonal antibody which binds the same epitope as 5E1.

29. The method of claim 26, wherein said hedgehog antibody which antagonizes hedgehog signaling is formulated in a pharmaceutically acceptable carrier.

30. The method of claim 26, wherein said hedgehog antibody is administered as part of a cancer treatment regimen.

31. The method of claim 26, wherein contacting said tissue with said hedgehog antagonist inhibits at least one of unwanted growth, proliferation or survival of cells of the diseased or disordered tissue.

32. The method of claim 26, wherein said hedgehog antibody is a humanized antibody.

33. The method of claim 26, wherein said hedgehog antibody is selected from 5E1 or a humanized antibody thereof.

34. The method of claim 26, wherein said cancer is testicular cancer.

35. The method of claim 26, wherein said urogenital cancer is associated with one or more of prostate, bladder, kidney, or testicle.

36. The method of claim 26, wherein determining whether said tissue overexpresses a Sonic hedgehog gene comprises obtaining a tissue sample from a patient, and determining whether said sample overexpresses said Sonic hedgehog gene.

37. A method of treating a diseased or disordered tissue, comprising
(a) determining whether said tissue overexpresses a Sonic hedgehog gene, and
(b) contacting said tissue which overexpresses said Sonic hedgehog gene with an effective amount of a hedgehog antibody that binds to Sonic hedgehog protein, which hedgehog antibody is 5E1 or an antibody which binds the same epitope as 5E1;

wherein the diseased or disordered tissue is tissue exhibiting urogenital cancer, and wherein contacting said tissue with said hedgehog antibody decreases unwanted cell proliferation and treats said diseased or disordered tissue.

38. The method of claim 37, wherein said hedgehog antibody which antagonizes hedgehog signaling is formulated in a pharmaceutically acceptable carrier.

39. The method of claim 37, wherein said hedgehog antibody is administered as part of a cancer treatment regimen.

40. The method of claim 37, wherein contacting said tissue with said hedgehog antagonist inhibits at least one of unwanted growth, proliferation or survival of cells of the diseased or disordered tissue.

41. The method of claim 37, wherein said hedgehog antibody is a humanized antibody.

42. The method of claim 37, wherein said cancer is testicular cancer.

43. The method of claim 37, wherein said urogenital cancer is associated with one or more of prostate, bladder, kidney, or testicle.

44. The method of claim 37, wherein determining whether said tissue overexpresses a Sonic hedgehog gene comprises obtaining a tissue sample from a patient, and determining whether said sample overexpresses said Sonic hedgehog gene.

45. A method of treating a urogenital cancer in a patient in need thereof, comprising ascertaining whether cells in the cancer overexpress a Sonic hedgehog gene, and contacting diseased or disordered tissue of said patient exhibiting urogenital cancer with an effective amount of a hedgehog antibody that binds to Sonic hedgehog protein and inhibits hedgehog signaling, wherein the diseased or disordered tissue exhibiting urogenital cancer overexpresses a Sonic hedgehog gene.

46. The method of claim 45, wherein the hedgehog antibody is a humanized antibody.

47. A method of treating a urogenital cancer in a patient in need thereof, comprising ascertaining whether cells in the cancer overexpress a Sonic hedgehog gene, and administering to said patient in need thereof an amount of a hedgehog antagonist sufficient to decrease at least one of the growth or proliferation of urogenital cancer tissue, wherein the hedgehog antagonist is a hedgehog antibody that binds to Sonic hedgehog protein and inhibits hedgehog signaling, and wherein the urogenital cancer tissue overexpresses a Sonic hedgehog gene.

48. The method of claim 47, wherein the hedgehog antibody is a humanized antibody.

49. The method of claim 48, wherein said urogenital cancer is associated with one or more of prostate, bladder, kidney, or testicle.

50. The method of claim 49, wherein the urogenital cancer is testicular cancer.

51. The method of claim 47, wherein said urogenital cancer is associated with one or more of prostate, bladder, kidney, or testicle.

52. The method of claim 51, wherein the urogenital cancer is testicular cancer.

53. A method of treating a diseased or disordered tissue in a patient in need thereof, comprising ascertaining whether the diseased or disordered tissue overexpresses a gli-1 gene or a Sonic hedgehog gene, and administering to said patient in need thereof an amount of a hedgehog antagonist effective to decrease at least one of the growth or proliferation of the disease or disordered tissue; wherein the hedgehog antagonist is a hedgehog antibody that binds to Sonic hedgehog protein and inhibits hedgehog signaling; and wherein the diseased or disordered tissue is tissue exhibiting urogenital cancer and that overexpresses a gli-1 gene or a Sonic hedgehog gene.

54. The method of claim 53, wherein the hedgehog antibody is a humanized antibody.

55. The method of claim 53, wherein the hedgehog antibody is a monoclonal antibody.

56. The method of claim 53, wherein the diseased or disordered tissue overexpresses a gli-1 gene.

57. The method of claim 53, wherein the diseased or disordered tissue overexpresses a Sonic hedgehog gene.

58. The method of claim 53, wherein said urogenital cancer is associated with one or more of prostate, bladder, kidney, or testicle.

59. The method of claim 58, wherein the diseased or disordered tissue overexpresses a gli-1 gene.

60. The method of claim 58, wherein the diseased or disordered tissue overexpresses a Sonic hedgehog gene.

61. The method of claim 53, wherein the urogenital cancer is testicular cancer.

62. The method of claim 61, wherein the diseased or disordered tissue overexpresses a gli-1 gene.

63. The method of claim 61, wherein the diseased or disordered tissue overexpresses a Sonic hedgehog gene.

* * * * *

UNITED STATES PATENT AND TRADEMARK OFFICE
CERTIFICATE OF CORRECTION

PATENT NO. : 7,708,998 B2
APPLICATION NO. : 10/652298
DATED : May 4, 2010
INVENTOR(S) : Dudek et al.

It is certified that error appears in the above-identified patent and that said Letters Patent is hereby corrected as shown below:

On the Title Page, under Related U.S. Application Data on page 1, item (60), please add the following:
-- and provisional application No. 60/407,145, filed on Aug. 29, 2002. --

In Column 1, Line 7, please insert:
-- This application claims priority to United States provisional application 60/407,145, filed August 29, 2002, the disclosure of which is hereby incorporated by reference in its entirety. --

Signed and Sealed this

Twenty-ninth Day of June, 2010

David J. Kappos
*Director of the United States Patent and Trademark Office*